US011976117B2

(12) United States Patent
Bramson et al.

(10) Patent No.: US 11,976,117 B2
(45) Date of Patent: *May 7, 2024

(54) T CELL-ANTIGEN COUPLER WITH VARIOUS CONSTRUCT OPTIMIZATIONS

(71) Applicant: McMaster University, Hamilton (CA)

(72) Inventors: Jonathan Lorne Bramson, Oakville (CA); Christopher W. Helsen, Oakville (CA); Joanne Alicia Hammill, Hamilton (CA); Kenneth Anthony Mwawasi, Hamilton (CA)

(73) Assignee: McMaster University, Hamilton (CA)

( * ) Notice: Subject to any disclaimer, the term of this patent is extended or adjusted under 35 U.S.C. 154(b) by 1034 days.

This patent is subject to a terminal disclaimer.

(21) Appl. No.: 16/826,053

(22) Filed: Mar. 20, 2020

(65) Prior Publication Data

US 2020/0239571 A1 Jul. 30, 2020

Related U.S. Application Data

(63) Continuation of application No. 16/442,274, filed on Jun. 14, 2019, now Pat. No. 10,640,562.

(60) Provisional application No. 62/839,235, filed on Apr. 26, 2019, provisional application No. 62/828,879, filed on Apr. 3, 2019, provisional application No. 62/826,853, filed on Mar. 29, 2019, provisional application No. 62/773,120, filed on Nov. 29, 2018, provisional application No. 62/703,037, filed on Jul. 25, 2018, provisional application No. 62/699,173, filed on Jul. 17, 2018.

(51) Int. Cl.
| | | |
|---|---|---|
| *A61K 35/17* | (2015.01) | |
| *C07K 14/73* | (2006.01) | |
| *C07K 16/28* | (2006.01) | |

(52) U.S. Cl.
CPC .... *C07K 16/2803* (2013.01); *C07K 14/70514* (2013.01); *C07K 16/2809* (2013.01); *C07K 2317/622* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 9,718,893 | B2 | 8/2017 | Jung et al. |
| 10,435,453 | B2 | 10/2019 | Bramson et al. |
| 10,640,562 | B2 | 5/2020 | Bramson et al. |
| 10,822,408 | B2 | 11/2020 | Hamburger et al. |
| 11,001,621 | B1 | 5/2021 | Bramson et al. |
| 11,008,376 | B2 | 5/2021 | Bramson et al. |
| 11,110,123 | B2 | 9/2021 | Bramson et al. |
| 11,111,298 | B2 | 9/2021 | Bramson et al. |
| 11,198,737 | B2 | 12/2021 | Helsen et al. |
| 11,406,667 | B2 | 8/2022 | Bramson et al. |
| 11,421,014 | B2 | 8/2022 | Bader et al. |
| 11,453,723 | B1 | 9/2022 | Bramson et al. |
| 2002/0107869 | A1 | 8/2002 | Leroy |
| 2004/0162411 | A1 | 8/2004 | Lanzavecchia |
| 2006/0233791 | A1 | 10/2006 | Tedder et al. |
| 2008/0044413 | A1 | 2/2008 | Hammond et al. |
| 2008/0095766 | A1 | 4/2008 | Koenig et al. |
| 2009/0004186 | A1 | 1/2009 | Shitara et al. |
| 2012/0009190 | A1 | 1/2012 | Gaffen et al. |
| 2013/0171152 | A1 | 7/2013 | Spriggs et al. |
| 2015/0119555 | A1 | 4/2015 | Jung et al. |
| 2015/0322169 | A1 | 11/2015 | June et al. |
| 2016/0228546 | A1 | 8/2016 | Stagliano et al. |
| 2016/0362472 | A1 | 12/2016 | Bitter et al. |
| 2016/0368964 | A1 | 12/2016 | Bramson et al. |
| 2019/0153115 | A1 | 5/2019 | Schellenberger et al. |
| 2020/0024345 | A1 | 1/2020 | Bramson et al. |
| 2020/0071377 | A1 | 3/2020 | Bramson et al. |
| 2020/0239571 | A1 | 7/2020 | Bramson et al. |
| 2020/0261500 | A1* | 8/2020 | Bramson .......... C07K 14/70517 |
| 2020/0270330 | A1 | 8/2020 | Bramson et al. |
| 2020/0308278 | A1 | 10/2020 | Bramson et al. |
| 2020/0392247 | A1 | 12/2020 | Helsen et al. |
| 2021/0369780 | A1 | 12/2021 | Bramson et al. |
| 2022/0127372 | A1 | 4/2022 | Li et al. |
| 2022/0331364 | A1 | 10/2022 | Bramson et al. |
| 2022/0332790 | A1 | 10/2022 | Bramson et al. |

(Continued)

FOREIGN PATENT DOCUMENTS

| | | |
|---|---|---|
| CN | 1229436 | 9/1999 |
| CN | 101679966 A | 3/2010 |

(Continued)

OTHER PUBLICATIONS

Kimchi-Sarfaty Cet al., A "silent" polymorphism in the MDR1 gene changes substrate specificity.Science. Jan. 26, 2007;315(5811):525-8.*
Voet et al., Biochemistry, John Wiley and Sons, 1990, p. 126-129.*
Acuto et al. T cell activation and the cytoskeleton. Annu. Rev. Immunol. 18:165-184 (2000).
Apuri, S., et al., "Outcomes in Patients with Acute Myeloid Leukemia Preceded by Breast Cancer", Blood, 120(21): 4316 (2012).
Arcaro et al. Essential role of CD8 palmitoylation in CD8 coreceptor function. J. Immunol. 165:2068-2076 (2000).
Chames et al. Bispecific antibodies for cancer therapy: the light at the end of the tunnel? MAbs 1 :539-547 (2009).
Chervin et al. The impact of TCR-binding properties and antigen presentation format on T cell responsiveness. J. Immunol. 183:1166-1178 (2009).

(Continued)

*Primary Examiner* — Maria G Leavitt
(74) *Attorney, Agent, or Firm* — Goodwin Procter LLP

(57) ABSTRACT

A trifunctional molecule is provided, comprising (i) a target-specific ligand, (ii) a ligand that binds a protein associated with a TCR complex, and (iii) a T cell receptor signaling domain polypeptide. Variants of the molecule are provided, including variants that exhibit optimized surface expression, transduction efficiency, and effector functionality. Variations include, for example, different ligands that bind CD3 epsilon (e.g., OKT3, L2K, F6A, UCHT1 and humanized UCHT1), different signaling domains, and different linkers between domains.

8 Claims, 46 Drawing Sheets

Specification includes a Sequence Listing.

(56) References Cited

U.S. PATENT DOCUMENTS

| | | | |
|---|---|---|---|
| 2023/0212258 A1 | 7/2023 | Bramson et al. | |
| 2023/0265207 A1 | 8/2023 | Helsen et al. | |

FOREIGN PATENT DOCUMENTS

| | | |
|---|---|---|
| CN | 103562221 | 2/2014 |
| JP | 2003111595 A | 4/2003 |
| WO | WO-199744461 A2 | 11/1997 |
| WO | WO-9957268 A1 | 11/1999 |
| WO | WO-2004106380 A2 | 12/2004 |
| WO | WO-2005040220 A1 | 5/2005 |
| WO | WO-2010037835 A2 | 4/2010 |
| WO | WO-2012066058 A1 | 5/2012 |
| WO | WO-2012106587 A1 | 8/2012 |
| WO | WO-2012135345 A1 | 10/2012 |
| WO | WO-2013059885 A2 | 5/2013 |
| WO | WO-2013092001 A1 | 6/2013 |
| WO | WO-2013123061 A1 | 8/2013 |
| WO | WO-2014011988 A2 | 1/2014 |
| WO | WO-2014122144 A1 | 8/2014 |
| WO | WO-2015006749 A2 | 1/2015 |
| WO | WO-2015061694 A2 | 4/2015 |
| WO | WO-2015117229 A1 | 8/2015 |
| WO | WO-2015/142675 A2 | 9/2015 |
| WO | WO-2016166139 A1 | 10/2016 |
| WO | WO-2017040344 A2 | 3/2017 |
| WO | WO-2017087723 A1 | 5/2017 |
| WO | WO-2018027155 A1 | 2/2018 |
| WO | WO 2018121605 * | 5/2018 |
| WO | WO-2018121605 A1 | 7/2018 |
| WO | WO-2019071358 A1 | 4/2019 |
| WO | WO-2020018727 A1 | 1/2020 |
| WO | WO-2020156554 A1 | 8/2020 |
| WO | WO-2022099076 A1 | 5/2022 |
| WO | WO-2022256449 A1 | 12/2022 |
| WO | WO-2022266778 A1 | 12/2022 |

OTHER PUBLICATIONS

Deshayes, S., et al., Cell-penetrating peptides: tools for intracellular delivery of therapeutics, Cell Mol Life Sci, 62(16): 1839-1849 (2005).
Dotti et al. Fifteen years of gene therapy based on chimeric antigen receptors: "are we nearly there yet?" Hum. Gene Ther. 20:1229-1239 (2009).
Finney et al. Activation of resting human primary T cells with chimeric receptors: costimulation from CD28, inducible costimulator, CD134, and CD137 in series with signals from the TCR zeta chain. J. Immunol. 172:104-113 (2004).
Fragoso et al. Lipid raft distribution of CD4 depends on its palmitoylation and association with Lek, and evidence for CD4-induced lipid raft aggregation as an additional mechanism to enhance CD3 signaling. J. Immunol. 170:913-921 (2003).
Fry et al. T-cell adoptive immunotherapy for acute lymphoblastic leukemia. Hematology Am. Soc. Hematol. Educ. Program 2013:348-353 (2013).
Han et al. Chimeric antigen receptor-engineered T cells for cancer immunotherapy: progress and challenges. J. Hematol. Oncol. 6:4 7 (2013).
He et al. T-cell antigen receptor triggering and lipid rafts: a matter of space and time scales. Talking Point on the involvement of lipid rafts in T-cell activation. EMBO Rep. 9:525-530 (2008).
Jamal, S., et al., "Immunophenotypic Analysis of Peripheral T-Cell Neoplasms", Am. J. Clin. Pathol., vol. 116, pp. 512-526, (2001).
Kiewe, P., et al., "Phase I Trial of the Trifunctional Anti-HER2 x Anti-CD3 Antibody Ertumaxomab in Matastatic Breast Cancer", Clin. Cancer Res., 12(10), pp. 3085-3091, (2006).
Kim et al. A zinc clasp structure tethers Lek to T cell coreceptors CD4 and CD8. Science 301 :1725-1728 (2003).
Kimchi-Sarfaty, C., et al., "A 'silent' polymorphiosm in the MDR1 gene changes substrate specificity", Science, 315:525-528, (2007).

Kochenderfer et al. Treating B-cell cancer with T cells expressing anti-CD19 chimeric antigen receptors. Nat. Rev. Clin. Oncol. 10:267-276 (2013).
Kuhns et al. TCR Signaling Emerges from the Sum of Many Parts. Front. Immunol. 3:159 (2012).
Marsden, H.R., et al., Model systems for membrane fusion, Chem Soc Rev, 40(3): 1572-1585 (2011).
Methi et al. Short-interfering RNA-mediated Lek knockdown results in augmented downstream T cell responses. J. Immunol. 175(11):7398-7406 (2005).
Milone et al. Chimeric receptors containing CD137 signal transduction domains mediate enhanced survival of T cells and increased antileukemic efficacy in vivo. Mol. Ther. 17: 1453-1464 (2009).
PCT/CA2015/000068 International Preliminary Report on Patentability dated Aug. 9, 2016.
Pllozzi et al. Co-expression of CD79a (JCB117) and CD3 by lymphoblastic lymphoma. J Pathol 186(2):140-143. (1998).
Popik, et al. CD4 receptor localized to non-raft membrane microdomains supports HIV-1 entry. Identification of a novel raft localization marker in CD4. J Biol Chem 279(1):704-712 (2004).
Portell et al. Clinical and pharmacologic aspects of blinatumomab in the treatment of B-cell acute lymphoblastic leukemia. Clin. Pharmacol. 5(Suppl 1):5-11 (2013).
Rosenberg, et al. Use of tumor-infiltrating lymphocytes and interleukin-2 in the immunotherapy of patients with matastatic melanoma. A preliminary report. NEJM 319: 1676 (1988).
Thompson et al. CLUSTAL W: improving the sensitivity of progressive multiple sequence alignment through sequence weighting, position-specific gap penalties and weight matrix choice. Nucleic Acid Res. 22:4673-4680 (1994).
U.S. Appl. No. 17/301,884, filed Apr. 16, 2021.
U.S. Appl. No. 15/929,510 Office Action dated Nov. 9, 2020.
U.S. Appl. No. 15/929,513 Office Action dated May 11, 2021.
U.S. Appl. No. 15/929,513 Office Action dated Nov. 30, 2020.
U.S. Appl. No. 16/547,421 Office Action dated Nov. 24, 2021.
U.S. Appl. No. 16/904,451 Office Action dated Dec. 1, 2020.
U.S. Appl. No. 16/904,451 Office Action dated May 10, 2021.
U.S. Appl. No. 17/248,174 Office Action dated Mar. 11, 2021.
U.S. Appl. No. 17/304,924, filed Jun. 28, 2021.
U.S. Appl. No. 17/394,280, filed Aug. 4, 2021.
U.S. Appl. No. 17/394,280 Office Action dated Dec. 10, 2021.
Voet, D., et al., Biochemistry, John Wiley and Sons, New York, pp. 126-128, (1990).
Wang, M., et al., Efficient delivery of genome-editing proteins using bioreducible lipid nanoparticles, PNAS, 113(11): 2868-2873 (2016).
Wykosky, J., et al. The EphA2 repector and ephrinA1 ligand in solid tumors: function and therapeutic targeting, Mol Cancer Res, 6(12):1795-1806 (2008).
Yin et al. Crystal structure of a complete ternary complex of T-cell receptor, peptide-MHC, and CD4. PNAS USA 109:5405-5410 (2012).
Alabanza et al. Function of Novel Anti-CD19 Chimeric Antigen Receptors with Human Variable Regions Is Affected by Hinge and Transmembrane Domains. Mol Ther 25(11):2452-2465 (2017).
Anderson et al. Comodulation of CD3 and CD4. Evidence for a specific association between CD4 and approximately 5% of the CD3:T cell receptor complexes on helper T lymphocytes. J Immunol 140:1732-1737 (1988).
Compte et al. Inhibition of tumor growth in vivo by in situ secretion of bispecific anti-CEA x anti-CD3 diabodies from lentivirally transduced human lymphocytes. Cancer Gene Therapy 14:380-388 (2007).
Deans et al. Interaction of CD4:lck with the T cell receptor/CD3 complex induces early signaling events in the absence of CD45 tyrosine phosphatase. Eur J Immunol 22:661-668 (1992).
EP15746948.7 Communication pursuant to Rule 114(2) EPC dated Jan. 21, 2019.
Fournier et al. Bispecific antibodies and trispecific immunocytokines for targeting the immune system against cancer: preparing for the future. BioDrugs 27:35-53 (2013).
Frankel et al. Targeting T cells to tumor cells using bispecific antibodies. Curr Opin Chem Biol 17(3):385-392 (2013).

(56) References Cited

OTHER PUBLICATIONS

Geiger et al. Integrated src kinase and costimulatory activity enhances signal transduction through single-chain chimeric receptors in T lymphocytes. Blood 98(8):2364-2371 (2001).
Geyer et al. Review: Current clinical applications of chimeric antigen receptor (CAR) modified T cells. Cytotherapy 18(11):1393-1409 (2016).
Hammond et al. Selective targeting and potent control of tumor growth using an EphA2/CD3-Bispecific single-chain antibody construct. 67(8):3927-3935 (2007).
Helsen et al. The chimeric TAC receptor co-opts the T cell receptor yielding robust anti-tumor activity without toxicity. Nature Communications 9:3049 (2018).
Helsen et al. Tri-functional T cell receptor antigen coupler (Tri-TAC): a novel methodto direct T cells against tumors. J Immunother Cancer 2(Supp 3):P17 (2014).
Hexham et al. Optimization of the anti-(human CD3) immunotoxin DT389-scFv(UCHT1) N-terminal sequence to yield a homogeneous protein. Biotechnol Appl Biochem 34(Pt 3):183-187 (2010).
Humphries. Adoptive cell therapy: Honing that killer instinct. Nature 504:S13-15 (2013).
Itano et al. The cytoplasmic domain of CD4 promotes the development of CD4 lineage T cells. J Exp Med. 183(3):731-741 (1996).
Klinger et al. Harnessing T cells to fight cancer with BiTER antibody constructs—past developments and future directions. Immunol Rev. 270(1):193-208 (2016).
Löffler et al. A recombinant bispecific single-chain antibody, CD19 X CD3, induces rapid and high lymphoma-directed cytotoxicity by unstimulated T lymphocytes. Blood 95(6):2098-2103 (2000).
Molhoj, et al. CD19-/CD3-bispecific antibody of the BiTE class is far superior to tandem diabody with respect to redirected tumor cell lysis. Mol Immunol. Mar. 2007;44(8):1935-43. Epub Nov. 2, 2006.
Nagorsen et al. Immunomodulatory therapy of cancer with T cell-engaging BiTE antibody blinatumomab. Exp Cell Res 317(9):1255-1260 (2011).
Nagorsen et al. Immunotherapy of lymphoma and leukemia with T-cell engaging BiTE antibody blinatumomab. Leuk Lymph 50(6): 886-891 (2009).
Panka et al. Variable region framework differences result in decreased or increased affinity of variant anti-digoxin antibodies. PNAS USA 85:3080-3084 (1988).
PCT/CA2015/000068 International Search Report and Written Opinion dated May 4, 2015.
PCT/CA2018/051290 International Search Report and Written Opinion dated Jan. 17, 2019.
PCT/US2019/042297 International Search Report and Written Opinion dated Oct. 30, 2019.
Rudikoff et al. Single amino acid substitution altering antigen-binding specificity. PNAS USA 79:1979-1983 (1982).
Till et al. CD20-specific adoptive immunotherapy for lymphoma using a chimeric antigen receptor with both CD28 and 4-1BB domains: pilot clinical trial results. Blood 119(17):3940-3950 (2012).
U.S. Appl. No. 15/117,173 Office Action dated Jan. 24, 2018.
U.S. Appl. No. 15/117,173 Office Action dated Jun. 21, 2019.
U.S. Appl. No. 15/117,173 Office Action dated Oct. 24, 2018.
U.S. Appl. No. 16/442,274 Office Action dated Nov. 6, 2019.
Velasquez. T cells expressing CD19-specific Engager Molecules for the Immunotherapy of CD19-positive Malignancies. Sci Rep 6:27130 (2016).
Wels et al. Construction, Bacterial Expression and Characterization of a Bifunctional Single-Chain Antibody-Phosphatase Fusion Protein Targeted to the human ERBB-2 receptor. Nature Biotech 10:1128-1132 (1992).
Wittlich et al. Structural characterization of the transmembrane and cytoplasmic domains of human CD4. Biochimica et Biophysica Acta 1768:2949-2960 (2007).
Zahnd et al. Efficient Tumor Targeting with High-Affinity Designed Ankyrin Repeat Proteins: Effects of Affinity and Molecular Size. Cancer Res 70:1595-1605 (2010).
Zahnd et al. Selection and Characterization of Her2 Binding-designed Ankyrin Repeat Proteins. The Journal Of Biological Chemistry 281(46):35167-35175 (2006).
Zhang et al. Sequestration of CD4-associated Lck from the TCR complex may elicit T cell hyporesponsiveness in nonobese diabetic mice. J Immunol 160:1148-1157 (1998).
Zhukovsky et al. Bispecific antibodies and CARs: generalized immunotherapeutics harnessing T cell redirection. Curr Opin Immunol 40:24-35 (2016).
U.S. Appl. No. 15/117,173, filed Aug. 5, 2016, U.S. Pat. No. 10,435,453, Oct. 8, 2019, Issued.
U.S. Appl. No. 16/547,421, filed Aug. 21, 2019, Allowed.
U.S. Appl. No. 15/929,510, filed May 6, 2020, U.S. Pat. No. 11,008,376, May 18, 2021, Issued.
U.S. Appl. No. 17/248,174, filed Jan. 12, 2021, U.S. Pat. No. 11,001,621, May 11, 2021, Issued.
U.S. Appl. No. 16/753,577, filed Apr. 3, 2020, Pending.
U.S. Appl. No. 17/301,884, filed Apr. 16, 2021, U.S. Pat. No. 11,198,737, Dec. 14, 2021, Issued.
U.S. Appl. No. 16/442,274, filed Jun. 14, 2019, U.S. Pat. No. 10,640,562, May 5, 2020, Issued.
U.S. Appl. No. 15/929,513, filed May 6, 2020, U.S. Pat. No. 11,110,123, Sep. 7, 2021, Issued.
U.S. Appl. No. 16/904,451, filed Jun. 17, 2020, U.S. Pat. No. 11,111,298, Sep. 7, 2021, Issued.
U.S. Appl. No. 17/394,280, filed Aug. 4, 2021, Allowed.
U.S. Appl. No. 17/304,924, filed Jun. 28, 2021, Pending.
Bezverbnaya, K., et al., Development of a B-cell maturation antigen-specific T-cell antigen coupler receptor for multiple myeloma, Cytotherapy, 23(9): 820-832 (2021).
Bezverbnaya, K., et al., Preclinical evaluation of BCMA-specific TAC receptor-engineered T cells for multiple myeloma, 32nd annual meeting and pre-conference programs of the society for immunotherapy of cancer (SITC 2017): Part one, J Immunother Cancer, 5(Suppl 2): 86 (2017).
Borst, J., et al., Distinct molecular forms of human T cell receptor γ/δ detected on viable T cells by a monoclonal antibody, J Exp Med, 167(5): 1625-1644 (1988).
Hammill, J.A., Pre-clinical development of synthetic receptor-engineered T lymphocytes for the treatment of cancer-novel receptors and understanding toxicity, Thesis submitted to McMaster University, pp. 1-220 (2017).
Lang, J.M., et al., Pilot trial of interleukin-2 and zoledronic acid to augment γδ T cells as treatment for patients with refractory renal cell carcinoma, Cancer Immunol Immunother, 60(10): 1447-1460 (2011).
PCT/CA2022/051024 International Search Report and Written Opinion dated Aug. 22, 2022.
PCT/US2021/058339 International Search Report and Written Opinion mailed Mar. 10, 2022.
PCT/US2022/031836 International Search Report and Written Opinion dated Nov. 3, 2022.
U.S. Appl. No. 18/188,312 Office Action dated Sep. 12, 2023.
U.S. Appl. No. 18/188,318 Office Action dated Sep. 7, 2023.
U.S. Appl. No. 18/188,326 Office Action dated May 18, 2023.
U.S. Appl. No. 16/547,421, filed Aug. 21, 2019, U.S. Pat. No. 11,421,014, Issue Date Aug. 23, 2022, Issued.
U.S. Appl. No. 17/808,361, filed Jun. 23, 2022, Pending.
U.S. Appl. No. 18/188,312, filed Mar. 22, 2023, Pending.
U.S. Appl. No. 16/753,577, filed Apr. 3, 2020, U.S. Pat. No. 11,643,472, Issue Date May 9, 2023, Issued.
U.S. Appl. No. 18/188,318, filed Mar. 22, 2023, Pending.
U.S. Appl. No. 17/394,280, filed Aug. 4, 2021, U.S. Pat. No. 11,406,667, Issue Date Aug. 4, 2021, Issued.
U.S. Appl. No. 17/810,238, filed Jun. 30, 2022, Pending.
U.S. Appl. No. 17/304,924, filed Jun. 28, 2021, U.S. Pat. No. 11,453,723, Issue Date Sep. 27, 2022, Issued.

* cited by examiner

Tri-TAC
Configuration-1

Tri-TAC
Configuration-2

Tri-TAC

Anti-Her2 DARPin Tri-TAC

Anti-CD19
scFv Tri-TAC

Anti-BCMA
scFv Tri-TAC

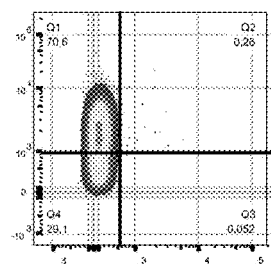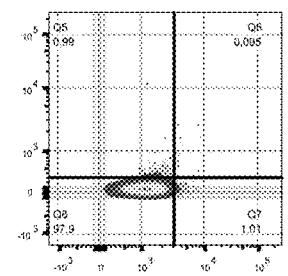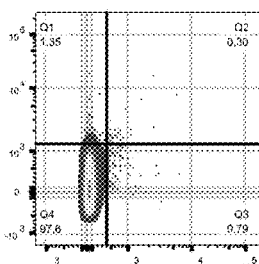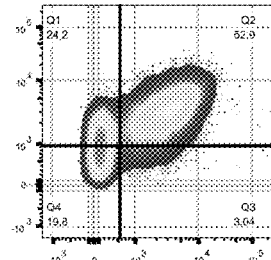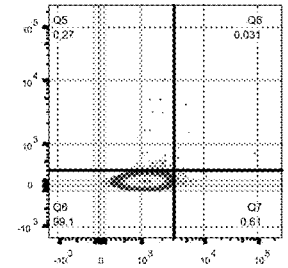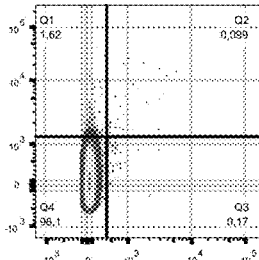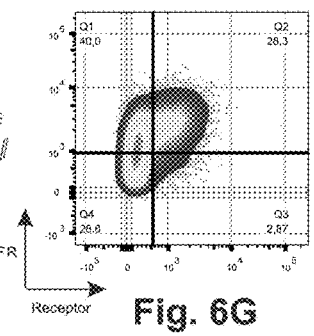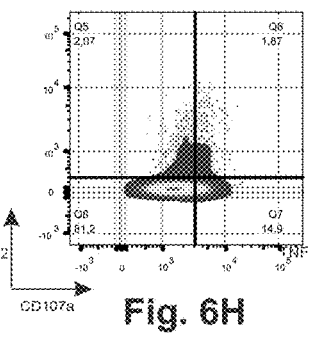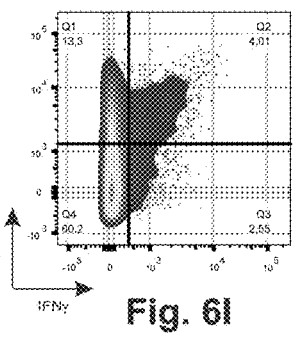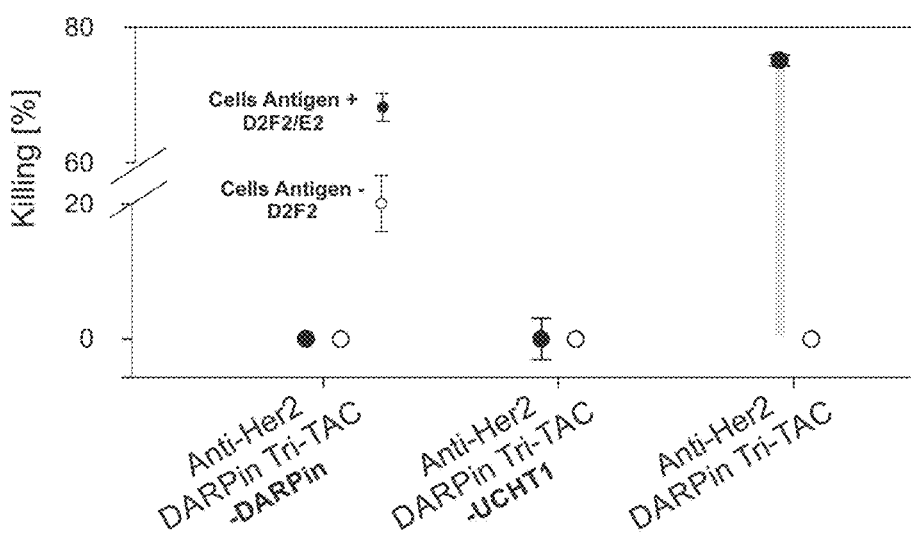

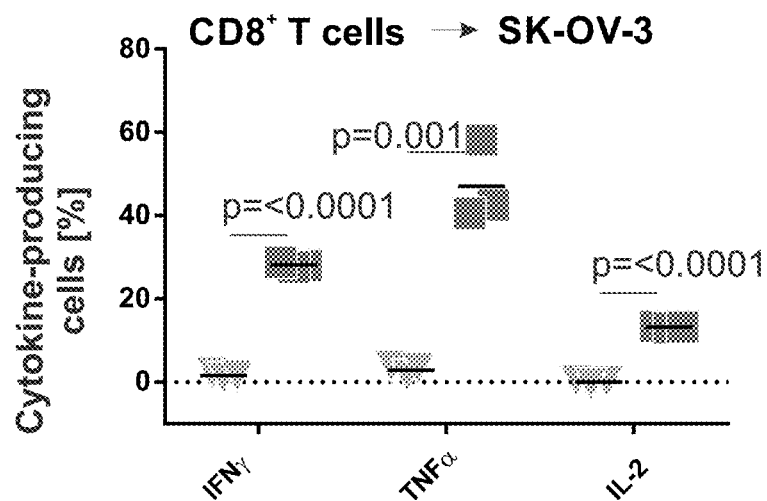
Fig. 8C
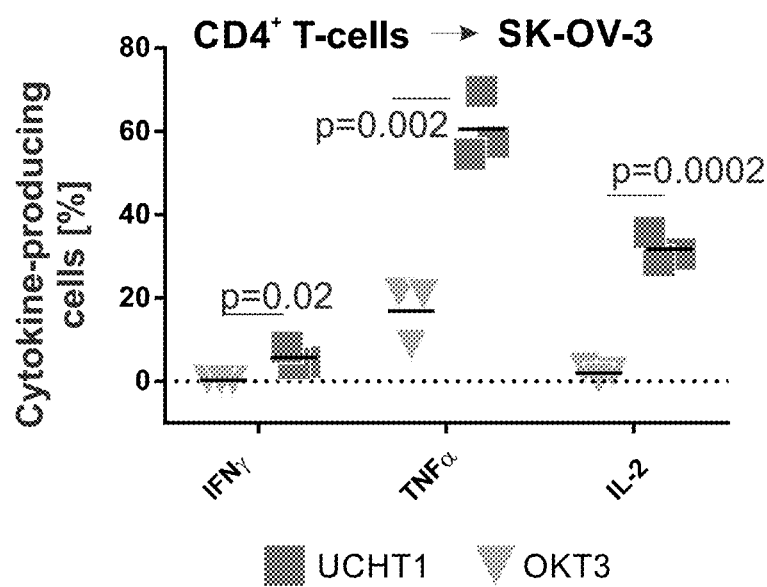
Fig. 8C1

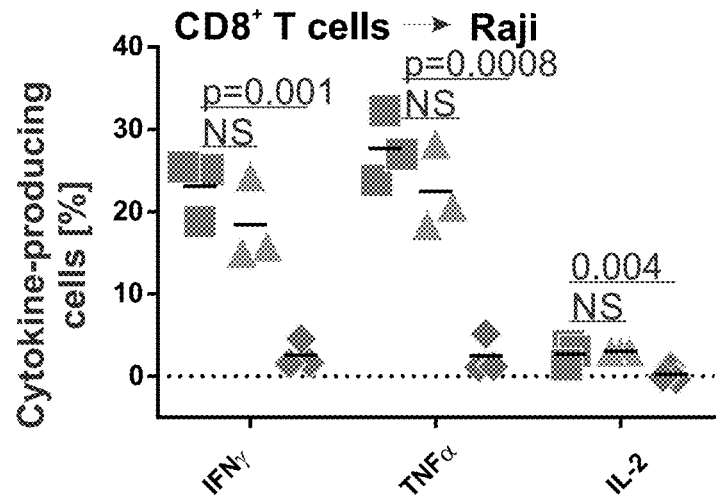
Fig. 8G
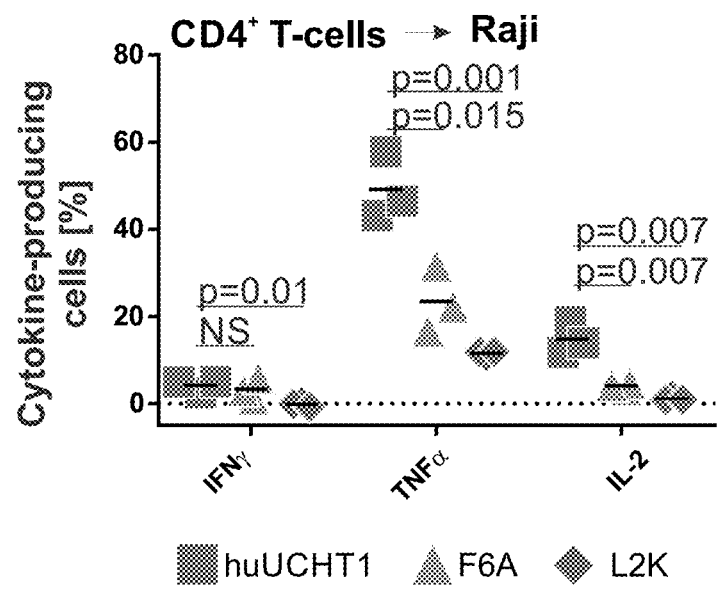
Fig. 8G1

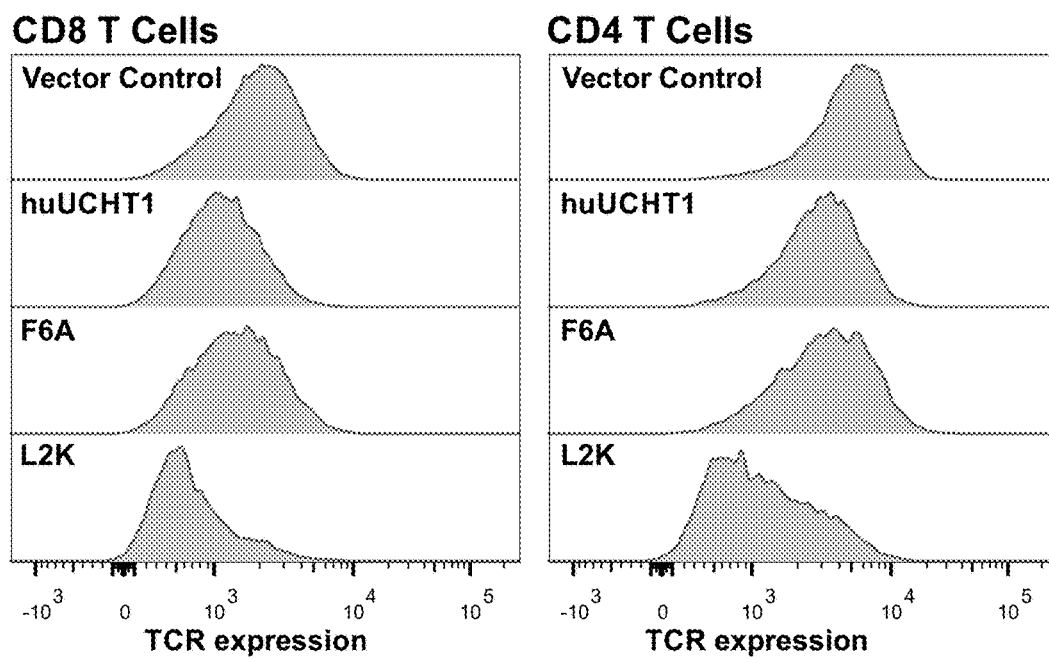
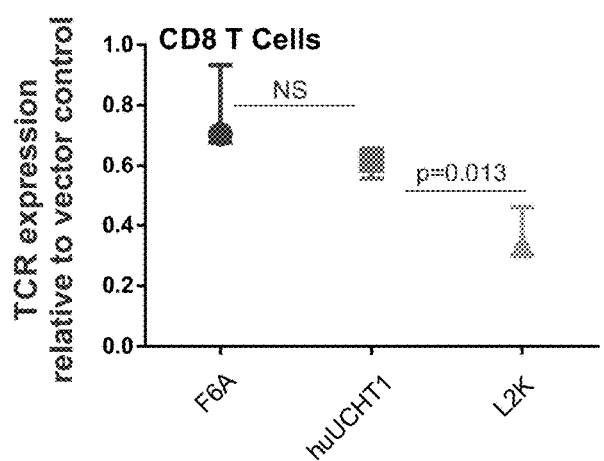
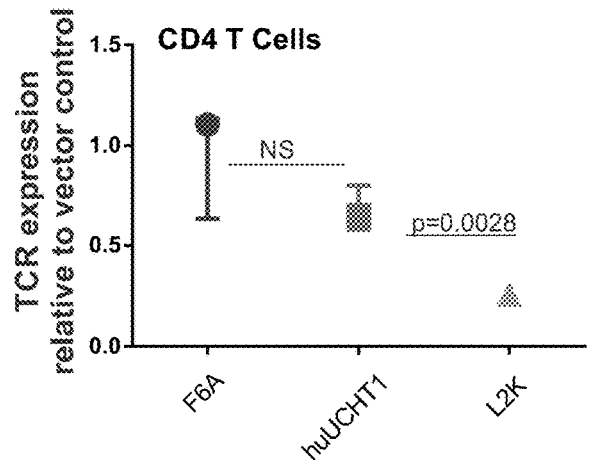
Fig. 9D
Fig. 9H

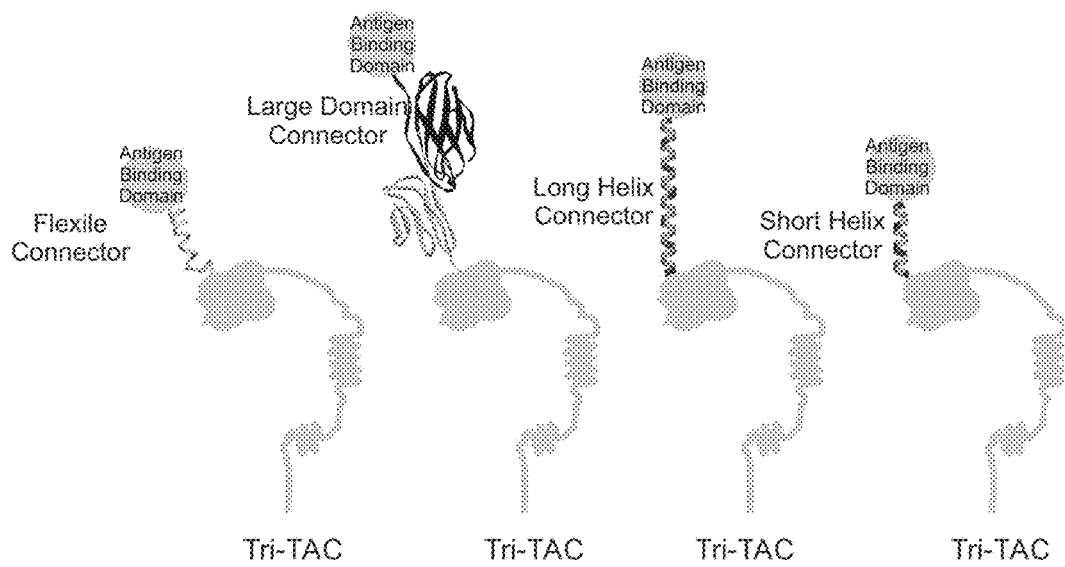

Fig. 10A

Flexible connector
GGGGSGGGGSGGGGSGGGGS

Short Helix connector
AEAAAKEAAAKEAAAKA

Long Helix connector
AEAAAKEAAAKEAAAKEAAAKA

Large Domain connector
IVVLAFQKASSIVYKKEGEQVEFSFPLAFTVEKLTGSGELWWQAERASSSKSWITFDLKNKE
VSVKRVTQDPKLQMGKKLPLHLTLPQALPQYAGSGNLTLALEAKTGKLHQEVNLVVMRATQ
LQKNLTCEVWGPTSPKLMLSLKLENKEAKVSKREKAVWVLNPEAGMWQCLLSDSGQVLLE
SNIKVLPAA

Fig. 10B

CD8α Tri TAC

CD8α+R(β) Tri TAC

CD8β+Lck Tri TAC

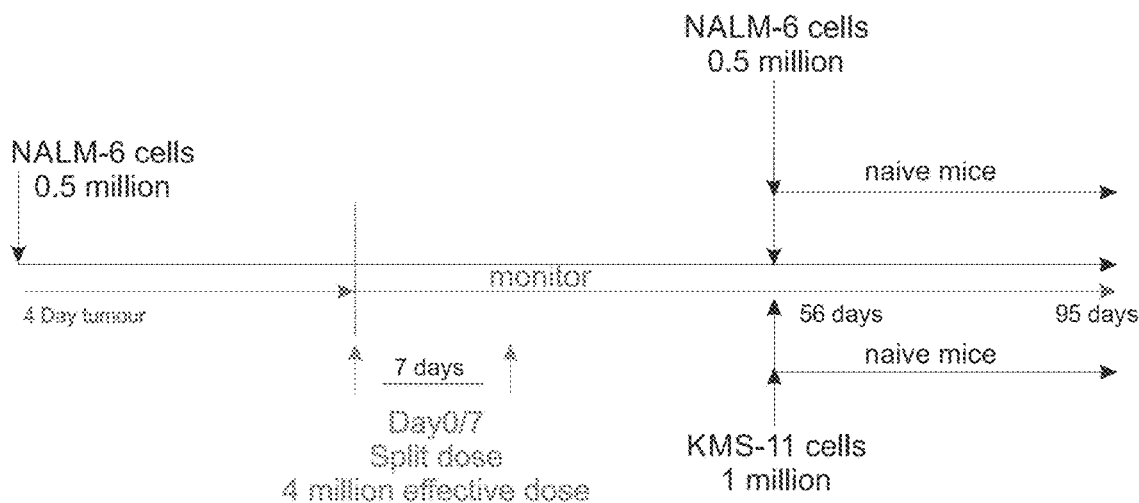
Fig. 20A
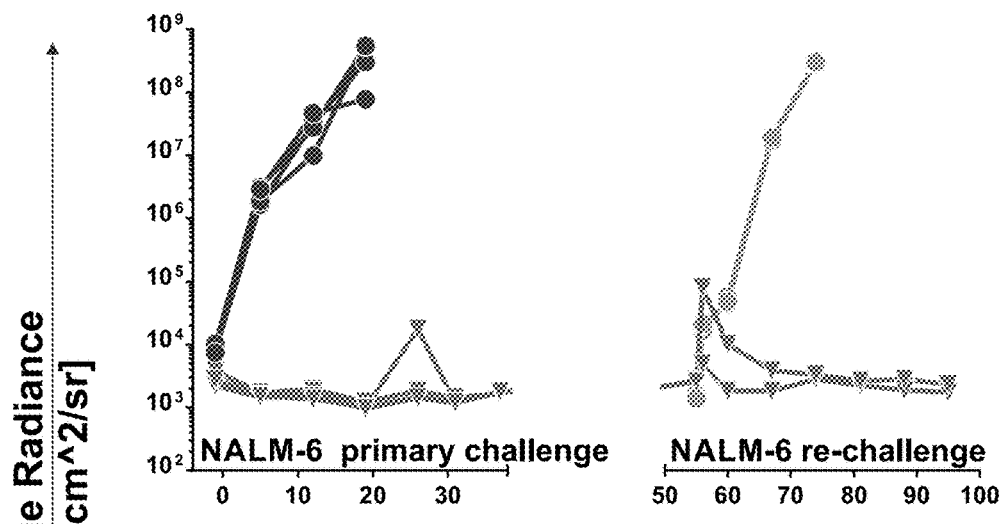
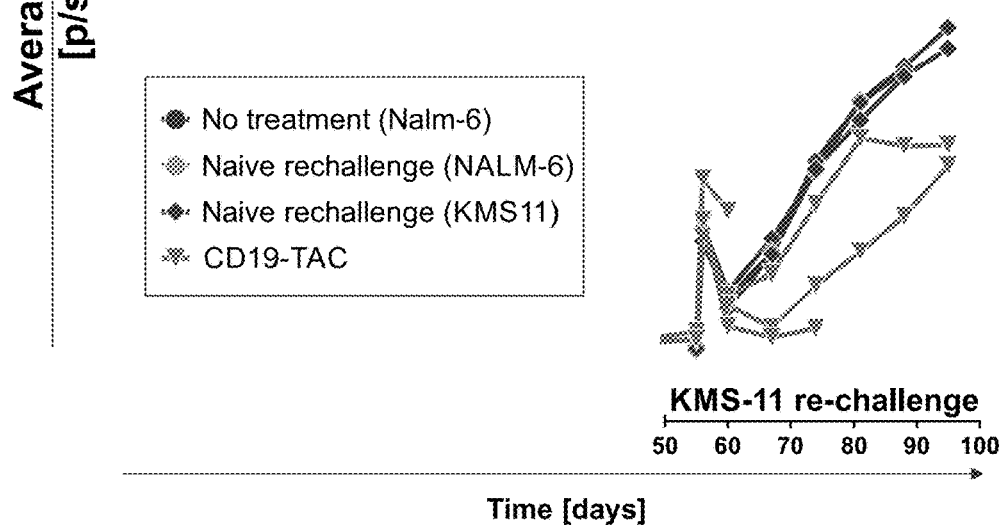
Fig. 20B

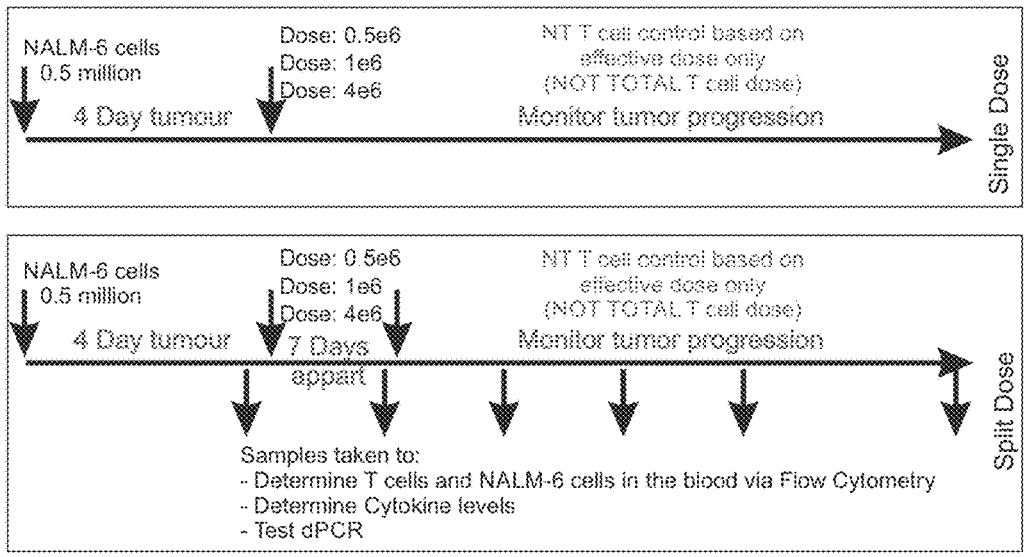
Fig. 21A
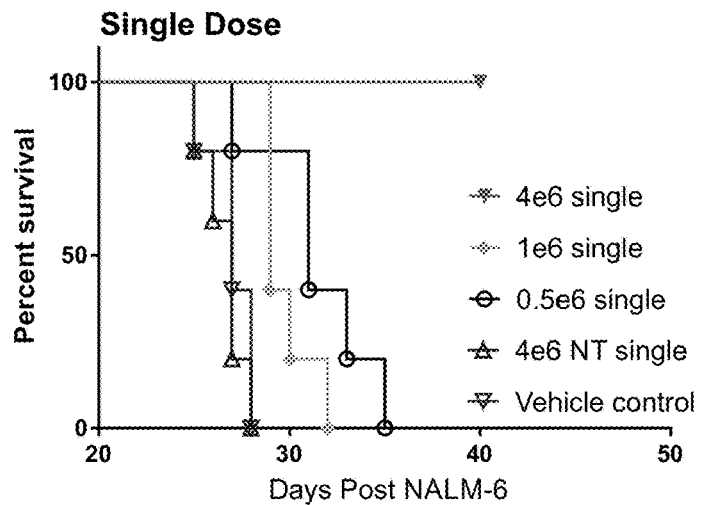
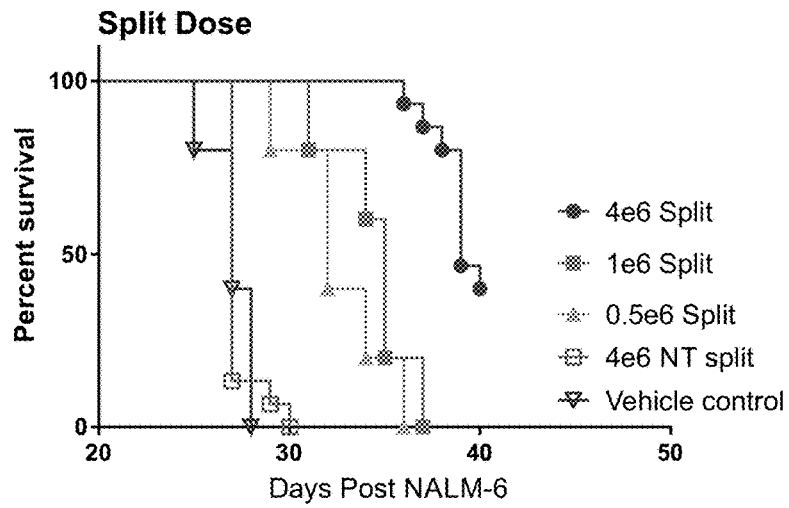
Fig. 21B

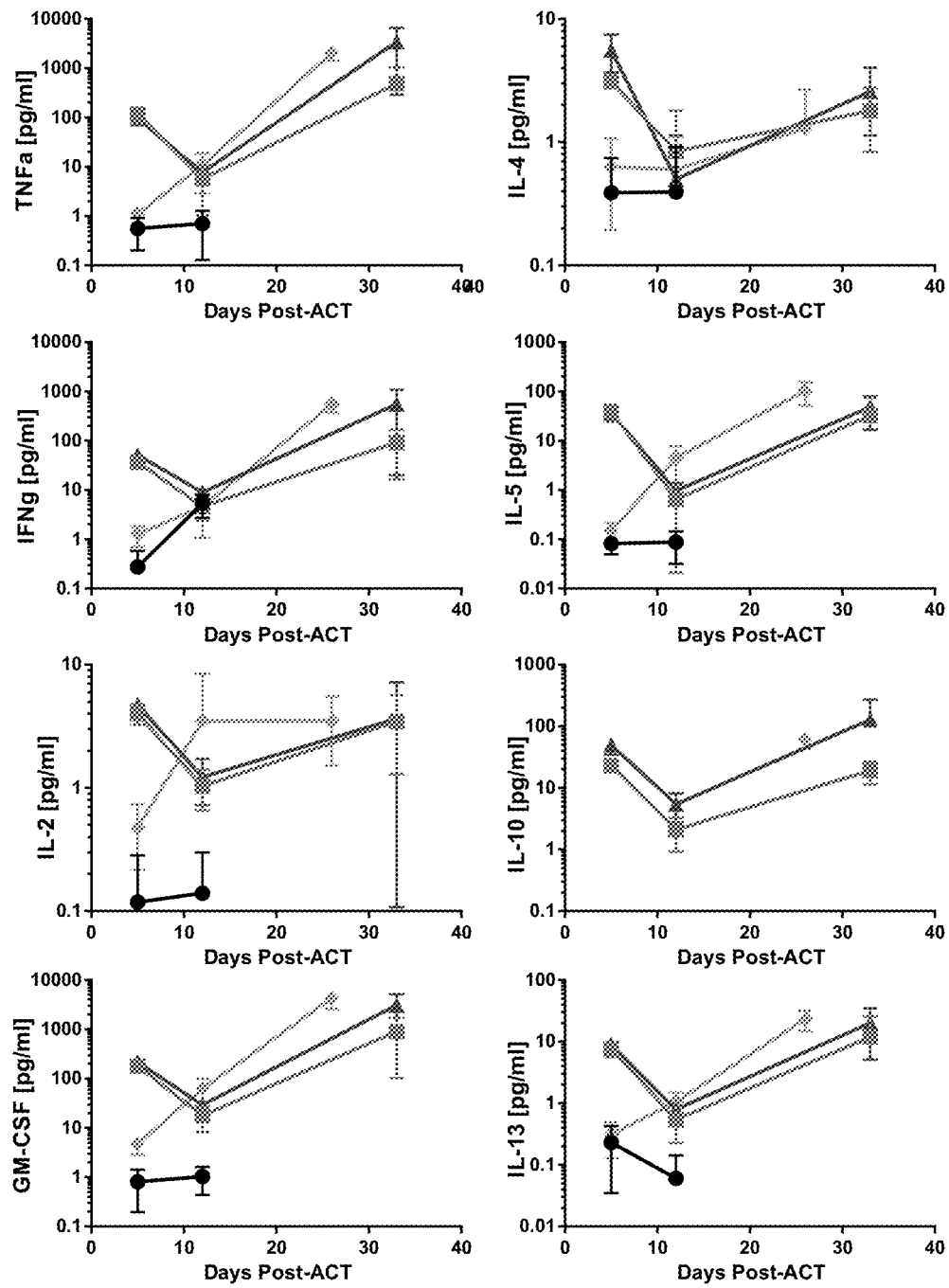
IL-6 was below detection level at all time points
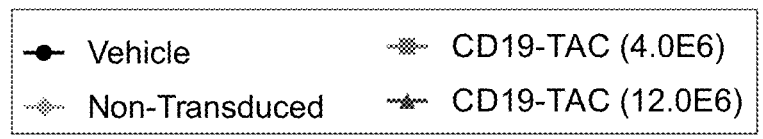
Fig. 25

| ID | Linker | Single chain |
|---|---|---|
| 872 | G4S | -------- |
| 888 | G4S | C11D5.3 |
| 1001 | G4S | 3625 H-L |
| 1002 | Short Helix | 3625 L-H |
| 1042 | Short Helix | 3625 H-L |
| 1043 | G4S | 3625 L-H |

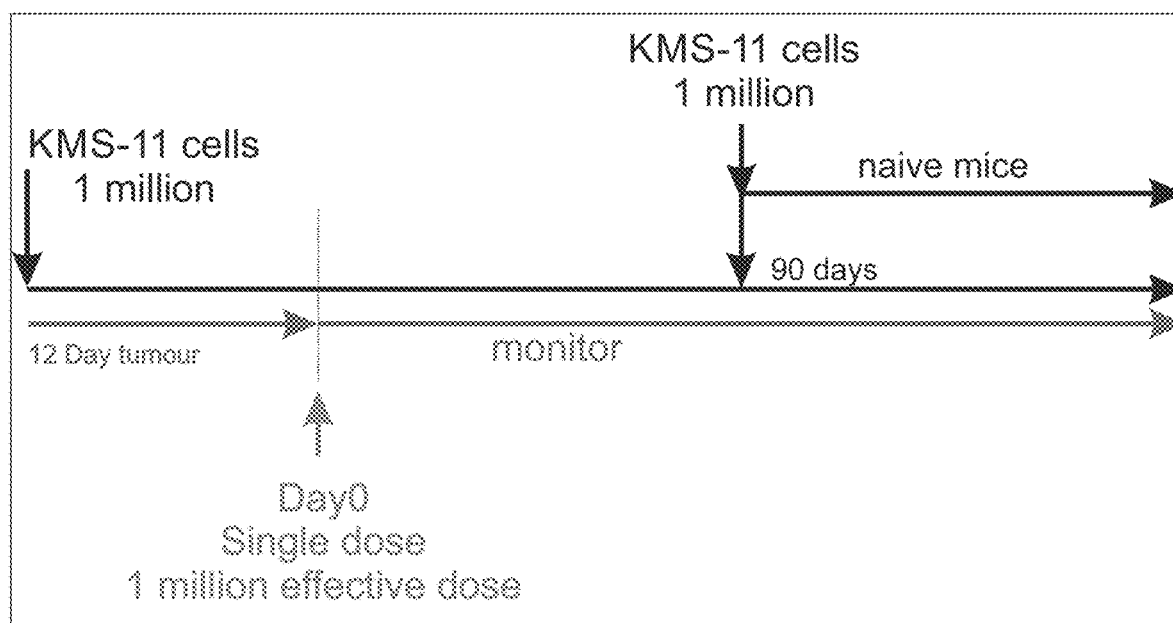
Fig. 28-A

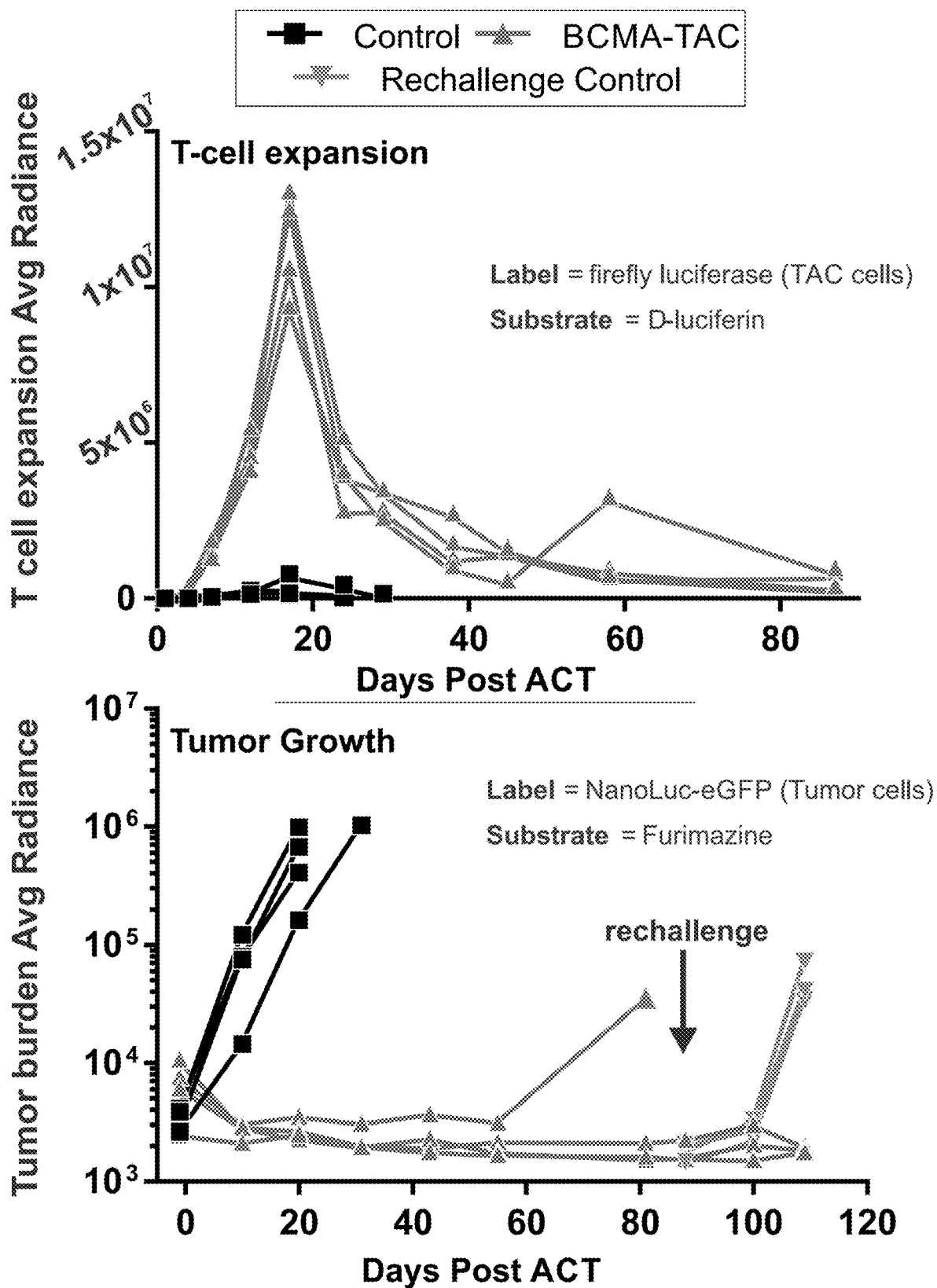
Fig. 28-B

T CELL-ANTIGEN COUPLER WITH VARIOUS CONSTRUCT OPTIMIZATIONS

CROSS-REFERENCE

This application is a continuation of U.S. application Ser. No. 16/442,274, filed on Jun. 14, 2019, now issued as U.S. Pat. No. 10,640,562 on May 5, 2020, which claims the benefit of U.S. Provisional Application No. 62/699,173, filed on Jul. 17, 2018, U.S. Provisional Application No. 62/703, 037, filed on Jul. 25, 2018, U.S. Provisional Application No. 62/773,120, filed on Nov. 29, 2018, U.S. Provisional Application No. 62/826,853, filed on Mar. 29, 2019, U.S. Provisional Application No. 62/828,879, filed on Apr. 3, 2019, and U.S. Provisional Application No. 62/839,235, filed on Apr. 26, 2019, each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Mar. 20, 2020, is named "55247704301_SL.txt" and is 123,289 bytes in size.

SUMMARY

Disclosed herein, in certain embodiments, are nucleic acid sequences encoding a CD19 Trifunctional T cell-antigen coupler (CD19-TAC). In some embodiments, the nucleic acid sequence encoding a CD19 Trifunctional T cell-antigen coupler (CD19-TAC) comprises: (a) a first polynucleotide encoding a ligand that selectively binds a CD19 antigen. In some embodiments, the nucleic acid sequence encoding a CD19 Trifunctional T cell-antigen coupler (CD19-TAC) comprises: (b) a second polynucleotide encoding a UCHT1 ligand that binds CD3. In some embodiments, the nucleic acid sequence encoding a CD19 Trifunctional T cell-antigen coupler (CD19-TAC) comprise: (c) a third polynucleotide encoding a TCR signaling domain polypeptide comprising a cytosolic domain and a transmembrane domain. In some embodiments, the components encoded by the first, second, and/or third polynucleotides are connected in any suitable manner, such as in any suitable order and/or comprising any suitable linker(s). In some embodiments, the components encoded by (a), components encoded by (b), and components encoded by (c) are fused directly to each other, or joined by at least one linker. In some embodiments, the ligand that selectively binds the CD19 antigen is a single chain variable fragment (scFv). In some embodiments, the ligand that selectively binds the CD19 antigen comprises an amino acid sequence having at least 80%, at least 85%, at least 90%, at least 95%, at least 96%, at least 97%, at least 98%, at least 99%, or 100% sequence identity with SEQ ID NO: 36. In some embodiments, the UCHT1 ligand is a single chain antibody. In some embodiments, the UCHT1 ligand comprises a Y182T mutation (SEQ ID NO: 72). In some embodiments, the UCHT1 ligand is a humanized variant of UCHT1 (huUCHT1) ligand (SEQ ID NO: 44). In some embodiments, the UCHT1 ligand is a humanized variant of UCHT1 comprising a Y177T mutation (huUCHT1 (Y177T)) (SEQ ID NO: 46). In some embodiments, the UCHT1 ligand comprises an amino acid sequence having at least 80%, at least 85%, at least 90%, at least 95%, at least 96%, at least 97%, at least 98%, at least 99%, or 100% sequence identity with SEQ ID NO: 14, SEQ ID NO: 72, SEQ ID NO: 44, or SEQ ID NO: 46. In some embodiments, the cytosolic domain is a CD4 cytosolic domain and the transmembrane domain is a CD4 transmembrane domain. In some embodiments, the third polynucleotide encodes a polypeptide comprises an amino acid sequence having at least 80%, at least 85%, at least 90%, at least 95%, at least 96%, at least 97%, at least 98%, at least 99%, or 100% sequence identity with SEQ ID NO: 18. In some embodiments, the component encoded by (a) and the component encoded by (c) are fused to the component encoded by (b). In some embodiments, the component encoded by (b) and the component encoded by (c) are fused to the component encoded by (a). In some embodiments, at least one linker joins the component encoded by (a) to the component encoded by (b). In some embodiments, the at least one linker is a $G_4S$ flexible linker (SEQ ID NO: 73), a large protein domain, a long helix structure, or a short helix structure. In some embodiments, the at least one linker comprises an amino acid sequence having at least 80%, at least 85%, at least 90%, at least 95%, at least 96%, at least 97%, at least 98%, at least 99%, or 100% sequence identity with SEQ ID NO: 12 ($G_4S$ flexible linker ("$G_4S$" disclosed as SEQ ID NO: 73)), SEQ ID NO: 32 (large protein domain), SEQ ID NO: 30 (long helix structure), or SEQ ID NO: 28 (short helix structure). In some embodiments, the CD3 is of a TCR complex on a cell expressing the second polynucleotide. In some embodiments, the binding of the CD3 induces activation of a cell expressing the second polynucleotide. In some embodiments, the CD19-TAC comprises a nucleic acid sequence having at least 80%, at least 85%, at least 90%, at least 95%, at least 96%, at least 97%, at least 98%, at least 99%, or 100% sequence identity with SEQ ID NO: 63. In some embodiments, the CD19-TAC comprises an amino acid sequence having at least 80%, at least 85%, at least 90%, at least 95%, at least 96%, at least 97%, at least 98%, at least 99%, or 100% sequence identity with SEQ ID NO: 64. In some embodiments, the nucleic acid sequence does not encode a co-stimulatory domain. In some embodiments, the nucleic acid sequence does not encode an activation domain.

Disclosed herein, in certain embodiments, are vector constructs comprising: (a) a nucleic acid sequence disclosed herein (e.g., a nucleic acid sequence encoding a CD19-TAC); and (b) a promoter functional in a mammalian cell.

Disclosed herein, in certain embodiments, are T cells comprising a nucleic acid sequence disclosed herein (e.g., a nucleic acid sequence encoding a CD19-TAC).

Disclosed herein, in certain embodiments, are pharmaceutical compositions comprising the T cell disclosed herein, and a pharmaceutically acceptable excipient.

Disclosed herein, in certain embodiments, are methods of treating cancer expressing CD19 in an individual in need thereof, comprising administering to the individual a pharmaceutical composition disclosed herein. (e.g., a pharmaceutical composition comprising a T cell comprising any nucleic acid sequence described herein, such as any nucleic acid sequence or sequences described herein as encoding a CD19 Trifunctional T cell-antigen coupler (CD19-TAC)). In some embodiments, the cancer is a B cell malignancy. In some embodiments, the cancer is B cell lymphoma, acute lymphoblastic leukemia (ALL), chronic lymphocytic leukemia (CLL), or Non-Hodgkins Lymphoma. In some embodiments, the pharmaceutical composition is administered transarterially, subcutaneously, intradermally, intratumorally, intranodally, intramedullary, intramuscularly, intravenously or intraperitoneally.

Disclosed herein, in certain embodiments, are nucleic acid sequences encoding a Trifunctional T cell-antigen coupler (Tri-TAC) comprising: (a) a first polynucleotide encoding a target-specific ligand; (b) a second polynucleotide encoding a ligand that binds a protein associated with a TCR complex; and (c) a third polynucleotide encoding a T cell receptor signaling domain polypeptide; wherein the ligand that binds the protein associated with the TCR complex is selected from OKT3, F6A or L2K. In some embodiments, component encoded by (a), component encoded by (b), and component encoded by (c) are fused directly to each other, or joined by at least one linker. In some embodiments, the component encoded by (a) and the component encoded by (b) are directly fused and joined to the component encoded by (c) by a linker. In some embodiments, the component encoded by (b) and the component encoded by (c) are directly fused and joined to the component encoded by (a) by a linker. In some embodiments, the at least one linker is a G$_4$S flexible linker (SEQ ID NO: 73), a large protein domain, a long helix structure, or a short helix structure. In some embodiments, the at least one linker has an amino acid sequence having at least 80%, at least 85%, at least 90%, at least 95%, at least 96%, at least 97%, at least 98%, at least 99%, or 100% sequence identity with SEQ ID NO: 12 (G$_4$S flexible linker ("G$_4$S" disclosed as SEQ ID NO: 73)), SEQ ID NO: 32 (large protein domain), SEQ ID NO: 30 (long helix structure), or SEQ ID NO: 28 (short helix structure). In some embodiments, the ligand that binds the protein associated with the TCR complex is OKT3. In some embodiments, the ligand that binds a protein associated with the TCR complex comprises an amino acid sequence having at least 80%, at least 85%, at least 90%, at least 95%, at least 96%, at least 97%, at least 98%, at least 99%, or 100% sequence identity with SEQ ID NO: 22. In some embodiments, the ligand that binds the protein associated with the TCR complex is F6A. In some embodiments, the ligand that binds the protein associated with the TCR complex comprises an amino acid sequence having at least 80%, at least 85%, at least 90%, at least 95%, at least 96%, at least 97%, at least 98%, at least 99%, or 100% sequence identity with SEQ ID NO: 24. In some embodiments, the ligand that binds the protein associated with the TCR complex is L2K. In some embodiments, the ligand that binds the protein associated with the TCR complex comprises an amino acid sequence having at least 80%, at least 85%, at least 90%, at least 95%, at least 96%, at least 97%, at least 98%, at least 99%, or 100% sequence identity with SEQ ID NO: 26. In some embodiments, the protein associated with the TCR complex is CD3. In some embodiments, the target-specific ligand selectively binds a tumor antigen. In some embodiments, the target-specific ligand is a designed ankyrin repeat (DARPin) polypeptide, or a single chain variable fragment (scFv). In some embodiments, the target-specific ligand selectively binds a CD19 antigen, a HER2 antigen, or a BCMA antigen. In some embodiments, the target-specific ligand selectively binds a HER-2 antigen comprises an antigen binding domain of an antibody selected from Trastuzumab, Pertuzumab, Lapatinib, Neratinib, Ado-trastuzmab Emtansine, Gancotamab, Margetuximab, Timigutuzumab, and Ertumaxomab. In some embodiments, the target-specific ligand selectively binds a BCMA antigen comprises an antigen binding domain of an antibody selected from Belantamab mafodotin, and GSK2857916. In some embodiments, the target-specific ligand comprises an amino acid sequence having at least 80%, at least 85%, at least 90%, at least 95%, at least 96%, at least 97%, at least 98%, at least 99%, or 100% sequence identity with SEQ ID NO: 36, SEQ ID NO: 8 or SEQ ID NO: 34. In some embodiments, the T cell receptor signaling domain polypeptide comprises a cytosolic domain and a transmembrane domain. In some embodiments, the cytosolic domain is a CD4 cytosolic domain and the transmembrane domain is a CD4 transmembrane domain, or wherein the cytosolic domain is a CD8 cytosolic domain and the transmembrane domain is a CD8 transmembrane domain. In some embodiments, the nucleic acid sequences further comprise a leader sequence. In some embodiments, the leader sequence comprises an amino acid sequence having at least 80%, at least 85%, at least 90%, at least 95%, at least 96%, at least 97%, at least 98%, at least 99%, or 100% sequence identity with SEQ ID NO: 6, SEQ ID NO: 48, or SEQ ID NO: 50. In some embodiments, the CD3 is of a TCR complex on a cell expressing the second polynucleotide. In some embodiments, the binding of the CD3 induces activation of a cell expressing the second polynucleotide. In some embodiments, the Tri-TAC comprises a nucleic acid sequence having at least 80%, at least 85%, at least 90%, at least 95%, at least 96%, at least 97%, at least 98%, at least 99%, or 100% sequence identity with SEQ ID NO: 63, SEQ ID NO: 65, SEQ ID NO: 67, SEQ ID NO: 55, SEQ ID NO: 57, SEQ ID NO: 59, or SEQ ID NO: 61. In some embodiments, the Tri-TAC comprises an amino acid sequence having at least 80%, at least 85%, at least 90%, at least 95%, at least 96%, at least 97%, at least 98%, at least 99%, or 100% sequence identity with SEQ ID NO: 64, SEQ ID NO: 66, SEQ ID NO: 68, SEQ ID NO: 56, SEQ ID NO: 58, SEQ ID NO: 60, or SEQ ID NO: 62. In some embodiments, the nucleic acid sequence does not encode a co-stimulatory domain. In some embodiments, the nucleic acid sequence does not encode an activation domain.

Disclosed herein, in certain embodiments, are nucleic acid sequences encoding a Trifunctional T cell-antigen coupler (Tri-TAC) comprising: (a) a first polynucleotide encoding a target-specific ligand; (b) a second polynucleotide encoding a ligand that binds a protein associated with a TCR complex; and (c) a third polynucleotide encoding a T cell receptor signaling domain polypeptide; wherein the nucleic acid sequence further comprises a leader sequence, and wherein component encoded by (a), component encoded by (b), and component encoded by (c) are fused directly to each other, or joined by at least one linker. In some embodiments, the target-specific ligand selectively binds a tumor antigen. In some embodiments, the target-specific ligand is a designed ankyrin repeat (DARPin) polypeptide, or a single chain variable fragment (scFv). In some embodiments, the target-specific ligand selectively binds a CD19 antigen, a HER2 antigen, or a BCMA antigen. In some embodiments, the target-specific ligand selectively binds a HER-2 antigen comprises an antigen binding domain of an antibody selected from Trastuzumab, Pertuzumab, Lapatinib, Neratinib, Ado-trastuzmab Emtansine, Gancotamab, Margetuximab, Timigutuzumab, and Ertumaxomab. In some embodiments, the target-specific ligand selectively binds a BCMA antigen comprises an antigen binding domain of an antibody selected from Belantamab mafodotin, and GSK2857916. In some embodiments, the target-specific ligand comprises an amino acid sequence having at least 80%, at least 85%, at least 90%, at least 95%, at least 96%, at least 97%, at least 98%, at least 99%, or 100% sequence identity with SEQ ID NO: 36, SEQ ID NO: 8, SEQ ID NO: 34, SEQ ID NO: 52, or SEQ ID NO: 54. In some embodiments, the ligand that binds the protein associated with the TCR complex is selected from UCHT1, UCHT1 (Y182T), huUCHT1, huUCHT1 (Y177T), OKT3, F6A, or L2K. In some embodiments, the ligand that binds a protein associated with the TCR complex has an amino acid sequence having at least 80%, at least 85%, at least 90%, at least 95%, at least 96%, at least 97%, at least 98%, at least 99%, or 100% sequence identity with SEQ ID NO: 14, SEQ ID NO: 72, SEQ ID NO: 44, SEQ ID NO: 46, SEQ ID NO: 22, SEQ ID NO: 24, or SEQ ID NO: 26. In some embodiments, the protein associated with the TCR complex is CD3. In some embodiments, the T cell receptor signaling domain polypeptide comprises a cytosolic domain and a transmembrane domain. In some embodiments, the cytosolic domain is a CD4 cytosolic domain and the transmembrane domain is a CD4 transmembrane domain, or wherein the cytosolic domain is a CD8 cytosolic domain and the transmembrane domain is a CD8 transmembrane domain. In some embodiments, the leader sequence comprises an amino acid sequence having at least 80%, at least 85%, at least 90%, at least 95%, at least 96%, at least 97%, at least 98%, at least 99%, or 100% sequence identity with SEQ ID NO: 6, SEQ ID NO: 48, or SEQ ID NO: 50. In some embodiments, the component encoded by (a) and the component encoded by (b) are directly fused and joined to the component encoded by (c) by a linker. In some embodiments, the component encoded by (b) and the component encoded by (c) are directly fused and joined to the component encoded by (a) by a linker. In some embodiments, the at least one linker is a $G_4S$ flexible linker (SEQ ID NO: 73), a large protein domain, a long helix structure, or a short helix structure. In some embodiments, the at least one linker has an amino acid sequence having at least 80%, at least 85%, at least 90%, at least 95%, at least 96%, at least 97%, at least 98%, at least 99%, or 100% sequence identity with SEQ ID NO: 12 ($G_4S$ flexible linker ("$G_4S$" disclosed as SEQ ID NO: 73)), SEQ ID NO: 32 (large protein domain), SEQ ID NO: 30 (long helix structure), or SEQ ID NO: 28 (short helix structure). In some embodiments, the CD3 is of a TCR complex on a cell expressing the second polynucleotide. In some embodiments, the binding of the CD3 induces activation of a cell expressing the second polynucleotide. In some embodiments, the Tri-TAC comprises a nucleic acid sequence having at least 80%, at least 85%, at least 90%, at least 95%, at least 96%, at least 97%, at least 98%, at least 99%, or 100% sequence identity with SEQ ID NO: 63, SEQ ID NO: 65, SEQ ID NO: 67, SEQ ID NO: 55, SEQ ID NO: 57, SEQ ID NO: 59, or SEQ ID NO: 61. In some embodiments, the Tri-TAC comprises an amino acid sequence having at least 80%, at least 85%, at least 90%, at least 95%, at least 96%, at least 97%, at least 98%, at least 99%, or 100% sequence identity with SEQ ID NO: 64, SEQ ID NO: 66, SEQ ID NO: 68, SEQ ID NO: 56, SEQ ID NO: 58, SEQ ID NO: 60, or SEQ ID NO: 62. In some embodiments, the nucleic acid sequence does not encode a co-stimulatory domain. In some embodiments, the nucleic acid sequence does not encode an activation domain.

Disclosed herein, in certain embodiments, are polypeptides encoded by the nucleic acid sequence disclosed herein.

Disclosed herein, in certain embodiments, are vector constructs comprising: (a) a nucleic acid sequence disclosed herein; and (b) a promoter functional in a mammalian cell.

Disclosed herein, in certain embodiments, are T cells comprising the nucleic acid sequence disclosed herein.

Disclosed herein, in certain embodiments, are pharmaceutical compositions comprising the T cell disclosed herein, and a pharmaceutically acceptable excipient.

Disclosed herein, in certain embodiments, are methods of treating a cancer in an individual in need thereof, comprising administering to the individual a pharmaceutical composition disclosed herein. In some embodiments, the subject is a mammal. In some embodiments, the cancer is a solid cancer or a liquid cancer. In some embodiments, the cancer is a lung cancer, a breast cancer, multiple myeloma, glioblastoma, gastric cancer, ovarian cancer, stomach cancer, colorectal cancer, urothelial cancer, endometrial cancer, or a colon cancer. In some embodiments, the cancer comprises a CD19 expressing cancer cell. In some embodiments, the cancer is a B cell malignancy. In some embodiments, the cancer is B cell lymphoma, acute lymphoblastic leukemia (ALL), chronic lymphocytic leukemia (CLL), or Non-Hodgkins Lymphoma. In some embodiments, the cancer comprises a HER-2 expressing cancer cell. In some embodiments, the cancer is breast cancer, bladder cancer, pancreatic cancer, ovarian cancer, or stomach cancer. In some embodiments, the cancer comprises a BCMA expressing cancer cell. In some embodiments, the cancer is leukemia, lymphoma, or multiple myeloma. In some embodiments, the pharmaceutical composition is administered to the individual transarterially, subcutaneously, intradermally, intratumorally, intranodally, intramedullary, intramuscularly, intravenously or intraperitoneally. In some embodiments, the pharmaceutical composition is in a unit dose form. In some embodiments, the pharmaceutical composition is comprises about $0.5\text{-}2\times10^9$ T cells. In some embodiments, the pharmaceutical composition is administered daily, weekly, bi-weekly, monthly, bi-month or yearly.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4A exemplifies the surface expression of the Tri-TAC and CAR compared to T cells that express no chimeric receptor. FIG. 4B exemplifies growth of three cell populations. FIG. 4C-FIG. 4D exemplify the percentage of engineered cells positive for various T cell activation markers following stimulation with antigen.

FIG. 6A-FIG. 6J illustrate receptor surface expression and activation of various anti-HER-2 DARPin Tri-TAC controls. T cells were engineered with a Tri-TAC variant that lacks the targeting element (−DARPin), a Tri-TAC variant that lacks UCHT1 (−UCHT1), or the full-length Tri-TAC. FIG. 6A, FIG. 6D, FIG. 6G illustrate T cell transduction and Her2 binding ability (left); FIG. 6B, FIG. 6E, FIG. 6H degranulation (middle) and FIG. 6C, FIG. 6F, FIG. 6I cytokine production (right). FIG. 6J illustrates that only full length anti-HER-2 DARPin Tri-TAC is able to elicit a cytotoxic response.

FIG. 7A exemplifies the change in tumor growth relative to the day of T cell infusion (day 35). FIG. 7B exemplifies the change in weight, a measure of toxicity, in the same mice. FIG. 7C illustrates cytokine concentrations in serum of mice on day 7 post T-cell infusion.

FIG. 8A-FIG. 8H illustrate Tri-TACs designed with various alternatives to the UCHT1 scFv-CD3 recruitment domain. FIG. 8A provides a schematic representation of TAC receptor constructs utilizing the anti-HER-2 DARPin, paired with either the UCHT1 or OKT3 anti-CD3 scFv. FIG. 8B illustrates HER-2 TAC surface expression of CD8+ NGFR+ (left) or CD4+ NGFR+ T cells (right).

FIG. 8C, FIG. 8C1 illustrate cytokine production by HER-2-specific TAC-T cells stimulated with antigen-positive SK-OV-3 tumor cells. FIG. 8D illustrates killing of SK-OV-3 tumor cells by HER-2 TAC and vector control (vector only carrying tNGFR) T cells. Vector control T cells (circles) are compared against HER-2-specific TAC-T cells bearing UCHT1 (square) or OKT3 (triangle). FIG. 8E provides a schematic representation of TAC receptor constructs utilizing the anti-CD19 scFv, paired with either huUCHT1, F6A, or L2K anti-CD3 scFv. FIG. 8F illustrates CD19-TAC surface expression of CD8+ NGFR+ (left) or CD4+ NGFR+ T cells (right). FIG. 8G, FIG. 8G1 illustrate cytokine production by CD19-specific TAC-T cells stimulated with antigen-positive Raji tumor cells. Cytokine producing cells are compared from TAC-T cells bearing huUCHT1 (square), F6A (triangle), or L2K (diamond). FIG. 8H illustrates killing of NALM-6 tumor cells by CD19 TAC and vector control (vector only carrying tNGFR) T cells. Vector control T cells (circles) are compared against CD19-specific TAC-T cells bearing huUCHT1 (square), F6A (triangle), or L2K (diamond).

FIG. 9A-FIG. 9H illustrates the effect of various anti-CD3 scFv on TCR surface expression. FIG. 9A, FIG. 9E illustrate TCR surface expression of T cells engineered with either control vector (tNGFR), UCHT1, or OKT3 TAC variants. FIG. 9B, FIG. 9F illustrate that T cells engineered with OKT3-TAC have significantly reduced TCR surface expression relative to UCHT1-TAC. FIG. 9C, FIG. 9G illustrate TCR surface expression of T cells engineered with control vector (tNGFR), huUCHT1, F6A or L2K TAC variants. FIG. 9D, FIG. 9H illustrates that T cells engineered with L2K TAC have significantly reduced TCR surface expression relative to huUCHT1-TAC.

FIG. 10A-FIG. 10B illustrate connector domain variants. The domain the connecting antigen binding domain with the TCR recruitment domain is termed the connector domain. FIG. 10A provides schematics of TAC variants with different connector domains: (i) a flexible connector, (ii) a large domain connector (constructed from domains 3 and 4 derived from the extracellular CD4 domain), (iii) a long helical connector, and (iv) a short helical connector. FIG. 10B provides exemplary amino acid sequence of the domains represented in FIG. 10A. (SEQ ID NOS 69, 28, 30, and 32, respectively, in order of appearance)

FIG. 11A illustrates TAC variant surface expression in both CD4 and CD8 cells. FIG. 11B illustrates surface expression of TAC comprising flexible connectors relative to TAC comprising helical or large domain connectors. FIG. 11C illustrates overall transduction of TAC comprising alternative connectors relative to the flexible connector. FIG. 11D, FIG. 11E illustrate relative cell reactivity to antigen positive Raji cells.

FIG. 13A, FIG. 13C illustrate surface expression. FIG. 13B illustrates cytokine production.

FIG. 14A illustrates a Tri-TAC comprising a CD4 transmembrane and cytosolic domain (left), and comparable regions of a CD8α/CD8β heterodimer (right). Key regions for co-receptor functionality (arginine rich domain and CXCP motif) are highlighted. FIG. 14B is a schematic of a CD8α Tri-TAC comprising a Cysteine to Serine mutation to ensure a monomeric receptor distribution, and a CD8α cytosolic domain. FIG. 14C is a schematic of a CD8α+Rβ Tri-TAC comprising a Cysteine to Serine mutation to ensure a monomeric receptor distribution, and a chimeric CD8α cytosolic domain where the CD8α arginine rich region is replaced with the CD8β arginine rich region. FIG. 14D is a schematic of a CD8β+Lck Tri-TAC comprising a Cysteine to Serine mutation to ensure a monomeric receptor distribution, and a chimeric CD8β cytosolic domain, where the CD8α CXCP domain, which contains an Lck binding motif, was added to the C-terminus of the CD8β cytosolic domain.

FIG. 15A-FIG. 15B illustrate surface expression of CD8-Tri TAC variants relative to the prototypic Tri-TAC. FIG. 15C illustrates in vitro cytotoxicity of CD8-Tri TAC variants co-cultured with LOX IMVI (HER-2 negative) or A549, SKOV3, SKBR3 or MBA MB 231 (HER-2 positive). FIG. 15D illustrates cell division of T cells engineered with either the CD8 Tri-TAC variants or the prototypic Tri-TAC. FIG. 15E illustrates TCR surface expression of engineered T cells comprising CD8 Tri-TAC variants or the prototypic Tri-TAC.

FIG. 17 illustrates the various domains of a TAC-CD19 (a CD8α leader, FMC63 scFv, Myc Tag, huUCHT1 Y177T mutant and a truncated CD4 anchoring co-receptor domain).

FIG. 19A NALM-6 (acute lymphoblastic leukemia), FIG. 19B Jeko-1 (Mantle Cell Lymphoma) and FIG. 19C Raji (Burkitt's lymphoma).

FIG. 20A illustrates the experimental set up of TAC-CD19 treated mice with NALM-6 tumor. Following successful treatment mice are then re-challenged with either NALM-6 (CD19 positive) or KMS11 (CD19 negative) tumor cells.

FIG. 20B illustrates in vivo efficacy of mice treated with TAC-CD19.

FIG. 21A illustrates the experimental design of evaluating dose regime and dosing impact on efficacy and cell expansion.

FIG. 21B illustrates in vivo survival of NALM-6 bearing mice treated with either a single or split dose of TAC-CD19.

FIG. 22A illustrates the gating strategy used to identify T cells in mouse blood. FIG. 22B illustrates in vivo results of T cell expansion in blood.

FIG. 23A illustrates an experimental protocol of NALM-6 bearing mice being treated with various controls and TAC-CD19 at two dose levels. FIG. 23B illustrates in vivo efficacy of control vs two dose levels of TAC-CD19 treatment groups. FIG. 23C illustrates long term survival of low dose TAC-CD19 treated mice.

FIG. 25 illustrates human cytokine released in mice blood following treatment with TAC-CD19 or non-transduced T cells.

FIG. 26A illustrates an experimental design. FIG. 26B illustrates various controls and test articles. FIG. 26C illustrates in vivo efficacy of various TAC constructs. FIG. 26A-FIG. 26C disclose "G$_4$S" as SEQ ID NO: 73.

FIG. 28A-FIG. 28B illustrate TAC engineered T cells expand in vivo and provide long term protection, indicating cell persistence in a model of myeloma. FIG. 28A-FIG. 28B illustrate BCMA-TAC T cells reject multiple myeloma tumors in a KMS-11 xenograft model engineered with NanoLuc (KMS 11-NanoLuc) (BCMA$^{pos}$). Following tumor engraftment mice were treated with BCMA TAC-T cells (carrying Firefly Luciferase). TAC-T cells expand significantly following administration. This correlates with tumor regression. Treated mice were resistant to tumor rechallenge indicating long term persistence of TAC-T cells.

DETAILED DESCRIPTION

Figure 1A:
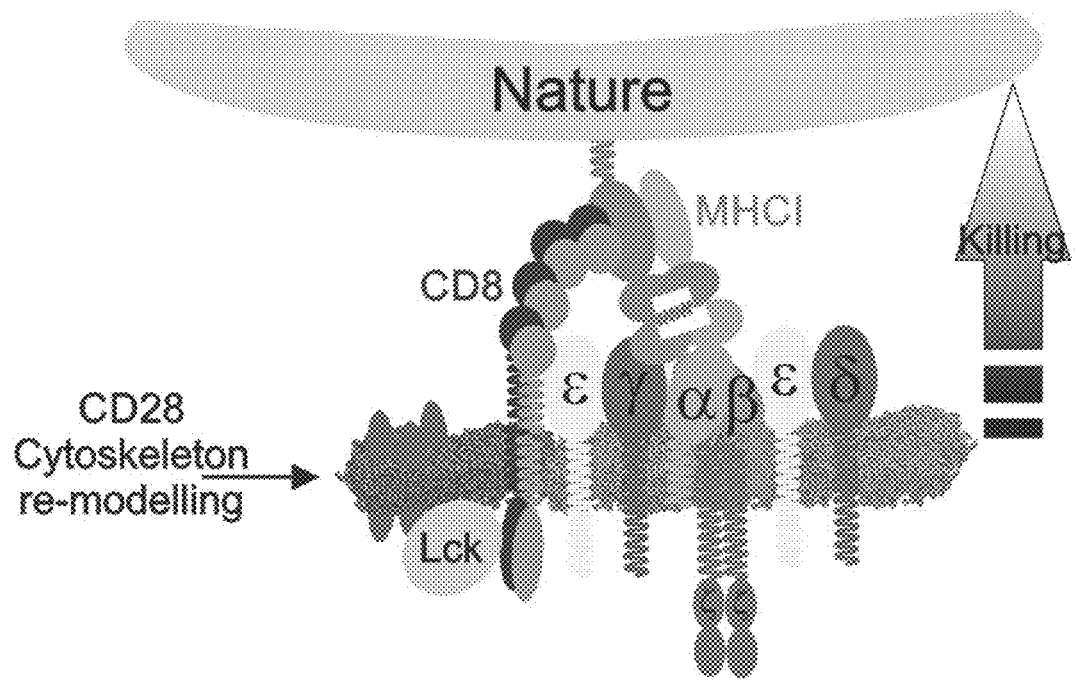
FIG. 1A is a schematic of natural T-cell activation.

Cancer is a major health challenge, with over 150,000 cases of cancer expected to be diagnosed in Canada alone. While patients with early stage disease are sometimes treated effectively by conventional therapies (surgery, radiation, chemotherapy), few options are available to patients with advanced disease, and those options are typically palliative in nature.

Active immunotherapy seeks to employ the patient's immune system to clear tumors and offers an option to patients who have failed conventional therapies. Generally, this treatment involves infusing patients with large numbers of tumor-specific T cells. This approach has proven to be successful in early phase clinical trials for a number of diseases, including melanoma, myeloma, leukemia, lymphoma and synovial sarcoma. As a specific example, several clinical studies have demonstrated that immunotherapy with T cells are curative in patients with advanced melanoma, confirming the utility of this approach. Additionally, patients suffering from chronic lymphocytic leukemia (CLL) and acute lymphoblastic leukemia (ALL) have also been effectively treated and cured with T cell immunotherapy.

A key challenge facing the clinical application of adoptive T cell therapy is the source of the T cells. Typically, T cells isolated from a tumor-bearing patient are grown to large numbers ex vivo and are administered back into the patient to induce a robust anti-tumor immune response. Tumor specificity is achieved by either: (i) isolating naturally-occurring tumor-specific T cells from the patient; or (ii) engineering bulk T cells from the peripheral blood to express tumor-specific receptors. Naturally occurring tumor-specific T cells are rare and isolating such cells in therapeutic quantities from cancer patients is a laborious and costly procedure. In contrast, it is becoming more efficient to engineer readily available peripheral T cells with tumor-specific receptors through genetic manipulation. Techniques have been developed for this engineering process, which are clinically viable, and several clinical trials have demonstrated the feasibility and efficacy of genetically-engineered T cells for the treatment of cancer.

To this point, most engineered T cell therapies involving genetic modification of the T cells yield: (i) forced expression of T cell receptor (TCR); or (ii) a chimeric antigen receptor (CAR) specific for antigen targets on the tumor. To date, the chimeric antigen receptors used for engineering T cells consist of: (i) a targeting domain, usually a single-chain fragment variable (scFv); (ii) a transmembrane domain; and (iii) a cytosolic domain that contains signaling elements from the T cell receptor and associated proteins. Such chimeric antigen receptors have also been referred to as "T-body" or "Chimeric Immune Receptor" (CTR), but currently, most researchers use the term "CAR". One advantage of the CAR approach is that it allows any patient's immune cells to be targeted against any desirable target in a major histocompatibility complex (MHC) independent manner. This is appealing as MHC presentation is often defective in tumor cells.

CARs are considered in modular terms and scientists have spent considerable time investigating the influence of different cytoplasmic signaling domains on CAR function. Conventional CARs generally share two main components: (i) the CD3 zeta cytoplasmic domain, which contains immunotyrosine activation motifs (ITAMs) critical for T cell activation; and (ii) components of costimulatory receptors that trigger important survival pathways such as the Akt pathway.

The first-generation CARs employed a single signaling domain from either CD3ζ or FcεRIγ. Second-generation CARs combined the signaling domain of CD3ζ with the cytoplasmic domain of costimulatory receptors from either the CD28 or TNFR family of receptors. Most CAR-engineered T cells that are currently being tested in the clinic employ second-generation CARs where CD3ζ is coupled to the cytoplasmic domain of either CD28 or CD137. These second generation CARs have demonstrated anti-tumor activity in CD19-positive tumors. Third-generation CARs combined multiple costimulatory domains, but there is concern that third-generation CARs may lose antigen-specificity.

While CAR-engineered T cells have shown considerable promise in clinical application, they rely on a synthetic method for replacing the native activation signal that is provided by the T cell receptor (TCR). Since this synthetic receptor does not deliver all of the signaling components associated with the TCR (ex. ITAMs on CD3γ, CD3δ, CD3ε), it remains unclear whether the T cells are optimally activated by the CAR or how the CAR activation affects T cell differentiation (ex. progression to memory). Furthermore, since the CAR signaling domains are disconnected from their natural regulatory partners by the very nature of the CAR structure, there is an inherent risk that CARs may lead to a low-level of constitutive activation, which could result in off-target toxicities. Therefore, the synthetic nature of the prototypic CAR may disrupt canonical mechanisms that limit TCR activation, and may underpin the severe toxicity often associated with therapeutic doses of conventional CAR T cells.

Given these limitations, it is preferable to re-direct T cells to attack tumors via their natural TCR. To this end, a class of recombinant proteins termed "Bispecific T-cell Engagers" (BiTEs) has been created. These proteins employ bispecific antibody fragments to crosslink T-cell TCR receptors with target antigens. This leads to efficient T-cell activation, triggering cytotoxicity. Similarly, bi-specific antibodies have been generated that accomplish this goal and some scientists have simply linked anti-CD3 antibodies to tumor-specific antibodies employing chemical linkage. While these bi-specific proteins have demonstrated some activity in vitro, GMP production, short biological half-lives, and limited bioavailability represent significant challenges to the successful use of these molecules in cancer treatment. Additionally, these molecules also fail to properly recapitulate natural TCR signaling because they do not engage the TCR co-receptors (CD8 and CD4).

In view of the above, a need remains for chimeric receptors with enhanced activity and safety.

An alternate chimeric receptor, termed a Trifunctional T cell Antigen Coupler (Tri-TAC or TAC) receptor, has been developed which employs a distinct biology to direct the T cell to attack tumors. While the CAR is a fully synthetic receptor that stitches together components of T cell receptor (TCR) signaling complex, the TAC receptor re-directs the TCR towards tumor targets and recapitulates the native TCR signaling structure. For example, in some embodiments, the TACs disclosed herein activate natural Major Histocompatibility complex (MHC) signaling through the T-cell receptor (TCR), while retaining MHC-unrestricted targeting. Further, the TACs disclosed herein recruit the T-Cell Receptor (TCR) in combination with co-receptor stimulation. Moreover, in some embodiments, Tri-TACs disclosed herein show enhanced activity and safety.

Certain Terminology

The term "T cell" as used herein refers to a type of lymphocyte that plays a central role in cell-mediated immunity. T cells, also referred to as T lymphocytes, are distinguished from other lymphocytes, such as B cells and natural killer cells, by the presence of a T-cell receptor (TCR) on the cell surface. There are several subsets of T cells with distinct functions, including but not limited to, T helper cells, cytotoxic T cells, memory T cells, regulatory T cells and natural killer T cells.

The term "T cell antigen coupler" or TAC is used interchangeably with "trifunctional T cell antigen coupler" or Tri-TAC and refers to an engineered nucleic acid construct or polypeptide, that when expressed on a T cell, helps to facilitate the targeting of the T cell to a particular antigen. In some embodiments, the TAC comprises (a) a target-specific ligand, (b) a ligand that binds a protein associated with a T cell receptor (TCR) complex, and (c) a T cell receptor signaling domain.

The term "polynucleotide" and/or "nucleic acid sequence" and/or "nucleic acid" as used herein refers to a sequence of nucleoside or nucleotide monomers consisting of bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acids of the present disclosure may be isolated from biological organisms, formed by laboratory methods of genetic recombination or obtained by chemical synthesis or other known protocols for creating nucleic acids.

The term "isolated polynucleotide" or "isolated nucleic acid sequence" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and is either double stranded or single stranded, and represents the sense or antisense strand. Further, the term "nucleic acid" includes the complementary nucleic acid sequences.

The term "recombinant nucleic acid" or "engineered nucleic acid" as used herein refers to a nucleic acid or polynucleotide that is not found in a biological organism. For example, recombinant nucleic acids may be formed by laboratory methods of genetic recombination (such as molecular cloning) to create sequences that would not otherwise be found in nature. Recombinant nucleic acids may also be created by chemical synthesis or other known protocols for creating nucleic acids.

The term "polypeptide" or "protein" as used herein describes a chain of amino acids. A polypeptide or protein of this disclosure is a peptide, which usually describes a chain of amino acids. The term protein as used herein also describes a large molecule comprising one or more chains of amino acids and, in some embodiments, is a fragment or domain of a protein or a full length protein. Furthermore, as used herein, the term protein either refers to a linear chain of amino acids or to a chain of amino acids that has been processed and folded into a functional protein. The protein structure is divided into four distinct levels: (1) primary structure—referring to the sequence of amino acids in the polypeptide chain, (2) secondary structure—referring to the regular local sub-structures on the polypeptide backbone chain, such as α-helix and β-sheets, (3) tertiary structure—referring to the three-dimensional structure if monomeric and multimeric protein molecules, and (4) quaternary structure—referring to the three-dimensional structure comprising the aggregation of two or more individual polypeptide chains that operate as a single functional unit. The proteins of the present disclosure, in some embodiments, are obtained by isolation and purification of the proteins from cells where they are produced naturally, by enzymatic (e.g., proteolytic) cleavage, and/or recombinantly by expression of nucleic acid encoding the proteins or fragments of this disclosure. The proteins and/or fragments of this disclosure, in some embodiments, is obtained by chemical synthesis or other known protocols for producing proteins and fragments.

The term "isolated polypeptide" refers to a polypeptide substantially free of cellular material or culture medium when produced by recombinant DNA techniques, or chemical precursors or other chemicals when chemically synthesized.

The term "antibody" as used herein is intended to include monoclonal antibodies, polyclonal antibodies, single chain antibodies, chimeric antibodies, and antibody fusions. The antibody may be from recombinant sources and/or produced in transgenic animals. The term "antibody fragment" as used herein is intended to include without limitations Fab, Fab', F(ab')2, scFv, dsFv, ds-scFv, dimers, minibodies, diabodies, and multimers thereof, multispecific antibody fragments and Domain Antibodies.

The term "vector" as used herein refers to a polynucleotide that is used to deliver a nucleic acid to the inside of a cell. In some embodiments, a vector is an expression vector comprising expression control sequences (for example, a promoter) operatively linked to a nucleic acid to be expressed in a cell. Vectors known in the art include, but are not limited to, plasmids, phages, cosmids and viruses.

The term "tumor antigen" or "tumor associated antigen" as used herein refers to an antigenic substance produced in tumor cells that triggers an immune response in a host (e.g. which is presented by MHC complexes). In some embodiments, a tumor antigen is on the surface of a tumor cell.

The term "T cell receptor" or TCR as used herein refers to a complex of integral membrane proteins that participates in the activation of T cells in response to the binding of an antigen. The TCR is a disulfide-linked membrane-anchored heterodimer normally consisting of the highly variable alpha (α) and beta (β) chains expressed as part of a complex with the invariant CD3 (cluster of differentiation 3) chain molecules. T cells expressing this receptor are referred to as α:β (or αβ) T cells, though a minority of T cells express an alternate receptor, formed by variable gamma (γ) and delta (δ) chains, referred as γδ T cells. CD3 is a protein complex composed of four distinct chains. In mammals, the complex contains a CD3γ chain, a CD3δ chain, two CD3ε chains and two CD3ζ chains.

As used herein, the term "transmembrane and cytosolic domain" refers to a polypeptide that comprises a transmembrane domain and a cytosolic domain of a protein associated with the T cell receptor (TCR) complex. In some embodiments, such transmembrane and cytosolic domain may include, but is not limited to, protein domains that (a) associate with the lipid raft and/or (b) bind Lck.

A "TCR co-receptor" as used herein, refers to a molecule that assists the T cell receptor (TCR) in communicating with an antigen-presenting cell and may be considered part of the first signal that leads to the activation of the TCR. Examples of TCR co-receptors include, but are not limited to, CD4, LAG3, and CD8.

A "TCR co-stimulator" as used herein, refers to a molecule that enhances the response of a T cell to an antigen and may be considered as the second signal that leads to the activation of the TCR. Examples of TCR co-stimulators include, but are not limited to, ICOS, CD27, CD28, 4-1BB (CD 137), OX40 (CD134), CD30, CD40, lymphocyte fiction-associated antigen 1 (LFA-1), CD2, CD7, LIGHT, NKG2C, B7-H3, and a ligand that specifically binds CD83.

A "TCR co-inhibitor" or "checkpoint receptor" as used herein, refers to a molecule that inhibits the response of a T cell to an antigen. Examples of TCR co-inhibitors include, but are not limited to, PD-1, TIM3, LAG-3, TIGIT, BTLA, CD160, and CD37.

The terms "recipient", "individual", "subject", "host", and "patient", are used interchangeably herein and in some embodiments, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human. None of these terms require the supervision of medical personnel.

As used herein, the terms "treatment," "treating," and the like, in some embodiments, refer to administering an agent, or carrying out a procedure, for the purposes of obtaining an effect. The effect may be prophylactic in terms of completely or partially preventing a disease or symptom thereof and/or may be therapeutic in terms of affecting a partial or complete cure for a disease and/or symptoms of the disease. "Treatment," as used herein, may include treatment of a disease or disorder (e.g. cancer) in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of a cancer, including any objective or subjective parameter such as abatement; remission; diminishing of symptoms; or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent, delay, alleviate, arrest or inhibit development of the symptoms or conditions associated with diseases (e.g. cancer). The term "therapeutic effect" refers to the reduction, elimination, or prevention of the disease, symptoms of the disease, or side effects of the disease in the subject.

As used herein, singular forms "a", "and," and "the" include plural referents unless the context clearly indicates otherwise. Thus, for example, reference to "an antibody" includes a plurality of antibodies and reference to "an antibody" in some embodiments includes multiple antibodies, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 96%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

"About" a number, as used herein, refers to range including the number and ranging from 10% below that number to 10% above that number. "About" a range refers to 10% below the lower limit of the range, spanning to 10% above the upper limit of the range.

"Percent (%) identity" refers to the extent to which two sequences (nucleotide or amino acid) have the same residue at the same positions in an alignment. For example, "an amino acid sequence is X % identical to SEQ ID NO: Y" refers to % identity of the amino acid sequence to SEQ ID NO:Y and is elaborated as X % of residues in the amino acid sequence are identical to the residues of sequence disclosed in SEQ ID NO: Y. Generally, computer programs are employed for such calculations. Exemplary programs that compare and align pairs of sequences, include ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984).

As used herein, the term "selective binding" refers to the higher affinity with which a molecule (e.g. protein such as a target-binding ligand of TAC) binds its target molecule (e.g. target antigen such as HER-2, BCMA, or CD19) over other molecules.

T Cell Antigen Coupler (Tri-TAC or TAC)

Disclosed herein, in certain embodiments, are nucleic acids encoding a Trifunctional T cell-antigen coupler (Tri-TAC). In some embodiments, the nucleic acids encoding a Tri-TAC comprises: (a) a first polynucleotide encoding a target-specific ligand; (b) a second polynucleotide encoding a ligand that binds a TCR complex; and (c) a third polynucleotide encoding a transmembrane domain and cytosolic domain. In some embodiments, the nucleic acids encoding a Tri-TAC do not encode a co-stimulatory domain. In some embodiments, the nucleic acids encoding a Tri-TAC do not encode a co-activation domain.

Target-Specific Ligand

The target-specific ligand, also referred to as an antigen binding domain, refers to any substance or molecule that binds, directly or indirectly, to a target cell. In some embodiments, the target specific ligand binds to an antigen on the target cell. In some embodiments, a target cell is a cell associated with a disease state, including, but not limited to, cancer, hematologic malignancy, large B-cell lymphoma, diffuse large B-cell lymphoma, primary mediastinal B cell lymphoma, high grade B-cell lymphoma, or large B cell lymphoma arising from follicular lymphoma. In some embodiments, a target cell is a tumor cell. In some embodiments, a target-specific ligand binds to a tumor antigen or tumor associated antigen on a tumor cell. In some embodiments, the target antigen is a tumor antigen. In some embodiments, the tumor antigen when proteinaceous is a sequence of 8 or more amino acids up to the full protein. In some embodiments, the tumor antigen is any number of amino acids in between 8 and the full length protein which comprises at least one antigenic fragment of the full length protein that is presented in a Major Histocompatibility Complex (MHC). Examples of tumor antigens include, but are not limited to, CD19, HER-2 (erbB-2), B-cell maturation antigen (BCMA), alphafetoprotein (AFP), carcinoembryonic antigen (CEA), CA-125, MUC-1, epithelial tumor antigen (ETA), tyrosinase, melanoma-associated antigen (MAGE), prostate-specific antigen (PSA), glioma-associated antigen, 3-human chorionic gonadotropin, thyroglobulin, RAGE-1, MN-CA IX, human telomerase reverse transcriptase, RU1, RU2 (AS), intestinal carboxyl esterase, mut hsp70-2, M-CSF, prostase, PAP, NY-ESO-1, LAGE-1a, p53, prostein, PSMA, survivin and telomerase, prostate-carcinoma tumor antigen-1 (PCTA-1), ELF2M, neutrophil elastase, CD22, insulin growth factor (IGF)-I, IGF-II, IGF-I receptor and mesothelin.

In some embodiments, the target-specific ligands include, but are not limited to, antibodies and fragments thereof, for example single chain antibodies such as single-chain antibodies (scFvs), single domain antibodies, peptides, peptidomimetics, proteins, glycoproteins, or proteoglycans that bind to the target cell and/or antigen. In some embodiments, the target-specific ligands include, but are not limited to, designed ankyrin repeat proteins (DARPins), lectins, knottins, centryrins, anticalins, or naturally occurring ligands for the tumor antigen, such as growth factors, enzyme substrates, receptors or binding proteins. In some embodiments, target specific ligands include non-protein compounds that bind to target cells and/or antigens, including but not limited to carbohydrates, lipids, nucleic acids, or small molecules. In some embodiments, a target-specific ligand is a designed ankyrin repeat (DARPin) targeted to a specific cell and/or antigen. In some embodiments, a target-specific ligand is a single-chain variable fragment (ScFv) targeted to a specific cell and/or antigen.

In some embodiments, the tumor antigen is a HER-2 antigen. In some embodiments, the HER-2 specific ligand comprises an antigen binding domain of an antibody selected from Trastuzumab, Pertuzumab, Lapatinib, Neratinib, Ado-trastuzmab Emtansine, Gancotamab, Margetuximab, Timigutuzumab, and Ertumaxomab. In some embodiments, the target-specific ligand is a DARPin that selectively binds a HER-2 (erbB-2) antigen. In some embodiments, the target-specific ligand is a DARPin that specifically binds a HER-2 (erbB-2) antigen. In some embodiments, the DARPin targeted to HER-2 (erb-2) comprises SEQ ID NO: 7 or SEQ ID NO: 8.

In some embodiments, the first polynucleotide comprises a nucleotide sequence having at least 70% sequence identity with SEQ ID NO: 7. In some embodiments, the first polynucleotide comprises a nucleotide sequence having at least 75% sequence identity with SEQ ID NO: 7. In some embodiments, the first polynucleotide comprises a nucleotide sequence having at least 80% sequence identity with SEQ ID NO: 7. In some embodiments, the first polynucleotide comprises a nucleotide sequence having at least 85% sequence identity with SEQ ID NO: 7. In some embodiments, the first polynucleotide comprises a nucleotide sequence having at least 90% sequence identity with SEQ ID NO: 7. In some embodiments, the first polynucleotide comprises a nucleotide sequence having at least 95% sequence identity with SEQ ID NO: 7. In some embodiments, the first polynucleotide comprises a nucleotide sequence of SEQ ID NO: 7.

In some embodiments, the target-specific ligand comprises an amino acid sequence having at least 70% sequence identity with SEQ ID NO: 8. In some embodiments, the target-specific ligand comprises an amino acid sequence having at least 75% sequence identity with SEQ ID NO: 8. In some embodiments, the target-specific ligand comprises an amino acid sequence having at least 80% sequence identity with SEQ ID NO: 8. In some embodiments, the target-specific ligand comprises an amino acid sequence having at least 85% sequence identity with SEQ ID NO: 8. In some embodiments, the target-specific ligand comprises an amino acid sequence having at least 90% sequence identity with SEQ ID NO: 8. In some embodiments, the target-specific ligand comprises an amino acid sequence having at least 95% sequence identity with SEQ ID NO: 8. In some embodiments, the target-specific ligand comprises an amino acid sequence of SEQ ID NO: 8.

In some embodiments, the tumor antigen is a BCMA antigen. In some embodiments, the BCMA specific ligand comprises an antigen binding domain of an antibody selected from Belantamab mafodotin, and GSK2857916. In some embodiments, the target-specific ligand is a scFv that selectively binds BCMA. In some embodiments, the target-specific ligand is a scFv that specifically binds BCMA. In some embodiments, the scFv that binds BCMA comprises SEQ ID NO: 33 or SEQ ID NO: 34.

In some embodiments, the first polynucleotide comprises a nucleotide sequence having at least 70% sequence identity with SEQ ID NO: 33. In some embodiments, the first polynucleotide comprises a nucleotide sequence having at least 75% sequence identity with SEQ ID NO: 33. In some embodiments, the first polynucleotide comprises a nucleotide sequence having at least 80% sequence identity with SEQ ID NO: 33. In some embodiments, the first polynucleotide comprises a nucleotide sequence having at least 85% sequence identity with SEQ ID NO: 33. In some embodiments, the first polynucleotide comprises a nucleotide sequence having at least 90% sequence identity with SEQ ID NO: 33. In some embodiments, the first polynucleotide comprises a nucleotide sequence having at least 95% sequence identity with SEQ ID NO: 33. In some embodiments, the first polynucleotide comprises a nucleotide sequence of SEQ ID NO: 33.

In some embodiments, the target-specific ligand comprises an amino acid sequence having at least 70% sequence identity with SEQ ID NO: 34. In some embodiments, the target-specific ligand comprises an amino acid sequence having at least 75% sequence identity with SEQ ID NO: 34. In some embodiments, the target-specific ligand comprises an amino acid sequence having at least 80% sequence identity with SEQ ID NO: 34. In some embodiments, the target-specific ligand comprises an amino acid sequence having at least 85% sequence identity with SEQ ID NO: 34. In some embodiments, the target-specific ligand comprises an amino acid sequence having at least 90% sequence identity with SEQ ID NO: 34. In some embodiments, the target-specific ligand comprises an amino acid sequence having at least 95% sequence identity with SEQ ID NO: 34. In some embodiments, the target-specific ligand comprises an amino acid sequence of SEQ ID NO: 34.

In some embodiments, the tumor antigen is a CD19 antigen. In some embodiments, the target-specific ligand is a scFv that selectively binds CD19. In some embodiments, the target-specific ligand is a scFv that specifically binds CD19. In some embodiments, the scFv that binds CD19 comprises SEQ ID NO: 35 or SEQ ID NO: 36.

In some embodiments, the first polynucleotide comprises a nucleotide sequence having at least 70% sequence identity with SEQ ID NO: 35. In some embodiments, the first polynucleotide comprises a nucleotide sequence having at least 75% sequence identity with SEQ ID NO: 35. In some embodiments, the first polynucleotide comprises a nucleotide sequence having at least 80% sequence identity with SEQ ID NO: 35. In some embodiments, the first polynucleotide comprises a nucleotide sequence having at least 85% sequence identity with SEQ ID NO: 35. In some embodiments, the first polynucleotide comprises a nucleotide sequence having at least 90% sequence identity with SEQ ID NO: 35. In some embodiments, the first polynucleotide comprises a nucleotide sequence having at least 95% sequence identity with SEQ ID NO: 35. In some embodiments, the first polynucleotide comprises a nucleotide sequence of SEQ ID NO: 35.

In some embodiments, the target-specific ligand comprises an amino acid sequence having at least 70% sequence identity with SEQ ID NO: 36. In some embodiments, the target-specific ligand comprises an amino acid sequence having at least 75% sequence identity with SEQ ID NO: 36. In some embodiments, the target-specific ligand comprises an amino acid sequence having at least 80% sequence identity with SEQ ID NO: 36. In some embodiments, the target-specific ligand comprises an amino acid sequence having at least 85% sequence identity with SEQ ID NO: 36. In some embodiments, the target-specific ligand comprises an amino acid sequence having at least 90% sequence identity with SEQ ID NO: 36. In some embodiments, the target-specific ligand comprises an amino acid sequence having at least 95% sequence identity with SEQ ID NO: 36. In some embodiments, the target-specific ligand comprises an amino acid sequence of SEQ ID NO: 36.

Ligand that Binds a TCR Complex

In some embodiments, the TAC comprises a ligand that binds a protein associated with the TCR complex. In some embodiments, the ligand that binds a protein associated with a TCR complex comprises a substance that binds, directly or indirectly, to a protein of the TCR. In some embodiments, the ligand that binds a protein associated with a TCR complex comprises a substance that selectively binds to a protein of the TCR. In some embodiments, the ligand that binds a protein associated with a TCR complex comprises a substance that specifically binds to a protein of the TCR. Proteins associated with the TCR include, but are not limited to, the TCR alpha (α) chain, TCR beta (β) chain, TCR gamma (γ) chain, TCR delta (δ) chain, CD3γ chain, CD3δ chain and CD3ε chains. In some embodiments, a ligand that binds a protein associated with the TCR complex is an antibody to the TCR alpha (α) chain, TCR beta (β) chain, TCR gamma (γ) chain, TCR delta (δ) chain, CD3γ chain, CD3δ chain and/or CD3ε chain. In some embodiments, the protein associated with a TCR complex is CD3. In some embodiments, the protein associated with a TCR complex is CD3ε. Examples of CD3 antibodies, include, but are not limited to, for. In some embodiments, the antibody that binds CD3 is a single chain antibody, for example a single-chain variable fragment (scFv). In some embodiments, the ligand that binds a TCR is anti-CD3 antibody, or a fragment thereof, such as muromonab, otelixizumab, teplizumab, visilizumab, CD3-12, MEM-57, 4D10A6, CD3D, or TR66.

In some embodiments, the CD3 is of a TCR complex on a cell expressing the second polynucleotide. In some embodiments, the binding of the CD3 induces activation of a cell expressing the second polynucleotide.

In some embodiments, the ligand that binds a TCR complex is UCHT1, or a variant thereof. In some embodiments, the ligand that binds a TCR complex is UCHT1 (SEQ ID NO: 13, SEQ ID NO: 14 or homologs thereof). In some embodiments, the UCHT1 ligand binds CD3. In some embodiments, the UCHT1 ligand selectively binds CD3. In some embodiments, the UCHT1 ligand specifically binds CD3. In some embodiments, the UCHT1 ligand binds CD3ε. In some embodiments, the UCHT1 ligand selectively binds CD3ε. In some embodiments, the UCHT1 ligand specifically binds CD3ε. In some embodiments, the UCHT1 ligand is encoded by SEQ ID NO 13. In some embodiments, the UCHT1 ligand comprises SEQ ID NO 14. In some embodiments, the UCHT1 ligand is mutated. In some embodiments, the UCHT1 ligand comprises a Y182T mutation (also referred to as UCHT1 (Y182T)) (SEQ ID NO: 71 and SEQ ID NO: 72). In some embodiments, the UCHT1 (Y182T) ligand binds CD3. In some embodiments, the UCHT1 (Y182T) ligand selectively binds CD3. In some embodiments, the UCHT1 (Y182T) ligand specifically binds CD3. In some embodiments, the UCHT1 (Y182T) ligand binds CD3ε. In some embodiments, the UCHT1 (Y182T) ligand selectively binds CD3ε. In some embodiments, the UCHT1 (Y182T) ligand specifically binds CD3ε. In some embodiments, the UCHT1 (Y182T) ligand is encoded by SEQ ID NO 71. In some embodiments, the UCHT1 (Y182T) ligand comprises SEQ ID NO 72. In some embodiments, the ligand that binds a TCR complex is a humanized UCHT1 (huUCHT1). In some embodiments, the ligand that binds a TCR complex is huUCHT1 (SEQ ID NO 43, SEQ ID NO: 44 or homologs thereof). In some embodiments, the huUCHT1 ligand binds CD3. In some embodiments, the huUCHT1 ligand selectively binds CD3. In some embodiments, the huUCHT1 ligand specifically binds CD3. In some embodiments, the huUCHT1 ligand binds CD3ε. In some embodiments, the huUCHT1 ligand selectively binds CD3ε. In some embodiments, the huUCHT1 ligand specifically binds CD3ε. In some embodiments, the huUCHT1 ligand is encoded by SEQ ID NO 43. In some embodiments, the huUCHT1 ligand comprises SEQ ID NO 44. In some embodiments, the huUCHT1 has a Y177T mutation (also referred to as huUCHT1 (Y177T)) (SEQ ID NO: 45 and SEQ ID NO: 46). In some embodiments, the huUCHT1 (Y177T) ligand binds CD3. In some embodiments, the huUCHT1 (Y177T) ligand selectively binds CD3. In some embodiments, the huUCHT1 (Y177T) ligand specifically binds CD3. In some embodiments, the huUCHT1 (Y177T) ligand binds CD3ε. In some embodiments, the huUCHT1 (Y177T) ligand selectively binds CD3ε. In some embodiments, the huUCHT1 (Y177T) ligand specifically binds CD3ε. In some embodiments, the huUCHT1 (Y177T) ligand is encoded by SEQ ID NO 45. In some embodiments, the huUCHT1 ligand comprises SEQ ID NO 46.

In some embodiments, the second polynucleotide comprises a nucleotide sequence having at least 70% sequence identity with SEQ ID NO: 13. In some embodiments, the second polynucleotide comprises a nucleotide sequence having at least 75% sequence identity with SEQ ID NO: 13. In some embodiments, the second polynucleotide comprises a nucleotide sequence having at least 80% sequence identity with SEQ ID NO: 13. In some embodiments, the second polynucleotide comprises a nucleotide sequence having at least 85% sequence identity with SEQ ID NO: 13. In some embodiments, the second polynucleotide comprises a nucleotide sequence having at least 90% sequence identity with SEQ ID NO: 13. In some embodiments, the second polynucleotide comprises a nucleotide sequence having at least 95% sequence identity with SEQ ID NO: 13. In some embodiments, the second polynucleotide comprises a nucleotide sequence of SEQ ID NO: 13.

In some embodiments, the ligand that binds a TCR complex comprises an amino acid sequence having at least 70% sequence identity with SEQ ID NO: 14. In some embodiments, the ligand that binds a TCR complex comprises an amino acid sequence having at least 75% sequence identity with SEQ ID NO: 14. In some embodiments, the ligand that binds a TCR complex comprises an amino acid sequence having at least 80% sequence identity with SEQ ID NO: 14. In some embodiments, the ligand that binds a TCR complex comprises an amino acid sequence having at least 85% sequence identity with SEQ ID NO: 14. In some embodiments, the ligand that binds a TCR complex comprises an amino acid sequence having at least 90% sequence identity with SEQ ID NO: 14. In some embodiments, the ligand that binds a TCR complex comprises an amino acid sequence having at least 95% sequence identity with SEQ ID NO: 14. In some embodiments, the ligand that binds a TCR complex comprises an amino acid sequence of SEQ ID NO: 14.

In some embodiments, the second polynucleotide comprises a nucleotide sequence having at least 70% sequence identity with SEQ ID NO: 71. In some embodiments, the second polynucleotide comprises a nucleotide sequence having at least 75% sequence identity with SEQ ID NO: 71. In some embodiments, the second polynucleotide comprises a nucleotide sequence having at least 80% sequence identity with SEQ ID NO: 71. In some embodiments, the second polynucleotide comprises a nucleotide sequence having at least 85% sequence identity with SEQ ID NO: 71. In some embodiments, the second polynucleotide comprises a nucleotide sequence having at least 90% sequence identity with SEQ ID NO: 71. In some embodiments, the second polynucleotide comprises a nucleotide sequence having at least 95% sequence identity with SEQ ID NO: 71. In some embodiments, the second polynucleotide comprises a nucleotide sequence of SEQ ID NO: 71.

In some embodiments, the ligand that binds a TCR complex comprises an amino acid sequence having at least 70% sequence identity with SEQ ID NO: 72. In some embodiments, the ligand that binds a TCR complex comprises an amino acid sequence having at least 75% sequence identity with SEQ ID NO: 72. In some embodiments, the ligand that binds a TCR complex comprises an amino acid sequence having at least 80% sequence identity with SEQ ID NO: 72. In some embodiments, the ligand that binds a TCR complex comprises an amino acid sequence having at least 85% sequence identity with SEQ ID NO: 72. In some embodiments, the ligand that binds a TCR complex comprises an amino acid sequence having at least 90% sequence identity with SEQ ID NO: 72. In some embodiments, the ligand that binds a TCR complex comprises an amino acid sequence having at least 95% sequence identity with SEQ ID NO: 72. In some embodiments, the ligand that binds a TCR complex comprises an amino acid sequence of SEQ ID NO: 72.

In some embodiments, the second polynucleotide comprises a nucleotide sequence having at least 70% sequence identity with SEQ ID NO: 43. In some embodiments, the second polynucleotide comprises a nucleotide sequence having at least 75% sequence identity with SEQ ID NO: 43. In some embodiments, the second polynucleotide comprises a nucleotide sequence having at least 80% sequence identity with SEQ ID NO: 43. In some embodiments, the second polynucleotide comprises a nucleotide sequence having at least 85% sequence identity with SEQ ID NO: 43. In some embodiments, the second polynucleotide comprises a nucleotide sequence having at least 90% sequence identity with SEQ ID NO: 43. In some embodiments, the second polynucleotide comprises a nucleotide sequence having at least 95% sequence identity with SEQ ID NO: 43. In some embodiments, the second polynucleotide comprises a nucleotide sequence of SEQ ID NO: 43.

In some embodiments, the ligand that binds a TCR complex comprises an amino acid sequence having at least 70% sequence identity with SEQ ID NO: 44. In some embodiments, the ligand that binds a TCR complex comprises an amino acid sequence having at least 75% sequence identity with SEQ ID NO: 44. In some embodiments, the ligand that binds a TCR complex comprises an amino acid sequence having at least 80% sequence identity with SEQ ID NO: 44. In some embodiments, the ligand that binds a TCR complex comprises an amino acid sequence having at least 85% sequence identity with SEQ ID NO: 44. In some embodiments, the ligand that binds a TCR complex comprises an amino acid sequence having at least 90% sequence identity with SEQ ID NO: 44. In some embodiments, the ligand that binds a TCR complex comprises an amino acid sequence having at least 95% sequence identity with SEQ ID NO: 44. In some embodiments, the ligand that binds a TCR complex comprises an amino acid sequence of SEQ ID NO: 44.

In some embodiments, the second polynucleotide comprises a nucleotide sequence having at least 70% sequence identity with SEQ ID NO: 45. In some embodiments, the second polynucleotide comprises a nucleotide sequence having at least 75% sequence identity with SEQ ID NO: 45. In some embodiments, the second polynucleotide comprises a nucleotide sequence having at least 80% sequence identity with SEQ ID NO: 45. In some embodiments, the second polynucleotide comprises a nucleotide sequence having at least 85% sequence identity with SEQ ID NO: 45. In some embodiments, the second polynucleotide comprises a nucleotide sequence having at least 90% sequence identity with SEQ ID NO: 45. In some embodiments, the second polynucleotide comprises a nucleotide sequence having at least 95% sequence identity with SEQ ID NO: 45. In some embodiments, the second polynucleotide comprises a nucleotide sequence of SEQ ID NO: 45.

In some embodiments, the ligand that binds a TCR complex comprises an amino acid sequence having at least 70% sequence identity with SEQ ID NO: 46. In some embodiments, the ligand that binds a TCR complex comprises an amino acid sequence having at least 75% sequence identity with SEQ ID NO: 46. In some embodiments, the ligand that binds a TCR complex comprises an amino acid sequence having at least 80% sequence identity with SEQ ID NO: 46. In some embodiments, the ligand that binds a TCR complex comprises an amino acid sequence having at least 85% sequence identity with SEQ ID NO: 46. In some embodiments, the ligand that binds a TCR complex comprises an amino acid sequence having at least 90% sequence identity with SEQ ID NO: 46. In some embodiments, the ligand that binds a TCR complex comprises an amino acid sequence having at least 95% sequence identity with SEQ ID NO: 46. In some embodiments, the ligand that binds a TCR complex comprises an amino acid sequence of SEQ ID NO: 46.

In some embodiments, the ligand that binds to a CD3 is OKT3. In some embodiments, the OKT3 ligand binds CD3. In some embodiments, the OKT3 ligand selectively binds CD3. In some embodiments, the OKT3 ligand specifically binds CD3. In some embodiments, the OKT3 ligand binds CD3ε. In some embodiments, the OKT3 ligand selectively binds CD3ε. In some embodiments, the OKT3 ligand specifically binds CD3ε. In some embodiments, the murine OKT3 ligand is encoded by SEQ ID NO 21. In some embodiments, the OKT3 ligand comprises SEQ ID NO 22.

In some embodiments, the second polynucleotide comprises a nucleotide sequence having at least 70% sequence identity with SEQ ID NO: 21. In some embodiments, the second polynucleotide comprises a nucleotide sequence having at least 75% sequence identity with SEQ ID NO: 21. In some embodiments, the second polynucleotide comprises a nucleotide sequence having at least 80% sequence identity with SEQ ID NO: 21. In some embodiments, the second polynucleotide comprises a nucleotide sequence having at least 85% sequence identity with SEQ ID NO: 21. In some embodiments, the second polynucleotide comprises a nucleotide sequence having at least 90% sequence identity with SEQ ID NO: 21. In some embodiments, the second polynucleotide comprises a nucleotide sequence having at least 95% sequence identity with SEQ ID NO: 21. In some embodiments, the second polynucleotide comprises a nucleotide sequence of SEQ ID NO: 21.

In some embodiments, the ligand that binds a TCR complex comprises an amino acid sequence having at least 70% sequence identity with SEQ ID NO: 22. In some embodiments, the ligand that binds a TCR complex comprises an amino acid sequence having at least 75% sequence identity with SEQ ID NO: 22. In some embodiments, the ligand that binds a TCR complex comprises an amino acid sequence having at least 80% sequence identity with SEQ ID NO: 22. In some embodiments, the ligand that binds a TCR complex comprises an amino acid sequence having at least 85% sequence identity with SEQ ID NO: 22. In some embodiments, the ligand that binds a TCR complex comprises an amino acid sequence having at least 90% sequence identity with SEQ ID NO: 22. In some embodiments, the ligand that binds a TCR complex comprises an amino acid sequence having at least 95% sequence identity with SEQ ID NO: 22. In some embodiments, the ligand that binds a TCR complex comprises an amino acid sequence of SEQ ID NO: 22.

In some embodiments, the ligand that binds to a CD3 is F6A. In some embodiments, the F6A ligand binds CD3. In some embodiments, the F6A ligand selectively binds CD3. In some embodiments, the F6A ligand specifically binds CD3. In some embodiments, the F6A ligand binds CD3ε. In some embodiments, the F6A ligand selectively binds CD3ε. In some embodiments, the F6A ligand specifically binds CD3ε. In some embodiments, the murine F6A ligand is encoded by SEQ ID NO 23. In some embodiments, the F6A ligand comprises SEQ ID NO 24.

In some embodiments, the second polynucleotide comprises a nucleotide sequence having at least 70% sequence identity with SEQ ID NO: 23. In some embodiments, the second polynucleotide comprises a nucleotide sequence having at least 75% sequence identity with SEQ ID NO: 23. In some embodiments, the second polynucleotide comprises a nucleotide sequence having at least 80% sequence identity with SEQ ID NO: 23. In some embodiments, the second polynucleotide comprises a nucleotide sequence having at least 85% sequence identity with SEQ ID NO: 23. In some embodiments, the second polynucleotide comprises a nucleotide sequence having at least 90% sequence identity with SEQ ID NO: 23. In some embodiments, the second polynucleotide comprises a nucleotide sequence having at least 95% sequence identity with SEQ ID NO: 23. In some embodiments, the second polynucleotide comprises a nucleotide sequence of SEQ ID NO: 23.

In some embodiments, the ligand that binds a TCR complex comprises an amino acid sequence having at least 70% sequence identity with SEQ ID NO: 24. In some embodiments, the ligand that binds a TCR complex comprises an amino acid sequence having at least 75% sequence identity with SEQ ID NO: 24. In some embodiments, the ligand that binds a TCR complex comprises an amino acid sequence having at least 80% sequence identity with SEQ ID NO: 24. In some embodiments, the ligand that binds a TCR complex comprises an amino acid sequence having at least 85% sequence identity with SEQ ID NO: 24. In some embodiments, the ligand that binds a TCR complex comprises an amino acid sequence having at least 90% sequence identity with SEQ ID NO: 24. In some embodiments, the ligand that binds a TCR complex comprises an amino acid sequence having at least 95% sequence identity with SEQ ID NO: 24. In some embodiments, the ligand that binds a TCR complex comprises an amino acid sequence of SEQ ID NO: 24.

In some embodiments, the ligand that binds to a CD3 is L2K. In some embodiments, the L2K ligand binds CD3. In some embodiments, the L2K ligand selectively binds CD3. In some embodiments, the L2K ligand specifically binds CD3. In some embodiments, the L2K ligand binds CD3ε. In some embodiments, the L2K ligand selectively binds CD3ε. In some embodiments, the L2K ligand specifically binds CD3ε. In some embodiments, the murine L2K ligand is encoded by SEQ ID NO 25. In some embodiments, the L2K ligand comprises SEQ ID NO 26.

In some embodiments, the second polynucleotide comprises a nucleotide sequence having at least 70% sequence identity with SEQ ID NO: 25. In some embodiments, the second polynucleotide comprises a nucleotide sequence having at least 75% sequence identity with SEQ ID NO: 25. In some embodiments, the second polynucleotide comprises a nucleotide sequence having at least 80% sequence identity with SEQ ID NO: 25. In some embodiments, the second polynucleotide comprises a nucleotide sequence having at least 85% sequence identity with SEQ ID NO: 25. In some embodiments, the second polynucleotide comprises a nucleotide sequence having at least 90% sequence identity with SEQ ID NO: 25. In some embodiments, the second polynucleotide comprises a nucleotide sequence having at least 95% sequence identity with SEQ ID NO: 25. In some embodiments, the second polynucleotide comprises a nucleotide sequence of SEQ ID NO: 25.

In some embodiments, the ligand that binds a TCR complex comprises an amino acid sequence having at least 70% sequence identity with SEQ ID NO: 26. In some embodiments, the ligand that binds a TCR complex comprises an amino acid sequence having at least 75% sequence identity with SEQ ID NO: 26. In some embodiments, the ligand that binds a TCR complex comprises an amino acid sequence having at least 80% sequence identity with SEQ ID NO: 26. In some embodiments, the ligand that binds a TCR complex comprises an amino acid sequence having at least 85% sequence identity with SEQ ID NO: 26. In some embodiments, the ligand that binds a TCR complex comprises an amino acid sequence having at least 90% sequence identity with SEQ ID NO: 26. In some embodiments, the ligand that binds a TCR complex comprises an amino acid sequence having at least 95% sequence identity with SEQ ID NO: 26. In some embodiments, the ligand that binds a TCR complex comprises an amino acid sequence of SEQ ID NO: 26.

Transmembrane Domain and Cytosolic Domain

In some embodiments, a T cell antigen coupler includes a T cell receptor signaling domain polypeptide. In some embodiments, the TCR signaling domain polypeptide comprises a transmembrane domain. In some embodiments, the TCR signaling domain polypeptide comprises a cytosolic domain. In some embodiments, the TCR signaling domain polypeptide comprises a transmembrane domain and a cytosolic domain. In some embodiments, the cytosolic domain and transmembrane domains are optionally joined by a linker. In some embodiments, the T cell receptor signaling domain polypeptide comprises a TCR co-receptor domain. In some embodiments, the T cell receptor signaling domain polypeptide does not comprise a TCR co-stimulator domain. In some embodiments, the TCR signaling domain polypeptide comprises a transmembrane domain and/or a cytosolic domain of a TCR co-receptor. In some embodiments, the TCR co-receptor is CD4, CD8, LAG3, or a chimeric variation thereof.

In some embodiments, the TCR co-receptor is CD4. In some embodiments, the TCR signaling domain polypeptide comprises the transmembrane and cytosolic domains of the CD4 co-receptor encoded by SEQ ID NO: 17. In some embodiments, the TCR signaling domain polypeptide comprises the transmembrane and cytosolic domains of the CD4 co-receptor comprising SEQ ID NO: 18.

In some embodiments, the third polynucleotide comprises a nucleotide sequence having at least 70% sequence identity with SEQ ID NO: 17. In some embodiments, the third polynucleotide comprises a nucleotide sequence having at least 75% sequence identity with SEQ ID NO: 17. In some embodiments, the third polynucleotide comprises a nucleotide sequence having at least 80% sequence identity with SEQ ID NO: 17. In some embodiments, the third polynucleotide comprises a nucleotide sequence having at least 85% sequence identity with SEQ ID NO: 17. In some embodiments, the third polynucleotide comprises a nucleotide sequence having at least 90% sequence identity with SEQ ID NO: 17. In some embodiments, the third polynucleotide comprises a nucleotide sequence having at least 95% sequence identity with SEQ ID NO: 17. In some embodiments, the third polynucleotide comprises a nucleotide sequence of SEQ ID NO: 17.

In some embodiments, the transmembrane domain and cytosolic domain comprise an amino acid sequence having at least 70% sequence identity with SEQ ID NO: 18. In some embodiments, the transmembrane domain and cytosolic domain comprise an amino acid sequence having at least 75% sequence identity with SEQ ID NO: 18. In some embodiments, the transmembrane domain and cytosolic domain comprise an amino acid sequence having at least 80% sequence identity with SEQ ID NO: 18. In some embodiments, the transmembrane domain and cytosolic domain comprise an amino acid sequence having at least 85% sequence identity with SEQ ID NO: 18. In some embodiments, the transmembrane domain and cytosolic domain comprise an amino acid sequence having at least 90% sequence identity with SEQ ID NO: 18. In some embodiments, the transmembrane domain and cytosolic domain comprise an amino acid sequence having at least 95% sequence identity with SEQ ID NO: 18. In some embodiments, the transmembrane domain and cytosolic domain comprise an amino acid sequence of SEQ ID NO: 18.

In some embodiments, the TCR co-receptor is CD8. In some embodiments, the TCR co-receptor is CD8α. In some embodiments, the TCR signaling domain polypeptide comprises the transmembrane and cytosolic domains of the CD8α co-receptor encoded by SEQ ID NO: 37. In some embodiments, the TCR signaling domain polypeptide comprises the transmembrane and cytosolic domains of the CD8α co-receptor comprising SEQ ID NO: 38.

In some embodiments, the third polynucleotide comprises a nucleotide sequence having at least 70% sequence identity with SEQ ID NO: 37. In some embodiments, the third polynucleotide comprises a nucleotide sequence having at least 75% sequence identity with SEQ ID NO: 37. In some embodiments, the third polynucleotide comprises a nucleotide sequence having at least 80% sequence identity with SEQ ID NO: 37. In some embodiments, the third polynucleotide comprises a nucleotide sequence having at least 85% sequence identity with SEQ ID NO: 37. In some embodiments, the third polynucleotide comprises a nucleotide sequence having at least 90% sequence identity with SEQ ID NO: 37. In some embodiments, the third polynucleotide comprises a nucleotide sequence having at least 95% sequence identity with SEQ ID NO: 37. In some embodiments, the third polynucleotide comprises a nucleotide sequence of SEQ ID NO: 37.

In some embodiments, the transmembrane domain and cytosolic domain comprise an amino acid sequence having at least 70% sequence identity with SEQ ID NO: 38. In some embodiments, the transmembrane domain and cytosolic domain comprise an amino acid sequence having at least 75% sequence identity with SEQ ID NO: 38. In some embodiments, the transmembrane domain and cytosolic domain comprise an amino acid sequence having at least 80% sequence identity with SEQ ID NO: 38. In some embodiments, the transmembrane domain and cytosolic domain comprise an amino acid sequence having at least 85% sequence identity with SEQ ID NO: 38. In some embodiments, the transmembrane domain and cytosolic domain comprise an amino acid sequence having at least 90% sequence identity with SEQ ID NO: 38. In some embodiments, the transmembrane domain and cytosolic domain comprise an amino acid sequence having at least 95% sequence identity with SEQ ID NO: 38. In some embodiments, the transmembrane domain and cytosolic domain comprise an amino acid sequence of SEQ ID NO: 38.

In some embodiments, the TCR signaling domain polypeptide comprises a chimera of sequences or domains from co-receptors. In some embodiments, the TCR signaling domain polypeptide comprises a chimera of CD8α and CD8β, wherein the CD8α arginine rich region is replaced with the CD8β arginine rich region. In some embodiments, the T cell receptor signaling domain polypeptide comprises the transmembrane and cytosolic domains of the CD8α+R(β) co-receptor chimera encoded by SEQ ID NO: 39. In some embodiments, the T cell receptor signaling domain polypeptide comprises the transmembrane and cytosolic domains of the CD8α+R(β) co-receptor chimera provided by SEQ ID NO: 40. In some embodiments, the TCR signaling domain polypeptide comprises a chimera of CD8α and CD8β, the CD8α CXCP domain, which contains an Lck binding motif, is appended to the C-terminus of the CD8β cytosolic domain. In some embodiments, the T cell receptor signaling domain polypeptide comprises the transmembrane and cytosolic domains of the CD8β+Lck co-receptor chimera encoded by SEQ ID NO: 41. In some embodiments, the T cell receptor signaling domain polypeptide comprises the transmembrane and cytosolic domains of the CD8β+Lck co-receptor chimera provided by SEQ ID NO: 42.

In some embodiments, the third polynucleotide comprises a nucleotide sequence having at least 70% sequence identity with SEQ ID NO: 39. In some embodiments, the third polynucleotide comprises a nucleotide sequence having at least 75% sequence identity with SEQ ID NO: 39. In some embodiments, the third polynucleotide comprises a nucleotide sequence having at least 80% sequence identity with SEQ ID NO: 39. In some embodiments, the third polynucleotide comprises a nucleotide sequence having at least 85% sequence identity with SEQ ID NO: 39. In some embodiments, the third polynucleotide comprises a nucleotide sequence having at least 90% sequence identity with SEQ ID NO: 39. In some embodiments, the third polynucleotide comprises a nucleotide sequence having at least 95% sequence identity with SEQ ID NO: 39. In some embodiments, the third polynucleotide comprises a nucleotide sequence of SEQ ID NO: 39.

In some embodiments, the transmembrane domain and cytosolic domain comprise an amino acid sequence having at least 70% sequence identity with SEQ ID NO: 40. In some embodiments, the transmembrane domain and cytosolic domain comprise an amino acid sequence having at least 75% sequence identity with SEQ ID NO: 40. In some embodiments, the transmembrane domain and cytosolic domain comprise an amino acid sequence having at least 80% sequence identity with SEQ ID NO: 40. In some embodiments, the transmembrane domain and cytosolic domain comprise an amino acid sequence having at least 85% sequence identity with SEQ ID NO: 40. In some embodiments, the transmembrane domain and cytosolic domain comprise an amino acid sequence having at least 90% sequence identity with SEQ ID NO: 40. In some embodiments, the transmembrane domain and cytosolic domain comprise an amino acid sequence having at least 95% sequence identity with SEQ ID NO: 40. In some embodiments, the transmembrane domain and cytosolic domain comprise an amino acid sequence of SEQ ID NO: 40.

In some embodiments, the third polynucleotide comprises a nucleotide sequence having at least 70% sequence identity with SEQ ID NO: 41. In some embodiments, the third polynucleotide comprises a nucleotide sequence having at least 75% sequence identity with SEQ ID NO: 41. In some embodiments, the third polynucleotide comprises a nucleotide sequence having at least 80% sequence identity with SEQ ID NO: 41. In some embodiments, the third polynucleotide comprises a nucleotide sequence having at least 85% sequence identity with SEQ ID NO: 41. In some embodiments, the third polynucleotide comprises a nucleotide sequence having at least 90% sequence identity with SEQ ID NO: 41. In some embodiments, the third polynucleotide comprises a nucleotide sequence having at least 95% sequence identity with SEQ ID NO: 41. In some embodiments, the third polynucleotide comprises a nucleotide sequence of SEQ ID NO: 41.

In some embodiments, the transmembrane domain and cytosolic domain comprise an amino acid sequence having at least 70% sequence identity with SEQ ID NO: 42. In some embodiments, the transmembrane domain and cytosolic domain comprise an amino acid sequence having at least 75% sequence identity with SEQ ID NO: 42. In some embodiments, the transmembrane domain and cytosolic domain comprise an amino acid sequence having at least 80% sequence identity with SEQ ID NO: 42. In some embodiments, the transmembrane domain and cytosolic domain comprise an amino acid sequence having at least 85% sequence identity with SEQ ID NO: 42. In some embodiments, the transmembrane domain and cytosolic domain comprise an amino acid sequence having at least 90% sequence identity with SEQ ID NO: 42. In some embodiments, the transmembrane domain and cytosolic domain comprise an amino acid sequence having at least 95% sequence identity with SEQ ID NO: 42. In some embodiments, the transmembrane domain and cytosolic domain comprise an amino acid sequence of SEQ ID NO: 42.

In some embodiments, the T cell receptor signaling domain polypeptide comprises a TCR co-stimulator domain. In some embodiments, the TCR co-stimulator is ICOS. In some embodiments, the TCR co-stimulator is CD27. In some embodiments, the TCR co-stimulator is CD28. In some embodiments, the TCR co-stimulator is 4-1BB (CD137). In some embodiments, the TCR co-stimulator is OX40 (CD134). In some embodiments, the TCR co-stimulator is CD30. In some embodiments, the TCR co-stimulator is CD40. In some embodiments, the TCR co-stimulator is lymphocyte fiction-associated antigen 1 (LFA-1). In some embodiments, the TCR co-stimulator is CD2. In some embodiments, the TCR co-stimulator is CD7. In some embodiments, the TCR co-stimulator is LIGHT. In some embodiments, the TCR co-stimulator is NKG2C. In some embodiments, the TCR co-stimulator is B7-H3. In some embodiments, the TCR co-stimulator is a ligand that specifically binds CD83.

In some embodiments, the TCR signaling domain polypeptide comprises a transmembrane domain and/or a cytosolic domain of a TCR co-inhibitor. In some embodiments, the TCR co-inhibitor is PD-1. In some embodiments, the TCR co-inhibitor is TIM3. In some embodiments, the TCR co-inhibitor is LAG-3. In some embodiments, the TCR co-inhibitor is TIGIT. In some embodiments, the TCR co-inhibitor is BTLA. In some embodiments, the TCR co-inhibitor is CD160. In some embodiments, the TCR co-inhibitor is CD37.

In some embodiments, the TCR signaling domain polypeptide includes both a cytosolic domain and a transmembrane domain of a TCR co-receptor or co-stimulator protein. In some embodiments, the cytosolic domain and transmembrane domain are from the same co-receptor or co-stimulator or from different co-receptors or co-stimulators. In some embodiments, the TAC further comprises other polypeptides that directly or indirectly act to target or activate the T cell.

Linkers, Connectors, and Configurations

In some embodiments, a nucleic acid disclosed herein is in an order of (1) a first polynucleotide encoding a target-specific ligand; (2) a second polynucleotide encoding a ligand that binds a TCR complex; (3) a third polynucleotide encoding a transmembrane domain and a cytosolic domain. In some embodiments, a nucleic acid disclosed herein is in an order of (1) a first polynucleotide encoding a target-specific ligand; (2) a second polynucleotide encoding a ligand that binds a TCR complex; (3) a third polynucleotide encoding a transmembrane domain and a cytosolic domain, wherein the order is 5' end to 3' end. In some embodiments, a nucleic acid disclosed herein is in an order of (1) a first polynucleotide encoding a target-specific ligand; (2) a second polynucleotide encoding a ligand that binds a TCR complex; (3) a third polynucleotide encoding a transmembrane domain and a cytosolic domain, wherein the order is 3' end to 5' end. In some embodiments, a nucleic acid described herein is in an order of (1) a first polynucleotide encoding a ligand that binds a TCR complex; (2) a second polynucleotide encoding a target-specific ligand; (3) a third polynucleotide encoding a transmembrane domain and a cytosolic domain. In some embodiments, a nucleic acid described herein is in an order of (1) a first polynucleotide encoding a ligand that binds a TCR complex; (2) a second polynucleotide encoding a target-specific ligand; (3) a third polynucleotide encoding a transmembrane domain and a cytosolic domain, wherein the order is 5' end to 3' end. In some embodiments, a nucleic acid described herein is in an order of (1) a first polynucleotide encoding a ligand that binds a TCR complex; (2) a second polynucleotide encoding a target-specific ligand; (3) a third polynucleotide encoding a transmembrane domain and a cytosolic domain, wherein the order is 3' end to 5' end.

In some embodiments, the first nucleic acid encodes a first polypeptide, the second nucleic acid encodes a second polypeptide, and the third nucleic acid encodes a third polypeptide. In some embodiments, the first polypeptide, the second polypeptide, and the third polypeptide are directly fused. For example, the target-specific ligand and the T cell receptor signaling domain polypeptide are both fused to the ligand that binds the TCR complex. In some embodiments, the first polypeptide, the second polypeptide, and the third polypeptide are joined by at least one linker. In some embodiments, the first polypeptide and the second polypeptide are directly fused, and joined to the third polypeptide by a linker. In some embodiments, the second polypeptide and the third polypeptide are directly fused, and joined to the first polypeptide by a linker.

In some embodiments, the linker is a peptide linker. In some embodiments, the peptide linker comprises 1 to 40 amino acids. In some embodiments, the peptide linker comprises 1 to 30 amino acids. In some embodiments, the peptide linker comprises 1 to 15 amino acids. In some embodiments, the peptide linker comprises 1 to 10 amino acids. In some embodiments, the peptide linker comprises 1 to 6 amino acids. In some embodiments, the peptide linker comprises 30 to 40 amino acids. In some embodiments, the peptide linker comprises 32 to 36 amino acids. In some embodiments, the peptide linker comprises 5 to 30 amino acids. In some embodiments, the peptide linker comprises 5 amino acids. In some embodiments, the peptide linker comprises 10 amino acids. In some embodiments, the peptide linker comprises 15 amino acids. In some embodiments, the peptide linker comprises 20 amino acids. In some embodiments, the peptide linker comprises 25 amino acids. In some embodiments, the peptide linker comprises 30 amino acids.

In some embodiments, the peptide linker comprises a $G_4S_3$ linker (SEQ ID NO: 74). In some embodiments, the peptide linker comprises SEQ ID NOs: 11, 12, 15, 16, 19, 20, or variants or fragments thereof.

In some embodiments, the peptide linker that joins the target-specific ligand to the ligand that binds a TCR complex (e.g. UCHT1) is known as the connector to distinguish this protein domain from other linkers in the Tri-TAC. The connector is of any size. In some embodiments, the connector between ligand that binds a TCR complex and a target-specific ligand is a short helix comprising SEQ ID NO ID: 28. In some embodiments, the connector between ligand that binds a TCR complex and a target-specific ligand is a short helix encoded by SEQ ID NO ID: 27. In some embodiments, the connector between ligand that binds a TCR complex and a target-specific ligand is a long helix comprising SEQ ID NO ID: 30. In some embodiments, the connector between ligand that binds a TCR complex and a target-specific ligand is a long helix encoded by SEQ ID NO ID: 29. In some embodiments, the connector between ligand that binds a TCR complex and a target-specific ligand is a large domain comprising SEQ ID NO ID: 32. In some embodiments, the connector between ligand that binds a TCR complex and a target-specific ligand is a large domain encoded by SEQ ID NO ID: 31.

In some embodiments, a nucleic acid disclosed herein comprises a leader sequence. In some embodiments, the leader sequence comprises a nucleotide sequence having at least 70% sequence identity with SEQ ID NO: 5, 47, or 49. In some embodiments, the leader sequence comprises a nucleotide sequence having at least 75% sequence identity with SEQ ID NO: 5, 47, or 49. In some embodiments, the leader sequence comprises a nucleotide sequence having at least 80% sequence identity with SEQ ID NO: 5, 47, or 49. In some embodiments, the leader sequence comprises a nucleotide sequence having at least 85% sequence identity with SEQ ID NO: 5, 47, or 49. In some embodiments, the leader sequence comprises a nucleotide sequence having at least 90% sequence identity with SEQ ID NO: 5, 47, or 49. In some embodiments, the leader sequence comprises a nucleotide sequence having at least 95% sequence identity with SEQ ID NO: 5, 47, or 49. In some embodiments, the leader sequence comprises a nucleotide sequence of SEQ ID NO: 5, 47, or 49.

In some embodiments, a nucleic acid disclosed herein comprises a leader sequence. In some embodiments, the leader sequence comprises an amino acid sequence having at least 70% sequence identity with SEQ ID NO: 6, 48, or 50. In some embodiments, the leader sequence comprises an amino acid sequence having at least 75% sequence identity with SEQ ID NO: 6, 48, or 50. In some embodiments, the leader sequence comprises an amino acid sequence having at least 80% sequence identity with SEQ ID NO: 6, 48, or 50. In some embodiments, the leader sequence comprises an amino acid sequence having at least 85% sequence identity with SEQ ID NO: 6, 48, or 50. In some embodiments, the leader sequence comprises an amino acid sequence having at least 90% sequence identity with SEQ ID NO: 6, 48, or 50. In some embodiments, the leader sequence comprises an amino acid sequence having at least 95% sequence identity with SEQ ID NO: 6, 48, or 50. In some embodiments, the leader sequence comprises an amino acid sequence of SEQ ID NO: 6, 48, or 50.

The Tri-TAC is contemplated to be present in various configurations and combinations of (a) target-specific ligand, (b) a ligand that binds a TCR complex, and (c) a TCR signaling domain, as disclosed herein.

In some embodiments, the Tri-TAC comprises (a) a target-specific ligand, (b) a single-chain antibody (scFv) that binds CD3ε, and (c) a transmembrane and cytosolic domain of the CD4 co-receptor. In some embodiments, the Tri-TAC comprises (a) a target-specific ligand, (b) UCHT1, and (c) a transmembrane and cytosolic domain of the CD4 co-receptor. In some embodiments, the Tri-TAC comprises (a) a target-specific ligand, (b) UCHT1 (Y182T), and (c) a transmembrane and cytosolic domain of the CD4 co-receptor. In some embodiments, the Tri-TAC comprises (a) a target-specific ligand, (b) huUCHT1, and (c) a transmembrane and cytosolic domain of the CD4 co-receptor. In some embodiments, the Tri-TAC comprises (a) a target-specific ligand, (b) huUCHT1 (Y177T), and (c) a transmembrane and cytosolic domain of the CD4 co-receptor. In some embodiments, the Tri-TAC comprises (a) a target-specific ligand, (b) OKT3, and (c) a transmembrane and cytosolic domain of the CD4 co-receptor. In some embodiments, the Tri-TAC comprises (a) a target-specific ligand, (b) F6A, and (c) a transmembrane and cytosolic domain of the CD4 co-receptor. In some embodiments, the Tri-TAC comprises (a) a target-specific ligand, (b) L2K, and (c) a transmembrane and cytosolic domain of the CD4 co-receptor.

In some embodiments, the Tri-TAC comprises (a) a DARPin, (b) UCHT1, and (c) a transmembrane and cytosolic domain of the CD4 co-receptor. In some embodiments, the Tri-TAC comprises (a) a DARPin, (b) UCHT1 (Y182T), and (c) a transmembrane and cytosolic domain of the CD4 co-receptor. In some embodiments, the Tri-TAC comprises (a) a DARPin, (b) huUCHT1, and (c) a transmembrane and cytosolic domain of the CD4 co-receptor. In some embodiments, the Tri-TAC comprises (a) a DARPin, (b) huUCHT1 (Y177T), and (c) a transmembrane and cytosolic domain of the CD4 co-receptor. In some embodiments, the Tri-TAC comprises (a) a DARPin, (b) OKT3, and (c) a transmembrane and cytosolic domain of the CD4 co-receptor. In some embodiments, the Tri-TAC comprises (a) a DARPin, (b) F6A, and (c) a transmembrane and cytosolic domain of the CD4 co-receptor. In some embodiments, the Tri-TAC comprises (a) a DARPin, (b) L2K, and (c) a transmembrane and cytosolic domain of the CD4 co-receptor.

In some embodiments, the Tri-TAC comprises (a) a scFv, (b) UCHT1, and (c) a transmembrane and cytosolic domain of the CD4 co-receptor. In some embodiments, the Tri-TAC comprises (a) a scFv, (b) UCHT1 (Y182T), and (c) a transmembrane and cytosolic domain of the CD4 co-receptor. In some embodiments, the Tri-TAC comprises (a) a scFv, (b) huUCHT1, and (c) a transmembrane and cytosolic domain of the CD4 co-receptor. In some embodiments, the Tri-TAC comprises (a) a scFv, (b) huUCHT1 (Y177T), and (c) a transmembrane and cytosolic domain of the CD4 co-receptor. In some embodiments, the Tri-TAC comprises (a) a scFv, (b) OKT3, and (c) a transmembrane and cytosolic domain of the CD4 co-receptor. In some embodiments, the Tri-TAC comprises (a) a scFv, (b) F6A, and (c) a transmembrane and cytosolic domain of the CD4 co-receptor. In some embodiments, the Tri-TAC comprises (a) a scFv, (b) L2K, and (c) a transmembrane and cytosolic domain of the CD4 co-receptor.

In some embodiments, the Tri-TAC comprises (a) a HER-2-specific DARPin, (b) UCHT1, and (c) a transmembrane and cytosolic domain of the CD4 co-receptor. In some embodiments, the Tri-TAC comprises (a) a HER-2-specific DARPin, (b) UCHT1 (Y182T), and (c) a transmembrane and cytosolic domain of the CD4 co-receptor. In some embodiments, the Tri-TAC comprises (a) a HER-2-specific DARPin, (b) huUCHT1, and (c) a transmembrane and cytosolic domain of the CD4 co-receptor. In some embodiments, the Tri-TAC comprises (a) a target-specific ligand, (b) huUCHT1 (Y177T), and (c) a transmembrane and cytosolic domain of the CD4 co-receptor. In some embodiments, the Tri-TAC comprises (a) a HER-2-specific DARPin, (b) OKT3, and (c) a transmembrane and cytosolic domain of the CD4 co-receptor. In some embodiments, the Tri-TAC comprises (a) a HER-2-specific DARPin, (b) F6A, and (c) a transmembrane and cytosolic domain of the CD4 co-receptor. In some embodiments, the Tri-TAC comprises (a) a HER-2-specific DARPin, (b) L2K, and (c) a transmembrane and cytosolic domain of the CD4 co-receptor.

In some embodiments, the Tri-TAC comprises (a) a BCMA-specific ScFv, (b) UCHT1, and (c) a transmembrane and cytosolic domain of the CD4 co-receptor. In some embodiments, the Tri-TAC comprises (a) a BCMA-specific ScFv, (b) UCHT1 (Y182T), and (c) a transmembrane and cytosolic domain of the CD4 co-receptor. In some embodiments, the Tri-TAC comprises (a) a BCMA-specific ScFv, (b) huUCHT1, and (c) a transmembrane and cytosolic domain of the CD4 co-receptor. In some embodiments, the Tri-TAC comprises (a) a BCMA-specific ScFv, (b) huUCHT1 (Y177T), and (c) a transmembrane and cytosolic domain of the CD4 co-receptor. In some embodiments, the Tri-TAC comprises (a) a BCMA-specific ScFv, (b) OKT3, and (c) a transmembrane and cytosolic domain of the CD4 co-receptor. In some embodiments, the Tri-TAC comprises (a) a BCMA-specific ScFv, (b) F6A, and (c) a transmembrane and cytosolic domain of the CD4 co-receptor. In some embodiments, the Tri-TAC comprises (a) a BCMA-specific ScFv, (b) L2K, and (c) a transmembrane and cytosolic domain of the CD4 co-receptor.

In some embodiments, the Tri-TAC comprises (a) a CD19-specific ScFv, (b) UCHT1, and (c) a transmembrane and cytosolic domain of the CD4 co-receptor. In some embodiments, the Tri-TAC comprises (a) a CD19-specific ScFv, (b) UCHT1 (Y182T), and (c) a transmembrane and cytosolic domain of the CD4 co-receptor. In some embodiments, the Tri-TAC comprises (a) a CD19-specific ScFv, (b) huUCHT1, and (c) a transmembrane and cytosolic domain of the CD4 co-receptor. In some embodiments, the Tri-TAC comprises (a) a CD19-specific ScFv, (b) huUCHT1 (Y177T), and (c) a transmembrane and cytosolic domain of the CD4 co-receptor. In some embodiments, the Tri-TAC comprises (a) a CD19-specific ScFv, (b) OKT3, and (c) a transmembrane and cytosolic domain of the CD4 co-receptor. In some embodiments, the Tri-TAC comprises (a) a CD19-specific ScFv, (b) F6A, and (c) a transmembrane and cytosolic domain of the CD4 co-receptor. In some embodiments, the Tri-TAC comprises (a) a CD19-specific ScFv, (b) L2K, and (c) a transmembrane and cytosolic domain of the CD4 co-receptor.

In some embodiments, the Tri-TAC comprises (a) a target-specific ligand, (b) a single-chain antibody (scFv) that binds CD3ε, and (c) a transmembrane and cytosolic domain of the CD8 co-receptor. In some embodiments, the Tri-TAC comprises (a) a target-specific ligand, (b) UCHT1, and (c) a transmembrane and cytosolic domain of the CD8 co-receptor. In some embodiments, the Tri-TAC comprises (a) a target-specific ligand, (b) UCHT1 (Y182T), and (c) a transmembrane and cytosolic domain of the CD8 co-receptor. In some embodiments, the Tri-TAC comprises (a) a target-specific ligand, (b) huUCHT1, and (c) a transmembrane and cytosolic domain of the CD8 co-receptor. In some embodiments, the Tri-TAC comprises (a) a target-specific ligand, (b) huUCHT1 (Y177T), and (c) a transmembrane and cytosolic domain of the CD8 co-receptor. In some embodiments, the Tri-TAC comprises (a) a target-specific ligand, (b) OKT3, and (c) a transmembrane and cytosolic domain of the CD8 co-receptor. In some embodiments, the Tri-TAC comprises (a) a target-specific ligand, (b) F6A, and (c) a transmembrane and cytosolic domain of the CD8 co-receptor. In some embodiments, the Tri-TAC comprises (a) a target-specific ligand, (b) L2K, and (c) a transmembrane and cytosolic domain of the CD8 co-receptor.

In some embodiments, the Tri-TAC comprises (a) a DARPin, (b) UCHT1, and (c) a transmembrane and cytosolic domain of the CD4 co-receptor. In some embodiments, the Tri-TAC comprises (a) a DARPin, (b) UCHT1 (Y182T), and (c) a transmembrane and cytosolic domain of the CD8 co-receptor. In some embodiments, the Tri-TAC comprises (a) a DARPin, (b) huUCHT1, and (c) a transmembrane and cytosolic domain of the CD8 co-receptor. In some embodiments, the Tri-TAC comprises (a) a DARPin, (b) huUCHT1 (Y177T), and (c) a transmembrane and cytosolic domain of the CD8 co-receptor. In some embodiments, the Tri-TAC comprises (a) a DARPin, (b) OKT3, and (c) a transmembrane and cytosolic domain of the CD8 co-receptor. In some embodiments, the Tri-TAC comprises (a) a DARPin, (b) F6A, and (c) a transmembrane and cytosolic domain of the CD8 co-receptor. In some embodiments, the Tri-TAC comprises (a) a DARPin, (b) L2K, and (c) a transmembrane and cytosolic domain of the CD8 co-receptor.

In some embodiments, the Tri-TAC comprises (a) a scFv, (b) UCHT1, and (c) a transmembrane and cytosolic domain of the CD8 co-receptor. In some embodiments, the Tri-TAC comprises (a) a scFv, (b) UCHT1 (Y182T), and (c) a transmembrane and cytosolic domain of the CD8 co-receptor. In some embodiments, the Tri-TAC comprises (a) a scFv, (b) huUCHT1, and (c) a transmembrane and cytosolic domain of the CD8 co-receptor. In some embodiments, the Tri-TAC comprises (a) a scFv, (b) huUCHT1 (Y177T), and (c) a transmembrane and cytosolic domain of the CD8 co-receptor. In some embodiments, the Tri-TAC comprises (a) a scFv, (b) OKT3, and (c) a transmembrane and cytosolic domain of the CD8 co-receptor. In some embodiments, the Tri-TAC comprises (a) a scFv, (b) F6A, and (c) a transmembrane and cytosolic domain of the CD8 co-receptor. In some embodiments, the Tri-TAC comprises (a) a scFv, (b) L2K, and (c) a transmembrane and cytosolic domain of the CD8 co-receptor.

In some embodiments, the Tri-TAC comprises (a) a HER-2-specific DARPin, (b) UCHT1, and (c) a transmembrane and cytosolic domain of the CD8 co-receptor. In some embodiments, the Tri-TAC comprises (a) a HER-2-specific DARPin, (b) UCHT1 (Y182T), and (c) a transmembrane and cytosolic domain of the CD8 co-receptor. In some embodiments, the Tri-TAC comprises (a) a HER-2-specific DARPin, (b) huUCHT1, and (c) a transmembrane and cytosolic domain of the CD8 co-receptor. In some embodiments, the Tri-TAC comprises (a) a target-specific ligand, (b) huUCHT1 (Y177T), and (c) a transmembrane and cytosolic domain of the CD8 co-receptor. In some embodiments, the Tri-TAC comprises (a) a HER-2-specific DARPin, (b) OKT3, and (c) a transmembrane and cytosolic domain of the CD8 co-receptor. In some embodiments, the Tri-TAC comprises (a) a HER-2-specific DARPin, (b) F6A, and (c) a transmembrane and cytosolic domain of the CD8 co-receptor. In some embodiments, the Tri-TAC comprises (a) a HER-2-specific DARPin, (b) L2K, and (c) a transmembrane and cytosolic domain of the CD8 co-receptor.

In some embodiments, the Tri-TAC comprises (a) a BCMA-specific ScFv, (b) UCHT1, and (c) a transmembrane and cytosolic domain of the CD8 co-receptor. In some embodiments, the Tri-TAC comprises (a) a BCMA-specific ScFv, (b) UCHT1 (Y182T), and (c) a transmembrane and cytosolic domain of the CD8 co-receptor. In some embodiments, the Tri-TAC comprises (a) a BCMA-specific ScFv, (b) huUCHT1, and (c) a transmembrane and cytosolic domain of the CD8 co-receptor. In some embodiments, the Tri-TAC comprises (a) a BCMA-specific ScFv, (b) huUCHT1 (Y177T), and (c) a transmembrane and cytosolic domain of the CD8 co-receptor. In some embodiments, the Tri-TAC comprises (a) a BCMA-specific ScFv, (b) OKT3, and (c) a transmembrane and cytosolic domain of the CD8 co-receptor. In some embodiments, the Tri-TAC comprises (a) a BCMA-specific ScFv, (b) F6A, and (c) a transmembrane and cytosolic domain of the CD8 co-receptor. In some embodiments, the Tri-TAC comprises (a) a BCMA-specific ScFv, (b) L2K, and (c) a transmembrane and cytosolic domain of the CD8 co-receptor.

In some embodiments, the Tri-TAC comprises (a) a CD19-specific ScFv, (b) UCHT1, and (c) a transmembrane and cytosolic domain of the CD8 co-receptor. In some embodiments, the Tri-TAC comprises (a) a CD19-specific ScFv, (b) UCHT1 (Y182T), and (c) a transmembrane and cytosolic domain of the CD8 co-receptor. In some embodiments, the Tri-TAC comprises (a) a CD19-specific ScFv, (b) huUCHT1, and (c) a transmembrane and cytosolic domain of the CD8 co-receptor. In some embodiments, the Tri-TAC comprises (a) a CD19-specific ScFv, (b) huUCHT1 (Y177T), and (c) a transmembrane and cytosolic domain of the CD8 co-receptor. In some embodiments, the Tri-TAC comprises (a) a CD19-specific ScFv, (b) OKT3, and (c) a transmembrane and cytosolic domain of the CD8 co-receptor. In some embodiments, the Tri-TAC comprises (a) a CD19-specific ScFv, (b) F6A, and (c) a transmembrane and cytosolic domain of the CD8 co-receptor. In some embodiments, the Tri-TAC comprises (a) a CD19-specific ScFv, (b) L2K, and (c) a transmembrane and cytosolic domain of the CD8 co-receptor.

In some embodiments, the Tri-TAC draws CD3 and TCR into lipid raft regions of the membrane, and brings Lck into the proximity of the TCR, similar to natural MHC binding.

In some embodiments, the TAC disclosed herein is the anti-HER-2 DARPin Tri-TAC (also referred to as configuration 1; SEQ ID NO: 1 and 2) includes, in order:
  i) the anti-HER-2 Tri-TAC leader sequence (secretion signal) (SEQ ID NO: 5 and 6)
  ii) DARPin specific for HER-2 antigen (SEQ ID NO: 7 and 8)
  iii) Myc tag (SEQ ID NO: 9 and 10)
  iv) Connector (SEQ ID NO: 11 and 12)
  v) UCHT1 (SEQ ID NO: 13 and 14)
  vi) Linker (SEQ ID NO: 15 and 16)
  vii) CD4 (SEQ ID NO: 17 and 18).

In some embodiments, the TAC disclosed herein is a HER2-TAC. In some embodiments, the HER2-TAC comprises a nucleotide sequence having at least 70% sequence identity with SEQ ID NO: 65. In some embodiments, the HER2-TAC comprises a nucleotide sequence having at least 75% sequence identity with SEQ ID NO: 65. In some embodiments, the HER2-TAC comprises a nucleotide sequence having at least 80% sequence identity with SEQ ID NO: 65. In some embodiments, the HER2-TAC comprises a nucleotide sequence having at least 85% sequence identity with SEQ ID NO: 65. In some embodiments, the HER2-TAC comprises a nucleotide sequence having at least 90% sequence identity with SEQ ID NO: 65. In some embodiments, the HER2-TAC comprises a nucleotide sequence having at least 95% sequence identity with SEQ ID NO: 65. In some embodiments, the HER2-TAC comprises a nucleotide sequence of SEQ ID NO: 65.

In some embodiments, the HER2-TAC comprises an amino acid sequence having at least 70% sequence identity with SEQ ID NO: 66. In some embodiments, the HER2-TAC comprises an amino acid sequence having at least 75% sequence identity with SEQ ID NO: 66. In some embodiments, the HER2-TAC comprises an amino acid sequence having at least 80% sequence identity with SEQ ID NO: 66. In some embodiments, the HER2-TAC comprises an amino acid sequence having at least 85% sequence identity with SEQ ID NO: 66. In some embodiments, the HER2-TAC an amino acid sequence having at least 90% sequence identity with SEQ ID NO: 66. In some embodiments, the HER2-TAC comprises an amino acid sequence having at least 95% sequence identity with SEQ ID NO: 66. In some embodiments, the HER2-TAC comprises an amino acid sequence of SEQ ID NO: 66.

In some embodiments, the TAC disclosed herein is a HER2-TAC. In some embodiments, the HER2-TAC comprises a nucleotide sequence having at least 70% sequence identity with SEQ ID NO: 67. In some embodiments, the HER2-TAC comprises a nucleotide sequence having at least 75% sequence identity with SEQ ID NO: 67. In some embodiments, the HER2-TAC comprises a nucleotide sequence having at least 80% sequence identity with SEQ ID NO: 67. In some embodiments, the HER2-TAC comprises a nucleotide sequence having at least 85% sequence identity with SEQ ID NO: 67. In some embodiments, the HER2-TAC comprises a nucleotide sequence having at least 90% sequence identity with SEQ ID NO: 67. In some embodiments, the HER2-TAC comprises a nucleotide sequence having at least 95% sequence identity with SEQ ID NO: 67. In some embodiments, the HER2-TAC comprises a nucleotide sequence of SEQ ID NO: 67.

In some embodiments, the HER2-TAC comprises an amino acid sequence having at least 70% sequence identity with SEQ ID NO: 68. In some embodiments, the HER2-TAC comprises an amino acid sequence having at least 75% sequence identity with SEQ ID NO: 68. In some embodiments, the HER2-TAC comprises an amino acid sequence having at least 80% sequence identity with SEQ ID NO: 68. In some embodiments, the HER2-TAC comprises an amino acid sequence having at least 85% sequence identity with SEQ ID NO: 68. In some embodiments, the HER2-TAC an amino acid sequence having at least 90% sequence identity with SEQ ID NO: 68. In some embodiments, the HER2-TAC comprises an amino acid sequence having at least 95% sequence identity with SEQ ID NO: 68. In some embodiments, the HER2-TAC comprises an amino acid sequence of SEQ ID NO: 68.

In some embodiments, the TAC disclosed herein is a BCMA-TAC. In some embodiments, the BCMA-TAC comprises a nucleotide sequence having at least 70% sequence identity with SEQ ID NO: 55, 57, 59 or 61. In some embodiments, the BCMA-TAC comprises a nucleotide sequence having at least 75% sequence identity with SEQ ID NO: 55, 57, 59 or 61. In some embodiments, the BCMA-TAC comprises a nucleotide sequence having at least 80% sequence identity with SEQ ID NO: 55, 57, 59 or 61. In some embodiments, the BCMA-TAC comprises a nucleotide sequence having at least 85% sequence identity with SEQ ID NO: 55, 57, 59 or 61. In some embodiments, the BCMA-TAC comprises a nucleotide sequence having at least 90% sequence identity with SEQ ID NO: 55, 57, 59 or 61. In some embodiments, the BCMA-TAC comprises a nucleotide sequence having at least 95% sequence identity with SEQ ID NO: 55, 57, 59 or 61. In some embodiments, the BCMA-TAC comprises a nucleotide sequence of SEQ ID NO: 55, 57, 59 or 61.

In some embodiments, the BCMA-TAC comprises an amino acid sequence having at least 70% sequence identity with SEQ ID NO: 56, 58, 60 or 62. In some embodiments, the BCMA-TAC comprises an amino acid sequence having at least 75% sequence identity with SEQ ID NO: 56, 58, 60 or 62. In some embodiments, the BCMA-TAC comprises an amino acid sequence having at least 80% sequence identity with SEQ ID NO: 56, 58, 60 or 62. In some embodiments, the BCMA-TAC comprises an amino acid sequence having at least 85% sequence identity with SEQ ID NO: 56, 58, 60 or 62. In some embodiments, the BCMA-TAC comprises an amino acid sequence having at least 90% sequence identity with SEQ ID NO: 56, 58, 60 or 62. In some embodiments, the BCMA-TAC comprises an amino acid sequence having at least 95% sequence identity with SEQ ID NO: 56, 58, 60 or 62. In some embodiments, the BCMA-TAC comprises an amino acid sequence of SEQ ID NO: 56, 58, 60 or 62.

In some embodiments, the TAC disclosed herein is a CD19-TAC. In some embodiments, the CD19-TAC comprises a nucleotide sequence having at least 70% sequence identity with SEQ ID NO: 63. In some embodiments, the CD19-TAC comprises a nucleotide sequence having at least 75% sequence identity with SEQ ID NO: 63. In some embodiments, the CD19-TAC comprises a nucleotide sequence having at least 80% sequence identity with SEQ ID NO: 63. In some embodiments, the CD19-TAC comprises a nucleotide sequence having at least 85% sequence identity with SEQ ID NO: 63. In some embodiments, the CD19-TAC comprises a nucleotide sequence having at least 90% sequence identity with SEQ ID NO: 63. In some embodiments, the CD19-TAC comprises a nucleotide sequence having at least 95% sequence identity with SEQ ID NO: 63. In some embodiments, the CD19-TAC comprises a nucleotide sequence of SEQ ID NO: 63.

In some embodiments, the CD19-TAC comprises an amino acid sequence having at least 70% sequence identity with SEQ ID NO: 64. In some embodiments, the CD19-TAC comprises an amino acid sequence having at least 75% sequence identity with SEQ ID NO: 64. In some embodiments, the CD19-TAC comprises an amino acid sequence having at least 80% sequence identity with SEQ ID NO: 64. In some embodiments, the CD19-TAC comprises an amino acid sequence having at least 85% sequence identity with SEQ ID NO: 64. In some embodiments, the CD19-TAC comprises an amino acid sequence having at least 90% sequence identity with SEQ ID NO: 64. In some embodiments, the CD19-TAC comprises an amino acid sequence having at least 95% sequence identity with SEQ ID NO: 64. In some embodiments, the CD19-TAC comprises an amino acid sequence of SEQ ID NO: 64.

Polypeptides and Vector Constructs

Disclosed herein, in certain embodiments, are polypeptides encoded by the nucleic acid sequence as disclosed herein. Also disclosed herein, are vectors comprising the nucleic acid sequence as disclosed herein. In some embodiments, the vectors further comprise a promoter. In some embodiments, the promoter is functional in a mammalian cell. Promoters, regions of DNA that initiate transcription of a particular nucleic acid sequence, are well known in the art. A "promoter functional in a mammalian cell" refers to a promoter that drives expression of the associated nucleic acid sequence in a mammalian cell. A promoter that drives expression of a nucleic acid sequence is referred to as being "operably connected" to the nucleic acid sequence.

A variety of delivery vectors and expression vehicles are employed to introduce nucleic acids described herein into a cell.

Disclosed herein, in certain embodiments, are polynucleotides comprised in a vector to provide a vector construct, also herein referred to as a vector. In some embodiments, the present disclosure provides a vector comprising:
 a. a first polynucleotide encoding a target-specific ligand;
 b. a second polynucleotide encoding a ligand that binds a protein associated with a TCR complex;
 c. a third polynucleotide encoding a T cell receptor signaling domain polypeptide; and
 d. a promoter that is functional in a mammalian cell.

In some embodiments, the target of the target-specific ligand binds to HER-2, BCMA, or CD19. In some embodiments, the target-specific ligand is a DARPin that selectively binds a HER-2 (erbB-2) antigen. In some embodiments, the target-specific ligand is a DARPin that specifically binds a HER-2 (erbB-2) antigen. In some embodiments, the DARPin targeted to HER-2 (erb-2) comprises SEQ ID NO: 7 or SEQ ID NO: 8. In some embodiments, the target-specific ligand is a scFv that selectively binds BCMA. In some embodiments, the target-specific ligand is a scFv that specifically binds BCMA. In some embodiments, the scFv that binds BCMA comprises SEQ ID NO: 33 or SEQ ID NO: 34. In some embodiments, the target-specific ligand is a scFv that selectively binds CD19. In some embodiments, the target-specific ligand is a scFv that specifically binds CD19. In some embodiments, the scFv that binds CD19 comprises SEQ ID NO: 35 or SEQ ID NO: 36.

In some embodiments, the ligand that binds a protein associated with a TCR complex is UCHT1, humanized UCHT1 (huUCHT1), OKT3, F6A, or L2K. In some embodiments, the ligand that binds a protein associated with a TCR complex is UCHT1, or a variant thereof. In some embodiments, the ligand that binds a protein associated with a TCR complex is UCHT1 and is encoded by SEQ ID NO: 13. In some embodiments, the ligand that binds a protein associated with a TCR complex is UCHT1 and comprises SEQ ID NO: 14 In some embodiments, the UCHT1 ligand that binds a protein associated with a TCR complex has a Y182T mutation (UCHT1 (Y182T)) and is encoded by SEQ ID NO: 71. In some embodiments, the ligand that binds a protein associated with a TCR complex is UCHT1 (Y182T) and comprises SEQ ID NO: 72. In some embodiments, the ligand that binds a protein associated with a TCR complex is humanized UCHT1 (huUCHT1), or a variant thereof. In some embodiments, the ligand that binds a protein associated with a TCR complex is humanized UCHT1 (huUCHT1) and is encoded by SEQ ID NO: 43. In some embodiments, the ligand that binds a protein associated with a TCR complex is huUCHT1 and comprises SEQ ID NO: 44. In some embodiments, the huUCHT1 ligand that binds a protein associated with a TCR complex has a Y177T mutation (huUCHT1 (Y177T)) and is encoded by SEQ ID NO: 45. In some embodiments, the ligand that binds a protein associated with a TCR complex is huUCHT1 (Y177T) and comprises SEQ ID NO: 46.

In some embodiments, the ligand that binds a protein associated with a TCR complex is OKT3, or a variant thereof. In some embodiments, the ligand that binds a protein associated with a TCR complex is OKT3 and is encoded by SEQ ID NO: 21. In some embodiments, the ligand that binds a protein associated with a TCR complex is OKT3 and comprises SEQ ID NO: 22.

In some embodiments, the ligand that binds a protein associated with a TCR complex is F6A, or a variant thereof. In some embodiments, the ligand that binds a protein associated with a TCR complex is F6A and is encoded by SEQ ID NO: 23. In some embodiments, the ligand that binds a protein associated with a TCR complex is F6A and comprises SEQ ID NO: 24.

In some embodiments, the ligand that binds a protein associated with a TCR complex is L2K, or a variant thereof. In some embodiments, the ligand that binds a protein associated with a TCR complex is L2K and is encoded by SEQ ID NO: 25. In some embodiments, the ligand that binds a protein associated with a TCR complex is L2K and comprises SEQ ID NO: 26.

In some embodiments, the protein associated with a TCR complex is CD3. In some embodiments, the protein associated with a TCR complex is CD3ε.

In some embodiments, the TCR signaling domain polypeptide comprises a transmembrane domain and/or a cytosolic domain of a TCR co-receptor. In some embodiments, the TCR co-receptor is CD4, CD8, LAG3, or a chimeric variation thereof.

In some embodiments, the first polynucleotide and third polynucleotide are fused to the second polynucleotide and the coding sequence is operably connected to the promoter. In some embodiments, the second polynucleotide and third polynucleotide are fused to the first polynucleotide and the coding sequence is operably connected to the promoter. In some embodiments, the vector is designed for expression in mammalian cells such as T cells. In some embodiments, the vector is a viral vector. In some embodiments, the viral vector is a retroviral vector.

In some embodiments, vectors that are useful comprise vectors derived from lentiviruses, Murine Stem Cell Viruses (MSCV), pox viruses, oncoretroviruses, adenoviruses, and adeno-associated viruses. Other delivery vectors that are useful comprise vectors derived from herpes simplex viruses, transposons, vaccinia viruses, human papilloma virus, Simian immunodeficiency viruses, HTLV, human foamy virus and variants thereof. Further vectors that are useful comprise vectors derived from spumaviruses, mammalian type B retroviruses, mammalian type C retroviruses, avian type C retroviruses, mammalian type D retroviruses and HTLV/BLV type retroviruses. One example of a lentiviral vector useful in the disclosed compositions and methods is the pCCL4 vector.

In some embodiments, the nucleic acid is a recombinant, or engineered, nucleic acid. In some embodiments, the first, second and/or third polynucleotides are recombinant, or engineered, polynucleotides. In some embodiments, the polynucleotides described herein are be modified or mutated to optimize the function of the encoded polypeptide and/or the function, activity and/or expression of the T cell antigen coupler. In some embodiments, the nucleic acid encodes a polypeptide.

In some embodiments, modifications are made to the polynucleotide sequences including vector sequences and polypeptides sequences disclosed herein. Modifications include substitution, insertion or deletion of nucleotides or amino acids or altering the relative positions or order of nucleotides or amino acids.

Expression in T Cells

Disclosed herein, in certain embodiments, are engineered T cells comprising the nucleic acid sequences disclosed herein, or the vectors disclosed herein. Disclosed herein, in certain embodiments, are human T cells engineered to express a Tri-TAC disclosed herein. In some embodiments, the T cell expresses a Tri-TAC disclosed herein. Further disclosed herein, are T cells transduced or transfected with T cell antigen coupler or a vector comprising a Tri-TAC. In some embodiments, the T cell is an isolated T cell.

In some embodiments, the human T cells engineered to express a Tri-TAC demonstrate functionality equivalent to a conventional CAR in vitro. In some embodiments, T cells engineered with the Tri-TAC demonstrate functionality superior to a conventional CAR in vitro. Disclosed herein, in some embodiments, are human T cells engineered with a Tri-TAC that demonstrate enhanced safety compared to traditional CARs. In some embodiments, human T cells engineered to express a Tri-TAC demonstrate enhanced safety compared to traditional CARs.

T cells, in some embodiments, are obtained from a number of sources, including, but not limited to blood (for example, peripheral blood mononuclear cells), bone marrow, thymus tissue, lymph node tissue, cord blood, thymus tissue, tissue from an infection site, spleen tissue, or tumors. In some embodiments, the T cells are autologous T cells. In some embodiments, the T cells are obtained from a cell line of T cells. In some embodiments, the T cells are obtained from donors (allogeneic T cells). In some embodiments, the T cells are obtained by differentiation of embryonic or adult stem cells or from induced pluripotent stem cells. In some embodiments, regardless of the source of T cells, the T cells have been modified so that they lack expression of an endogenous TCR and/or permanently or transiently lack expression of MHC/HLA molecules (universal donor T cells). In some embodiments, the T cells are autologous with respect to the subject. In some embodiments, the cells are allogeneic, syngeneic, or xenogeneic with respect to the subject.

In some embodiments, once obtained, the T cells are optionally enriched in vitro. In some embodiments, a population of cells is enriched by positive or negative selection. Further, the T cells are optionally frozen or cryopreserved and then thawed at a later date.

In some embodiments, T cells are activated and/or expanded before or after introducing the Tri-TAC to the T cells. In some embodiments, the T cells are expanded by contact with a surface having attached thereto an agent that stimulates a CD3/TCR complex associated signal and a ligand that stimulates a co-stimulator molecule on the surface of the T cells. In some embodiments, the T cells are expanded by contact with one or more soluble agents that stimulate CD3/TCR complex signaling and co-stimulator molecule signaling.

In some embodiments, the T cells are transduced or transfected with nucleic acid sequences. The transduced or transfected T cells express proteins coded for by the transfected or transduced nucleic acid sequences. A nucleic acid may be introduced into a cell by physical, chemical, or biological means. Physical means include, but are not limited to, microinjection, electroporation, particle bombardment, lipofection and calcium phosphate precipitation. Biological means include the use of DNA and RNA vectors.

Viral vectors, including retroviral vectors, are used to introduce and express a nucleic acid into a T cell. Viral vectors include vectors derived from lentivirus, Murine Stem Cell Viruses (MSCV), pox viruses, herpes simplex virus I, adenovirus and adeno-associated viruses. The vector optionally includes a promoter that drives expression of the transduced nucleic acid molecule in a T cell (e.g., a CMV promoter, eF1a promoter, or MSCV promoter).

Any suitable assay is used to confirm the presence and/or expression of the transduced nucleic acid sequence and/or the polypeptide encoded by the nucleic acid in the T cell. Assays include, but are not limited to, Southern and Northern blotting, RT-PCR and PCR, ELISA, Western blotting, and flow cytometry.

A T cell expressing a TAC has increased T cell activation in the presence of an antigen compared to a T cell not expressing a TAC and/or as compared to a T cell expressing a traditional CAR. Increased T cell activation is ascertained by numerous methods, including but not limited to, increased tumor cell line killing, increased cytokine production, increased cytolysis, increased degranulation and/or increased expression of activation markers such as CD107α, IFNγ, IL2 or TNFα. In some embodiments, increases are measured in an individual cell or in a population of cells.

The terms "increased" or "increasing" as used herein refer to at least a 1%, 2%, 5%, 10%, 25%, 50%, 100% or 200% increase in a T cell or population of T cells expressing a TAC compared to a T cell or population of T cells not expressing a TAC and/or as compared to a T cell or population of T cells expressing a traditional CAR.

Pharmaceutical Compositions

Disclosed herein, in certain embodiments, are pharmaceutical compositions comprising an engineered T cell disclosed herein (transduced with and/or expressing a TAC), and a pharmaceutically acceptable carrier. Pharmaceutically acceptable carriers include, but are not limited to, buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); or preservatives. In some embodiments, the engineered T cells are formulated for intravenous administration.

Pharmaceutical compositions are administered in a manner appropriate to the disease to be treated (or prevented). The quantity and frequency of administration is determined by such factors as the condition of the patient, and the type and severity of the patient's disease, although appropriate dosages are determined by clinical trials. When "an immunologically effective amount," "an anti-tumor effective amount," "a tumor-inhibiting effective amount," or "therapeutic amount" is indicated, the precise amount of the compositions of the present invention to be administered is determined by a physician with consideration of individual differences in age, weight, tumor size, extent of infection or metastasis, and condition of the patient (subject).

In some embodiments, the modified T cells and/or pharmaceutical compositions described herein are administered at a dosage of $10^1$ to $10^{15}$ cells per kg body weight, $10^4$ to $10^9$ cells per kg body weight, optionally $10^5$ to $10^8$ cells per kg body weight, $10^6$ to $10^7$ cells per kg body weight or $10^5$ to $10^6$ cells per kg body weight, including all integer values within those ranges. In some embodiments, the modified T cells and/or pharmaceutical compositions described herein are administered at a dosage of greater than $10^1$ cells per kg body weight. In some embodiments, the modified T cells and/or pharmaceutical compositions described herein are administered at a dosage of less than $10^{15}$ cells per kg body weight.

In some embodiments, the modified T cells and/or pharmaceutical compositions described herein are administered at a dosage of $0.5\times10^6$ cells, $2\times10^6$ cells, $4\times10^6$ cells, $5\times10^6$ cells, $1.2\times10^7$ cells, $2\times10^7$ cells, $5\times10^7$ cells, $2\times10^8$ cells, $5\times10^8$ cells, $2\times10^9$ cells, $0.5-2000\times10^6$ cells, $0.5-2\times10^6$ cells, $0.5-2\times10^7$ cells, $0.5-2\times10^8$ cells, or $0.5-2\times10^9$ cells, including all integer values within those ranges.

In some embodiments, T cell compositions are administered multiple times at these dosages. In some embodiments, the dosage is administered a single time or multiple times, for example daily, weekly, biweekly, or monthly, hourly, or is administered upon recurrence, relapse or progression of the cancer being treated. The cells, in some embodiments, are administered by using infusion techniques that are commonly known in immunotherapy (see, e.g., Rosenberg et al., New Eng. J. of Med. 319:1676, 1988).

The pharmaceutical composition is substantially free of, e.g., there are no detectable levels of a contaminant, e.g., selected from the group consisting of endotoxin, mycoplasma, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium a fungus, mycoplasma, IL-2, and IL-7.

In some embodiments, engineered T-cells disclose herein are administered to a subject and blood is subsequently redrawn (or apheresis performed), T-cells therefrom are activated and reinfused into the patient with engineered T cells. This process, in some embodiments, is carried out multiple times every few weeks. T-cells are activated from blood draws of from 10 cc to 400 cc. T-cells are activated from blood draws of 20 cc, 30 cc, 40 cc, 50 cc, 60 cc, 70 cc, 80 cc, 90 cc, or 100 cc.

The modified/engineered T cells and/or pharmaceutical compositions are administered by methods including, but not limited to, aerosol inhalation, injection, infusion, ingestion, transfusion, implantation or transplantation. The modified T cells and/or pharmaceutical compositions are administered to a subject transarterially, subcutaneously, intradermally, intratumorally, intranodally, intramedullary, intramuscularly, by intravenous (i.v.) injection, by intravenous (i.v.) infusion, or intraperitoneally. The modified/engineered T cells and/or pharmaceutical compositions thereof are administered to a patient by intradermal or subcutaneous injection. The modified/engineered T cells and/or pharmaceutical compositions thereof are administered by i.v. injection. The modified/engineered T cells and/or pharmaceutical compositions thereof are injected directly into a tumor, lymph node, or site of infection.

The modified/engineered T cells T cells and/or pharmaceutical compositions are administered in a volume of about 5 mL, 10 mL, 15 mL, 20 mL, 25 mL, 30 mL, 35 mL, 40 mL, 45 mL, 50 mL, 60 mL, 70 mL, 80 mL, 90 mL, 100 mL, 110 mL, 120 mL, 130 mL, 140 mL, 150 mL, 200 mL, 300 mL, 400 mL, or 500 mL.

The modified/engineered T cells T cells and/or pharmaceutical compositions are administered in a volume of at greater than at most about 5 mL, 10 mL, 15 mL, 20 mL, 25 mL, 30 mL, 35 mL, 40 mL, 45 mL, 50 mL, 60 mL, 70 mL, 80 mL, 90 mL, 100 mL, 110 mL, 120 mL, 130 mL, 140 mL, 150 mL, 200 mL, 300 mL, 400 mL, or 500 mL.

The modified/engineered T cells T cells and/or pharmaceutical compositions are administered in a volume of at least about 5 mL, 10 mL, 15 mL, 20 mL, 25 mL, 30 mL, 35 mL, 40 mL, 45 mL, 50 mL, 60 mL, 70 mL, 80 mL, 90 mL, 100 mL, 110 mL, 120 mL, 130 mL, 140 mL, 150 mL, 200 mL, 300 mL, 400 mL, or 500 mL.

A pharmaceutical composition is prepared by per se known methods for the preparation of pharmaceutically acceptable compositions that are administered to subjects, such that an effective quantity of the T cells are combined in a mixture with a pharmaceutically acceptable carrier. Suitable carriers are described, for example, in Remington's Pharmaceutical Sciences (Remington's Pharmaceutical Sciences, 20$^{th}$ ed., Mack Publishing Company, Easton, Pa., USA, 2000). On this basis, the compositions include, albeit not exclusively, solutions of the substances in association with one or more pharmaceutically acceptable carriers or diluents, and contained in buffered solutions with a suitable pH and iso-osmotic with the physiological fluids.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, N-(1(2,3-dioleyloxy)propyl)N,N,N-trimethylammonium chloride (DOTMA), diolesylphosphotidyl-ethanolamine (DOPE), and liposomes. In some embodiments, such compositions contain a therapeutically effective amount of the compound, together with a suitable amount of carrier so as to provide the form for direct administration to the patient.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions.

A pharmaceutical composition disclosed herein is formulated into a variety of forms and administered by a number of different means. A pharmaceutical formulation is administered orally, rectally, or parenterally, in formulations containing conventionally acceptable carriers, adjuvants, and vehicles as desired. The term "parenteral" as used herein includes subcutaneous, intravenous, intramuscular, or intrasternal injection and infusion techniques. Administration includes injection or infusion, including intra-arterial, intracardiac, intracerebroventricular, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration. In some exemplary embodiments, a route of administration is via an injection such as an intramuscular, intravenous, subcutaneous, or intraperitoneal injection.

Liquid formulations include an oral formulation, an intravenous formulation, an intranasal formulation, an ocular formulation, an otic formulation, an aerosol, and the like. In certain embodiments, a combination of various formulations are administered. In certain embodiments a composition is formulated for an extended release profile.

Methods of Treatment and Use

Disclosed herein, in certain embodiments, are methods of use of Tri-TACs disclosed herein in the treatment of cancer in an individual in need thereof. In some embodiments, a target-specific ligand of the TACs disclosed herein bind to a tumor antigen or tumor associated antigen on a tumor cell. In some embodiments, a target-specific ligand of the TACs disclosed herein selectively bind to a tumor antigen or tumor associated antigen on a tumor cell. In some embodiments, a target-specific ligand of the TACs disclosed herein specifically bind to a tumor antigen or tumor associated antigen on a tumor cell. In some embodiments, the target antigen is a tumor antigen. Examples of tumor antigens include, but are not limited to, CD19, HER-2 (erbB-2), B-cell maturation antigen (BCMA), alphafetoprotein (AFP), carcinoembryonic antigen (CEA), CA-125, MUC-1, epithelial tumor antigen (ETA), tyrosinase, melanoma-associated antigen (MAGE), prostate-specific antigen (PSA), glioma-associated antigen, β-human chorionic gonadotropin, thyroglobulin, RAGE-1, MN-CA IX, human telomerase reverse transcriptase, RU1, RU2 (AS), intestinal carboxyl esterase, mut hsp70-2, M-CSF, prostase, PAP, NY-ESO-1, LAGE-la, p53, prostein, PSMA, survivin and telomerase, prostate-carcinoma tumor antigen-1 (PCTA-1), ELF2M, neutrophil elastase, CD22, insulin growth factor (IGF)-I, IGF-II, IGF-I receptor and mesothelin.

Disclosed herein, in certain embodiments, are methods of treating a cancer expressing a target antigen in an individual in need thereof, comprising administering to the individual engineered T cells disclosed herein. In some embodiments, the target antigen is CD19. In some embodiments, the method of treating a cancer expressing CD19 in an individual in need thereof comprises administering to the individual engineered T cells comprising a TAC comprising a CD19-targeting ligand. In some embodiments, examples of cancers that are treated by a TAC comprising a CD19-targeting ligand include, but are not limited to B cell malignancies. In some embodiments, examples of cancers that are treated by a TAC comprising a CD19-targeting ligand include, but are not limited to B cell lymphomas, acute lymphoblastic leukemia (ALL), and chronic lymphocytic leukemia (CLL). In some embodiments, examples of cancers that are treated by a TAC comprising a CD19-targeting ligand include, but are not limited to Non-Hodgkin's lymphoma (NHL).

In some embodiments, the target antigen is HER-2. In some embodiments, the method of treating a cancer wherein a cancer cell expresses HER-2 in an individual in need thereof comprises administering to the individual engineered T cells comprising a TAC comprising a HER-2-targeting ligand. In some embodiments, examples of cancers that are treated by a TAC comprising a HER-2-targeting ligand include, but are not limited to breast cancer, bladder cancer, pancreatic cancer, ovarian cancer, and stomach cancer.

In some embodiments, the target antigen is BCMA. In some embodiments, the method of treating a cancer wherein a cancer cell expresses BCMA in an individual in need thereof comprises administering to the individual engineered T cells comprising a TAC comprising a BCMA-targeting ligand. In some embodiments, examples of cancers that are treated by a TAC comprising a BCMA-targeting ligand include, but are not limited to leukemia, lymphomas, and multiple myeloma.

Further disclosed herein is use of an engineered T cell disclosed herein in the preparation of a medicament to treat cancer in an individual in need thereof. Also disclosed herein is the use of a mixture of T cells comprising modified and unmodified cells, or comprising different populations of modified cells with or without unmodified cells. One of ordinary skill in the art would understand that a therapeutic quantity of modified T cells need not be homogenous in nature.

In some embodiment, the engineered T cells disclosed herein are part of a combination therapy. In some embodiments, effectiveness of a therapy disclosure herein is assessed multiple times. In some embodiments, patients are stratified based on a response to a treatment disclosed herein. In some embodiments, an effectiveness of treatment determines entrance into a trial.

In some embodiments, cancers that are treated engineered T cells comprising any one of the TAC disclosed herein include any form of neoplastic disease. In some embodiments, examples of cancers that are treated include, but are not limited to breast cancer, lung cancer and leukemia, for example mixed lineage leukemia (MLL), chronic lymphocytic leukemia (CLL) acute lymphoblastic leukemia (ALL). In some embodiments, examples of cancers that are treated include, but are not limited to large B-cell lymphoma, diffuse large B-cell lymphoma, primary mediastinal B cell lymphoma, high grade B-cell lymphoma, or large B cell lymphoma arising from follicular lymphoma. Other cancers include carcinomas, blastomas, melanomas, sarcomas, hematological cancers, lymphoid malignancies, benign and malignant tumors, and malignancies. In some embodiments, the cancer comprises non-solid tumors or solid tumors. In some embodiments, cancers that are treated include tumors that are not vascularized, or not yet substantially vascularized, as well as vascularized tumors. In some embodiments, the cancer is a solid cancer or comprises a solid tumor. In some embodiments, the cancer is a liquid cancer or comprises a liquid tumor. In some embodiments, the cancer is a lung cancer, a breast cancer, a colon cancer, multiple myeloma, glioblastoma, gastric cancer, ovarian cancer, stomach cancer, colorectal cancer, urothelial cancer, endometrial cancer, or a melanoma. In some embodiments, the cancer is a lung cancer. In some embodiments, the cancer is a breast cancer. In some embodiments, the cancer is a colon cancer. In some embodiments, the cancer is multiple myeloma. In some embodiments, the cancer is a glioblastoma. In some embodiments, the cancer is a gastric cancer. In some embodiments, the cancer is an ovarian cancer. In some embodiments, the cancer is a stomach cancer. In some embodiments, the cancer is a colorectal cancer. In some embodiments, the cancer is urothelial cancer. In some embodiments, the cancer is an endometrial cancer. In some embodiments, the cancer is a melanoma.

TABLE 1

Table of Sequences

| SEQ ID NO | Description | Nucleotide/Amino Acid |
|---|---|---|
| SEQ ID NO: 1 | Tri TAC Configuration 1 | Nucleotide |
| SEQ ID NO: 2 | Tri TAC Configuration 1 | Amino Acid |
| SEQ ID NO: 3 | Tri TAC Configuration 2 | Nucleotide |
| SEQ ID NO: 4 | Tri TAC Configuration 2 | Amino Acid |
| SEQ ID NO: 5 | muIgG leader (secretion signal) | Nucleotide |
| SEQ ID NO: 6 | muIgG leader (secretion signal) | Amino Acid |
| SEQ ID NO: 7 | DARPin specific for Her2 antigen | Nucleotide |
| SEQ ID NO: 8 | DARPin specific for Her2 antigen | Amino Acid |
| SEQ ID NO: 9 | Myc Tag | Nucleotide |
| SEQ ID NO: 10 | Myc Tag | Amino Acid |
| SEQ ID NO: 11 | Linker 1 | Nucleotide |
| SEQ ID NO: 12 | Linker 1 | Amino Acid |
| SEQ ID NO: 13 | UCHT1[1] | Nucleotide |
| SEQ ID NO: 14 | UCHT1[2] | Amino Acid |
| SEQ ID NO: 15 | Linker 2 | Nucleotide |
| SEQ ID NO: 16 | Linker 2 | Amino Acid |
| SEQ ID NO: 17 | CD4 Domain[3] | Nucleotide |
| SEQ ID NO: 18 | CD4 Domain[4] | Amino Acid |
| SEQ ID NO: 19 | CD4 based linker | Nucleotide |
| SEQ ID NO: 20 | CD4 based linker | Amino Acid |
| SEQ ID NO: 21 | OKT3 | Nucleotide |
| SEQ ID NO: 22 | OKT3 | Amino Acid |
| SEQ ID NO: 23 | F6A | Nucleotide |
| SEQ ID NO: 24 | F6A | Amino Acid |
| SEQ ID NO: 25 | L2K | Nucleotide |
| SEQ ID NO: 26 | L2K | Amino Acid |
| SEQ ID NO: 27 | Short Helix connector | Nucleotide |
| SEQ ID NO: 28 | Short Helix connector | Amino Acid |
| SEQ ID NO: 29 | Long Helix connector | Nucleotide |
| SEQ ID NO: 30 | Long Helix connector | Amino Acid |
| SEQ ID NO: 31 | Large domain connector | Nucleotide |
| SEQ ID NO: 32 | Large domain connector | Amino Acid |
| SEQ ID NO: 33 | ScFv specific for BCMA antigen | Nucleotide |
| SEQ ID NO: 34 | ScFv specific for BCMA antigen | Amino Acid |
| SEQ ID NO: 35 | ScFv specific for CD19 antigen | Nucleotide |
| SEQ ID NO: 36 | ScFv specific for CD19 antigen | Amino Acid |
| SEQ ID NO: 37 | CD8α Domain | Nucleotide |
| SEQ ID NO: 38 | CD8α Domain | Amino Acid |
| SEQ ID NO: 39 | CD8α + R(β) Domain | Nucleotide |
| SEQ ID NO: 40 | CD8α + R(β) Domain | Amino Acid |
| SEQ ID NO: 41 | CD8 α + Lck Domain | Nucleotide |
| SEQ ID NO: 42 | CD8 α + Lck Domain | Amino Acid |
| SEQ ID NO: 43 | huUCHT1 | Nucleotide |
| SEQ ID NO: 44 | huUCHT1 | Amino Acid |

TABLE 1-continued

Table of Sequences

| SEQ ID NO | Description | Nucleotide/Amino Acid |
|---|---|---|
| SEQ ID NO: 45 | huUCHT1 (Y177T) | Nucleotide |
| SEQ ID NO: 46 | huUCHT1 (Y177T) | Amino Acid |
| SEQ ID NO: 47 | huIgG | Nucleotide |
| SEQ ID NO: 48 | huIgG | Amino Acid |
| SEQ ID NO: 49 | huCD8a | Nucleotide |
| SEQ ID NO: 50 | huCD8a | Amino Acid |
| SEQ ID NO: 51 | 3625 scFv BCMA Vh-Vl | Nucleotide |
| SEQ ID NO: 52 | 3625 scFv BCMA Vh-Vl | Amino Acid |
| SEQ ID NO: 53 | 3625 scFv BCMA Vl-Vh | Nucleotide |
| SEQ ID NO: 54 | 3625 scFv BCMA Vl-Vh | Amino Acid |
| SEQ ID NO: 55 | 3625 TAC Helix Vh-Vl huUCHT1 | Nucleotide |
| SEQ ID NO: 56 | 3625 TAC Helix Vh-Vl huUCHT1 | Amino Acid |
| SEQ ID NO: 57 | 3625 TAC Helix Vl-Vh huUCHT1 | Nucleotide |
| SEQ ID NO: 58 | 3625 TAC Helix Vl-Vh huUCHT1 | Amino Acid |
| SEQ ID NO: 59 | 3625 TAC G4S Vh-Vl huUCHT1 | Nucleotide |
| SEQ ID NO: 60 | 3625 TAC G4S Vh-Vl huUCHT1 | Amino Acid |
| SEQ ID NO: 61 | 3625 TAC G4S VL-VH huUCHT1 | Nucleotide |
| SEQ ID NO: 62 | 3625 TAC G4S VL-VH huUCHT1 | Amino Acid |
| SEQ ID NO: 63 | CD19-TAC | Nucleotide |
| SEQ ID NO: 64 | CD19-TAC | Amino Acid |
| SEQ ID NO: 65 | huIgG Her2 TAC huUCHT1 | Nucleotide |
| SEQ ID NO: 66 | huIgG Her2 TAC huUCHT1 | Amino Acid |
| SEQ ID NO: 67 | CD8a Her2 TAC huUCHT1 | Nucleotide |
| SEQ ID NO: 68 | CD8a Her2 TAC huUCHT1 | Amino Acid |
| SEQ ID NO: 69 | Flexible Connector | Amino Acid |
| SEQ ID NO: 70 | Flexible Connector | Nucleotide |
| SEQ ID NO: 71 | UCHT1 (Y182T) | Nucleotide |
| SEQ ID NO: 72 | UCHT1 (Y182T) | Amino Acid |

[1]Light chain, nucleotides 1-324; Linker, nucleotides 325-387; Heavy chain, nucleotides 388-750
[2]Light chain, amino acids 1-108; Linker, amino acids 109-128; Heavy chain, amino acids 129-250
[3]Extracellular linker, nucleotides 1-66; Transmembrane domain, nucleotides 67-132; Cytosolic domain, nucleotides 133-254
[4]Extracellular linker, amino acids 1-22; Transmembrane domain, amino acids 23-44; Cytosolic domain, amino acids 45-84

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Characterization of the Tri-TAC Technology

Figure 1B:
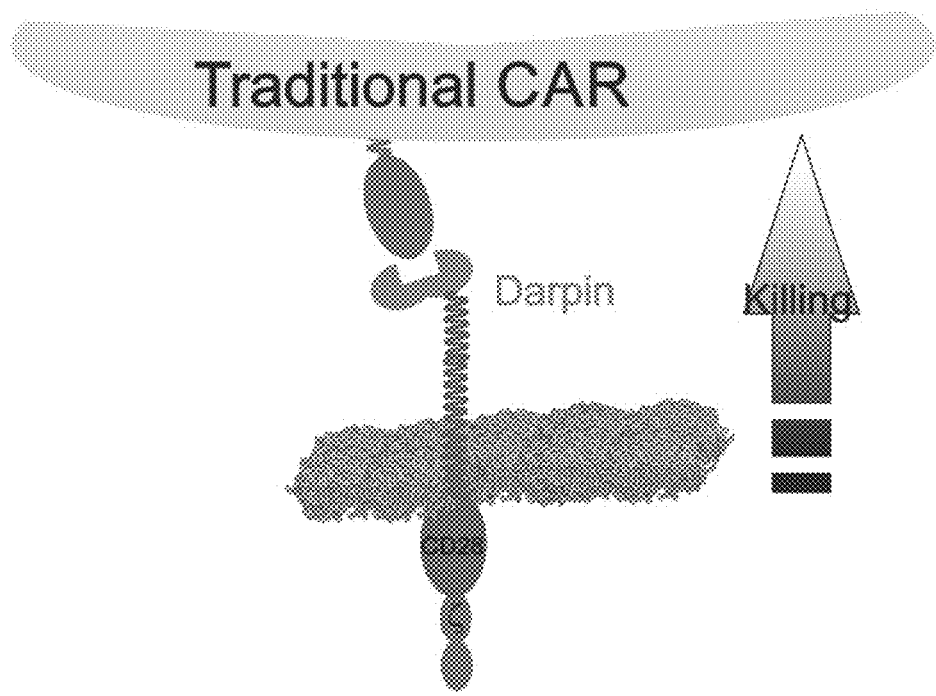
FIG. 1B is a schematic of CAR based T-cell activation.
Figure 1C:
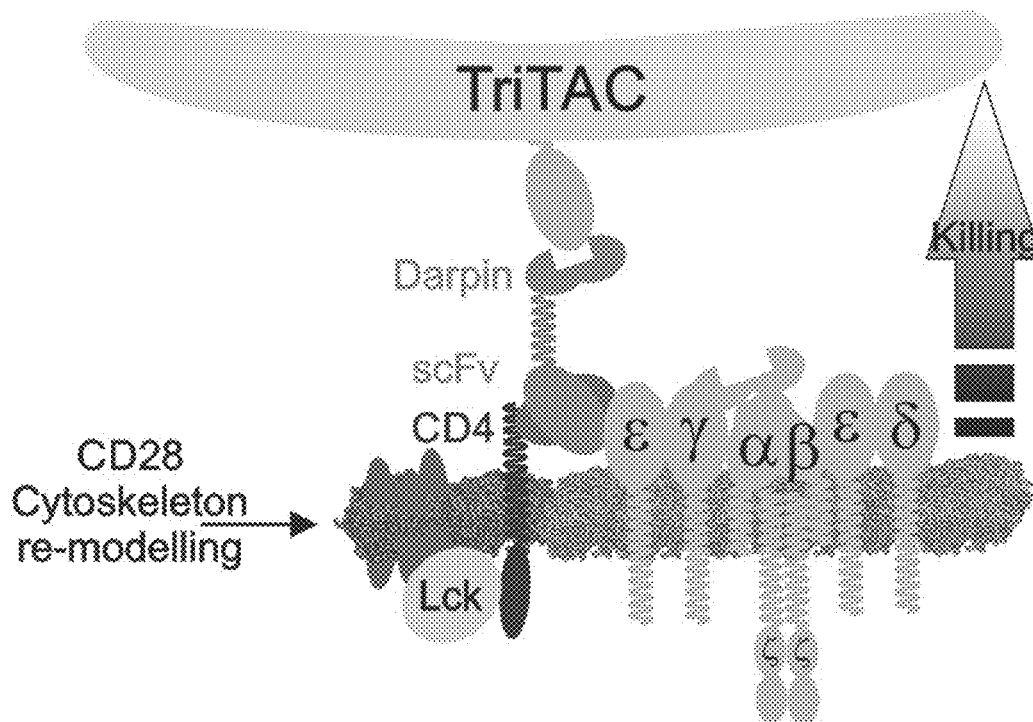
FIG. 1C is a schematic of a trifunctional-T cell-antigen coupler (Tri-TAC) based T cell activation.
Figure 1D:
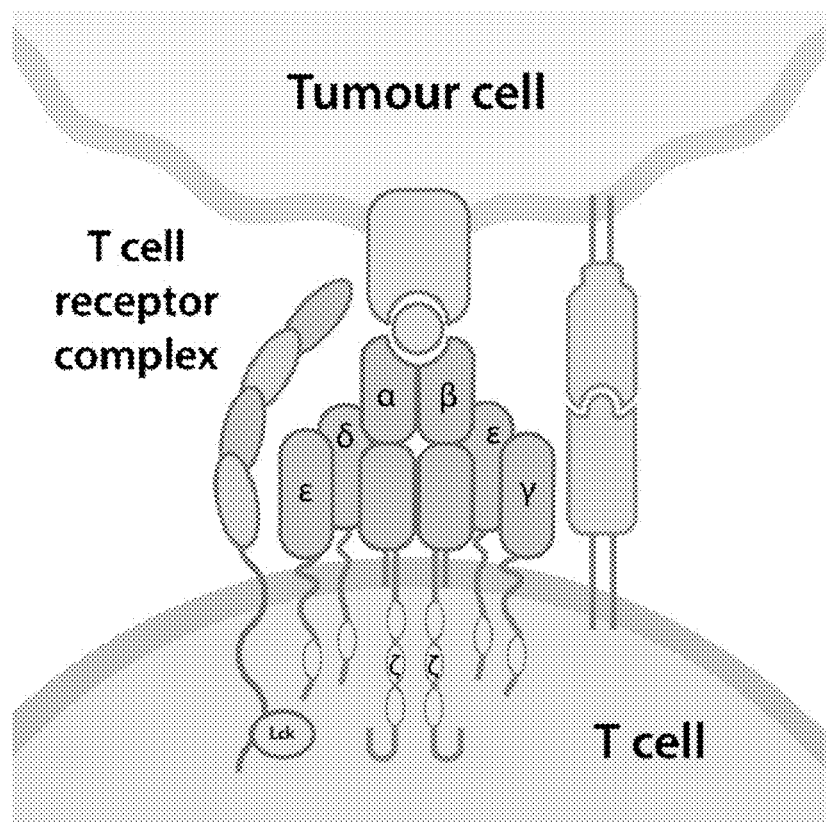
FIG. 1D is a schematic of natural T-cell activation.
Figure 1E:
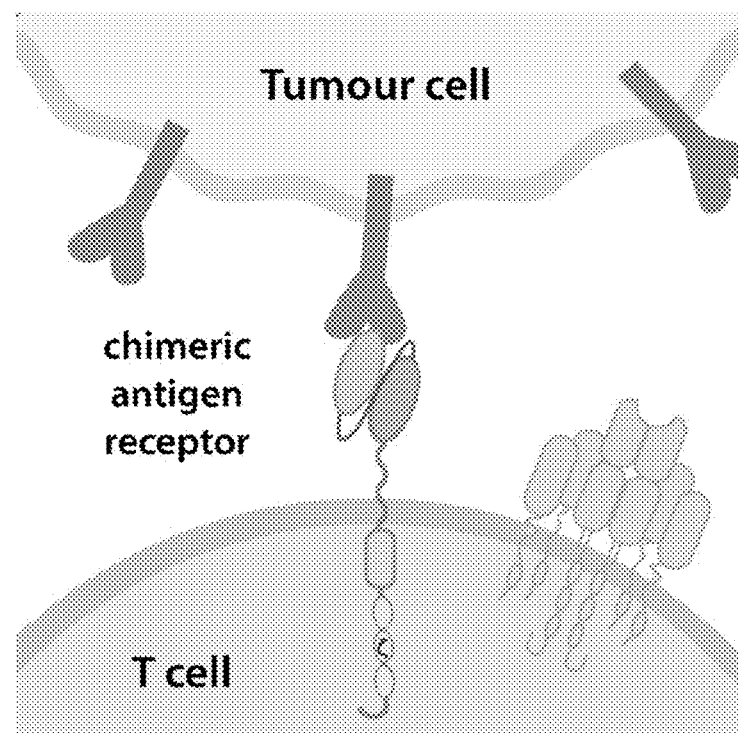
FIG. 1E is a schematic of CAR based T-cell activation.
Figure 1F:
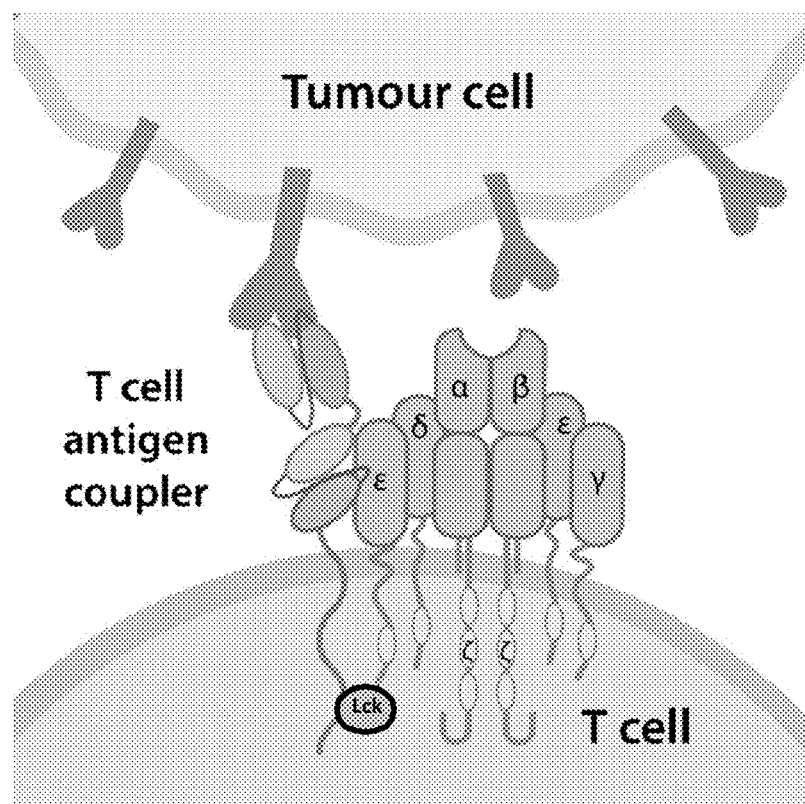
FIG. 1F is a schematic of Tri-TAC based T cell activation.

An overview of the Tri-TAC technology is provided in FIG. 1A-FIG. 1C.

FIG. 1A shows an example of CD8 T-cell activation based on the co-assembly of different receptors and their associated protein partners. Initially, the major histocompatibility complex I is presenting an antigen (helix). This is recognized by a T cell receptor (TCR) complex capable of binding the antigen. The TCR complex contains several individual subunits. The α/β domains are able to interact directly with the antigen presented on MHC-I. The α/β domains then interact with several other domains (ε, γ, δ, and ζ), all of which participate in T-cell activation via various intracellular activation domains. The TCR complex interacts with MHC-I concurrently with the CD8 co-receptor. The CD8 co-receptor binds to the MHC-I in an antigen independent manner. CD8 directly interacts with Lck, a protein kinase important for activating the TCR receptor complex. The CD8 and Lck interaction also ensures their association with lipid rafts (membrane portion) microdomains, which are hypothesized to organize and encapsulate other relevant signaling moieties (dark spheres). Later stages of activation then lead to CD28 recruitment. If this interaction cascade occurs several times in parallel, T-cells become activated and are able to exert their cytotoxic effects.

FIG. 1B provides an overview of Chimeric Antigen Receptors (CAR). CARs seek to reproduce the complex mechanism of T-cell activation by combining several key activation domains, such as CD3ζ and CD28 in a single synthetically engineered molecule. The CAR then directly interacts with an antigen of choice using specific binding domains. Depicted here is an ankyrin repeat protein (DARPin). It is believed that several such interactions occurring in parallel lead to T-cell activation.

FIG. 1C is an overview of the Tri-TAC technology mimicking the natural activation process. The Tri-TAC was developed to better recapitulate the natural signaling through the TCR, while retaining MHC unrestricted targeting. T-cell activation occurs following ligation of MHC by the TCR and T cell co-receptor (either CD4 or CD8), which simultaneously bind to conserved regions within the MHC molecule. The co-receptors are specifically located within "lipid rafts", membrane micro domains that are particularly important for TCR signal complex formation. In addition to ensuring the correct microdomain localization of the TCR activation complex, these co-receptors also bind directly to Lck, a protein kinase that is crucial for T-cell activation. None of the traditional chimeric receptors or bi-functional proteins engage the co-receptor molecules or Lck. A molecule was created where the transmembrane and intracellular regions of the CD4 co-receptor, which localize to the lipid raft and bind Lck, respectively, were fused to single-chain antibody that binds CD3 (UCHT1; SEQ ID NO: 13, 14 and homologs thereof). This construct is designed to draw the CD3 molecule and the TCR into regions of lipid rafts and bring Lck into the proximity of the TCR, similar to natural MHC binding. To target this receptor, a designed ankyrin repeat (DARPin) was linked to the CD4-UCHT1 chimera to generate a Trifunctional T cell-antigen coupler (Tri-TAC). In this example, the DARPin was specific for the proto-oncogene, HER-2 (erbB-2).

Figure 2A:
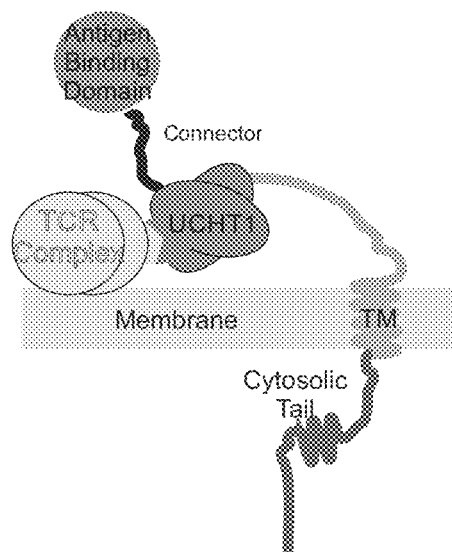
FIG. 2A is a schematic of a Tri-TAC configuration with the UCHT1 domain being centered between the trans-membrane domain (TM) and the antigen binding domain.
Figure 2B:
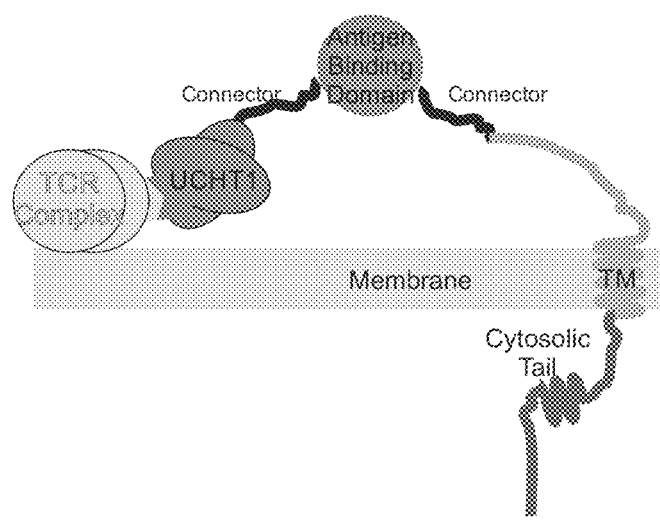
FIG. 2B is a schematic of a Tri-TAC configuration in which the UCHT1 domain is N-terminal, followed by the antigen binding domain and the trans-membrane domain.
Figure 2C:
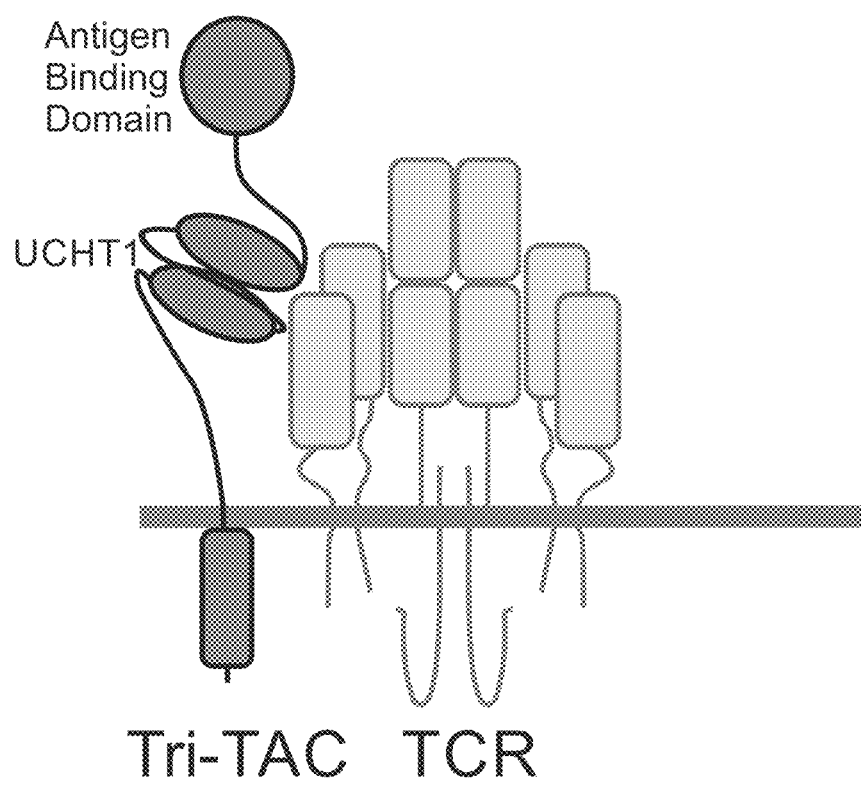
FIG. 2C is a schematic of a Tri-TAC molecule with a generic antigen binding domain and a UCHT1 domain.

Multiple Tri-TAC configurations are possible (FIG. 2A and FIG. 2B). In configuration 1 (FIG. 2A) the Antigen binding domain is located N-terminal, connected to the CD3 ligand binding domain and then the co-receptor domain. In configuration 2 (FIG. 2B) the CD3 ligand binding domain is located N-terminal, connected to the antigen binding domain which in turn connects to the co-receptor domain.

Figure 3A:
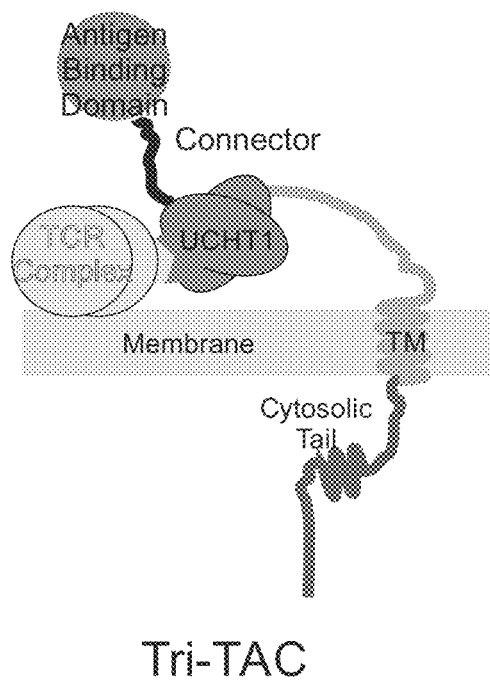
FIG. 3A is a schematic of a Tri-TAC molecule with a generic antigen binding domain.
Figure 3B:
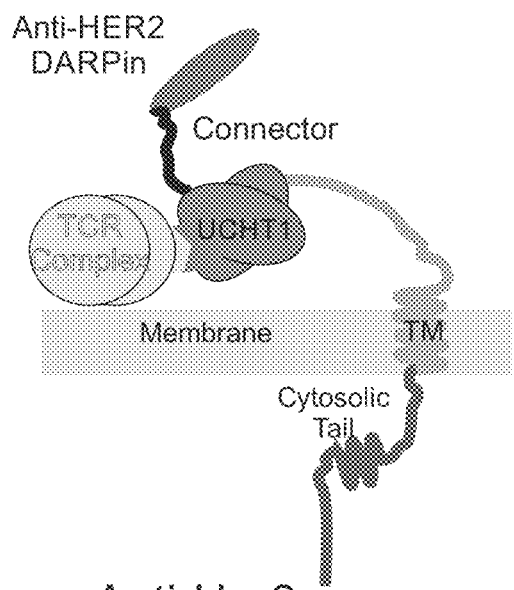
FIG. 3B is a schematic of a Tri-TAC with an anti-HER-2 DARPin antigen binding domain.
Figure 3C:
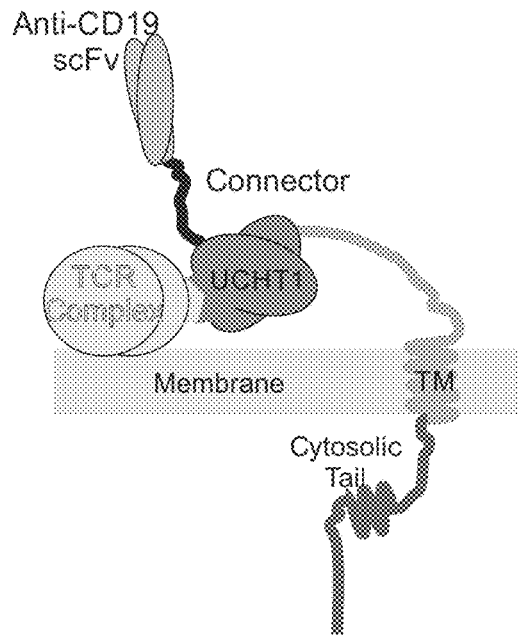
FIG. 3C is a schematic of a Tri-TAC with an anti-CD19 scFv antigen binding domain.
Figure 3D:
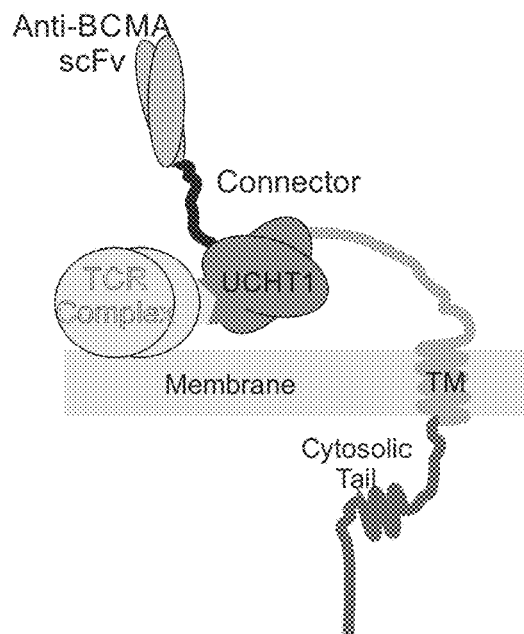
FIG. 3D is a schematic of a Tri-TAC with an anti-BCMA scFv antigen binding domain.
Figure 3E:
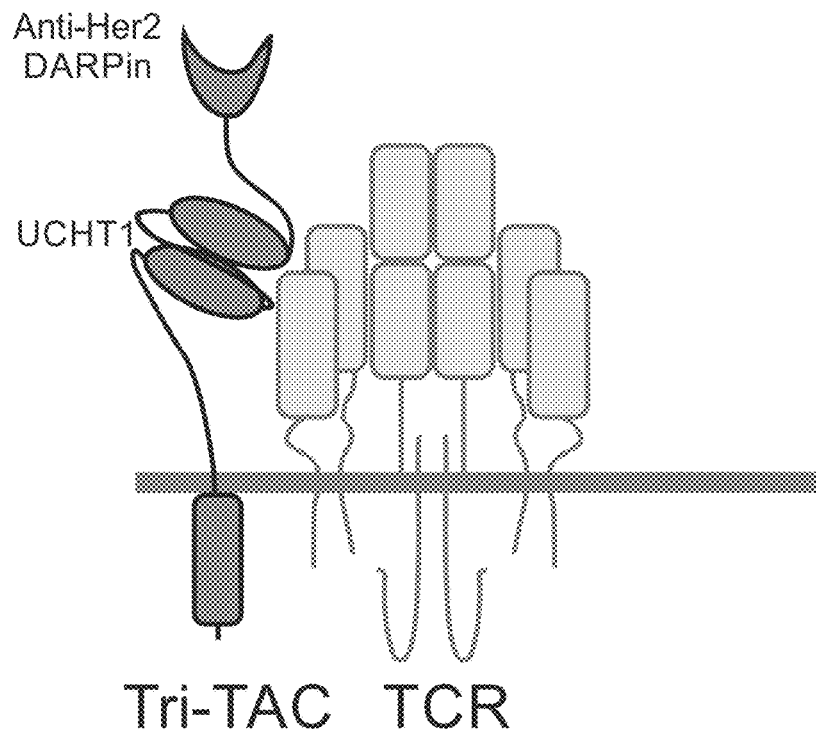
FIG. 3E is a schematic of a Tri-TAC molecule with the Anti-HER-2 DARPin antigen binding domain.
Figure 3F:
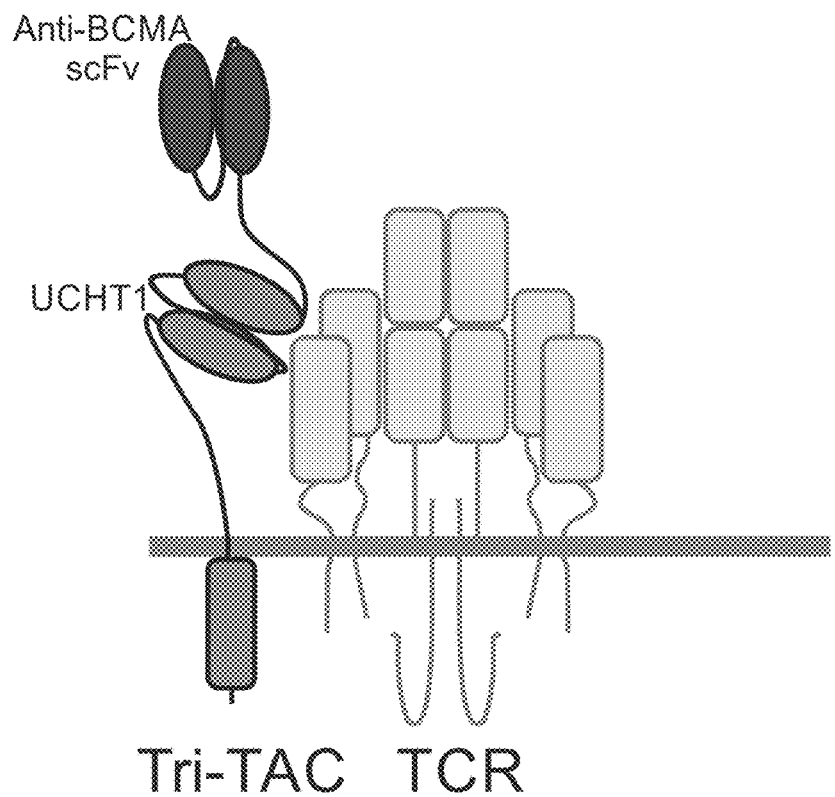
FIG. 3F is a schematic of a Tri-TAC molecule with the Anti-BCMA scFv antigen binding domain.

Multiple classes of ligand binding domains can be incorporated into the Tri-TAC molecule (FIG. 3A-FIG. 3D). The examples herein illustrate a general schematic of a configuration 1 Tri-TAC (FIG. 3A), a Tri-TAC bearing a HER-2-specific DARPin (FIG. 3B), a Tri-TAC bearing a CD19-specific scFv (FIG. 3C), and a Tri-TAC bearing a BCMA-specific scFv (FIG. 3D).

FIG. 4A-FIG. 4D illustrate the functionality of a Tri-TAC bearing the HER-2-specific DARPin. Human T cells were engineered to express either the Tri-TAC as disclosed herein or a conventional CAR with the same DARPin. It was determined that in all aspects, T cells engineered with the Tri-TAC demonstrated functionality at least equivalent to a conventional CAR. Interestingly, with regard to 2 parameters (TNF-α production and CD107a mobilization), it was observed that the Tri-TAC was more active than a conventional CAR in some circumstances.

Figure 4A:
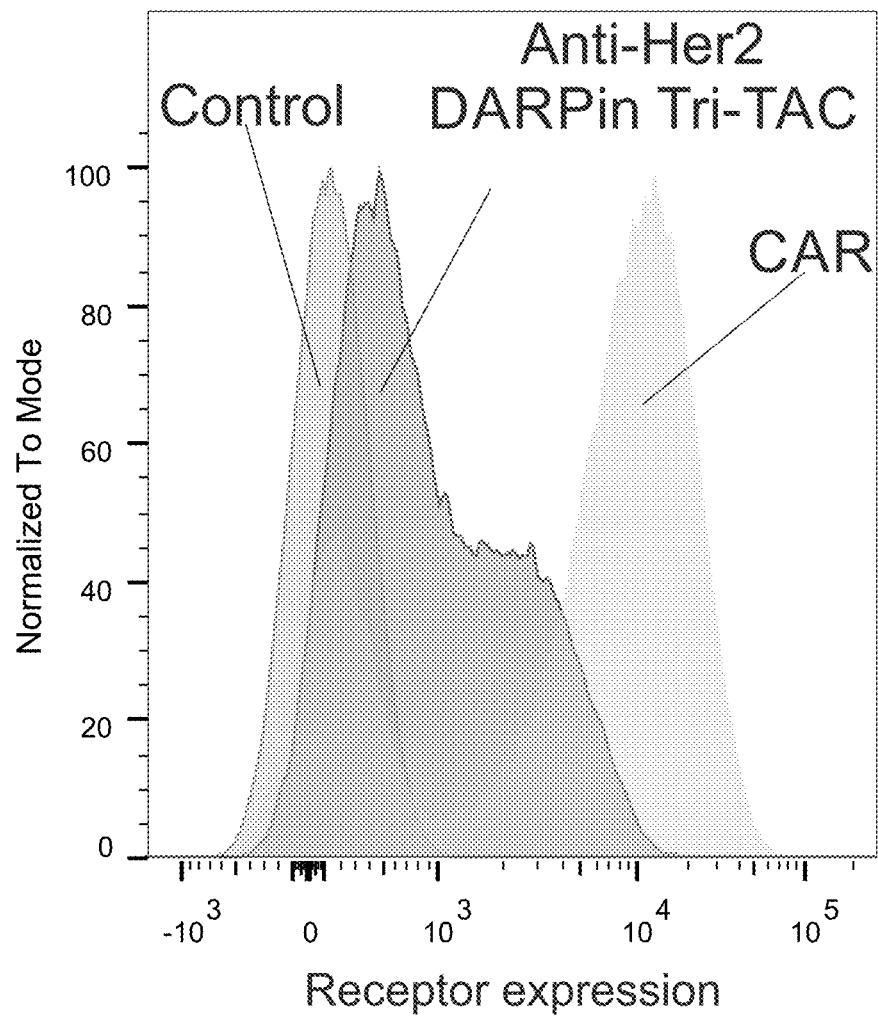
FIG. 4A-FIG. 4D exemplify T cells engineered with a Tri-TAC or a CD28-based CAR directed against HER-2 using a DARPin.
Figure 4B:
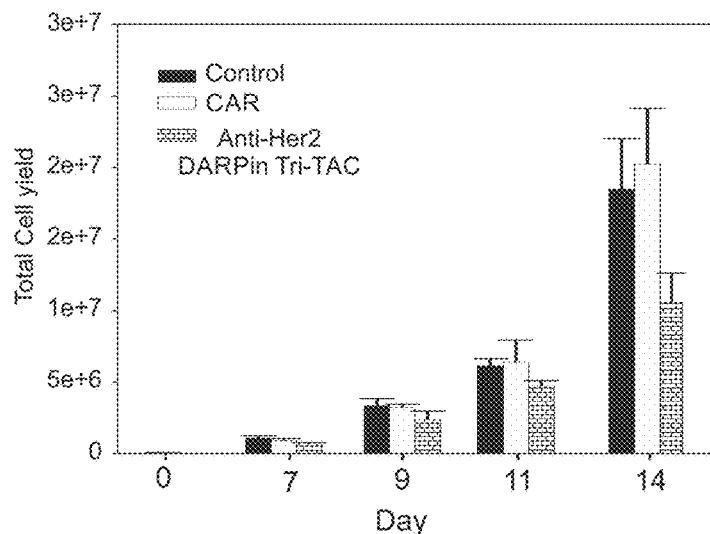
Figure 4C:
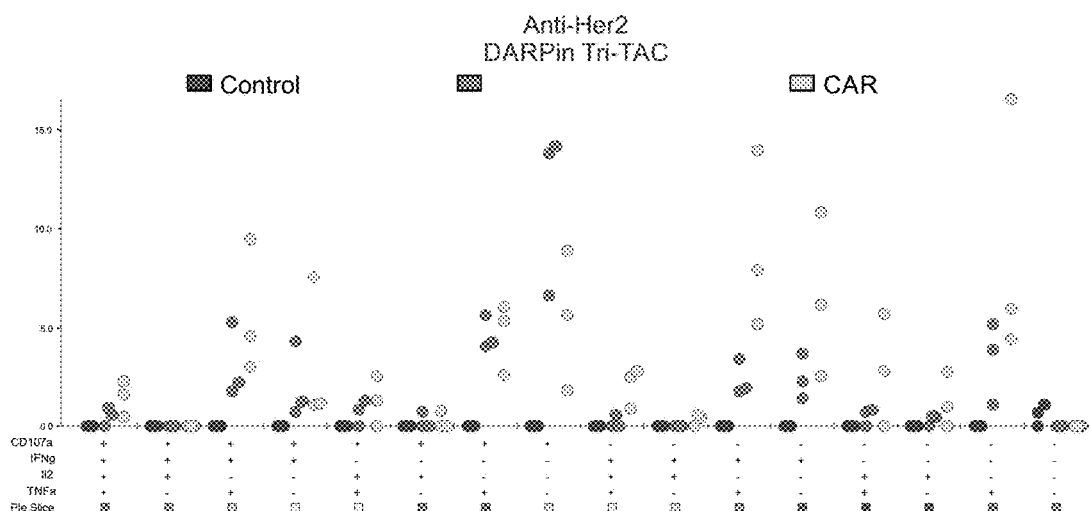
Figure 4D:
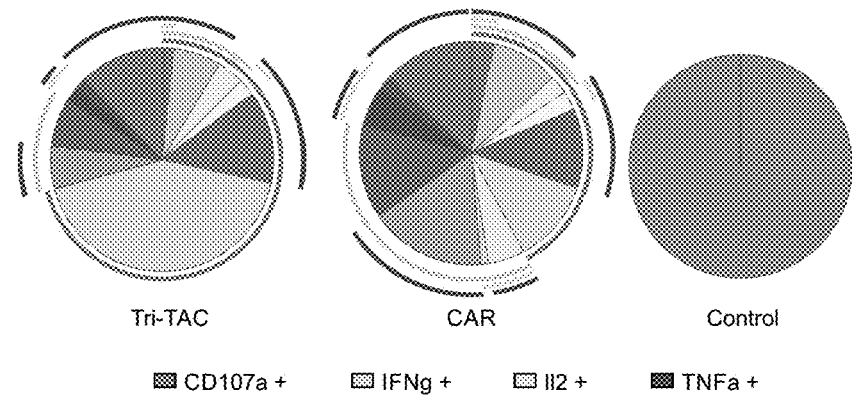
Figure 5:
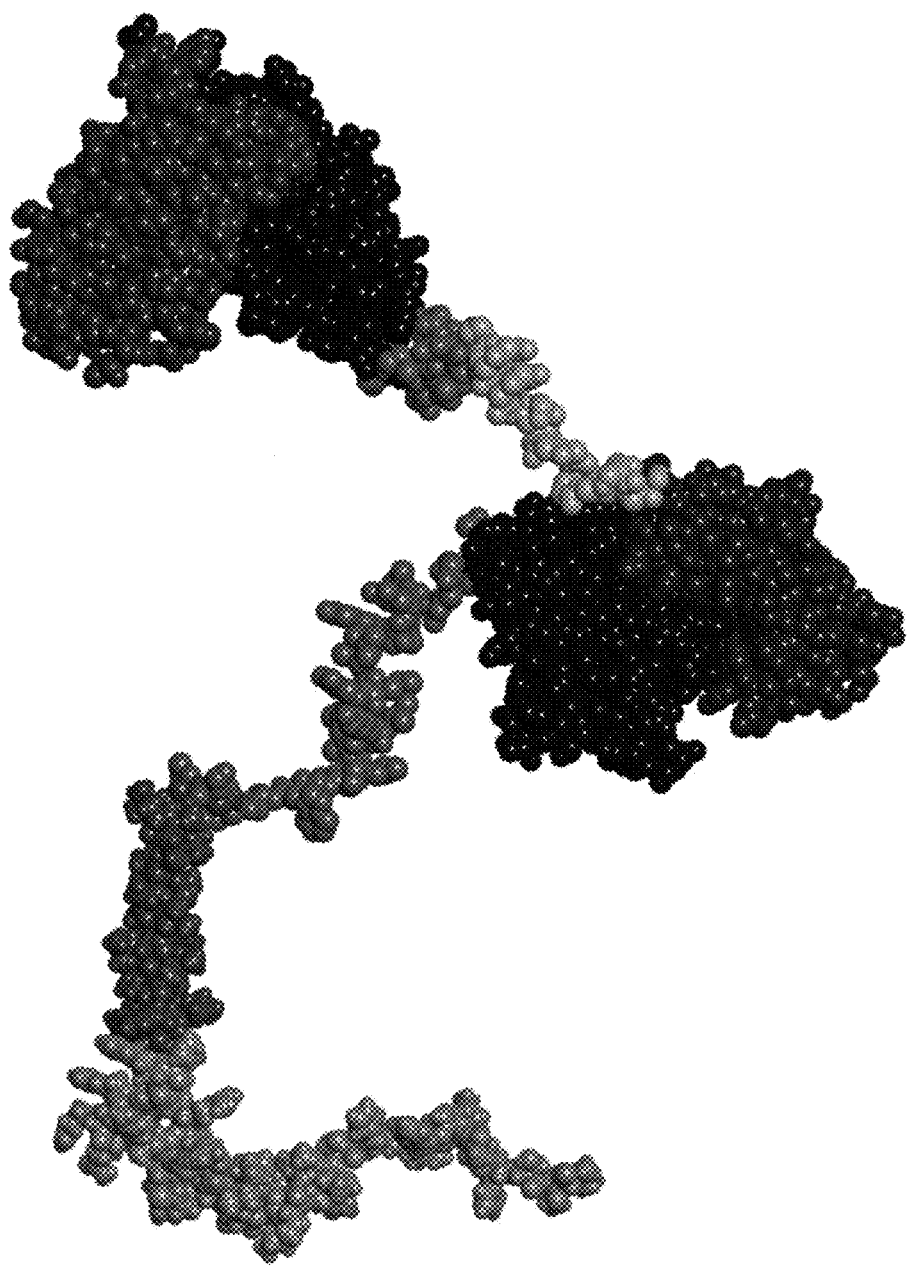
FIG. 5 illustrates a model of the CD19-TAC protein structure.

FIG. 4A shows surface expression of Anti-HER-2 DARPin Tri-TAC compared to Anti-HER-2 DARPin CAR, and control T cells. The chimeric receptors were detected by incubation with recombinant HER-2. The Anti-HER-2 DARPin Tri-TAC was expressed well on the surface of the engineered T cells. FIG. 4B shows growth of the engineered T cells cultures. T cells were activated with anti-CD3/anti-CD28 Dynabeads and engineered with lentiviruses encoding the Tri-TAC, CAR or no receptor (control). After 2 weeks, the CAR and control cultures had grown to similar numbers while the Tri-TAC cultures grew slightly more slowly. FIG. 4C and FIG. 4D show the functional attributes of the engineered T cells. T cells engineered to express the Tri-TAC or the CAR bearing the HER-2 DARPin were stimulated with plate-bound antigen. The T cells engineered to express the Tri-TAC and CAR could elaborate all measured functions (TNF-α production, IFN-7 production and CD107a mobilization, FIG. 3C and FIG. 3D). T cells engineered with the Tri-TAC exhibited elevated frequencies of CD107a-positive cells following stimulation relative to T cells engineered with a CAR (FIG. 3D), suggesting enhanced cytotoxicity on a per-cell basis.

FIG. 6A-FIG. 6J provides data confirming the importance of both ligand binding domain and the UCHT1 CD3 binding domain for Tri-TAC functionality. T cells were engineered with the full-length Tri-TAC bearing the HER-2 DARPin (FIG. 6G, FIG. 6H, FIG. 6I, bottom row), a Tri-TAC variant that lacks the DARPin (FIG. 6A, FIG. 6B, FIG. 6C, top row), or a Tri-TAC variant that lacks the UCHT1 (FIG. 6D, FIG. 6E, FIG. 6F, middle row). All three engineered T cell populations were stimulated with HER-2-positive tumor cells. The T cells engineered with the full-length Tri-TAC could produce IFN-g, TNF- and IL-2 following stimulation, whereas the variants failed to produce any cytokine following stimulation. The three T cell populations were also co-cultured with D2F2/E2 cells (HER-2-expressing) or D2F2 cells (HER-2-negative) at an effector: target of 4:1 (FIG. 6J). T cells engineered with full-length Tri-TAC demonstrated robust killing against D2F2/E2 cells but did not kill the D2F2 cells. The other Tri-TAC variants lacking either the DARPin or the UCHT1, exhibited no killing.

Figure 7A:
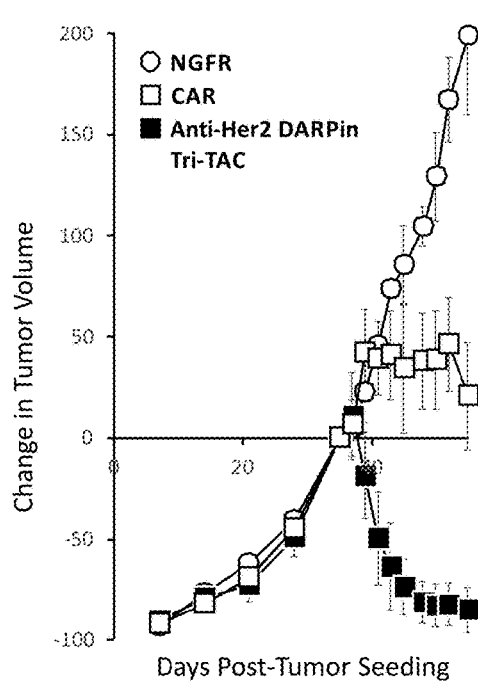
FIG. 7A-FIG. 7C illustrate anti-tumor activity, toxicity, and cytokine production of T cells engineered with either the anti-HER-2 DARPin Tri-TAC or the anti-HER-2 DARPin CD28-based CAR. Mice bearing established OVCAR-3 tumors were treated with T cells engineered with the anti-HER-2 DARPin Tri-TAC or the anti-HER-2 DARPin CAR.
Figure 7B:
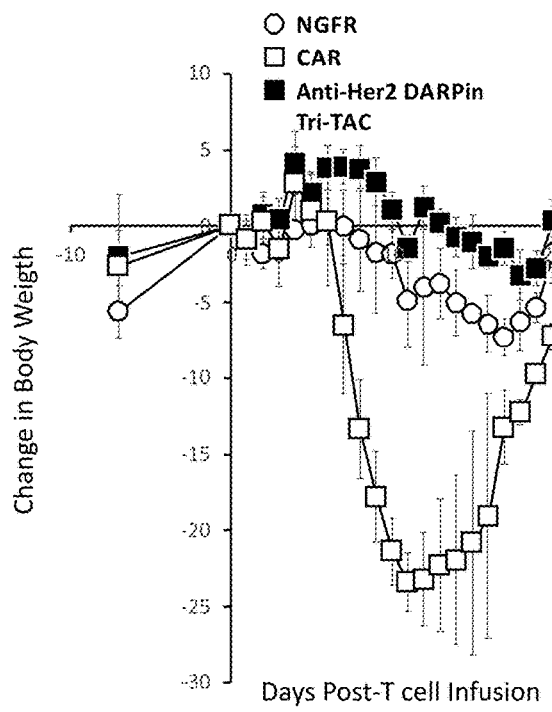
Figure 7C:
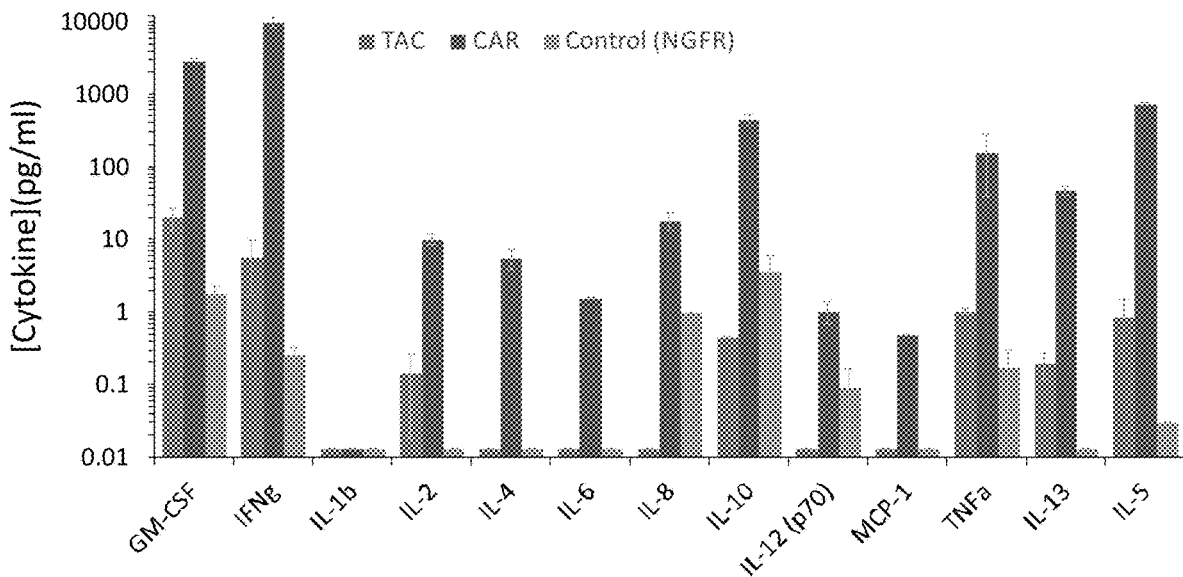

FIG. 7A-FIG. 7C show the results of mice treated with vector control (NGFR), Anti-HER-2 DARPin CAR or Anti-HER-2 DARPin Tri-TAC. A xenograft mouse model was used. OVCAR-3 tumor cells were administered to mice subcutaneously and allowed to grow until the tumors reached a size of 100-200 mm$^3$. FIG. 7A shows relative tumor progression normalized to tumor size at day of treatment. Anti-HER-2 DARPin Tri-TAC engineered T-cells caused a rapid decrease in tumor volume, control had no effect, and CAR cells slowed tumor growth and showed a delayed reduction in tumor size. FIG. 7B illustrates relative changes in body weight post T-cell infusion. Both control and anti-HER-2 DARPin Tri-TAC engineered cells show no significant changes in mouse body weight post treatment. In contrast, Anti-HER-2 DARPin CAR-treated mice show significant loss in body weight indicative of severe toxicity. FIG. 7C illustrates cytokine concentrations in serum of mice on day 7 post T-cell infusion. Cytokine levels were higher in CAR-treated mice compared to Tri-TAC-treated mice.

Example 2. Substitutions of UCHT1 Influence Tri-TAC Function

Figure 8A:
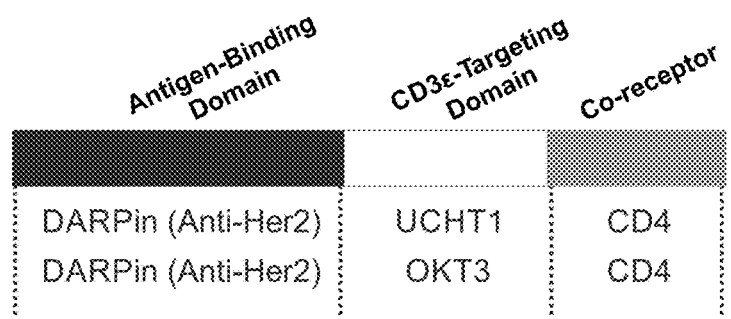
Figure 8B:
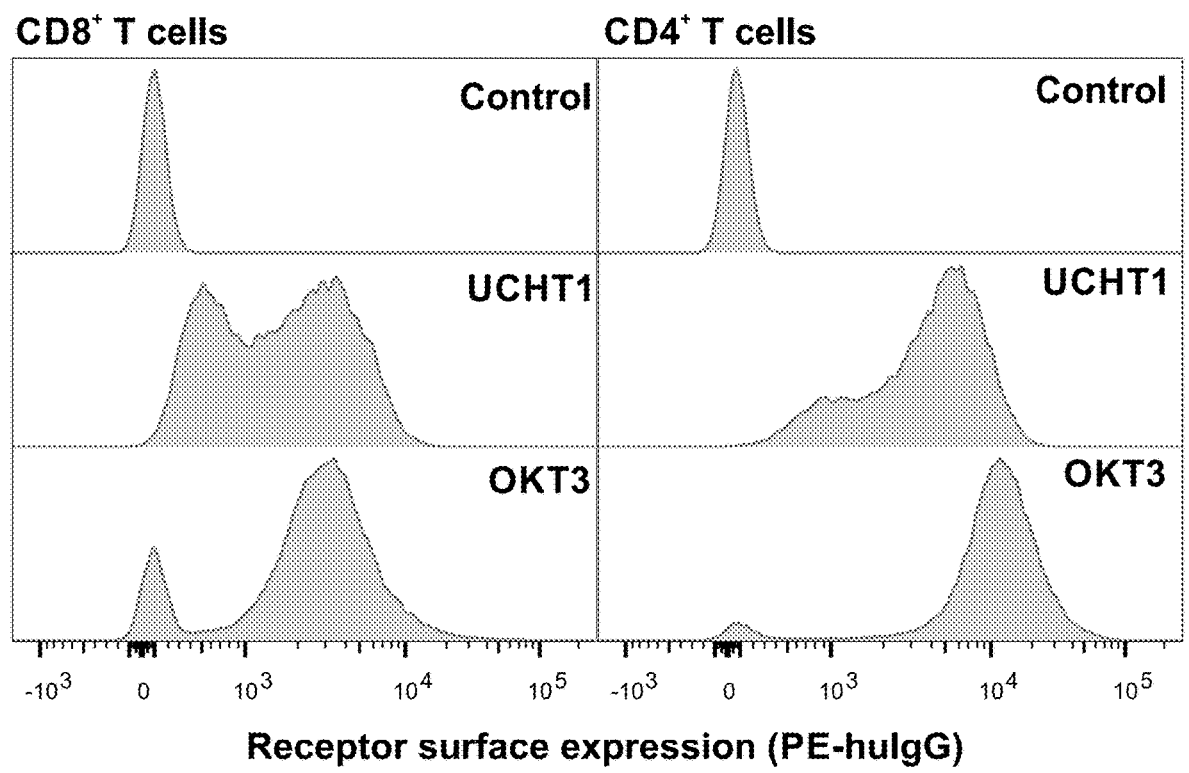
Figure 8D:
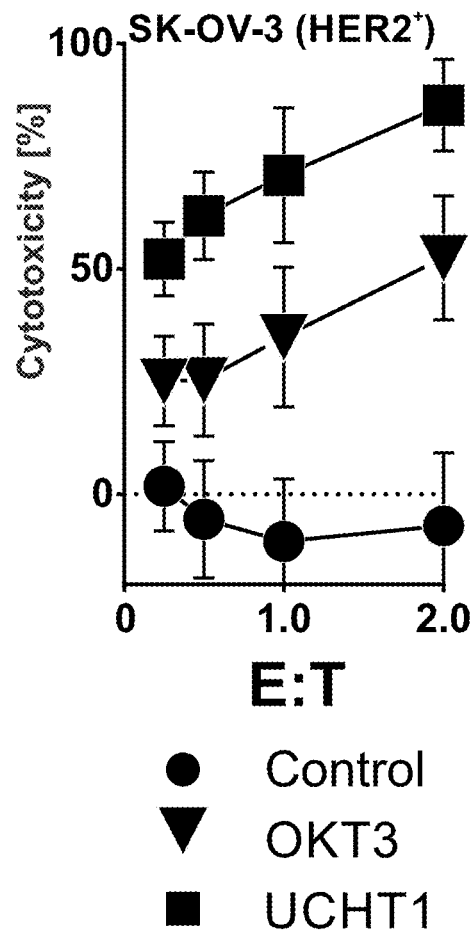
Figure 8E:
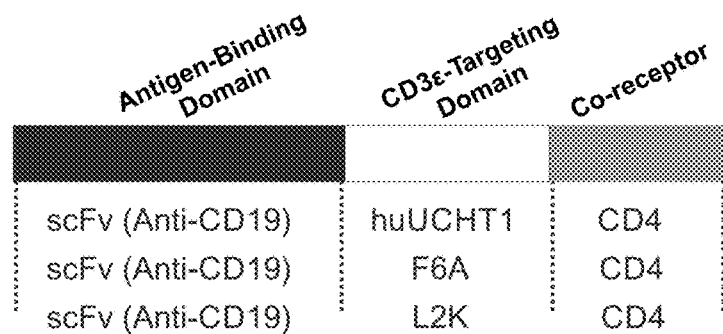
Figure 8F:
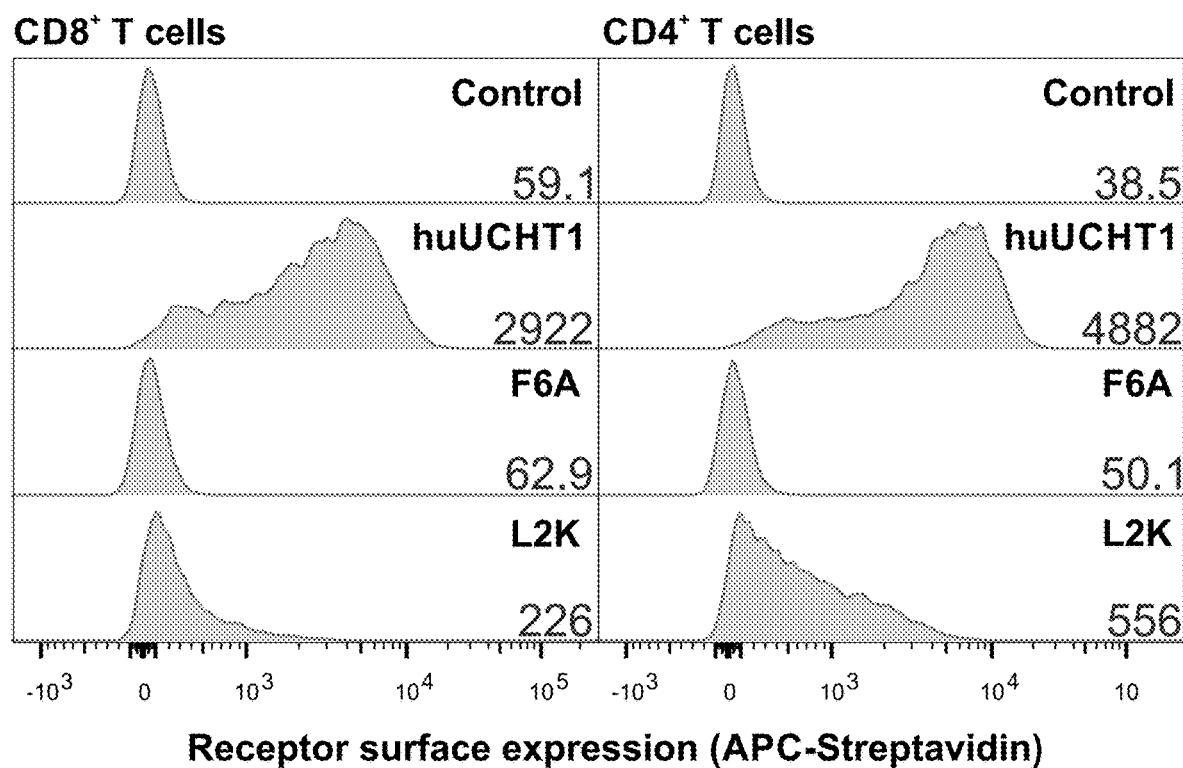
Figure 8H:
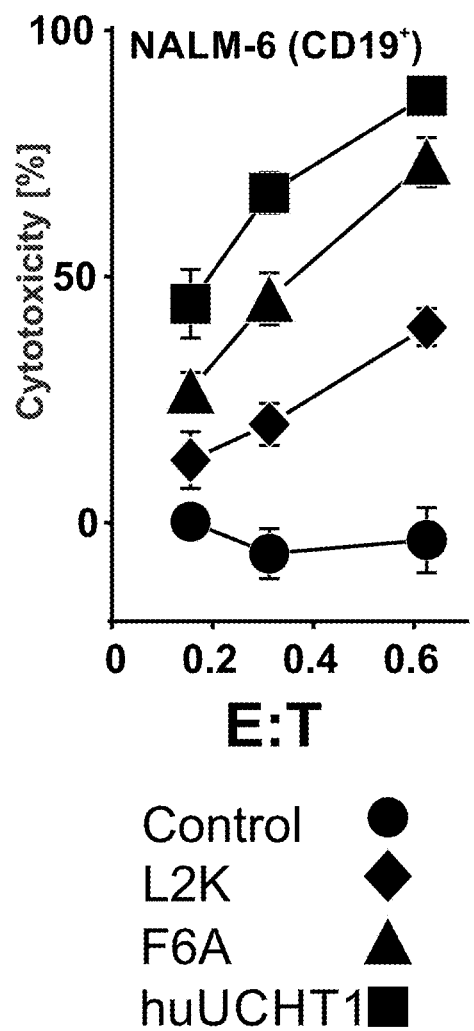
Figures 9A, 9E:
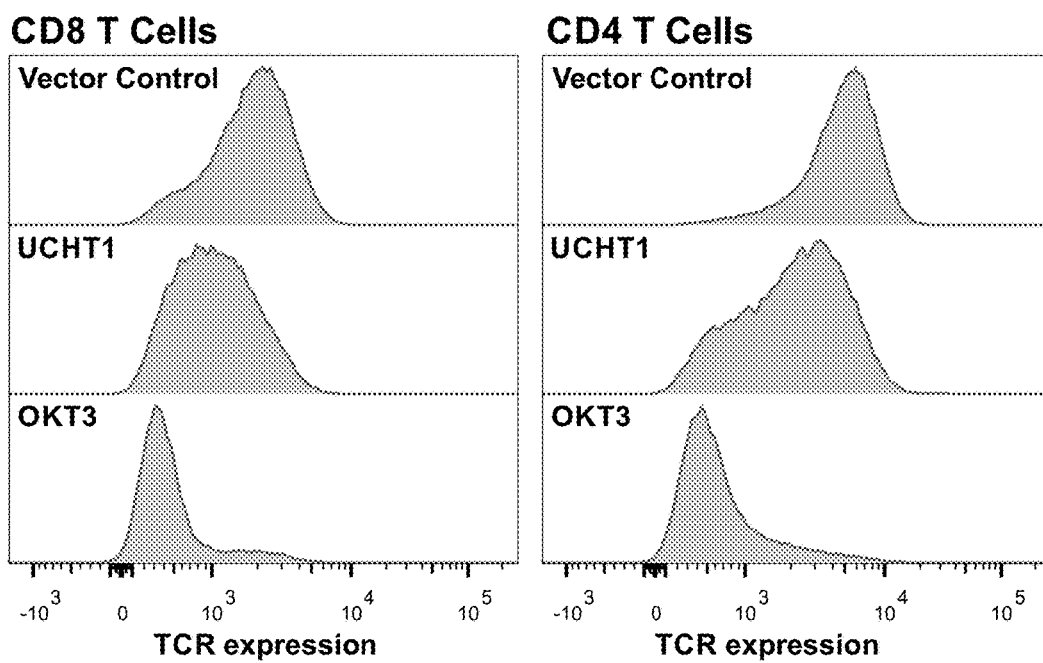
Figures 9B, 9F:
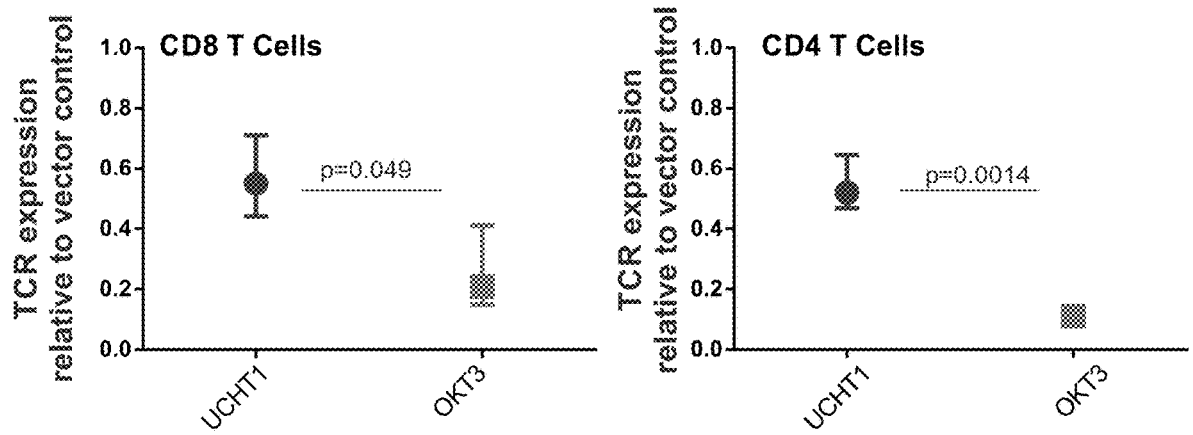

FIG. 8A-FIG. 8H illustrate the functionality of Tri-TACs bearing alternate CD3 binding domains. The domains are listed in FIG. 8A and FIG. 8E. Tri-TACs containing UCHT1 (FIG. 8B), OKT3 (FIG. 8B) and huUCHT1 (FIG. 8F) displayed high surface expression, whereas the Tri-TACs containing F6A (FIG. 8F) and L2K (FIG. 8F) revealed lower surface expression. Cells expressing the Tri-TAC containing OKT3 exhibited low cytokine production (FIG. 8C, FIG. 8C1) and intermediate cytotoxicity (FIG. 8D) upon Tri-TAC ligation. Cells expressing the Tri-TAC containing F6A exhibited strong cytokine production (FIG. 8G, FIG. 8G1) and cytotoxicity (FIG. 8H) following Tri-TAC ligation. Cells expressing the Tri-TAC containing L2K exhibited low cytokine production (FIG. 8G, FIG. 8G1) and intermediate cytotoxicity (FIG. 8H).

FIG. 9A-FIG. 9H illustrates TCR surface expression on T cells engineered with different Tri-TAC variants shown in FIG. 8A and FIG. 8E. T cells engineered with the Tri-TAC variants comprising OKT3 (FIG. 9A, FIG. 9E and FIG. 9B, FIG. 9F) or L2K (FIG. 9C, FIG. 9G and FIG. 9D, FIG. 9H) exhibited lower TCR surface expression relative to the T cells engineered with Tri-TACs comprising UCHT1 or huUCHT1, respectively. In contrast, T cells engineered with the Tri-TAC variant comprising F6A did not reveal TCR downregulation relative to the Tri-TAC carrying huUCHT1 (FIG. 9C, FIG. 9G and FIG. 9D, FIG. 9H). The F6A substitution reduced Tri-TAC receptor surface expression, while retaining moderate cytokine production and cytotoxicity. The L2K substitution moderately reduced surface expression and reduced cytokine production, but retained intermediate cytotoxicity. The OKT3 substitution resulted in high Tri-TAC surface expression, low cytokine production, and intermediate cytotoxicity. These data indicate that Tri-TAC surface expression and T cell effector functions are not inherently proportional, and that Tri-TAC domain substitutions, in some instances, alters effector functions independent of surface expression levels. It is conceivable that a TAC variant with reduced cytotoxicity and low surface expression could be of value in certain clinical applications.

In many cases, the scFv substitutions attenuated the ability of the engineered T cell to elaborate IFN-γ, TNF-α, and IL-2, yet the engineered T cells retained the ability to kill target cells. Excessive cytokine production has been associated with adverse events in clinical settings, limiting current CAR technologies to life-threatening diseases. The ability to modify TAC molecules to reduce their cytokine production while retaining moderate cytotoxicity will allow generation Tri-TAC receptors with the exact level of reactivity required to satisfy clinical efficacy and safety.

The capacity of the Tri-TAC variant comprising OKT3 to suppress TCR surface expression and cytokine production, while retaining cytotoxicity, could be of great value in allogeneic situations where the suppression of TCR could suppress graft versus host disease.

These data demonstrate that scFv substitutions of UCHT1 influences the function of Tri-TACs. Further modifications will be result in Tri-TACs useful in various applications (e.g., oncology, autoimmunity, allergy).

Example 3. Introducing Various Linkers Connecting the Ligand that Binds a TCR Complex to the Target-Binding Ligand Domain FIG. 10A-FIG. 10B illustrate several TAC variants with different linkers connecting the ligand that binds a TCR complex and the target-binding ligand domain. The flexible connector allows movement between the two domains. The large domain connector contains two folded domains and is very large and rigid. The small and long helix connectors also introduce rigidity but are less restrictive when compared to the large domain linker.

Figure 11A:
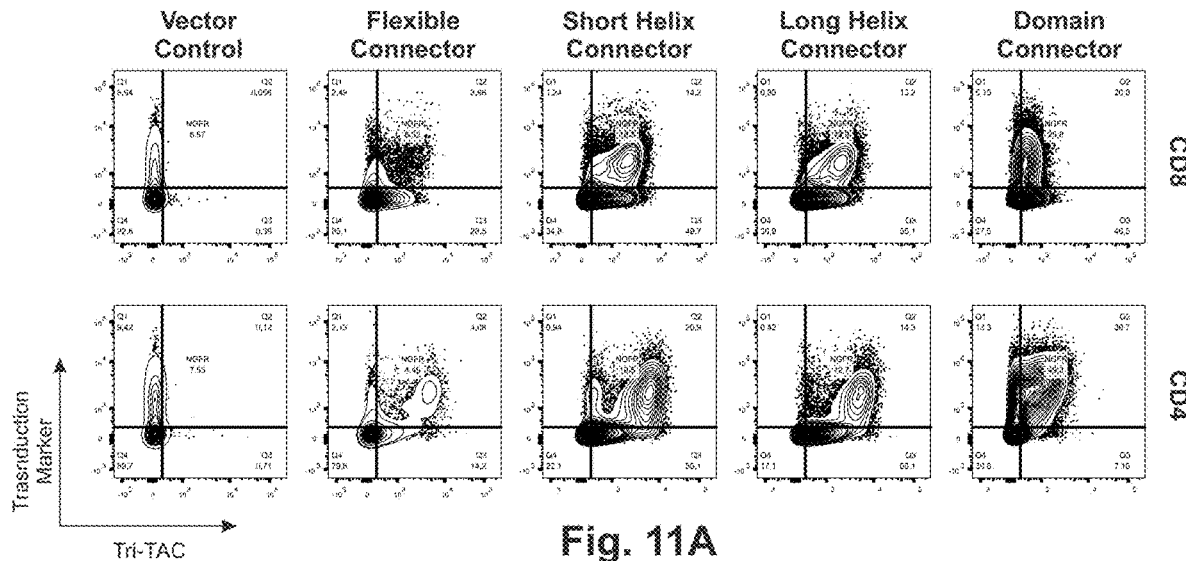
FIG. 11A-FIG. 11E illustrate exemplary in vitro parameters of CD19 TAC engineered with different connector variants.
Figure 11B:
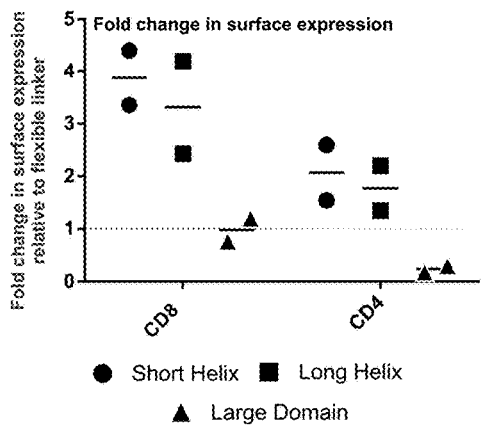
Figure 11C:
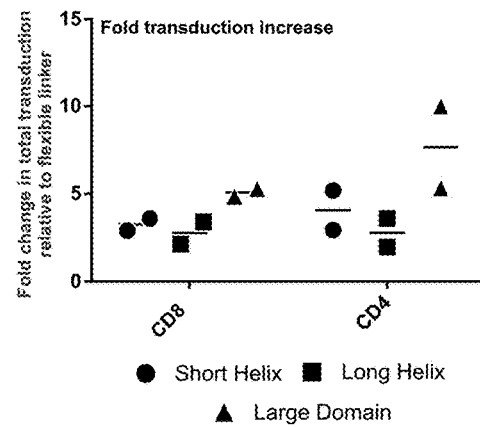
Figure 11D:
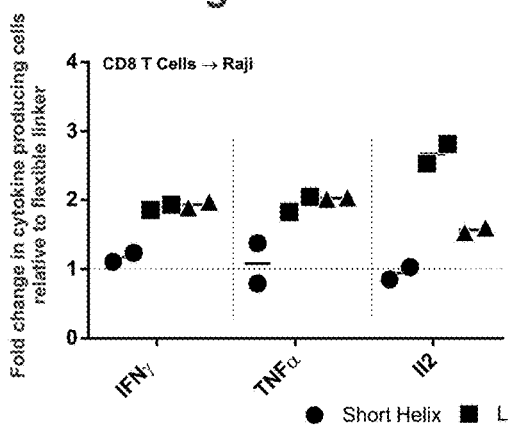
Figure 11E:
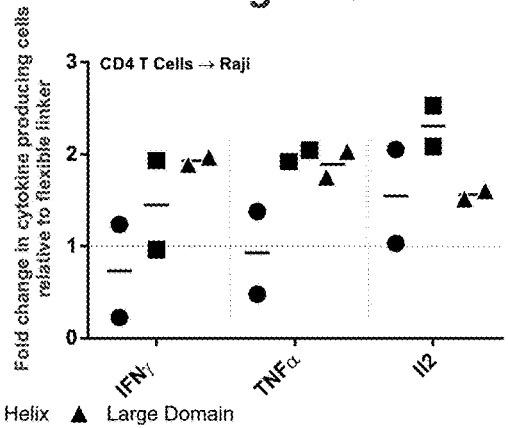

FIG. 11A-FIG. 11E illustrate the impact of connector substitution on Tri-TAC surface expression, Tri-TAC transduction efficiency, and cytokine production upon Tri-TAC ligation. FIG. 11A and FIG. 11B show that the helical linkers enhance surface expression and transduction efficiency when compared to the flexible linker, while the large domain connector enhances transduction efficiency but not surface expression. FIG. 11D, FIG. 11E illustrates cytokine production by cells expressing Tri-TACs with short helix, long helix, or large domain connectors.

Figure 12A:
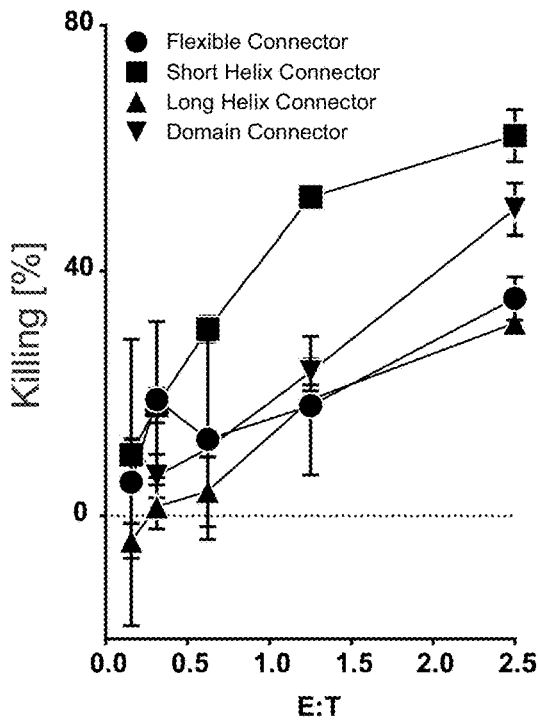
FIG. 12A illustrates in vitro cytotoxicity of BCMA Tri-TAC variants engineered with different connectors.
Figure 12B:
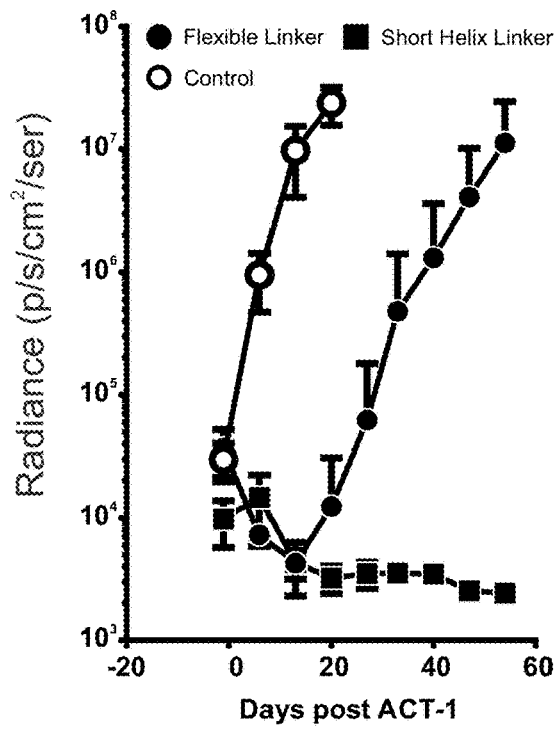
FIG. 12B illustrates in vivo tumor control of BCMA Tri-TAC variants engineered with the flexible connector compared to the short helical connector.

FIG. 12A illustrates enhanced in vitro cytotoxicity of T cells expressing Tri-TACs with the short helix connector. FIG. 12B illustrates enhanced in vivo tumor control of T cells expressing Tri-TACs with the short helix connector. The short helical connector was associated with high in vitro cytotoxicity and effective in vivo tumor control.

Example 4. Introducing a CD8α/β Cytosolic Domain

Figure 13A:
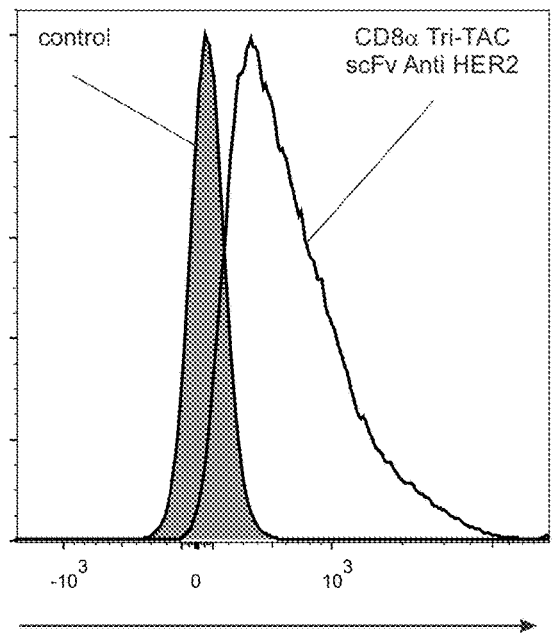
FIG. 13A-FIG. 13C illustrate properties of CD8a Tri-TAC scFv anti HER-2, and CD8a Tri-TAC DARPin anti-HER-2.
Figure 13C:
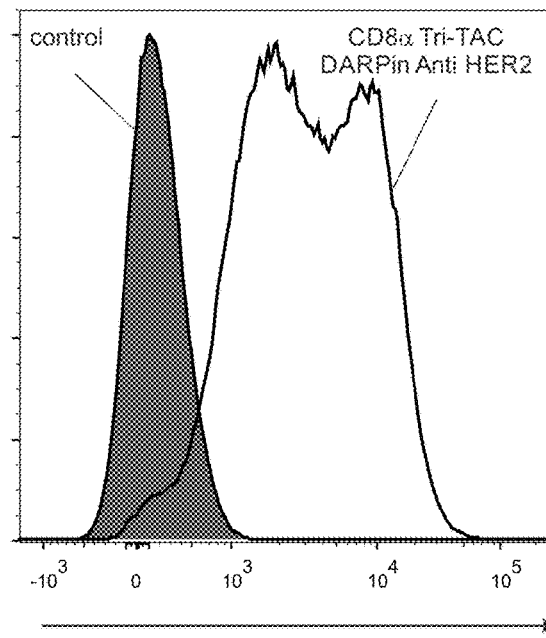
Figure 13B:
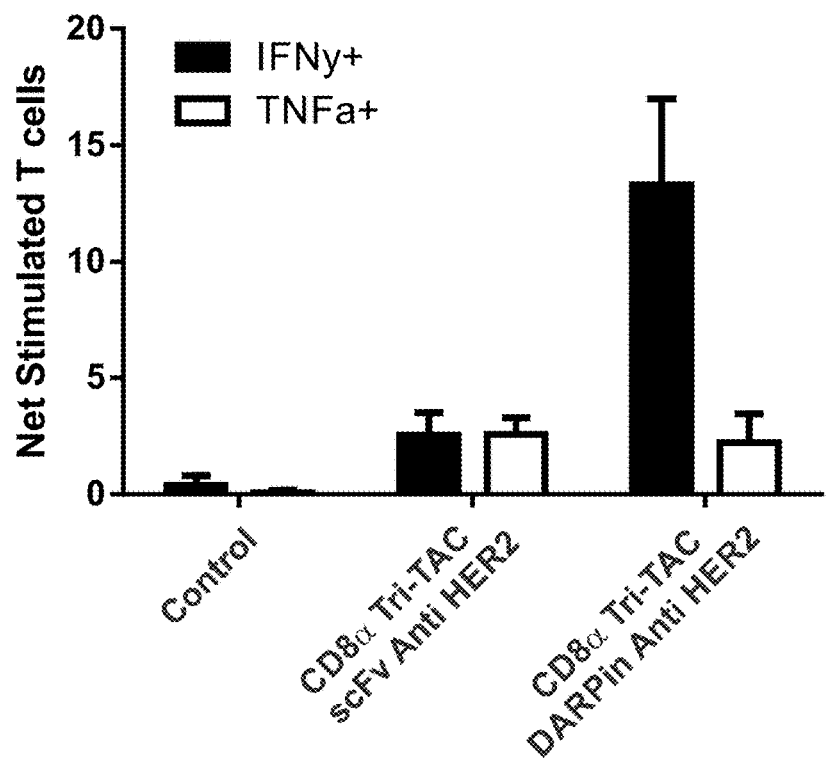

FIG. 13A illustrates surface expression of CD8α Tri-TAC paired with an anti-HER-2 scFv or FIG. 13C anti-HER-2 DARPin. FIG. 13B illustrates cytokine production by T cells expressing CD8α Tri-TAC paired with an anti-HER-2 scFv or anti-HER-2 DARPin.

Figures 14A, 14B, 14C, 14D:
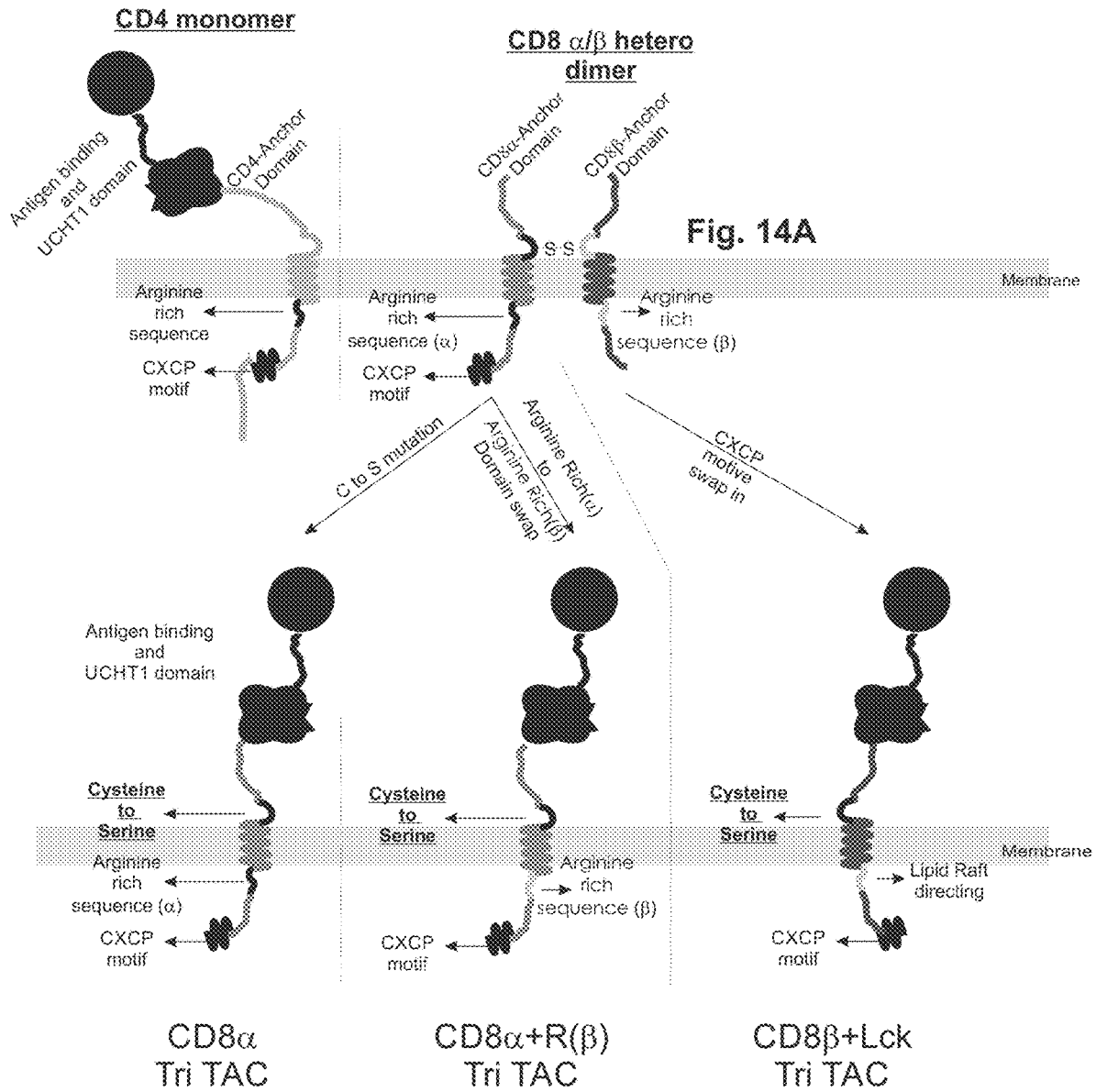
FIG. 14A-FIG. 14D provide schematics of CD8 Tri-TAC variants. The anti HER-2-DARPin is used as an exemplary antigen-binding domain and the UCHT1 CD3 recruitment domain is used as an exemplary recruitment domain.

FIG. 14A illustrates a CD4 Tri-TAC monomer and a CD8α/β heterodimer. TCR co-receptors, both CD4 and CD8, carry functional domains that are important for the co-receptor functionality. These regions include the arginine rich region that is hypothesized to be important for lipid raft association, and the CXCP motif required for Lck binding. Unlike CD4, which is a monomer, the CD8 co-receptor is a heterodimer composed of an α and a β subunit (FIG. 14A). Both the α and β CD8 subunits contain arginine rich regions, but only the α subunit contains the CXCP motif.

FIG. 14B-FIG. 14D provide schematics of Tri-TAC variants that incorporate elements from the CD8 co-receptor shown in FIG. 14A. The cysteine responsible for dimerizing CD8α and CD8β was replaced with an alanine in all CD8 Tri-TAC variants. FIG. 14B is a schematic of a CD8α Tri-TAC comprising a Cysteine to Serine mutation to ensure a monomeric receptor distribution, and a CD8α cytosolic domain. FIG. 14C is a schematic of a CD8α+Rβ Tri-TAC comprising a Cysteine to Serine mutation to ensure a monomeric receptor distribution, and a chimeric CD8α cytosolic domain where the CD8α arginine rich region is replaced with the CD8β arginine rich region. FIG. 14D is a schematic of a CD8β+Lck Tri-TAC comprising a Cysteine to Serine mutation to ensure a monomeric receptor distribution, and a chimeric CD8β cytosolic domain, where the CD8α CXCP domain, which contains an Lck binding motif, was added to the C-terminus of the CD8β cytosolic domain.

Figure 15A:
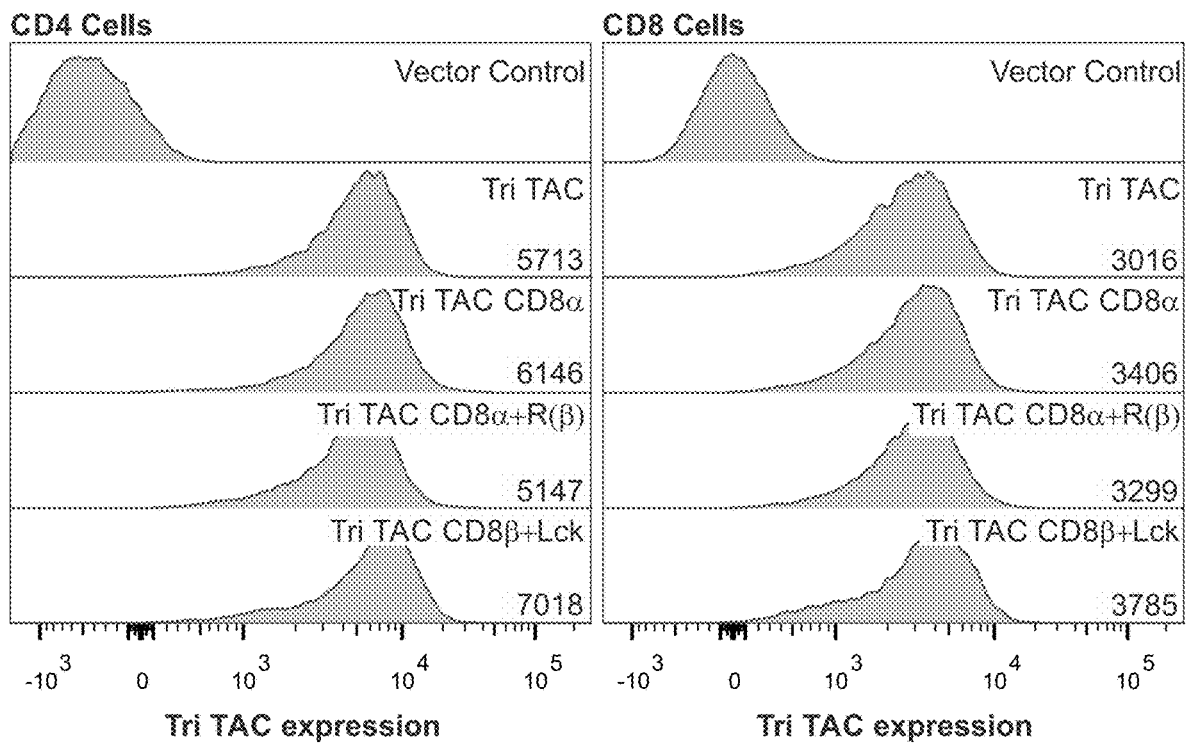
FIG. 15A-FIG. 15E illustrate in vitro characterization of CD8 Tri-TAC variants relative to the prototypic Tri-TAC containing CD4 regions.
Figure 15B:
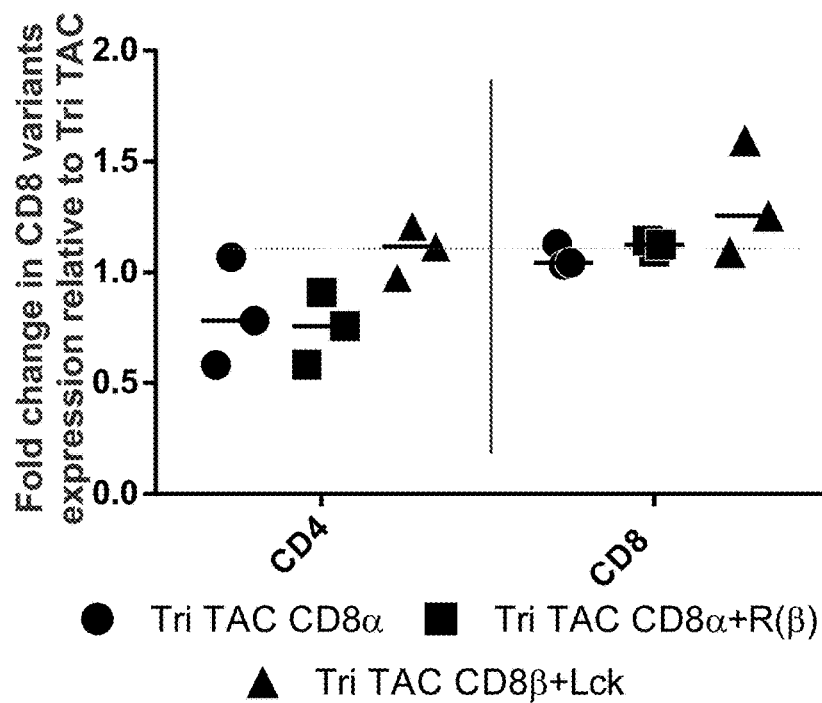
Figure 15C:
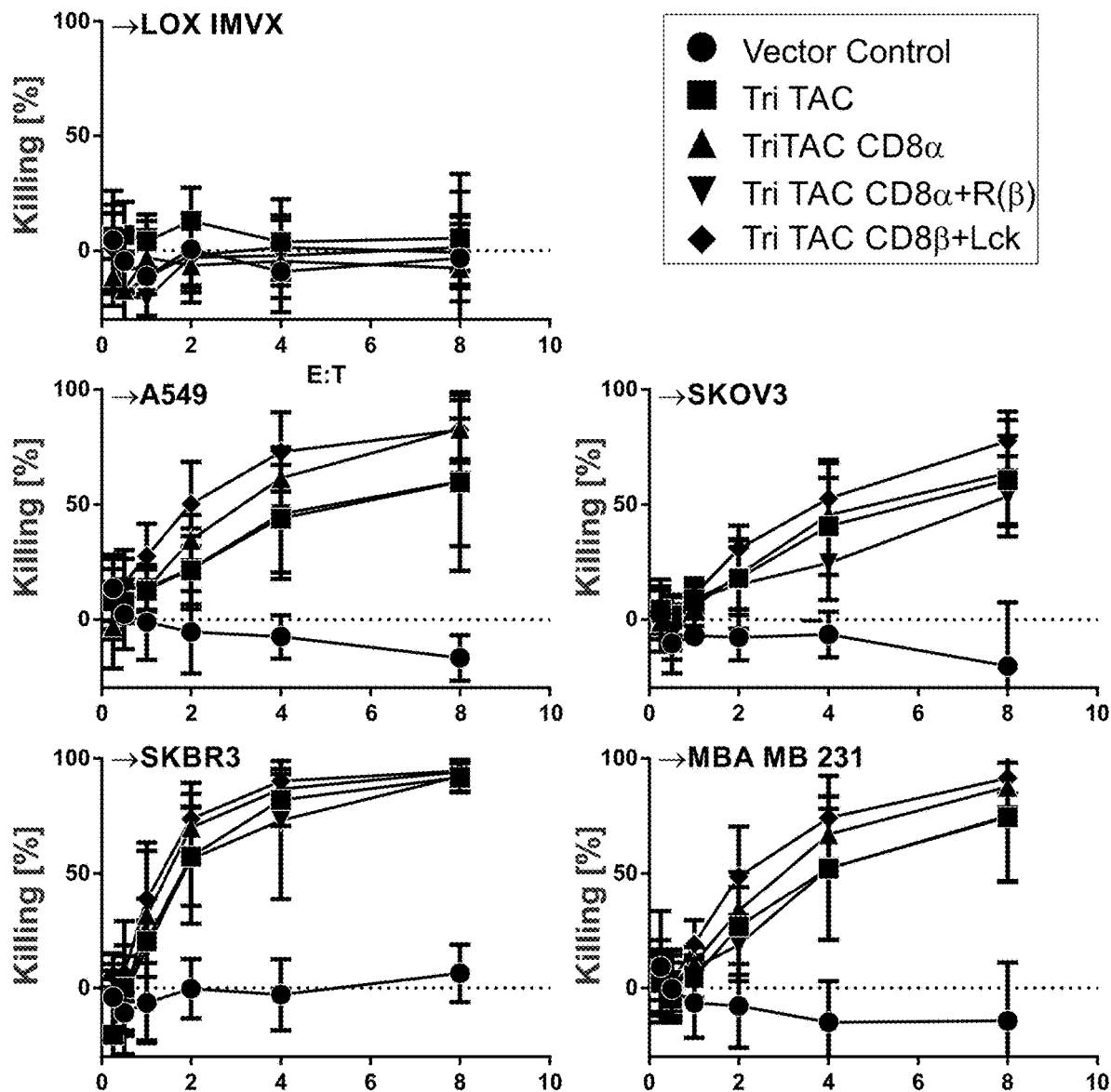
Figure 15D:
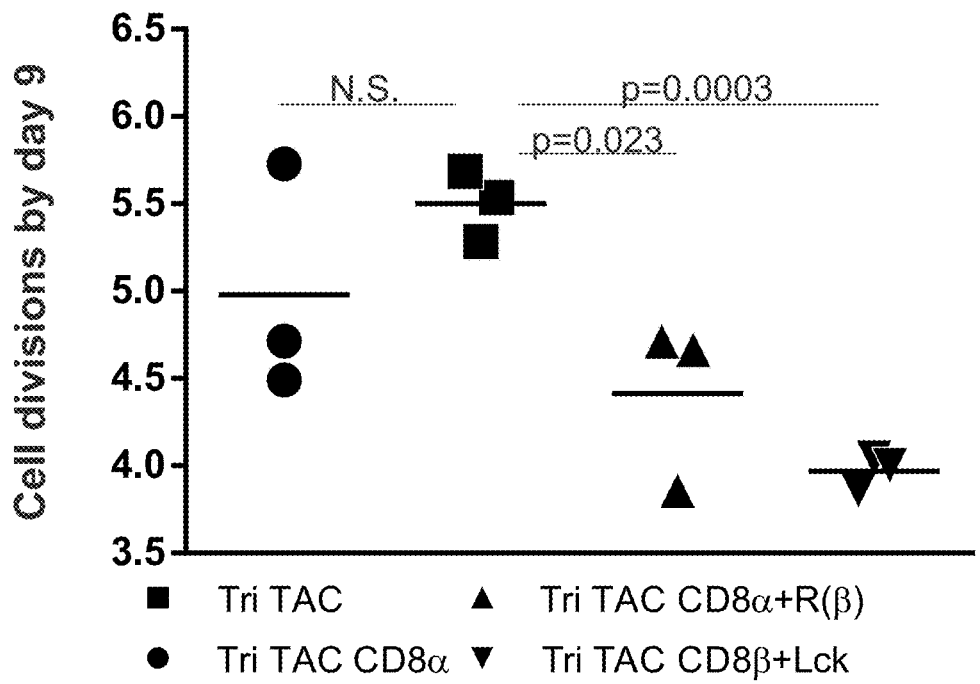
Figure 15E:
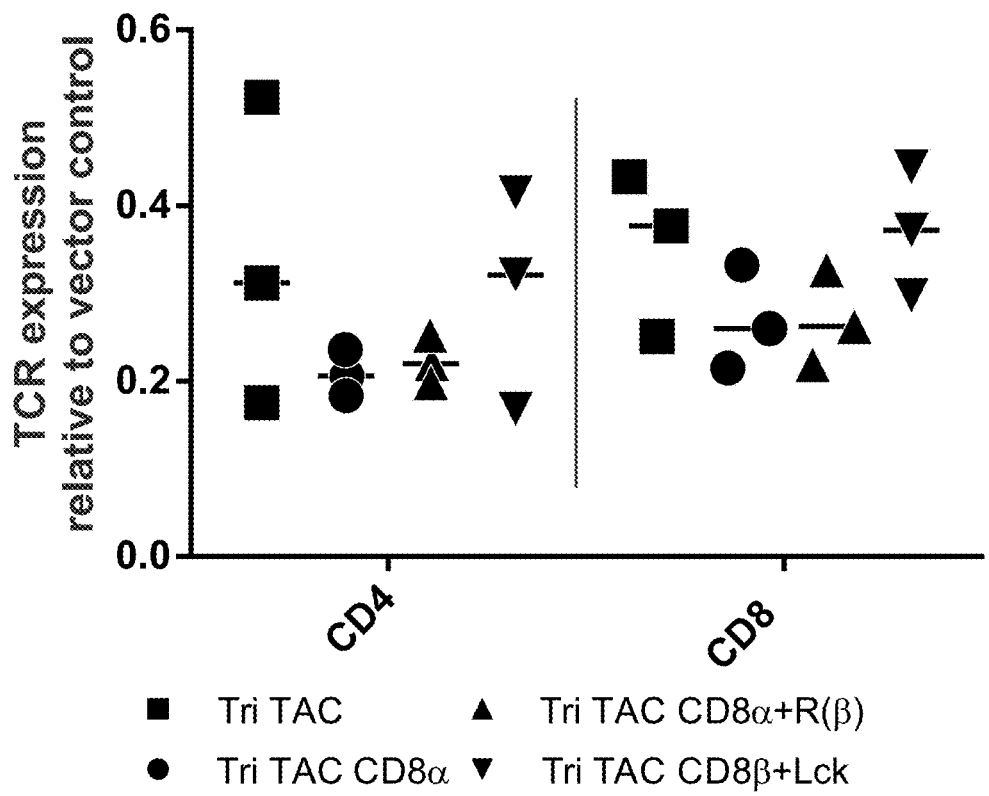

FIG. 15A-FIG. 15D illustrate various phenotypic and functional attributes of the CD8-based Tri-TAC variants relative to the prototypical Tri-TAC. FIG. 15A-FIG. 15B illustrate surface expression of CD8-Tri TAC variants relative to the prototypic Tri-TAC. Surface expression was comparable among the different Tri-TACs. FIG. 15C illustrates in vitro cytotoxicity of CD8-Tri TAC variants co-cultured with LOX IMVI (HER-2 negative) and A549, SKOV3, SKBR3 or MBA MB 231 (all are HER-2 positive). All T cells engineered with Tri-TACs exhibited cytotoxicity. FIG. 15D illustrates cell division of T cells engineered with either the CD8 Tri-TAC variants or the prototypic Tri-TAC (FIG. 15D). FIG. 15E illustrates TCR surface expression of engineered T cells comprising CD8 Tri-TAC variants or the prototypic Tri-TAC. All Tri-TAC variants had a similar effect on TCR expression. While the CD4 co-receptor demonstrated good surface expression and functionality with both the scFv and DARPin anti HER-2, the CD8α construct showed activity only in the context of the DARPin antigen binding domain. When testing different CD8α cytosolic domains, all the configurations contained the reported key sequence attributes associated with co receptor functionality (Arginine rich region and CXCP). All CD8α/β constructs showed similar performance when compared to the CD4 prototype. This emphasizes that the retention of specific biochemical properties, such as lipid raft affinity and Lck binding, is more important to determine Tri TAC performance than a specific cytosolic polypeptide sequence.

The growth of T cells engineered with the CD8α+R(β) and the CD8β+Lck Tri-TACs was significantly impaired relative to the growth of T cells engineered with the other variations. Despite a significant impact on growth, these Tri-TACs all displayed a comparable ability to activate T cells. The reduced growth of the CD8α+R(β) and the CD8β+Lck Tri-TACs may be advantageous for certain application where maximal T cell expansion is not desirable.

Example 5. Development of a CD19-TAC Construct

Figure 16:
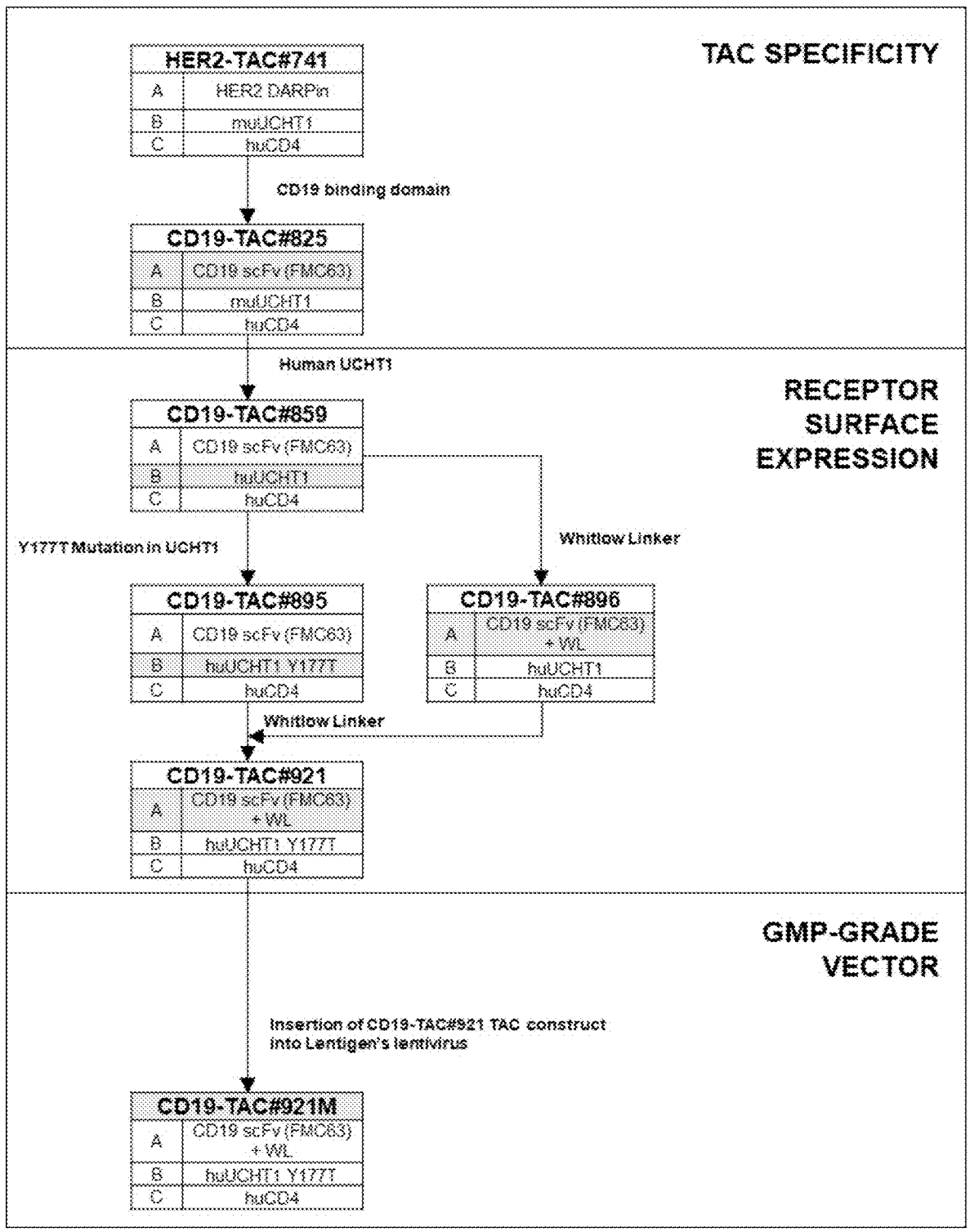
FIG. 16 illustrates various Tri-TACs.

FIG. 16 illustrates the step-wise development of a CD19-TAC construct. Several generations of lentiviral vectors are created with various alterations in design elements to ensure CD19-specificity, proper TAC expression, and GMP-grade lentivirus production. Each box represents a lentiviral vector and specifies the 3 major design elements: (A) the antigen-binding domain, (B) the TCR/CD3-binding domain, and (C) the co-receptor domain. Shaded areas indicate domains that have been the subject of modification during the vector development process.

The TAC in the first step comprises a HER-2-specific designed ankyrin repeat protein (DARPin), a murine UCHT1 CD3-specific scFv, and a flexible transmembrane and cytosolic CD4 polypeptide. The TAC is cloned into a pCCL4 lentiviral vector.

To generate a CD19-specific Tri-TAC, the HER-2-specific DARPin was replaced with a polypeptide comprising an N-terminal CD8α leader peptide fused to an anti-CD19 scFv. The heavy and light chains of the CD19 scFv were connected via glycine-serine linker region.

The UCHT1 domain was replaced with a humanized version (huUCHT1) to reduce immunogenicity. This TAC construct exhibited superior surface expression levels than its precursor.

To further improve receptor expression on the cellular surface of T cells without impairing functionality, two separate modifications were evaluated in parallel. To increase single chain stabilization, the $G_4S$ linker (SEQ ID NO: 73) used in the anti-CD19 scFv was replaced with the more structured Whitlow linker. Separately, a Y177T mutation was introduced into the huUCHT1 domain. Both strategies enhanced the expression of the TAC receptor, and a receptor was generated with both the Whitlow linker and the Y177T mutation.

Figure 17:
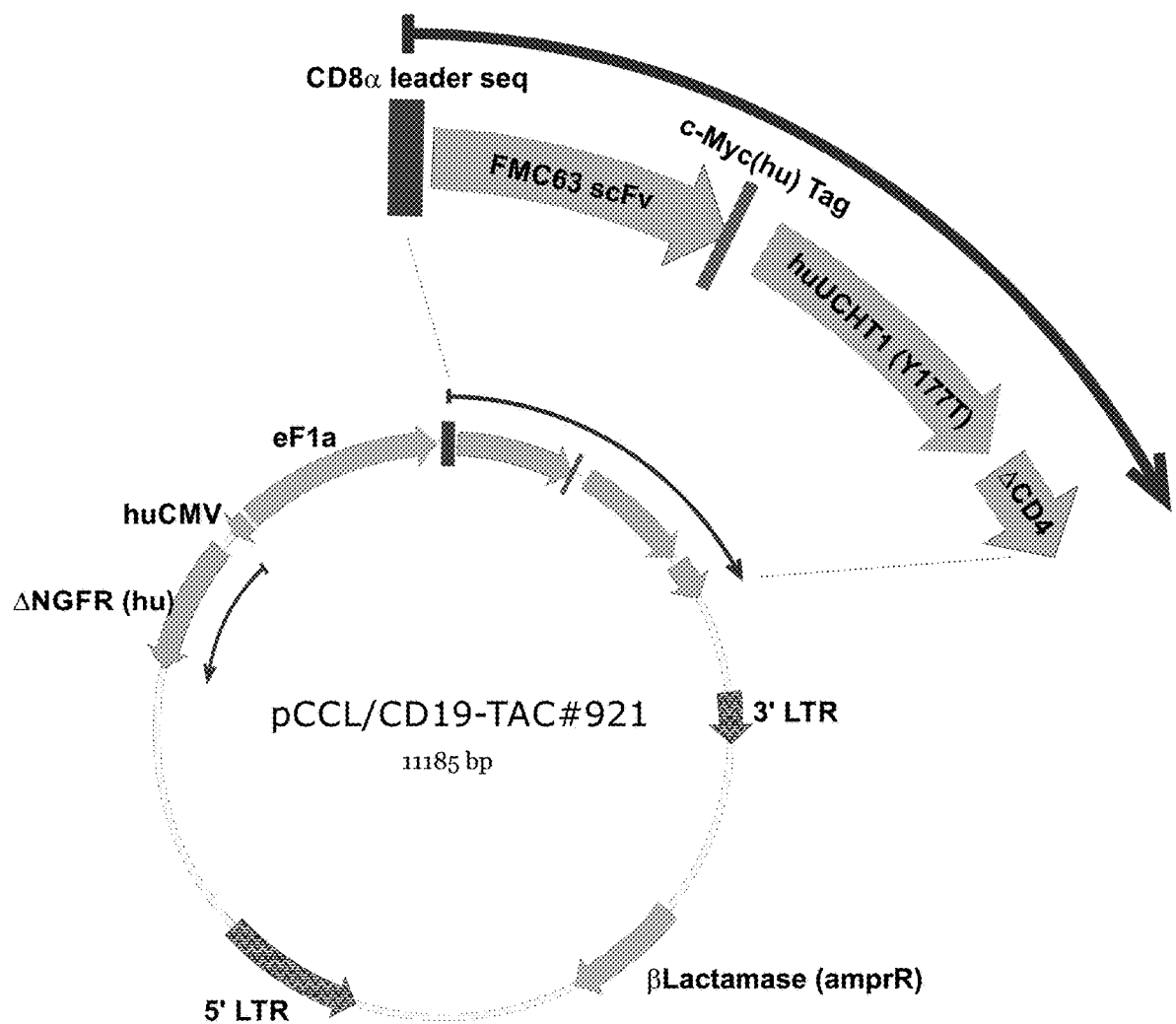
FIG. 17 illustrates TAC-CD19 insert in a pCCL lentiviral vector.

FIG. 17 illustrates a CD19-TAC insert in a pCCL lentiviral vector. The pCCL vector features a bi-directional promoter system with ΔNGFR(hu) under control of the mCMV promoter and TAC expression being driven by the EF-1α promoter. The ΔNGFR(hu) is a truncated human CD271 (Tumor necrosis factor receptor superfamily member 16), with transmembrane domain but lacking the cytosolic signaling domain. The ΔNGFR(hu) expression product is used to quantify lentiviral transduction. The CD19-TAC #921 open reading frame is enlarged to show the key elements of the TAC construct: The CD8α leader, FMC63 single chain (anti-CD19 scFv), the human c-Myc Tag, the huUCHT1 (Y177T) and the ΔCD4 domain. The huUCHT1 (Y177T) mutation was identified by examining point mutations randomly introduced into resides of the murine UCHT1 CD3 epsilon binding interface. In a screen the (Y177T) mutation was successfully identified. The (Y177T) mutation results in better Tri TAC surface expression while retaining T cell activation. ΔCD4 lacks the four CD4 extracellular immunoglobulin like domains and retains the extracellular linker, transmembrane and cytosolic domains.

To generate a GMP-grade lentiviral vector, the CD19-Tri-TAC construct was cloned into a new lentiviral vector under the control of a MSCV promoter. The CD19-Tri-TAC construct is the same as shown in FIG. 17.

Figure 18:
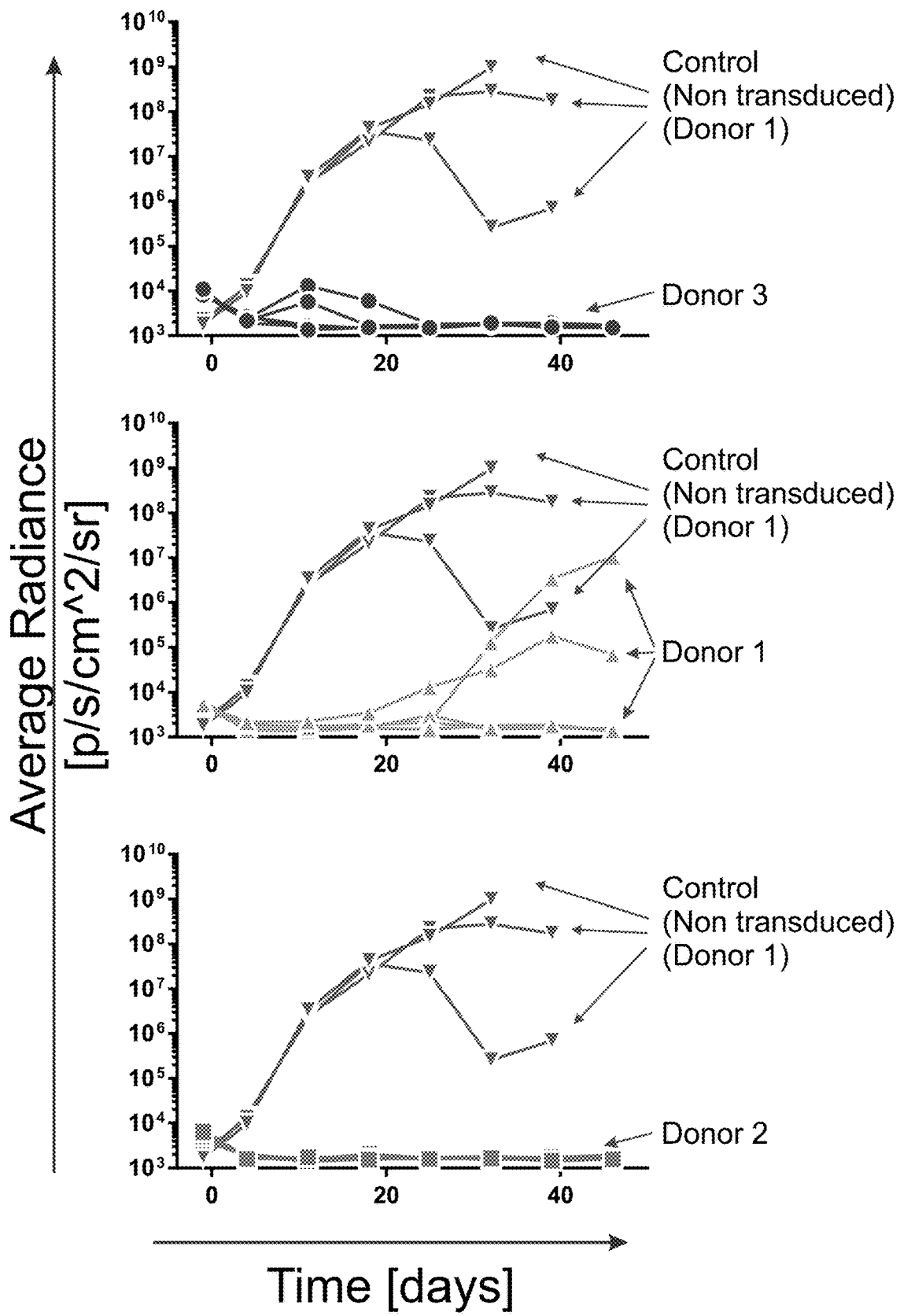
FIG. 18 illustrates the in vivo efficacy of TAC-CD19 generated from different donors.

Example 6. Ability to Manufacture CD19-TAC-Expressing T Cells from Different Donor Material FIG. 18 illustrates the efficacy of CD19 TAC-expressing T cells manufactured from multiple donors. CD19-TAC-expressing T cells were produced using T cells from three different donors, and tested in the NALM-6 tumor model. Mice bearing established NALM-6 tumors were treated with a single dose of $4 \times 10^6$ CD19 TAC-expressing T cells. Control mice showed rapid tumor outgrowth, with all mice reaching endpoint by the termination of the study. T cell products from Donors 1 & 2 resulted in complete control in all mice. T cell product from Donor 3 resulted in robust tumor control in all mice and long-term control in 2/4 treated mice. The study confirms that tumor rejection is achieved by CD19 TAC-expressing T cells derived from multiple healthy donors. The results of the NALM-6 tumor model in FIG. 18 suggest that efficacious CD19 TAC is produced from multiple donor source materials.

Example 7. In Vitro Cytotoxicity and In Vivo Efficacy of CD19-TAC-Expressing T Cells To evaluate the ability of CD19-TAC to effectively engage various CD19-positive cells, Tri-TAC-engineered T cells were co-cultured with either NALM-6 (acute lymphoblastic leukemia), Raji (Burkitt lymphoma) or Jeko-1 (Mantle Cell Lymphoma). NALM-6, Jeko-1 and Raji cells were engineered with enhanced firefly luciferase to enable tracking of tumor burden in vitro and in the live animal via bioluminescence imaging.

Figures 19A, 19B, 19C:
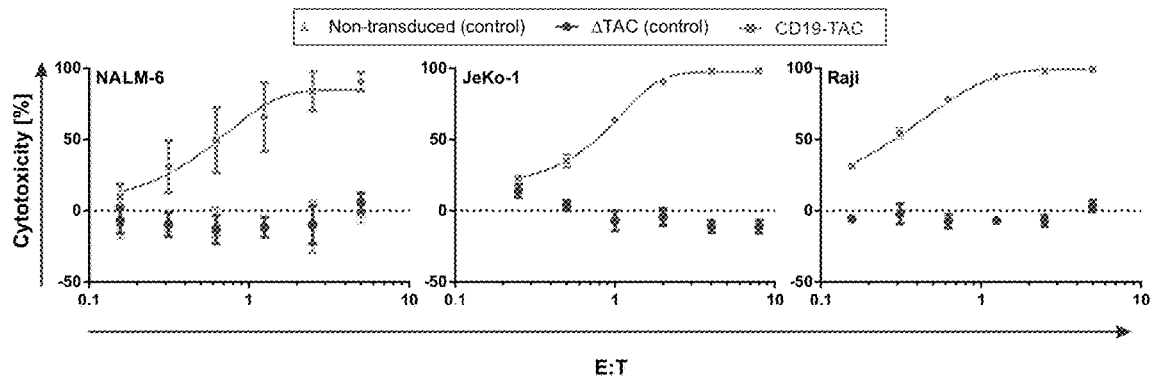
FIG. 19A-FIG. 19C illustrates an in vitro example of TAC-CD19 cytotoxicity against the tumor lines.

FIG. 19A-FIG. 19C illustrates killing of tumor cell lines by CD19-TAC-expressing T cells. The effects were dose-dependent and increased with increasing effector-to-target (E:T) ratios. As negative controls, cells engineered with ΔTAC (lacking an antigen-binding domain) or non-transduced T cells were used. These results demonstrate that CD19-TAC-expressing T cells kill CD19-positive tumor cells.

Figure 19D:
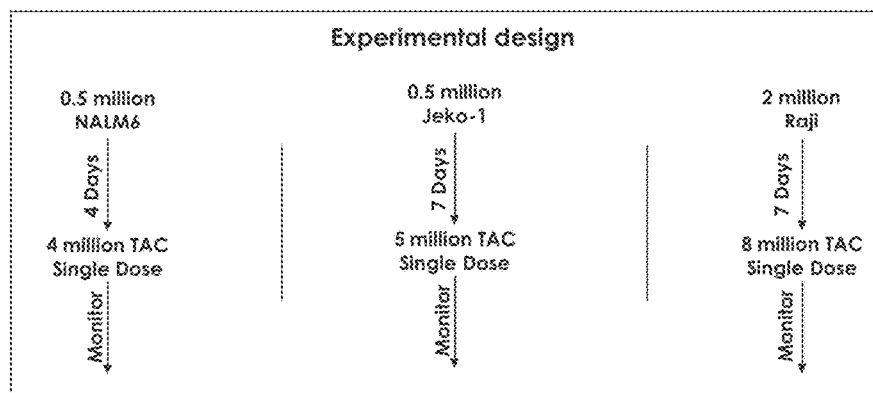
FIG. 19D illustrates the schematic of 3 different in vivo tumor models in NRG mice.
Figures 19E, 19F, 19G:
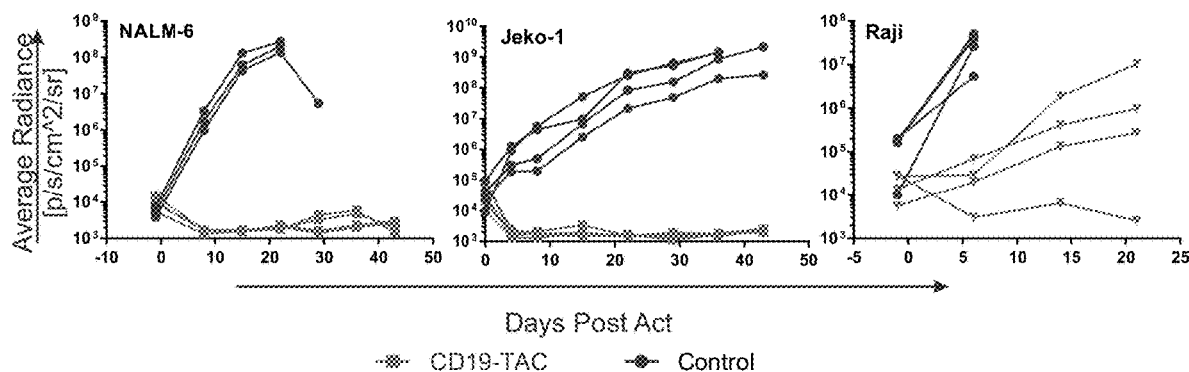
FIG. 19E-FIG. 19G illustrate in vivo efficacy of CD19-TAC in NALM-6 (acute lymphoblastic leukemia) FIG. 19E, Jeko-1 (Mantle Cell Lymphoma) FIG. 19F, and Raji (Burkitt's lymphoma) FIG. 19G.

FIG. 19 D-FIG. 19G illustrates the design and outcome of an in vivo study assessing efficacy of CD19-TAC in mice engrafted with either NALM-6 (acute lymphoblastic leukemia), Raji (Burkitt lymphoma) or Jeko-1 (Mantle Cell Lymphoma) liquid tumors. To initiate NALM-6, Raji and Jeko-1 tumors, mice were inoculated with NALM-6, Raji or Jeko-1 cells and housed 4 or 7 days, respectively, to allow the engraftment of tumors. On day 4 or 7, CD19-TAC-expressing T cells were given as an intravenous tail vein injection. Tumor burden was measured at weekly intervals, and the data are plotted as the average radiance [p/s/cm^2/sr].

FIG. 19 E-FIG. 19G illustrates that CD19-TAC engineered T cells are efficacious in inducing tumor regression and long-term tumor control in NALM-6 (acute lymphoblastic leukemia), Raji (Burkitt lymphoma) or Jeko-1 (Mantle Cell Lymphoma) liquid tumors.

The results of the NAML-6, Raji or Jeko-1 tumor models in FIG. 19A-FIG. 19G suggest that CD19-TAC is efficacious in a variety of CD19 positive tumor models.

Example 8. CD19-TAC-Expressing T Cell Persistence and Lasting Tumor Immunity

FIG. 20A-FIG. 20B illustrate persistence of tumor immunity and resistance to re-challenge in mice receiving CD19-TAC-expressing T cells. Mice bearing established NALM-6 tumors were treated with CD19-TAC-expressing T cells.

FIG. 20A illustrates the experimental set up to determine CD19-TAC persistence in mice. Mice were first inoculated with NALM-6 cells, which following a 4 day engraftment period were treated with CD19-TAC. All mice showed tumor regression and complete tumor control. 56 days after the initial treatment mice were re-challenged with either NALM-6 (CD19 positive) or KMS11 (CD19 negative) liquid tumors. In all cases naïve mice are co-injected with tumor cells and used as negative controls. Tumor burden is followed via luminescence signal.

FIG. 20B: Mice bearing established NALM-6 tumors were treated with CD19-TAC-expressing T cells given as split dose totaling $4 \times 10^6$ engineered cells. As controls, a group of un-treated animals was used. Following ACT, treated mice presented durable anti-tumor responses. In contrast, control mice showed exponential increases in tumor masses and reached tumor burden related endpoint. On day 56 post-ACT, mice were re-challenged with either NALM-6 tumor cells (CD19 positive) or KMS11 tumor cells (CD19 negative). CD19-TAC-treated mice remain protected from NALM-6 (CD19 positive) tumor cells, but not from KMS11 (CD19 negative) tumor cells.

The results of re-challenge experiments in FIG. 20A and FIG. 20B suggest that CD19-TAC, in some instances, differentiates into long-lived memory cells that retain anti-tumor properties.

Example 9. In Vivo Expansion and Dose Dependency of CD19-TAC-Expressing T Cells

FIG. 21 and FIG. 22 illustrate dose dependency, dose regime (split or single) and expansion of CD19-TAC-expressing T cells in a NALM-6 cancer model. FIG. 21A illustrates experimental design. Mice received either a single dose of CD19-TAC-expressing T cells on day four post-tumor inoculation, or a split dose delivered seven days apart. Multiple CD19-TAC-expressing T cells doses were tested: $0.5 \times 10^6$, $1 \times 10^6$, and $4 \times 10^6$ cells. FIG. 21B control groups of mice receive $4 \times 10^6$ non-transduced cells, or freezing media (vehicle control).

FIG. 21B illustrate survival of mice after NALM-6 injection and CD19-TAC injection. Dose-dependent promotion of survival were observed both in the single dose and split dose groups, with the highest single administration dose limiting tumor growth and promoting survival the mouse.

Figure 22A:
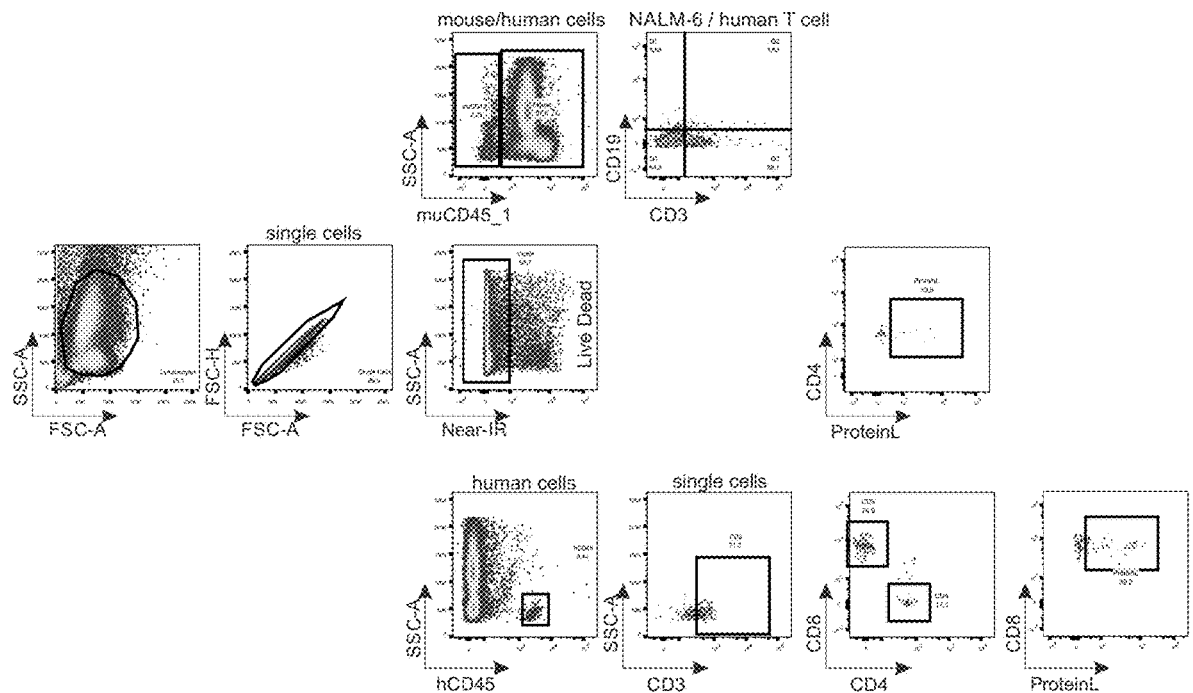
FIG. 22A-FIG. 22B illustrate an experimental setup and data with regard to in vivo expansion of TAC-CD19 following a split dose administration.

FIG. 22A illustrates the gating strategy used to assess T cell proliferation. Cells were first selected based on forward and sideways scatter to select for the lymphocyte population. Singlet cells were identified via a forward scatter area over height gate. Live cells were identified via near IR gating. Human cells were identified via a hCD45 gate. The resulting subset of cells was further divided into CD3 positive cells. These cells were then gated on CD4/CD8 and Protein L. The staining strategy also contained muCD45_1 to identify murine blood cells. CD19 was included to stain for NALM-6 cells.

Figure 22B:
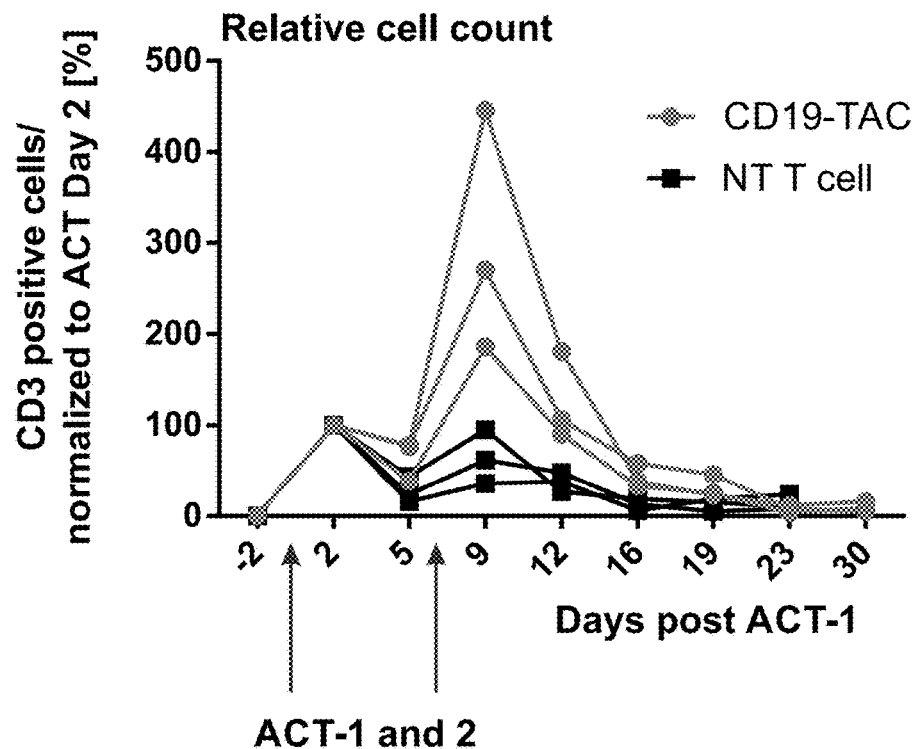

FIG. 22B expansion of T cells in mice after split dose adoptive T cell transfer (ACT). After ACT, blood samples were taken regularly and analyzed via flow cytometry. Values were normalized to the number of total T cells present in the blood post ACT1. Values were also normalized to the total number of CD45.1+ (murine) cells to account for differences in blood draw. T cells in mice treated with CD19-TAC engineered cells were shown to expand in recipient mice within approximately 1-2 weeks after the first ACT (FIG. 22B). Non-transduced cells did not expand (FIG. 22B).

The results of the various doses, dose regimen (FIG. 21B) and T cell counts (FIG. 22B) suggest that CD19-TAC efficacy is dose dependent, that engineered T cells expand in vivo, and that this expansion is specific to CD19-TAC engineered cells in animals carrying CD19-positive tumors.

Example 10. In Vivo Efficacy, Long Term Efficacy and Safety CD19-TAC Treatment

Figure 23A:
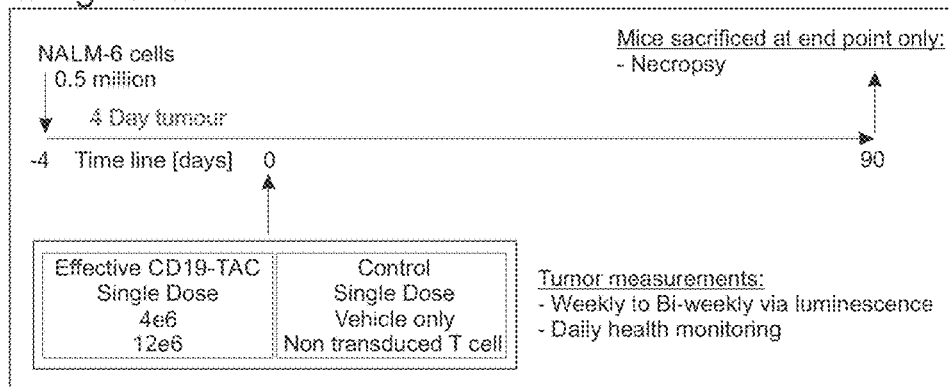
FIG. 23A-FIG. 23C illustrate long term in vivo studies of TAC-CD19 in mice.
Figure 23B:
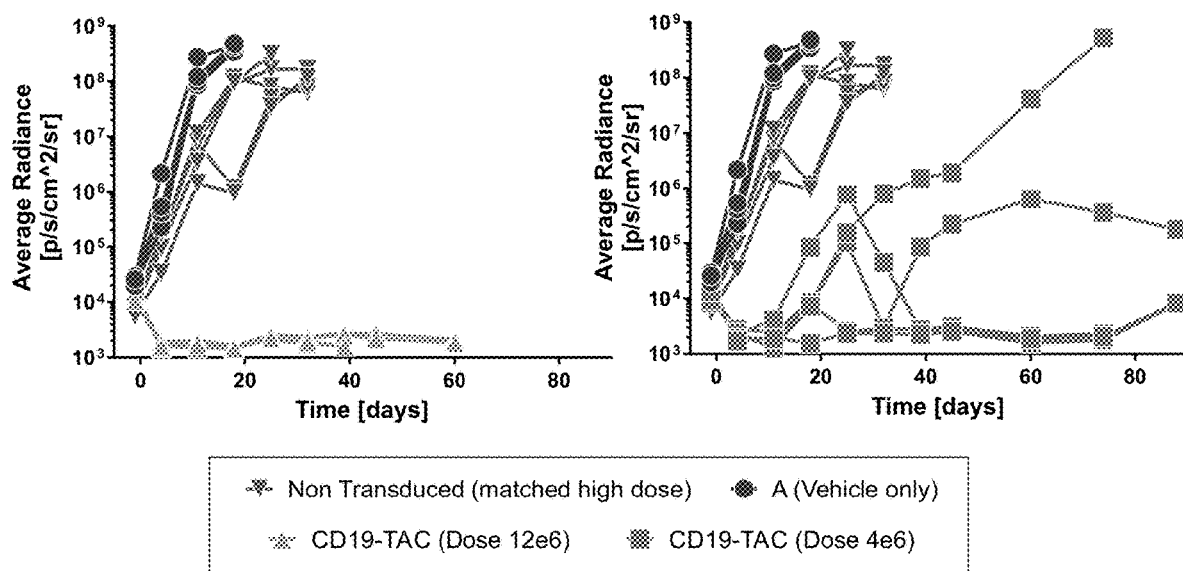
Figure 23C:
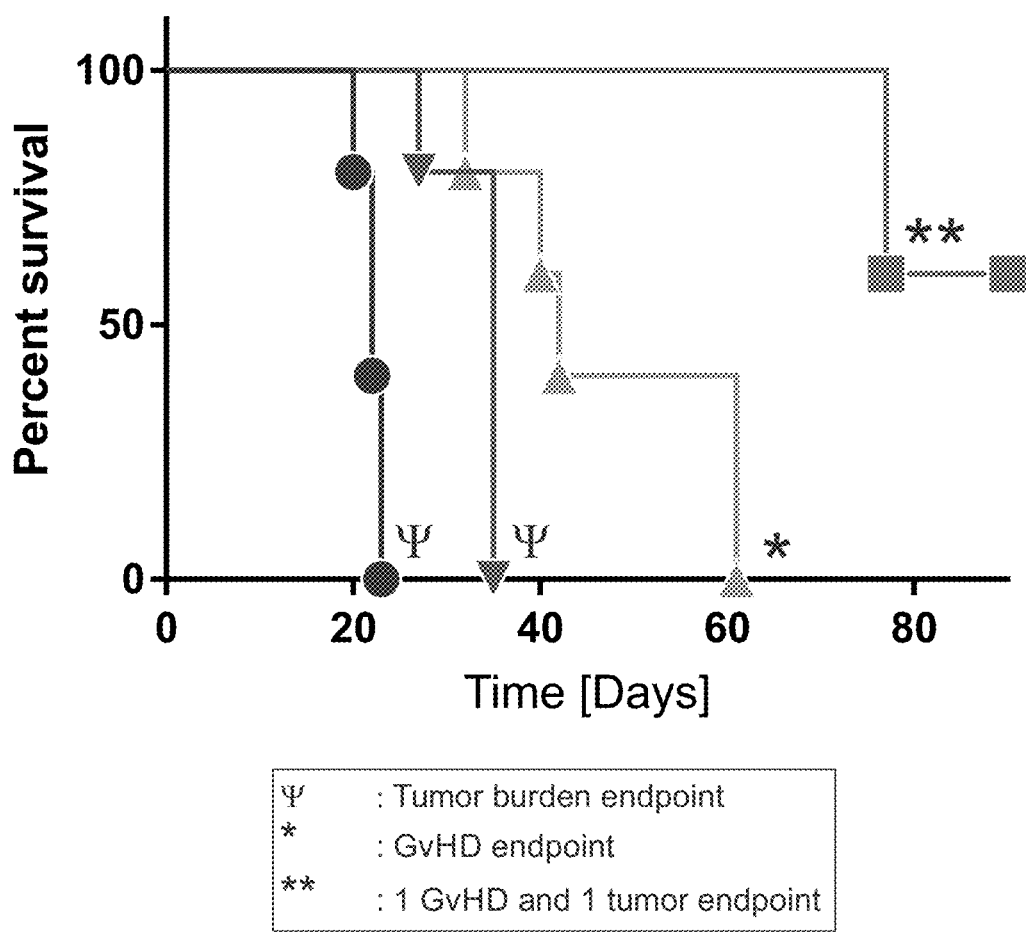
Figure 24:
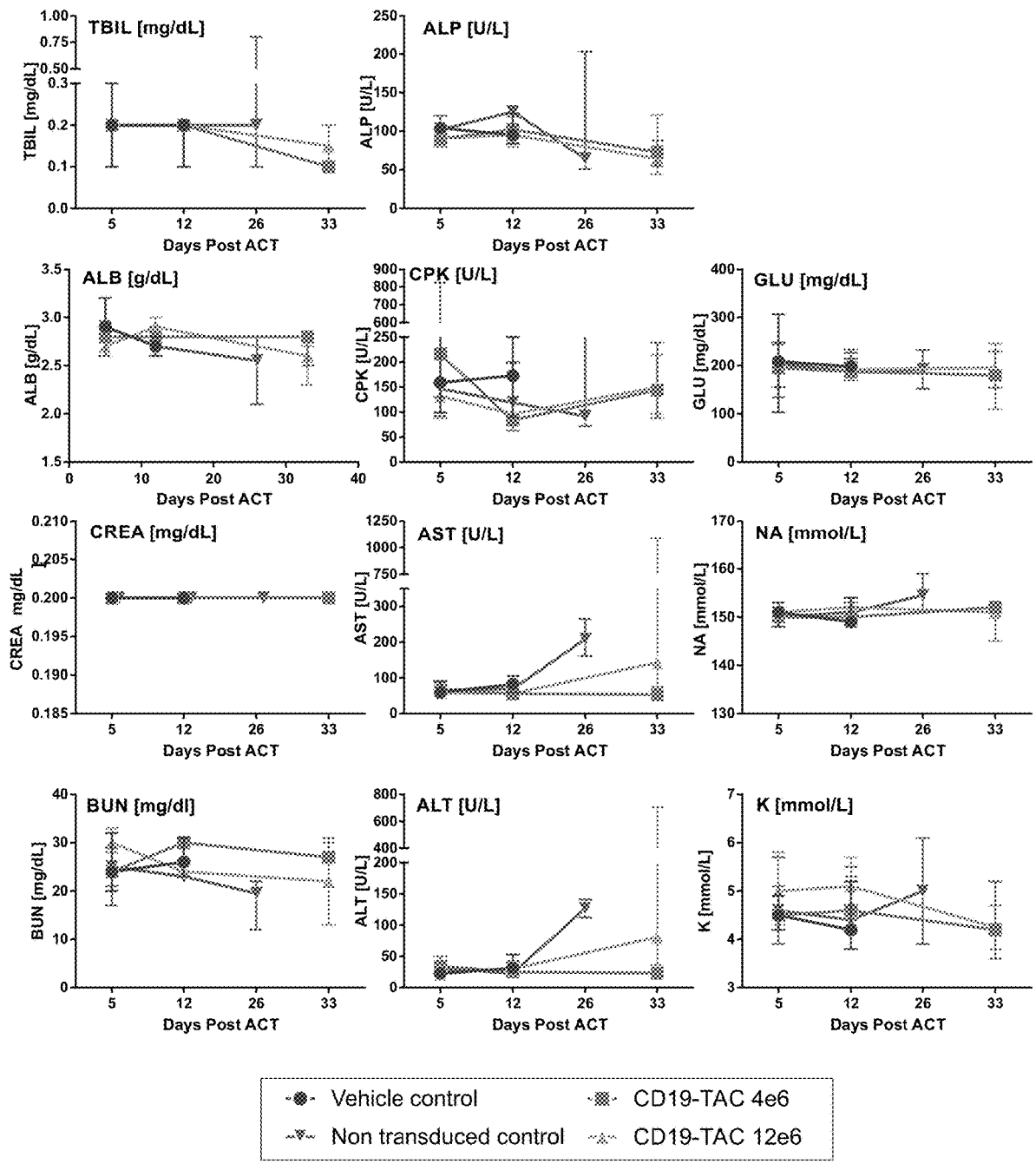
FIG. 24 illustrates clinical chemistry analysis results from mice treated with TAC-CD19 or non-transduced T cells.

FIG. 23-FIG. 25 demonstrate the long-term safety and efficacy (FIG. 23) and in the absence of any acute treatment associated toxicities (FIG. 24-FIG. 25).

FIG. 23A illustrates the experiment design. Mice were injected with $0.5 \times 10^6$ enhanced luciferase engineered NALM-6 cells, which were allowed to engraft for 4 days. Mice are then treated with two dose levels (4 and $12 \times 10^6$ engineered cells) of CD19-TAC-engineered T cells in a single dose administration. Tumor growth was then followed via regular luminesce measurements. Mouse health was regularly assessed via inspection of mouse behavior and physical characteristics (grooming, motility, fur integrity)

FIG. 23B illustrates the tumor burden via luminescence following treatment with either vehicle alone (Freezing media), non-engineered control cells (Total T cell dose equal to total T cell dose of highest engineered treatment group) and either 4 or $12 \times 10^6$ engineered CD19-TAC engineered T cells. Both controls show rapid tumor outgrowth and no anti-tumor efficacy. The control dose results in a delay in tumor outgrowth relative to vehicle alone, presumably due to competition between high dose T cell and tumor cells for engraftment niches. Engineered T cell show tumor regression in all cases. High dose treatment groups show complete tumor control in all cases. The $4 \times 10^6$ treatment group shows 3 mice with complete control, one with delayed tumor outgrowth and one with controlled but high tumor burden.

FIG. 23C illustrates overall survival of the different treatment groups. In both, the vehicle and non-engineered control mice, all mice succumb to the tumor within 23 to 35 days respectively. In case of high dose CD19-TAC treatment all mice develop GvHD symptoms and succumb to GvHD within 61 days. GvHD is a consequence of the mouse model itself and not the treatment with the modified T cells. Low dose mice show survival of 3 mice until end of study at 90 days, one mouse succumbs to high tumor burden, one mouse succumbs to GvHD.

FIG. 24 and FIG. 25 illustrates clinical chemistry parameters and cytokine levels from vehicle control, non-engineered and CD19-TAC (4 and 12×10$^6$ effective CD19-TAC engineered cells) treated mice. Mice were followed for 33 days with blood samples taken 5, 12 and 33 days post ACT. Only CD19-TAC treated mice survived for 33 days. Vehicle control mice succumbed to tumor burden before a 3$^{rd}$ blood sample could be collected, non-engineered cells were sacrificed early on day 26, immediately prior to mice reaching tumor burden related endpoint. All blood samples were analyzed for several clinical chemistry parameters and cytokine levels.

FIG. 24 illustrates that at day 5 and 12 CD19-TAC treated mice show no parameter that is significantly higher compared to control groups. At day 33 all treated mice show clinical chemistry parameters comparable to early treatment time points, with the exception of Alanine Aminotransferase (ALT) and Aspartate Aminotransferase (AST) where some mice experience high levels, similar to mice treated with non-engineered cells sampled on day 26.

Figure 29:
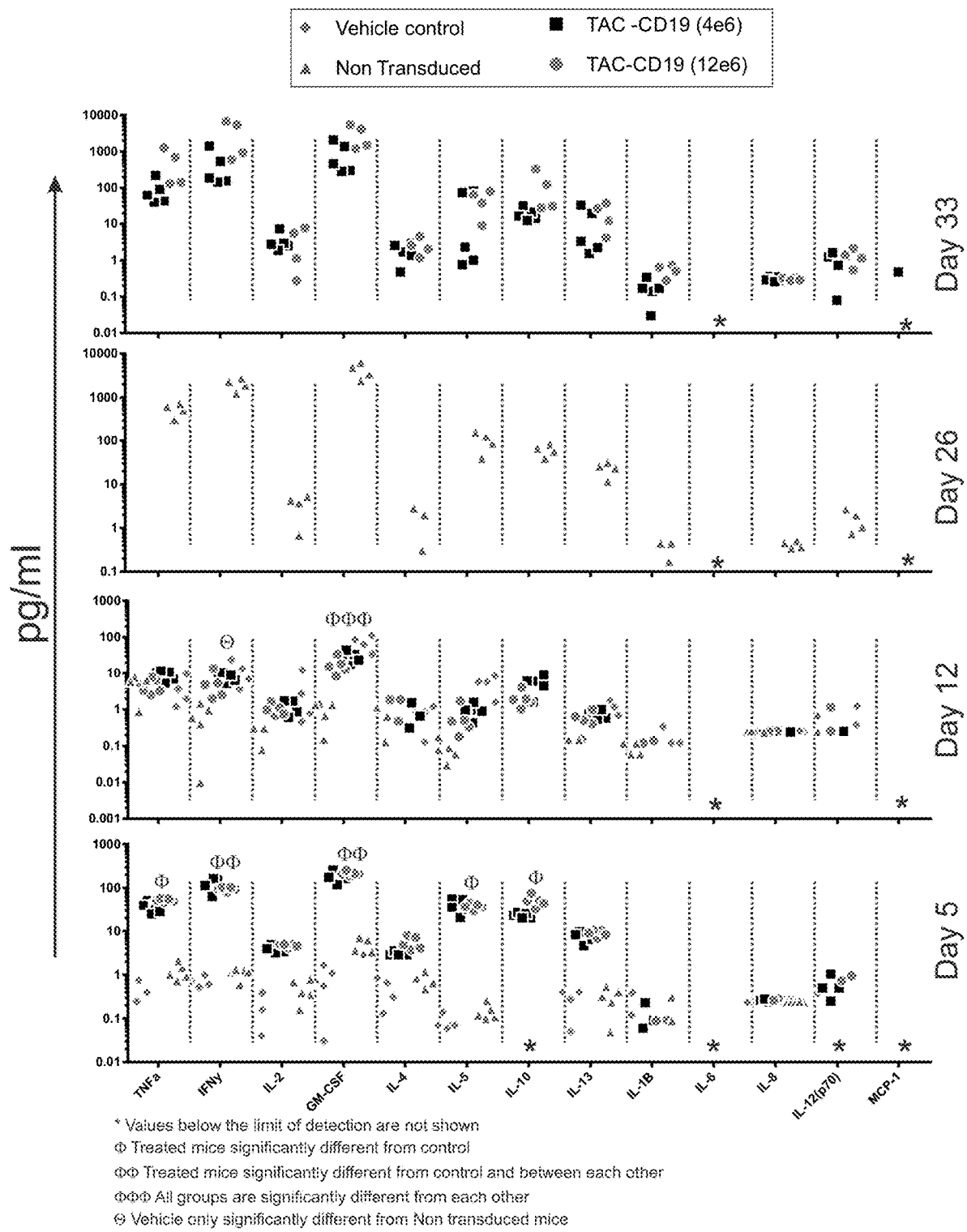
FIG. 29 illustrates human cytokine released in mice blood following treatment with TAC-CD19 or non-transduced T cells.

FIG. 25 illustrates the cytokine response on day 5, 12 and 33. On day 5 post ACT CD19-TAC but not control mice show elevation in all cytokines tested. The cytokine increase is in agreement with an inflammatory response of CD19-TAC engineered T cells recognizing and reacting to antigen positive NALM-6 tumor cells. Following their initial reaction by day 12 cytokine levels subside, which correlates with the by then induced tumor regression and generally low tumor burden. On day 12 cytokine levels between CD19-TAC treated are either similar or lower than non-engineered T cells except for IL10. At the later stage all mice treated with non-transduced or CD19-TAC engineered T cells show an increase in cytokines, presumably associated with GvHD onset. See also FIG. 29, which illustrates cytokine response on day 5, 12, 26 and 33.

The results of the long-term follow up of mice treated with CD19-TAC and their clinical chemistry profile demonstrate that engineered T cells are safe to use and do not show any indication of toxicity caused specifically by CD19-TAC engineering. The results of the cytokine study demonstrate an early inflammatory response associated with anti-tumor efficacy, following by a drop in all cytokine levels, suggesting that a controlled inflammatory response.

Example 11. In Vivo Efficacy of Several BCMA Tri-TAC Variants

Figures 26A, 26B:
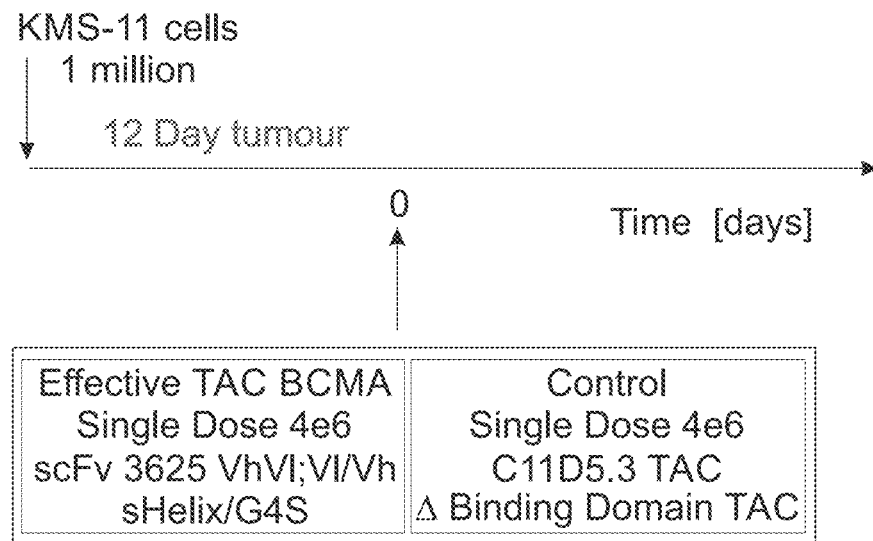
FIG. 26A-FIG. 26C illustrates efficacy of BCMA-TAC in different configurations.

FIG. 26 illustrates an in vivo efficacy study of various BCMA Tri-TAC constructs. FIG. 26A illustrates the overall experimental design. 1 million luciferase-engineered KMS11 (BCMA positive) tumor cells were allowed to engraft for 12 days. Mice were then treated with a single effective dose of 4 million BCMA constructs and controls (FIG. 26B). Tumor burden was regularly assessed via luminescence measurements. All mice that showed tumor regression and tumor control were then re-challenged on day 25 post ACT with 1 million KMS11 cells.

Figure 26C:
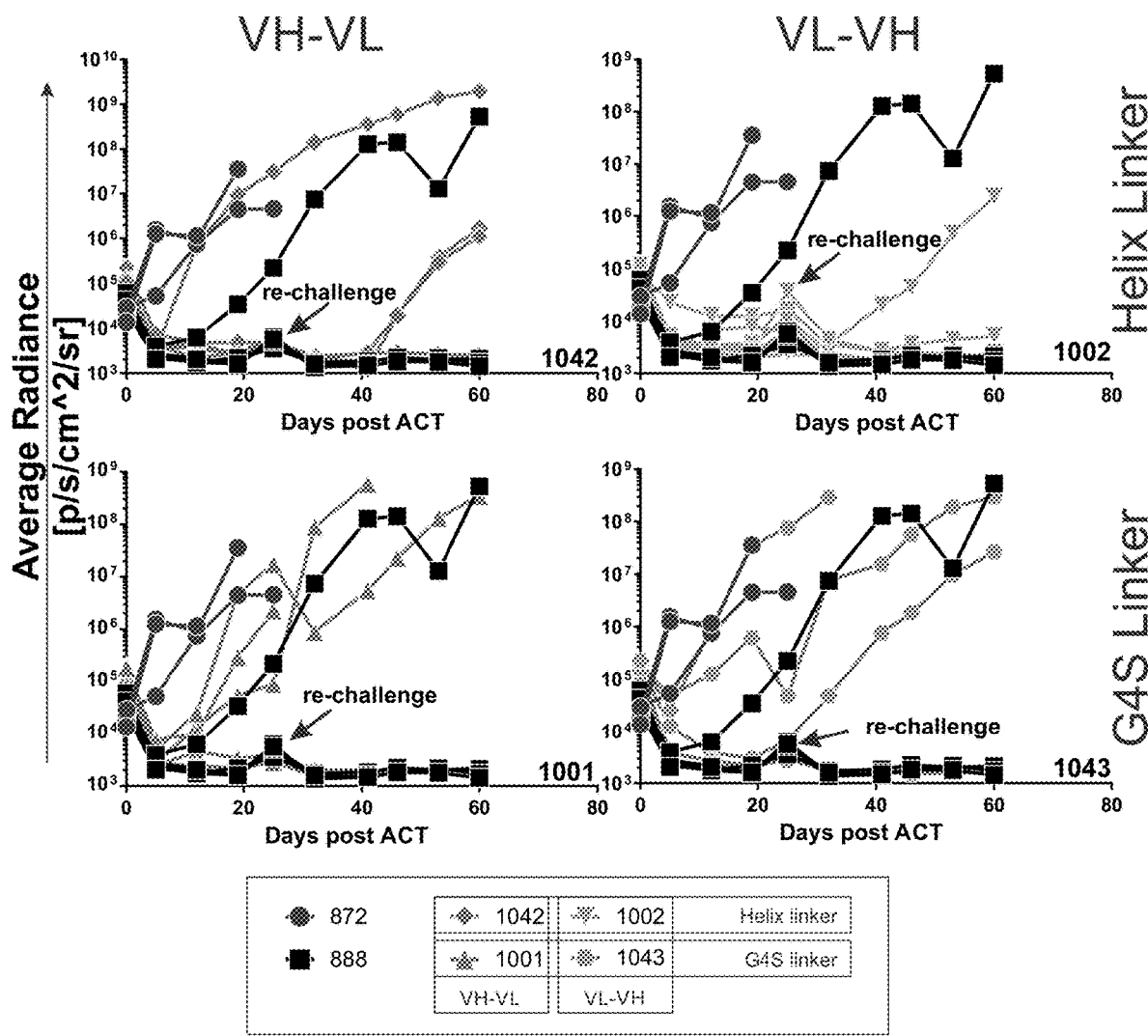

FIG. 26C: Following ACT, control mice exhibited a rapid outgrowth of tumor cells reaching tumor associated endpoint within 19 to 25 days. In contrast all BCMA-TAC treated mice showed initial tumor regression. Tumor control varied across constructs with the G$_4$S (SEQ ID NO: 73) 3625VH-VL showing the lowest level of initial tumor control and Short Helix 3625 VL-VH showing the highest level of initial tumor control. Following re-challenge, a majority of all constructs that had maintained tumor control until day 25 remained protected against re-challenge.

The results of this in vivo study demonstrate, that a variety of BCMA Tri-TAC constructs are effective in controlling KMS11 (BCMA positive) liquid tumors. But that certain preferred configurations provide superior efficacy. In general, the helical connector region provided a relative benefit when compared to the flexible linker within the same scFv configuration.

Example 12. In Vivo of TAC-Her2

Mice are inoculated at the hind flank with OVCAR3 solid tumors. Tumors are allowed to establish and grow to a size of 100 mm$^3$. Mice are then treated with a tail vain injection of TAC-Her2 engineered T cells. Tumor volume is measured regularly.

Example 13. Clinical Trial

A clinical study is undertaken wherein subjects of at least 18 years of age with CD19-positive Diffuse Large B-cell Lymphoma who have failed at least two prior lines of therapies including ASCT or who are ineligible for ASCT are treated with CD19-TAC-expressing T cells. The study is an open label, single arm, Phase 1/2 two-stage trial, featuring a dose escalation stage to determine the maximum tolerated dose (MTD) or recommended phase II dose (RPh2D), followed by an expansion cohort at the selected dose.

Upon enrollment, subjects undergo leukapheresis to obtain T cells for manufacture of CD19-TAC-expressing T cells. Upon successful manufacture, subjects enter the treatment phase. This phase involves a lymphodepleting chemotherapy with fludarabine and cyclophosphamide, followed by intravenous (IV) administration of CD19-TAC-expressing T cells. After treatment with CD19-TAC-expressing T cells, subjects enter post-treatment follow-up and are followed for safety, disease status, and survival for 2 years after their last dose of CD19-TAC-expressing T cells. After study completion, subjects are followed for survival, long-term toxicity, and viral vector safety in a separate long-term follow up protocol for up to 15 years after their last dose of CD19-TAC-expressing T cells.

In all groups, safety is assessed throughout the study. T cell expansion is assessed from the time of the first dose of CD19-TAC-expressing T cells until cells are no longer detectable. Radiographic disease assessment is performed by positron emission tomography (PET) and/or computed tomography (CT) scans pre-treatment and approximately 3, 6, 9, 12, 18, and 24 months following the last dose of CD19-TAC-expressing T cells, or until progressive disease, or treatment with additional anti-cancer therapy.

Example 14. Manufacturing of CD19-TAC-Expressing T Cell Drug Products

The manufacturing process of CD19-TAC-expressing T cells drug products involves selecting CD4/CD8 T cells from a leukapheresis product, activating the CD4/CD8 positive cells, transducing the cells with a lentiviral vector comprising the CD19-TAC construct (as described in example 5), expanding the transduced cells to level adequate for the proposed dosing schedule, and harvesting and cryopreserving the final product.

The patient's leukapheresis material with its associated unique subject identifier (UPN) is received into a manufacturing site and given a unique specimen number (ISN). The CD4/CD8 cells are selected are cryopreserved until initiation of the culture process steps.

The cryopreserved CD4/CD8 positively selected T cells are thawed at 37° C., resuspended in appropriate medium and seeded into culture bags with activating reagents, the cultures are incubated overnight at 37° C./5% CO2.

The cells are transduced with the CD19-TAC lentiviral vector at an appropriate multiplicity of infection (MOI) and incubated overnight at 37° C./5% CO2. On subsequent days, the culture is supplemented with complete medium to maintain a desired cell concentration and eventually pooled into transfer bags, pelleted, resuspended and seeded to larger culture bags at the targeted cell density.

For drug product formulation, the harvested cell suspension is resuspended in excipient and cryopreserved with a controlled-rate freezer then transferred to LN2 storage.

The product is shipped to the clinical site in its frozen state, thawed at the bedside and administered intravenously.

Prior to the clinical trial, engineering manufacturing runs are conducted inclusive of all in-process and release testing using healthy donor leukapheresis material. In addition to in-process and release testing, studies supportive of regulatory filings are conducted on final drug product from these engineering runs. These studies include post-thaw stability, initiation of long-term stability, residual testing to assure the clearance of growth-promoting cytokines and early assessment of potential functional/potency indicating assays.

Figure 27:
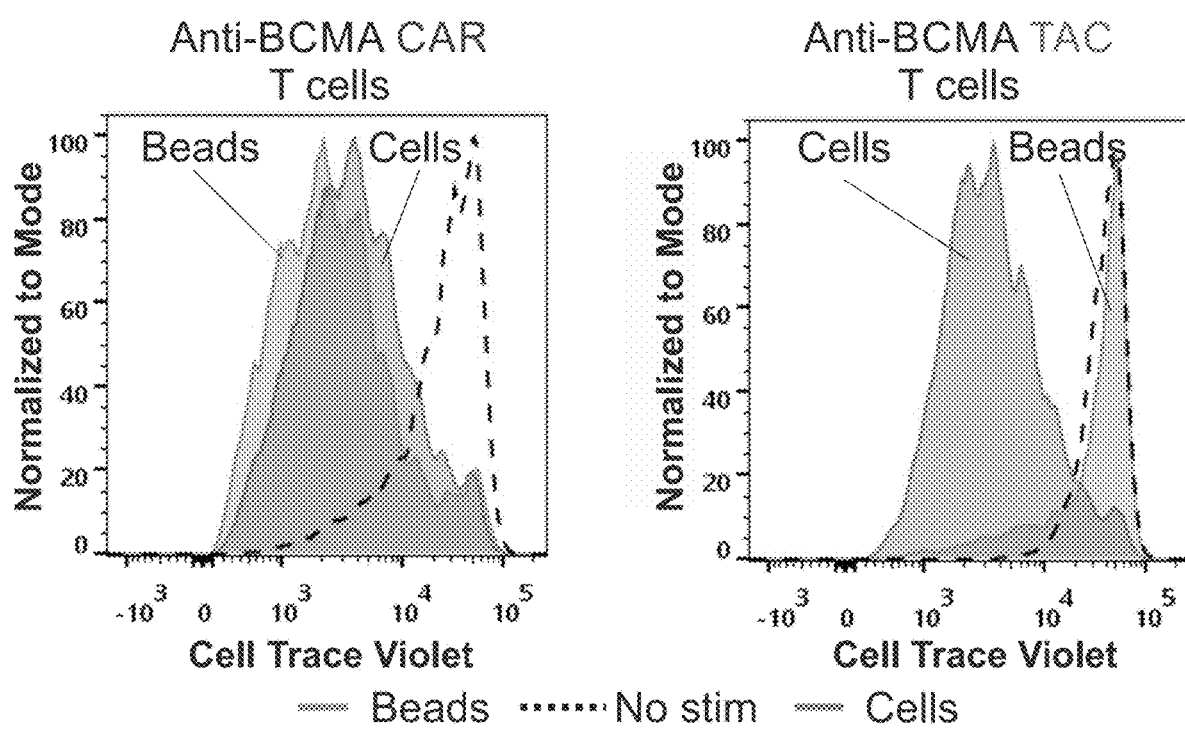
FIG. 27 illustrates that TACs proliferate when encountering antigen on cells, but not when the antigen is presented on artificial beads; but CARs proliferate irrespective if antigens are presented on beads or cells.

Example 15. Preclinical Development of BCMA Specific T-Cell Antigen Coupler (TAC) Therapy for the Treatment of BCMA Positive Malignancies FIG. 27 illustrates that TACs proliferate when encountering antigen on cells, but not when the antigen is presented on artificial beads; but CARs proliferate irrespective if antigens are presented on beads or cells.

FIG. 28A-FIG. 28B illustrate TAC engineered T cells expand in vivo and provide long term protection, indicating cell persistence in a model of myeloma. FIG. 28A-FIG. 28B illustrate BCMA-TAC T cells reject multiple myeloma tumors in a KMS-11 xenograft model engineered with NanoLuc (KMS 11-NanoLuc) ($BCMA^{pos}$). Following tumor engraftment mice were treated with BCMA TAC-T cells (carrying Firefly Luciferase). TAC-T cells expand significantly following administration. This correlates with tumor regression. Treated mice were resistant to tumor rechallenge indicating long term persistence of TAC-T cells.

The data illustrates that TAC-T cells destroy tumor cells likely via a mechanism that mimics the natural process of T cell activation. The TAC technology illustrates 1) strong efficacy in liquid, 2) in vivo proliferation, 3) T cell persistence, protecting mice from re-challenge, and 4) cell expansion following T cell administration.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A T-cell comprising a nucleic acid sequence encoding a CD19 Trifunctional T cell-antigen coupler (CD19-TAC), the nucleic acid sequence comprising:
   (a) a first polynucleotide encoding a ligand that selectively binds a CD19 antigen;
   (b) a second polynucleotide encoding a humanized variant of a UCHT1 (huUCHT1) that binds a CD3 protein associated with a TCR complex on a T cell expressing the CD19-TAC, wherein the huUCHT1 comprises an amino acid sequence having 100% sequence identity to the amino acid sequence of SEQ ID NO: 46; and
   (c) a third polynucleotide encoding a T cell anchoring co-receptor domain polypeptide comprising a CD4 cytosolic domain and a CD4 transmembrane domain;
   wherein the ligand that selectively binds a CD19 antigen encoded by (a), the huUCHT1 encoded by (b), and the T cell anchoring co-receptor domain polypeptide encoded by (c) are fused directly to each other, or joined by at least one linker.

2. The T-cell of claim 1, wherein the nucleic acid sequence comprises a nucleic acid sequence having 100% sequence identity to the nucleic acid sequence of SEQ ID NO: 63.

3. The T cell of claim 1, wherein the CD19-TAC comprises an amino acid sequence having 100% sequence identity to the amino acid sequence of SEQ ID NO: 64.

4. A pharmaceutical composition, comprising: (a) the T cell of claim 1; and (b) an excipient.

5. A method of treating a cancer that expresses a CD19 tumor antigen in an individual in need thereof, comprising administering to the individual the pharmaceutical composition of claim 4, wherein the ligand of the CD19-TAC binds to the CD19 tumor antigen, thereby treating the cancer.

6. The method of claim 5, wherein the cancer is a lymphoma.

7. The method of claim 5, wherein the cancer is a B cell lymphoma, acute lymphoblastic leukemia, chronic lymphocytic leukemia or non-Hodgkin's lymphoma.

8. The method of claim 5, wherein the pharmaceutical composition is administered transarterially, subcutaneously, intradermally, intratumorally, intranodally, intramedullary, intramuscularly, intravenously or intraperitoneally.

* * * * *

SEQUENCE LISTING

```
<160> NUMBER OF SEQ ID NOS: 74

<210> SEQ ID NO 1
<211> LENGTH: 1521
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgtcacggg gctccgacct gggcaaaaag ctgctggagg ccgctagggc cgggcaggac      60
gatgaagtga gaatcctgat ggccaacggg gctgacgtga atgctaagga tgagtacggc     120 ctgaccccccc tgtatctggc tacagcacac ggccatctgg agatcgtgga agtcctgctg     180
aaaaacggag ccgacgtgaa tgcagtcgat gccattgggt tcactcctct gcacctggca     240
gcctttatcg gacatctgga gattgcagaa gtgctgctga agcacggcgc tgacgtgaac     300
gcacaggata agttcggaaa aaccgctttt gacatcagca ttggcaacgg aaatgaagac     360
ctggctgaaa tcctgcagaa actgaatgaa cagaaactga ttagcaaga agacctgaac     420 cccggggag gaggagggag cggggggagga ggcagcggcg ggggaggctc tggaggagga     480
gggagcggat ccatggacat ccagatgact cagaccacaa gctccctgtc tgcaagtctg     540
ggcgaccggg tgacaatctc ctgcagagcc tctcaggata ttaggaacta cctgaattgg     600
tatcagcaga aacctgatgg cacagtcaag ctgctgatct actataccag ccggctgcac     660
tcaggcgtgc caagcaaatt ctcaggaagc ggctccggga ctgactactc cctgaccatc     720
```

```
tctaacctgg agcaggaaga tattgctacc tatttctgcc agcagggcaa tacactgccc    780
tggacttttg ccggaggcac caaactggag atcaagggg gaggcgggag tggaggcggg     840
ggatcaggag gaggaggcag cggaggagga gggtccgagg tccagctgca gcagagcgga    900 ccagaactg tgaagcccgg agcaagtatg aaaatctcct gtaaggcctc aggatacagc     960
ttcaccggct atacaatgaa ctgggtgaaa cagtcccatg caagaacct ggaatggatg    1020 gggctgatta tccttacaa aggcgtcagc acctataatc agaagtttaa agacaaggcc    1080
acactgactg tggataagtc tagttcaacc gcttacatgg agctgctgtc cctgacatct    1140
gaagacagtg ccgtgtacta ttgtgctcgg tctggctact atggggacag tgattggtac    1200
ttcgatgtct ggggacaggg cactaccctg accgtgtttt ctactagtgg cggaggagga    1260
tcactcgaga gcggacaggt gctgctggaa tccaatatca agtcctgcc cacttggtct    1320 accccgtgc agcctatggc tctgattgtg ctgggaggag tcgcaggact gctgctgttt    1380
atcgggctgg aattttctt ttgcgtgcgc tgccggcacc ggagaaggca ggccgagcgc    1440
atgagccaga tcaagcgact gctgagcgag aagaaaacct gtcagtgtcc ccatagattc    1500
cagaagacct gttcacccat t                                             1521

<210> SEQ ID NO 2
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asp Phe Gln Val Gln Ile Phe Ser Phe Leu Leu Ile Ser Ala Ser
1               5                   10                  15

Val Ile Met Ser Arg Gly Ser Asp Leu Gly Lys Lys Leu Leu Glu Ala
            20                  25                  30

Ala Arg Ala Gly Gln Asp Asp Glu Val Arg Ile Leu Met Ala Asn Gly
        35                  40                  45

Ala Asp Val Asn Ala Lys Asp Glu Tyr Gly Leu Thr Pro Leu Tyr Leu
    50                  55                  60

Ala Thr Ala His Gly His Leu Glu Ile Val Glu Val Leu Leu Lys Asn
65                  70                  75                  80

Gly Ala Asp Val Asn Ala Val Asp Ala Ile Gly Phe Thr Pro Leu His
                85                  90                  95

Leu Ala Ala Phe Ile Gly His Leu Glu Ile Ala Glu Val Leu Leu Lys
            100                 105                 110

His Gly Ala Asp Val Asn Ala Gln Asp Lys Phe Gly Lys Thr Ala Phe
        115                 120                 125

Asp Ile Ser Ile Gly Asn Gly Asn Glu Asp Leu Ala Glu Ile Leu Gln
    130                 135                 140

Lys Leu Asn Glu Gln Lys Leu Ile Ser Glu Glu Asp Leu Asn Pro Gly
145                 150                 155                 160

Gly Gly Gly Gly Ser Gly Gly Gly Ser Gly Gly Gly Ser Gly
                165                 170                 175

Gly Gly Gly Ser Gly Ser Met Asp Ile Gln Met Thr Gln Thr Thr Ser
            180                 185                 190

Ser Leu Ser Ala Ser Leu Gly Asp Arg Val Thr Ile Ser Cys Arg Ala
        195                 200                 205

Ser Gln Asp Ile Arg Asn Tyr Leu Asn Trp Tyr Gln Gln Lys Pro Asp
```

Gly Thr Val Lys Leu Leu Ile Tyr Tyr Thr Ser Arg Leu His Ser Gly
225                 230                 235                 240

Val Pro Ser Lys Phe Ser Gly Ser Gly Ser Gly Thr Asp Tyr Ser Leu
            245                 250                 255

Thr Ile Ser Asn Leu Glu Gln Glu Asp Ile Ala Thr Tyr Phe Cys Gln
            260                 265                 270

Gln Gly Asn Thr Leu Pro Trp Thr Phe Ala Gly Gly Thr Lys Leu Glu
        275                 280                 285

Ile Lys Gly Gly Gly Gly Ser Gly Gly Gly Gly Ser Gly Gly Gly Gly
    290                 295                 300

Ser Gly Gly Gly Gly Ser Glu Val Gln Leu Gln Gln Ser Gly Pro Glu
305                 310                 315                 320

Leu Val Lys Pro Gly Ala Ser Met Lys Ile Ser Cys Lys Ala Ser Gly
                325                 330                 335

Tyr Ser Phe Thr Gly Tyr Thr Met Asn Trp Val Lys Gln Ser His Gly
                340                 345                 350

Lys Asn Leu Glu Trp Met Gly Leu Ile Asn Pro Tyr Lys Gly Val Ser
            355                 360                 365

Thr Tyr Asn Gln Lys Phe Lys Asp Lys Ala Thr Leu Thr Val Asp Lys
    370                 375                 380

Ser Ser Ser Thr Ala Tyr Met Glu Leu Leu Ser Leu Thr Ser Glu Asp
385                 390                 395                 400

Ser Ala Val Tyr Tyr Cys Ala Arg Ser Gly Tyr Tyr Gly Asp Ser Asp
                405                 410                 415

Trp Tyr Phe Asp Val Trp Gly Gln Gly Thr Thr Leu Thr Val Phe Ser
                420                 425                 430

Thr Ser Gly Gly Gly Gly Ser Leu Glu Ser Gly Gln Val Leu Leu Glu
        435                 440                 445

Ser Asn Ile Lys Val Leu Pro Thr Trp Ser Thr Pro Val Gln Pro Met
    450                 455                 460

Ala Leu Ile Val Leu Gly Gly Val Ala Gly Leu Leu Leu Phe Ile Gly
465                 470                 475                 480

Leu Gly Ile Phe Phe Cys Val Arg Cys Arg His Arg Arg Arg Gln Ala
                485                 490                 495

Glu Arg Met Ser Gln Ile Lys Arg Leu Leu Ser Glu Lys Lys Thr Cys
                500                 505                 510

Gln Cys Pro His Arg Phe Gln Lys Thr Cys Ser Pro Ile
        515                 520                 525

<210> SEQ ID NO 3
<211> LENGTH: 1647
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggactttc aggtgcagat tttctctttt ctgctgattt ccgcaagcgt catcgagctc      60
gggggggggg ggtcaggatc catggacatc cagatgactc agaccacaag ctccctgagc     120
gcatccctgg gcgaccgagt gacaatctca tgcagagcca gcaggatat taggaactac     180 ctgaattggt atcagcagaa acctgacggc acagtcaagc tgctgatcta ctatacttcc     240
cggctgcact ctggcgtgcc aagtaaattc tctggagtg atcaggcac tgactactca     300

```
ctgaccatca gcaacctgga gcaggaagat attgctacct atttctgcca gcagggcaat    360
acactgccct ggacttttgc aggcgggacc aaactggaga tcaagggcgg cggcggaagt    420
ggaggaggag gctcaggcgg aggagggagc ggcggaggag gcagcgaggt ccagctgcag    480
cagagcggac cagaactggt gaagcctggc gcatccatga aaatctcttg taaggcctct    540
gggtacagtt tcaccggata tacaatgaac tgggtgaaac agtctcatgg caagaacctg    600
gaatggatgg gcctgattaa tccttacaaa ggcgtcagca cctataatca gaagtttaaa    660
gacaaggcca cactgactgt ggataagtct agttcaaccg cttacatgga gctgctgtca    720
ctgacaagcg aagactccgc cgtgtactat tgcgctagga gcggatacta tggcgactcc    780
gattggtact cgatgtctg ggggcaggga actaccctga ccgtgtttag cactagtgga    840
ggaggaggct ctggaggagg agggagtgga ggcgggggat caggaggagg aggcagcgat    900
atcatgtcac ggggctccga cctgggcaaa agctgctgg aggccgctag gccgggcag    960 gacgatgaag tgagaatcct gatggccaac ggggctgacg tgaatgctaa ggatgagtac    1020
ggcctgaccc ccctgtatct ggctacagca cacggccatc tggagatcgt ggaagtcctg    1080
ctgaaaaacg gagccgacgt gaatgcagtc gatgccattg gttcactcc tctgcacctg    1140 gcagccttta tcggacatct ggagattgca gaagtgctgc tgaagcacgg cgctgacgtg    1200
aacgcacagg ataagttcgg aaaaaccgct tttgacatca gcattggcaa cggaaatgaa    1260
gacctggctg aaatcctgca gaaactgaat gaacagaaac tgattagcga agaagacctg    1320
aacgtcgacg gaggaggagg gtctggagga ggggaagtg gcggggagg cagcggggga    1380 ggcgggtctc tcgagagtgg ccaggtgctg ctggaaagca atatcaaggt cctgccaact    1440
tggtccaccc cagtgcagcc tatggctctg attgtgctgg gagtcgc aggactgctg    1500 ctgtttatcg gcctggggat tttcttttgc gtgcgctgcc ggcaccggag aaggcaggct    1560
gagcgcatgt ctcagattaa gcgactgctg agcgagaaga gacctgtca gtgcccccat    1620 agattccaga aaacctgttc acccatt                                        1647
```

<210> SEQ ID NO 4
<211> LENGTH: 547
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Asp Phe Gln Val Gln Ile Phe Ser Phe Leu Leu Ile Ser Ala Ser
1               5                   10                  15

Val Ile Glu Leu Gly Gly Gly Ser Gly Ser Met Asp Ile Gln Met
            20                  25                  30

Thr Gln Thr Thr Ser Ser Leu Ser Ala Ser Leu Gly Asp Arg Val Thr
        35                  40                  45

Ile Ser Cys Arg Ala Ser Gln Asp Ile Arg Asn Tyr Leu Asn Trp Tyr
    50                  55                  60

Gln Gln Lys Pro Asp Gly Thr Val Lys Leu Leu Ile Tyr Tyr Thr Ser
65                  70                  75                  80

Arg Leu His Ser Gly Val Pro Ser Lys Phe Ser Gly Ser Gly Ser Gly
                85                  90                  95

Thr Asp Tyr Ser Leu Thr Ile Ser Asn Leu Glu Gln Glu Asp Ile Ala
            100                 105                 110
```

-continued

```
Thr Tyr Phe Cys Gln Asn Thr Leu Pro Trp Thr Phe Ala Gly Gly Thr
            115                 120                 125

Lys Leu Glu Ile Lys Gly Gly Gly Ser Gly Gly Gly Gly Ser Gly
130                 135                 140

Gly Gly Gly Ser Gly Gly Gly Ser Glu Val Gln Leu Gln Gln Ser
145                 150                 155                 160

Gly Pro Glu Leu Val Lys Pro Gly Ala Ser Met Lys Ile Ser Cys Lys
                165                 170                 175

Ala Ser Gly Tyr Ser Phe Thr Gly Tyr Thr Met Asn Trp Val Lys Gln
                180                 185                 190

Ser His Gly Lys Asn Leu Glu Trp Met Gly Leu Ile Asn Pro Tyr Lys
            195                 200                 205

Gly Val Ser Thr Tyr Asn Gln Lys Phe Lys Asp Lys Ala Thr Leu Thr
            210                 215                 220

Val Asp Lys Ser Ser Ser Thr Ala Tyr Met Glu Leu Leu Ser Leu Thr
225                 230                 235                 240

Ser Glu Asp Ser Ala Val Tyr Tyr Cys Ala Arg Ser Gly Tyr Tyr Gly
                245                 250                 255

Asp Ser Asp Trp Tyr Phe Asp Val Trp Gly Gln Gly Thr Thr Leu Thr
            260                 265                 270

Val Phe Ser Thr Ser Gly Gly Gly Gly Ser Gly Gly Gly Gly Ser Gly
            275                 280                 285

Gly Gly Gly Ser Gly Gly Gly Gly Ser Asp Ile Met Ser Arg Gly Ser
            290                 295                 300

Asp Leu Gly Lys Lys Leu Leu Glu Ala Ala Arg Ala Gly Gln Asp Asp
305                 310                 315                 320

Glu Val Arg Ile Leu Met Ala Asn Gly Ala Asp Val Asn Ala Lys Asp
                325                 330                 335

Glu Tyr Gly Leu Thr Pro Leu Tyr Leu Ala Thr Ala His Gly His Leu
                340                 345                 350

Glu Ile Val Glu Val Leu Leu Lys Asn Gly Ala Asp Val Asn Ala Val
            355                 360                 365

Asp Ala Ile Gly Phe Thr Pro Leu His Leu Ala Ala Phe Ile Gly His
            370                 375                 380

Leu Glu Ile Ala Glu Val Leu Leu Lys His Gly Ala Asp Val Asn Ala
385                 390                 395                 400

Gln Asp Lys Phe Gly Lys Thr Ala Phe Asp Ile Ser Ile Gly Asn Gly
                405                 410                 415

Asn Glu Asp Leu Ala Glu Ile Leu Gln Lys Leu Asn Glu Gln Lys Leu
            420                 425                 430

Ile Ser Glu Glu Asp Leu Asn Val Asp Gly Gly Gly Ser Gly Gly
            435                 440                 445

Gly Gly Ser Gly Gly Gly Gly Ser Gly Gly Gly Gly Ser Leu Glu Ser
            450                 455                 460

Gly Gln Val Leu Leu Glu Ser Asn Ile Lys Val Leu Pro Thr Trp Ser
465                 470                 475                 480

Thr Pro Val Gln Pro Met Ala Leu Ile Val Leu Gly Gly Val Ala Gly
                485                 490                 495

Leu Leu Leu Phe Ile Gly Leu Gly Ile Phe Phe Cys Val Arg Cys Arg
                500                 505                 510

His Arg Arg Arg Gln Ala Glu Arg Met Ser Gln Ile Lys Arg Leu Leu
            515                 520                 525

Ser Glu Lys Lys Thr Cys Gln Cys Pro His Arg Phe Gln Lys Thr Cys
```

```
                530                 535                 540

Ser Pro Ile
545

<210> SEQ ID NO 5
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atggatttcc aggtccagat tttctccttc ctgctgattt ccgcaagcgt catt          54

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Asp Phe Gln Val Gln Ile Phe Ser Phe Leu Leu Ile Ser Ala Ser
1               5                   10                  15

Val Ile

<210> SEQ ID NO 7
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgtcacggg gctccgacct gggcaaaaag ctgctggagg ccgctagggc cgggcaggac     60
gatgaagtga gaatcctgat ggccaacggg gctgacgtga atgctaagga tgagtacggc    120
ctgacccccc tgtatctggc tacagcacac ggccatctgg agatcgtgga agtcctgctg    180
aaaaacggag ccgacgtgaa tgcagtcgat gccattgggt tcactcctct gcacctggca    240
gcctttatcg acatctgga gattgcagaa gtgctgctga gcacggcgc tgacgtgaac     300 gcacaggata gttcggaaa accgcttttt gacatcagca ttggcaacgg aaatgaagac    360
ctggctgaaa tcctgcagaa actgaat                                       387

<210> SEQ ID NO 8
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ser Arg Gly Ser Asp Leu Gly Lys Lys Leu Leu Glu Ala Ala Arg
1               5                   10                  15

Ala Gly Gln Asp Asp Glu Val Arg Ile Leu Met Ala Asn Gly Ala Asp
                20                  25                  30

Val Asn Ala Lys Asp Glu Tyr Gly Leu Thr Pro Leu Tyr Leu Ala Thr
            35                  40                  45
```

```
Ala His Gly His Leu Glu Ile Val Glu Val Leu Leu Lys Asn Gly Ala
     50                  55                  60

Asp Val Asn Ala Val Asp Ala Ile Gly Phe Thr Pro Leu His Leu Ala
 65                  70                  75                  80

Ala Phe Ile Gly His Leu Glu Ile Ala Glu Val Leu Leu Lys His Gly
                 85                  90                  95

Ala Asp Val Asn Ala Gln Asp Lys Phe Gly Lys Thr Ala Phe Asp Ile
            100                 105                 110

Ser Ile Gly Asn Gly Asn Glu Asp Leu Ala Glu Ile Leu Gln Lys Leu
        115                 120                 125

Asn

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gaacagaaac tgattagcga agaagacctg                                     30

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Gln Lys Leu Ile Ser Glu Glu Asp Leu
  1               5                  10

<210> SEQ ID NO 11
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaccccgggg gaggaggagg gagcggggga ggaggcagcg gcggggagg ctctggagga    60 ggagggagcg gatcc                                                    75

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Pro Gly Gly Gly Gly Gly Ser Gly Gly Gly Gly Ser Gly Gly Gly
  1               5                  10                  15

Gly Ser Gly Gly Gly Gly Ser Gly Ser
             20                  25

<210> SEQ ID NO 13
<211> LENGTH: 750
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
atggacatcc agatgactca gaccacaagc tccctgtctg caagtctggg cgaccgggtg      60
acaatctcct gcagagcctc tcaggatatt aggaactacc tgaattggta tcagcagaaa     120
cctgatggca cagtcaagct gctgatctac tataccagcc ggctgcactc aggcgtgcca     180
agcaaattct caggaagcgg ctccgggact gactactccc tgaccatctc taacctggag     240
caggaagata ttgctaccta tttctgccag cagggcaata cactgccctg gacttttgcc     300
ggaggcacca aactggagat caaggggga ggcgggagtg gaggcggggg atcaggagga     360
ggaggcagcg gaggaggagg gtccgaggtc cagctgcagc agagcggacc agaactggtg     420
aagcccggag caagtatgaa aatctcctgt aaggcctcag gatacagctt caccggctat     480
acaatgaact gggtgaaaca gtcccatggc aagaacctgg aatggatggg gctgattaat     540
ccttacaaag gcgtcagcac ctataatcag aagtttaaag acaaggccac actgactgtg     600
gataagtcta gttcaaccgc ttacatggag ctgctgtccc tgcacatctg agacagtgcc     660
gtgtactatt gtgctcggtc tggctactat ggggacagtg attggtactt cgatgtctgg     720
ggacagggca ctaccctgac cgtgttttct                                      750
```

<210> SEQ ID NO 14
<211> LENGTH: 250
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Trp Thr Phe Ala Gly Gly Thr Lys Leu Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Gln Gln Ser Gly Pro Glu Leu Val Lys Pro Gly Ala
    130                 135                 140

Ser Met Lys Ile Ser Cys Lys Ala Ser Gly Tyr Ser Phe Thr Gly Tyr
145                 150                 155                 160

Thr Met Asn Trp Val Lys Gln Ser His Gly Lys Asn Leu Glu Trp Met
                165                 170                 175

Gly Leu Ile Asn Pro Tyr Lys Gly Val Ser Thr Tyr Asn Gln Lys Phe
```

```
            180                 185                 190
Lys Asp Lys Ala Thr Leu Thr Val Asp Lys Ser Ser Thr Ala Tyr
            195                 200                 205

Met Glu Leu Leu Ser Leu Thr Ser Glu Asp Ser Ala Val Tyr Tyr Cys
        210                 215                 220

Ala Arg Ser Gly Tyr Tyr Gly Asp Ser Asp Trp Tyr Phe Asp Val Trp
225                 230                 235                 240

Gly Gln Gly Thr Thr Leu Thr Val Phe Ser
                245                 250

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actagtggcg gaggaggatc actcgag                                        27

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Ser Gly Gly Gly Gly Ser Leu Glu
1               5

<210> SEQ ID NO 17
<211> LENGTH: 252
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
agcggacagg tgctgctgga atccaatatc aaagtcctgc ccacttggtc taccccgtg     60 cagcctatgg ctctgattgt gctgggagga gtcgcaggac tgctgctgtt tatcgggctg   120
ggaattttct tttgcgtgcg ctgccggcac cggagaaggc aggccgagcg catgagccag   180
atcaagcgac tgctgagcga aagaaaaacc tgtcagtgtc cccatagatt ccagaagacc   240
tgttcaccca tt                                                      252

<210> SEQ ID NO 18
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser Gly Gln Val Leu Leu Glu Ser Asn Ile Lys Val Leu Pro Thr Trp
1               5                   10                  15

Ser Thr Pro Val Gln Pro Met Ala Leu Ile Val Leu Gly Gly Val Ala
            20                  25                  30
```

Gly Leu Leu Leu Phe Ile Gly Leu Gly Ile Phe Phe Cys Val Arg Cys
            35                  40                  45

Arg His Arg Arg Arg Gln Ala Glu Arg Met Ser Gln Ile Lys Arg Leu
    50                  55                  60

Leu Ser Glu Lys Lys Thr Cys Gln Cys Pro His Arg Phe Gln Lys Thr
65                  70                  75                  80

Cys Ser Pro Ile

<210> SEQ ID NO 19
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agcggacagg tgctgctgga atccaatatc aaagtcctgc ccacttggtc taccccgtg      60 cagcct                                                               66

<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Gly Gln Val Leu Leu Glu Ser Asn Ile Lys Val Leu Pro Thr Trp
1               5                   10                  15

Ser Thr Pro Val Gln Pro
            20

<210> SEQ ID NO 21
<211> LENGTH: 769
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atggccgaca tcgtgctgac acagagcccc gccatcatgt ctgccagccc tggcgagaaa      60
gtgaccatga cctgtagcgc cagcagcagc gtgtcctaca tgaactggta tcagcagaag     120
tccggcacca gccccaagcg gtggatctac gacacaagca gctggcctc tggcgtgccc      180 gcccactta gaggctctgg cagcggcaca agctacagcc tgaccatcag cggcatggaa     240
gccgaggatg ccgccaccta ctactgccag cagtggtcca gcaaccctt cacctttggc     300 tccggcacaa agctggaaat caaccgggcc gacaccgccc taccaggcgg cggaggatct     360
ggcggaggcg gatctggggg cggaggaagt ggggggggag gatctatggc tcaggtgcag     420
ctgcagcagt ctggcgccga actggctaga cctggcgcct ccgtgaagat gagctgcaag     480
gccagcggct acaccttcac ccggtacacc atgcactggg tcaagcagag gcctggacag     540
ggcctggaat ggatcggcta catcaacccc agccgggct acaccaacta caaccagaag     600
ttcaaggaca aggccaccct gaccaccgac aagagcagca gcaccgccta catgcagctg     660
tcctccctga ccagcgagga cagcgccgtg tactactgcg cccggtacta cgacgaccac     720
tactccctgg actactgggg ccagggcacc acactgaccg tgtctagta                 769

<210> SEQ ID NO 22
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Ala Asp Ile Val Leu Thr Gln Ser Pro Ala Ile Met Ser Ala Ser
1               5                   10                  15

Pro Gly Glu Lys Val Thr Met Thr Cys Ser Ala Ser Ser Ser Val Ser
            20                  25                  30

Tyr Met Asn Trp Tyr Gln Gln Lys Ser Gly Thr Ser Pro Lys Arg Trp
        35                  40                  45

Ile Tyr Asp Thr Ser Lys Leu Ala Ser Gly Val Pro Ala His Phe Arg
    50                  55                  60

Gly Ser Gly Ser Gly Thr Ser Tyr Ser Leu Thr Ile Ser Gly Met Glu
65                  70                  75                  80

Ala Glu Asp Ala Ala Thr Tyr Tyr Cys Gln Gln Trp Ser Ser Asn Pro
                85                  90                  95

Phe Thr Phe Gly Ser Gly Thr Lys Leu Glu Ile Asn Arg Ala Asp Thr
            100                 105                 110

Ala Pro Thr Gly Gly Gly Gly Ser Gly Gly Gly Gly Ser Gly Gly Gly
        115                 120                 125

Gly Ser Gly Gly Gly Gly Ser Met Ala Gln Val Gln Leu Gln Gln Ser
130                 135                 140

Gly Ala Glu Leu Ala Arg Pro Gly Ala Ser Val Lys Met Ser Cys Lys
145                 150                 155                 160

Ala Ser Gly Tyr Thr Phe Thr Arg Tyr Thr Met His Trp Val Lys Gln
                165                 170                 175

Arg Pro Gly Gln Gly Leu Glu Trp Ile Gly Tyr Ile Asn Pro Ser Arg
            180                 185                 190

Gly Tyr Thr Asn Tyr Asn Gln Lys Phe Lys Asp Lys Ala Thr Leu Thr
        195                 200                 205

Thr Asp Lys Ser Ser Ser Thr Ala Tyr Met Gln Leu Ser Ser Leu Thr
    210                 215                 220

Ser Glu Asp Ser Ala Val Tyr Tyr Cys Ala Arg Tyr Tyr Asp Asp His
225                 230                 235                 240

Tyr Ser Leu Asp Tyr Trp Gly Gln Gly Thr Thr Leu Thr Val Ser Ser
                245                 250                 255

<210> SEQ ID NO 23
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
cagaccgtgg tgacccagga gcccagcctg accgtgagcc ccggcggcac cgtgaccctg      60
acctgcggca gcagcaccgg cgccgtgacc agcggctact accccaactg ggtgcagcag    120
aagcccggcc aggcccccag gggcctgatc ggcggcacca gttcctggc ccccggcacc     180 cccgccaggt tcagcggcag cctgctgggc ggcaaggccg ccctgaccct gagcggcgtg    240

```
cagcccgagg acgaggccga gtactactgc gccctgtggt acagcaacag gtgggtgttc    300
ggcggcggca ccaagctgac cgtgctgggc ggcggcggca gcggcggcgg cggcagcggc    360
ggcggcggca gcgaggtgca gctgctggag agcggcggcg gcctggtgca gcccggcggc    420
agcctgaagc tgagctgcgc cgccagcggc ttcaccttca acatctacgc catgaactgg    480
gtgaggcagg cccccggcaa gggcctggag tgggtggcca ggatcaggag caagtacaac    540
aactacgcca cctactacgc cgacagcgtg aagagcaggt tcaccatcag cagggacgac    600
agcaagaaca ccgcctacct gcagatgaac aacctgaaga ccgaggacac cgccgtgtac    660
tactgcgtga ggcacggcaa cttcggcaac agctacgtga gcttcttcgc ctactggggc    720
cagggcaccc tggtgaccgt gagcagc                                      747
```

<210> SEQ ID NO 24
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu Gly Gly Gly
            100                 105                 110

Gly Ser Gly Gly Gly Gly Ser Gly Gly Gly Ser Glu Val Gln Leu
        115                 120                 125

Leu Glu Ser Gly Gly Gly Leu Val Gln Pro Gly Gly Ser Leu Lys Leu
    130                 135                 140

Ser Cys Ala Ala Ser Gly Phe Thr Phe Asn Ile Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Ser
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Gly Asn Phe Gly Asn Ser Tyr Val Ser Phe Phe Ala Tyr Trp Gly
225                 230                 235                 240

Gln Gly Thr Leu Val Thr Val Ser Ser
                245
```

<210> SEQ ID NO 25

<210> SEQ ID NO 25
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
gacatccagc tgacccagag ccccgccatc atgagcgcca gccccggcga gaaggtgacc     60
atgacctgca gggccagcag cagcgtgagc tacatgaact ggtaccagca gaagagcggc    120
accagcccca gaggtggat ctacgacacc agcaaggtgg ccagcggcgt gccctacagg     180
ttcagcggca gcggcagcgg caccagctac agcctgacca tcagcagcat ggaggccgag    240
gacgccgcca cctactactg ccagcagtgg agcagcaacc ccctgacctt cggcgccggc    300
accaagctgg agctgaaggg cggcggcggc agcggcggcg gcggcagcgg cggcggcggc    360
agcgacatca agctgcagca gagcggcgcc gagctggcca ggcccggcgc cagcgtgaag    420
atgagctgca gaccagcgg ctacaccttc accaggtaca ccatgcactg ggtgaagcag     480
aggcccggcc agggcctgga gtggatcggc tacatcaacc ccagcagggg ctacaccaac    540
tacaaccaga gttcaagga caaggccacc ctgaccaccg acaagagcag cagcaccgcc     600
tacatgcagc tgagcagcct gaccagcgag gacagcgccg tgtactactg cgccaggtac    660
tacgacgacc actactgcct ggactactgg ggccagggca ccaccctgac cgtgagcagc    720
```

<210> SEQ ID NO 26
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Gly Gly Gly Gly Ser Gly
            100                 105                 110

Gly Gly Gly Ser Gly Gly Gly Ser Asp Ile Lys Leu Gln Gln Ser
        115                 120                 125

Gly Ala Glu Leu Ala Arg Pro Gly Ala Ser Val Lys Met Ser Cys Lys
    130                 135                 140

Thr Ser Gly Tyr Thr Phe Thr Arg Tyr Thr Met His Trp Val Lys Gln
145                 150                 155                 160

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
            180                 185                 190
```

```
Thr Asp Lys Ser Ser Thr Ala Tyr Met Gln Leu Ser Ser Leu Thr
        195                 200                 205

Ser Glu Asp Ser Ala Val Tyr Tyr Cys Ala Arg Tyr Tyr Asp Asp His
    210                 215                 220

Tyr Cys Leu Asp Tyr Trp Gly Gln Gly Thr Thr Leu Thr Val Ser Ser
225                 230                 235                 240

<210> SEQ ID NO 27
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gccgaagcag cagcaaagga ggccgcagcg aaggaagcag ctgcgaaggc c            51

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Glu Ala Ala Ala Lys Glu Ala Ala Ala Lys Glu Ala Ala Ala Lys
1               5                   10                  15

Ala

<210> SEQ ID NO 29
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gccgaggcag ctgcaaagga agctgcggcg aaggaggccg cagcgaaaga agcagcggca       60
aaagaagcag ccgccaaagc c                                                81

<210> SEQ ID NO 30
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
                20                  25

<210> SEQ ID NO 31
<211> LENGTH: 576
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 31

```
atcgtagtgt tggcatttca aaaagcgtct agcatcgtct ataagaagga aggtgaacaa      60
gtcgagtttt ctttcccct tgcatttacg gtggaaaagc ttacgggtag cggcgagctg     120
tggtggcaag ctgaacgggc ttcaagctca aaatcttgga ttacttttga cttgaagaac    180
aaagaggtga gtgtcaaaag agttactcag acccaaagc ttcaaatggg aagaaacttt     240
ccgctgcacc tgacgttgcc tcaggccctg cctcaatatg ccggctcagg caatctgacc    300
ctcgcgctgg aagctaagac cggaaaattg caccaggaag tcaatttggt tgtgatgcgc    360
gccactcagc tccaaaaaaa tctcacttgc gaggtatggg ggcctacgag cccaaaactt    420
atgctgtctt tgaagcttga aaacaaggaa gcgaaagttt ctaagcgcga aaagcggta     480
tgggttttga atcctgaggc tggaatgtgg caatgcctcc tgagcgatag cgggcaggtg    540
ctgttggaga gcaacatcaa ggttttgcca gcagcc                              576
```

<210> SEQ ID NO 32
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Ile Val Val Leu Ala Phe Gln Lys Ala Ser Ile Val Tyr Lys Lys
1               5                   10                  15

Glu Gly Glu Gln Val Glu Phe Ser Phe Pro Leu Ala Phe Thr Val Glu
            20                  25                  30

Lys Leu Thr Gly Ser Gly Glu Leu Trp Trp Gln Ala Glu Arg Ala Ser
        35                  40                  45

Ser Ser Lys Ser Trp Ile Thr Phe Asp Leu Lys Asn Lys Glu Val Ser
    50                  55                  60

Val Lys Arg Val Thr Gln Asp Pro Lys Leu Gln Met Gly Lys Lys Leu
65                  70                  75                  80

Pro Leu His Leu Thr Leu Pro Gln Ala Leu Pro Gln Tyr Ala Gly Ser
                85                  90                  95

Gly Asn Leu Thr Leu Ala Leu Glu Ala Lys Thr Gly Lys Leu His Gln
            100                 105                 110

Glu Val Asn Leu Val Val Met Arg Ala Thr Gln Leu Gln Lys Asn Leu
        115                 120                 125

Thr Cys Glu Val Trp Gly Pro Thr Ser Pro Lys Leu Met Leu Ser Leu
    130                 135                 140

Lys Leu Glu Asn Lys Glu Ala Lys Val Ser Lys Arg Glu Lys Ala Val
145                 150                 155                 160

Trp Val Leu Asn Pro Glu Ala Gly Met Trp Gln Cys Leu Leu Ser Asp
                165                 170                 175

Ser Gly Gln Val Leu Leu Glu Ser Asn Ile Lys Val Leu Pro Ala Ala
            180                 185                 190
```

<210> SEQ ID NO 33
<211> LENGTH: 801
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
atggatttte aggtgcagat tttcagcttc ctgctaatca gtgcctcagt cataatgtct      60
agagacatcg tgctgaccca gagccccccc agcctggcca tgtctctggg caagagagcc     120
accatcagct gccgggccag cgagagcgtg accatcctgg gcagccacct gatccactgg     180
tatcagcaga gcccggcca gccccccacc ctgctgatcc agctcgccag caatgtgcag     240
accggcgtgc cgccagatt cagcggcagc ggcagcagaa ccgacttcac cctgaccatc     300
gaccccgtgg aagaggacga cgtggccgtg tactactgcc tgcagagccg gaccatcccc     360
cggacctttg gcggaggcac caaactggaa atcaagggca gcaccagcgg ctccggcaag     420
cctggctctg gcgagggcag cacaaaggga cagattcagc tggtgcagag cggccctgag     480
ctgaagaaac ccggcgagac agtgaagatc agctgcaagg cctccggcta caccttcacc     540
gactacagca tcaactgggt gaaaagagcc cctggcaagg gcctgaagtg gatgggctgg     600
atcaacaccg agacaagaga gcccgcctac gcctacgact ccggggcag attcgccttc     660 agcctggaaa ccagcgccag caccgcctac ctgcagatca caacctgaa gtacgaggac     720 accgccacct actttgcgc cctggactac agctacgcca tggactactg ggccagggc     780 accagcgtga ccgtgtccag c                                               801
```

<210> SEQ ID NO 34
<211> LENGTH: 267
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Met Asp Phe Gln Val Gln Ile Phe Ser Phe Leu Leu Ile Ser Ala Ser
1               5                   10                  15

Val Ile Met Ser Arg Asp Ile Val Leu Thr Gln Ser Pro Pro Ser Leu
            20                  25                  30

Ala Met Ser Leu Gly Lys Arg Ala Thr Ile Ser Cys Arg Ala Ser Glu
        35                  40                  45

Ser Val Thr Ile Leu Gly Ser His Leu Ile His Trp Tyr Gln Gln Lys
    50                  55                  60

Pro Gly Gln Pro Pro Thr Leu Leu Ile Gln Leu Ala Ser Asn Val Gln
65                  70                  75                  80

Thr Gly Val Pro Ala Arg Phe Ser Gly Ser Gly Ser Arg Thr Asp Phe
                85                  90                  95

Thr Leu Thr Ile Asp Pro Val Glu Glu Asp Asp Val Ala Val Tyr Tyr
            100                 105                 110

Cys Leu Gln Ser Arg Thr Ile Pro Arg Thr Phe Gly Gly Gly Thr Lys
        115                 120                 125

Leu Glu Ile Lys Gly Ser Thr Ser Gly Ser Gly Lys Pro Gly Ser Gly
    130                 135                 140

Glu Gly Ser Thr Lys Gly Gln Ile Gln Leu Val Gln Ser Gly Pro Glu
145                 150                 155                 160

Leu Lys Lys Pro Gly Glu Thr Val Lys Ile Ser Cys Lys Ala Ser Gly
                165                 170                 175

Tyr Thr Phe Thr Asp Tyr Ser Ile Asn Trp Val Lys Arg Ala Pro Gly
            180                 185                 190

Lys Gly Leu Lys Trp Met Gly Trp Ile Asn Thr Glu Thr Arg Glu Pro
        195                 200                 205
```

Ala Tyr Ala Tyr Asp Phe Arg Gly Arg Phe Ala Phe Ser Leu Glu Thr
        210                 215                 220

Ser Ala Ser Thr Ala Tyr Leu Gln Ile Asn Asn Leu Lys Tyr Glu Asp
225                 230                 235                 240

Thr Ala Thr Tyr Phe Cys Ala Leu Asp Tyr Ser Tyr Ala Met Asp Tyr
                245                 250                 255

Trp Gly Gln Gly Thr Ser Val Thr Val Ser Ser
            260                 265

<210> SEQ ID NO 35
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gatatccaga tgactcagac gacctcatca ttgtccgcca gtttggggga cagggttaca      60
atatcctgcc gggcgagcca agacatcagt aaatatctta attggtacca gcagaaacca     120
gatggtacag taaaacttct tatctaccac acctctcggc tccactctgg ggttccctct     180
aggttcagtg gtagtgggtc aggcaccgac tacagcctta cgataagcaa cttggaacag     240
gaggatatcg caacttactt ctgccaacag gaaatacccc tgccttacac gttcggtgga     300
ggcactaaac tggagatcac tgggtcaacc tctggtagcg gtaagcctgg ctccggcgaa     360
ggctccacaa agggtgaggt gaaactccaa gagtcaggtc ccggtttggt agccccctca     420
caaagtttgt cagttacttg taccgtaagc ggcgtttccc tgcccgatta cggtgtgagc     480
tggataaggc agccaccgag aaaaggtctt gaatggctgg gagtgatctg ggggtctgag     540
acaacgtatt acaactcagc tcttaagagc aggcttacga tcattaaaga taacagcaaa     600
tctcaagtgt tcctcaaaat gaatagcctt caaactgatg atactgccat ctattattgt     660
gctaagcatt attactatgg cggcagttac gcaatggatt attgggggca aggtacctca     720
gtcactgtaa gcagc                                                       735

<210> SEQ ID NO 36
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

```
Thr Phe Gly Gly Gly Thr Lys Leu Glu Ile Thr Gly Ser Thr Ser Gly
                100                 105                 110

Ser Gly Lys Pro Gly Ser Gly Glu Gly Ser Thr Lys Gly Glu Val Lys
            115                 120                 125

Leu Gln Glu Ser Gly Pro Gly Leu Val Ala Pro Ser Gln Ser Leu Ser
        130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
        210                 215                 220

Tyr Tyr Gly Gly Ser Tyr Ala Met Asp Tyr Trp Gly Gln Gly Thr Ser
225                 230                 235                 240

Val Thr Val Ser Ser
                245

<210> SEQ ID NO 37
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
ctcgagctga ggcccgaggc ttctagacct gctgccggcg gagccgtgca caccagaggc    60
ctggacttcg ccagcgacat ctacatctgg gcccctctgg ccggcacctg tggcgtgctg   120
ctgctgagcc tggtcatcac cctgtactgc aaccaccgga accggcggag agtgtgcaag   180
tgccccagac ccgtggtcaa gagcggcgac aagcccagcc tgagcgccag atacgtg     237

<210> SEQ ID NO 38
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Leu Glu Leu Arg Pro Glu Ala Ser Arg Pro Ala Ala Gly Gly Ala Val
1               5                   10                  15

His Thr Arg Gly Leu Asp Phe Ala Ser Asp Ile Tyr Ile Trp Ala Pro
            20                  25                  30

Leu Ala Gly Thr Cys Gly Val Leu Leu Leu Ser Leu Val Ile Thr Leu
        35                  40                  45

Tyr Cys Asn His Arg Asn Arg Arg Val Cys Lys Cys Pro Arg Pro
    50                  55                  60

Val Val Lys Ser Gly Asp Lys Pro Ser Leu Ser Ala Arg Tyr Val
65                  70                  75

<210> SEQ ID NO 39
<211> LENGTH: 234
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 39

```
ctcgagctga ggcccgaggc ttctagacct gctgccggcg gagccgtgca caccagaggc    60
ctggacttcg ccagcgacat ctacatctgg gcccctctgg ccggcacctg tggcgtgctg   120
ctgctgagcc tggtcatcac cctgtacctg tgctgcagac ggcggagagt gtgcaagtgc   180
cccagacccg tggtcaagag cggcgacaag cccagcctga gcgccagata cgtg         234
```

<210> SEQ ID NO 40
<211> LENGTH: 78
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Leu Glu Leu Arg Pro Glu Ala Ser Arg Pro Ala Ala Gly Gly Ala Val
1               5                   10                  15
His Thr Arg Gly Leu Asp Phe Ala Ser Asp Ile Tyr Ile Trp Ala Pro
            20                  25                  30
Leu Ala Gly Thr Cys Gly Val Leu Leu Leu Ser Leu Val Ile Thr Leu
        35                  40                  45
Tyr Leu Cys Cys Arg Arg Arg Val Cys Lys Cys Pro Arg Pro Val
    50                  55                  60
Val Lys Ser Gly Asp Lys Pro Ser Leu Ser Ala Arg Tyr Val
65                  70                  75
```

<210> SEQ ID NO 41
<211> LENGTH: 213
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 41

```
ctcgagaaga agtccaccct gaagaaacgg gtgtcccggc tgcccagacc cgagacacag    60
aagggccccc tgagcagccc tatcaccctg ggactgctgg tggccggcgt gctggtgctg   120
ctggtgtctc tgggagtggc catccacctg tgctgccggc ggagaagggc ctgcaagtgc   180
cccagactgc ggttcatgaa gcagttctac aag                                213
```

<210> SEQ ID NO 42
<211> LENGTH: 71
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Leu Glu Lys Lys Ser Thr Leu Lys Lys Arg Val Ser Arg Leu Pro Arg
1               5                   10                  15
Pro Glu Thr Gln Lys Gly Pro Leu Ser Ser Pro Ile Thr Leu Gly Leu
            20                  25                  30
Leu Val Ala Gly Val Leu Val Leu Leu Val Ser Leu Gly Val Ala Ile
        35                  40                  45
```

His Leu Cys Cys Arg Arg Arg Ala Cys Lys Cys Pro Arg Leu Arg
        50                  55                  60

Phe Met Lys Gln Phe Tyr Lys
65                  70

<210> SEQ ID NO 43
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atggatatcc agatgaccca gtccccgagc tccctgtccg cctctgtggg cgatagggtc      60
accatcacct gccgtgccag tcaggacatc cgtaattatc tgaactggta tcaacagaaa     120
ccaggaaaag ctccgaaact actgatttac tatacctccc gcctggagtc tggagtccct     180
tctcgcttct ctggttctgg ttctgggacg gattacactc tgaccatcag cagtctgcaa     240
ccggaagact tcgcaactta ttactgtcag caaggtaata ctctgccgtg gacgttcgga     300
cagggcacca aggtggagat caaaggcggc ggcggaagtg gaggaggagg ctcaggcgga     360
ggagggagcg aggttcagct ggtggagtct ggcggtggcc tggtgcagcc agggggctca     420
ctccgtttgt cctgtgcagc ttctggctac tcctttaccg gctacactat gaactgggtg     480
cgtcaggccc caggtaaggg cctggaatgg gttgcactga ttaatcctta taaggtgtt      540 agtacctaca accagaagtt caaggaccgt ttcactataa gctagataaa atccaaaaac     600
acagcctacc tgcaaatgaa cagcctgcgt gctgaggaca ctgccgtcta ttattgtgct     660
agaagcggat actacggcga tagtgactgg tattttgacg tgtggggtca aggaaccctg     720
gtcaccgtct cctcg                                                      735

<210> SEQ ID NO 44
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Ile Arg Asn
            20                  25                  30

Tyr Leu Asn Trp Tyr Gln Gln Lys Pro Gly Lys Ala Pro Lys Leu Leu
        35                  40                  45

Ile Tyr Tyr Thr Ser Arg Leu Glu Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Asn Thr Leu Pro
                85                  90                  95

Trp Thr Phe Gly Gln Gly Thr Lys Val Glu Ile Lys Gly Gly Gly Gly
            100                 105                 110

Ser Gly Gly Gly Gly Ser Gly Gly Gly Ser Glu Val Gln Leu Val
        115                 120                 125

-continued

```
Glu Ser Gly Gly Gly Leu Val Gln Pro Gly Gly Ser Leu Arg Leu Ser
        130                 135                 140
Cys Ala Ala Ser Gly Tyr Ser Phe Thr Gly Tyr Thr Met Asn Trp Val
145                 150                 155                 160
Arg Gln Ala Pro Gly Lys Gly Leu Glu Trp Val Ala Leu Ile Asn Pro
                165                 170                 175
Tyr Lys Gly Val Ser Thr Tyr Asn Gln Lys Phe Lys Asp Arg Phe Thr
            180                 185                 190
Ile Ser Val Asp Lys Ser Lys Asn Thr Ala Tyr Leu Gln Met Asn Ser
        195                 200                 205
Leu Arg Ala Glu Asp Thr Ala Val Tyr Tyr Cys Ala Arg Ser Gly Tyr
    210                 215                 220
Tyr Gly Asp Ser Asp Trp Tyr Phe Asp Val Trp Gly Gln Gly Thr Leu
225                 230                 235                 240
Val Thr Val Ser Ser
                245

<210> SEQ ID NO 45
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
atggatatcc agatgaccca gtccccgagc tccctgtccg cctctgtggg cgatagggtc      60
accatcacct gccgtgccag tcaggacatc cgtaattatc tgaactggta tcaacagaaa     120
ccaggaaaag ctccgaaact actgatttac tatacctccc gcctggagtc tggagtccct     180
tctcgcttct ctggttctgg ttctgggacg gattacactc tgaccatcag cagtctgcaa     240
ccggaagact cgcaactta ttactgtcag caaggtaata tctctgccgt gacgttcgga      300
cagggcacca aggtggagat caaaggcggc ggcggaagtg gaggaggagg ctcaggcgga     360
ggagggagcg aggttcagct ggtggagtct ggcggtggcc tggtgcagcc aggggctca     420 ctccgtttgt cctgtgcagc ttctggctac tcctttaccg gctacactat gaactgggtg     480
cgtcaggccc caggtaaggg cctggaatgg gttgcactga ttaatcctac caaaggtgtt     540
agtacctaca accagaagtt caaggaccgt ttcactataa gctagataa atccaaaaac     600 acagcctacc tgcaaatgaa cagcctgcgt gctgaggaca ctgccgtcta ttattgtgct     660
agaagcggat actacggcga tagtgactgg tattttgacg tgtggggtca aggaaccctg     720
gtcaccgtct cctcg                                                      735

<210> SEQ ID NO 46
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Met Asp Ile Gln Met Thr Gln Ser Pro Ser Ser Leu Ser Ala Ser Val
1               5                   10                  15
Gly Asp Arg Val Thr Ile Thr Cys Arg Ala Ser Gln Asp Ile Arg Asn
            20                  25                  30
Tyr Leu Asn Trp Tyr Gln Gln Lys Pro Gly Lys Ala Pro Lys Leu Leu
```

35                  40                  45
Ile Tyr Tyr Thr Ser Arg Leu Glu Ser Gly Val Pro Ser Arg Phe Ser
 50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys Gln Gln Gly Asn Thr Leu Pro
                 85                  90                  95

Trp Thr Phe Gly Gln Gly Thr Lys Val Glu Ile Lys Gly Gly Gly Gly
            100                 105                 110

Ser Gly Gly Gly Gly Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Tyr Ser Phe Thr Gly Tyr Thr Met Asn Trp Val
145                 150                 155                 160

Arg Gln Ala Pro Gly Lys Gly Leu Glu Trp Val Ala Leu Ile Asn Pro
                165                 170                 175

Thr Lys Gly Val Ser Thr Tyr Asn Gln Lys Phe Lys Asp Arg Phe Thr
            180                 185                 190

Ile Ser Val Asp Lys Ser Lys Asn Thr Ala Tyr Leu Gln Met Asn Ser
        195                 200                 205

Leu Arg Ala Glu Asp Thr Ala Val Tyr Tyr Cys Ala Arg Ser Gly Tyr
    210                 215                 220

Tyr Gly Asp Ser Asp Trp Tyr Phe Asp Val Trp Gly Gln Gly Thr Leu
225                 230                 235                 240

Val Thr Val Ser Ser
                245

<210> SEQ ID NO 47
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atggagaccc ccgcccagct gctgttcctg ctgctgctgt ggctgcccga caccaccggc    60

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Glu Thr Pro Ala Gln Leu Leu Phe Leu Leu Leu Leu Trp Leu Pro
 1               5                  10                  15

Asp Thr Thr Gly
             20

<210> SEQ ID NO 49
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49

```
atggctttgc ctgtcacggc tcttctgctc cctctggccc tgcttctgca cgcggcgcga    60
ccc                                                                  63
```

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 51
<211> LENGTH: 732
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51

```
gaggtgcagc tggtggagtc tggaggaggc ctggtgcagc ctggcggctc cctgaggctg    60
tcttgcgcag caagcggctt caacatctac tatagctaca tgcactgggt gcgccaggcc   120
cctggcaagg gcctggagtg ggtggcctcc atctctccat actatggcta cacctcctat   180
gccgactctg tgaagggccg gtttacaatc agcgccgata cctccaagaa cacagcctat   240
ctgcagatga attccctgag gcagaggac accgccgtgt actattgcgc cagacacggc   300
tacgccctgg attattgggg ccagggcacc ctggtgacag tgagctccgg cagcacatcc   360
ggatctggca agccaggctc tgagaggga agcaccaagg gcgacatcca gatgacacag   420
tccccatcta gcctgagcgc ctccgtgggc gatagggtga ccatcacatg tcgcgcctct   480
cagagcgtgt cctctgccgt ggcatggtac cagcagaagc ccggcaaggc ccctaagctg   540
ctgatctaca gcgccagctc cctgtattcc ggcgtgcctt ctcggttctc cggctctaga   600
agcggcaccg actttaccct gacaatctct agcctgcagc ccgaggattt cgccacatac   660
tattgtcagc agagcgtgtg ggtgggctac tccctgatca cctttggcca gggcacaaag   720
gtggagatca ag                                                       732
```

<210> SEQ ID NO 52
<211> LENGTH: 244
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Tyr Met His Trp Val Arg Gln Ala Pro Gly Lys Gly Leu Glu Trp Val
```

```
                   35                  40                  45
Ala Ser Ile Ser Pro Tyr Tyr Gly Tyr Thr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg His Gly Tyr Ala Leu Asp Tyr Trp Gly Gln Gly Thr Leu Val
                100                 105                 110

Thr Val Ser Ser Gly Ser Thr Ser Gly Ser Gly Lys Pro Gly Ser Gly
                115                 120                 125

Glu Gly Ser Thr Lys Gly Asp Ile Gln Met Thr Gln Ser Pro Ser Ser
            130                 135                 140

Leu Ser Ala Ser Val Gly Asp Arg Val Thr Ile Thr Cys Arg Ala Ser
145                 150                 155                 160

Gln Ser Val Ser Ser Ala Val Ala Trp Tyr Gln Gln Lys Pro Gly Lys
                165                 170                 175

Ala Pro Lys Leu Leu Ile Tyr Ser Ala Ser Ser Leu Tyr Ser Gly Val
                180                 185                 190

Pro Ser Arg Phe Ser Gly Ser Arg Ser Gly Thr Asp Phe Thr Leu Thr
                195                 200                 205

Ile Ser Ser Leu Gln Pro Glu Asp Phe Ala Thr Tyr Tyr Cys Gln Gln
    210                 215                 220

Ser Val Trp Val Gly Tyr Ser Leu Ile Thr Phe Gly Gln Gly Thr Lys
225                 230                 235                 240

Val Glu Ile Lys

<210> SEQ ID NO 53
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
gacatccaga tgacacagtc cccaagctcc ctgtccgcct ctgtgggcga tagggtgacc      60
atcacatgca gggcaagcca gtccgtgtct agcgccgtgg catggtacca gcagaagccc    120
ggcaaggccc ctaagctgct gatctacagc gcctcctctc tgtattccgg cgtgccatct    180
cggttctctg gcagcagatc cggcaccgac tttaccctga caatcagctc cctgcagccc    240
gaggatttcg ccacatacta ttgccagcag agcgtgtggg tgggctactc cctgatcacc    300
tttggccagg gcacaaaggt ggagatcaag ggatctacca gcggatccgg caagcctggc    360
agcggagagg gatccacaaa gggagaggtg cagctggtgg agtctggagg aggcctggtg    420
cagcctggcg gctctctgag gctgagctgt gcagcatccg gcttcaacat ctactatagc    480
tacatgcact gggtgcgcca ggccccggc aagggcctgg agtgggtggc ctctatcagc    540
ccttactatg gctacaccct ttatgccgac agcgtgaagg gccggtttac aatctccgcc    600
gatacctcta gaacacagc ctatctgcag atgaattccc tgagggcaga ggacaccgcc    660
gtgtactatt gtgccagaca cggctacgcc ctggattatt ggggccaggg caccctggtg    720
acagtgtcta gc                                                        732

<210> SEQ ID NO 54
```

-continued

```
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Trp Val Gly Tyr
                85                  90                  95

Ser Leu Ile Thr Phe Gly Gln Gly Thr Lys Val Glu Ile Lys Gly Ser
            100                 105                 110

Thr Ser Gly Ser Gly Lys Pro Gly Ser Gly Glu Gly Ser Thr Lys Gly
        115                 120                 125

Glu Val Gln Leu Val Glu Ser Gly Gly Leu Val Gln Pro Gly Gly
    130                 135                 140

Ser Leu Arg Leu Ser Cys Ala Ala Ser Gly Phe Asn Ile Tyr Tyr Ser
145                 150                 155                 160

Tyr Met His Trp Val Arg Gln Ala Pro Gly Lys Gly Leu Glu Trp Val
                165                 170                 175

Ala Ser Ile Ser Pro Tyr Tyr Gly Tyr Thr Ser Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ala Arg His Gly Tyr Ala Leu Asp Tyr Trp Gly Gln Gly Thr Leu Val
225                 230                 235                 240

Thr Val Ser Ser

<210> SEQ ID NO 55
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atggccctgc cagtgaccgc cctgctgctg ccactggccc tgctgctgca cgccgccaga    60
cccgaggtgc agctggtgga gtctggagga ggcctggtgc agcctggcgg ctccctgagg   120
ctgtcttgcg cagcaagcgg cttcaacatc tactatagct acatgcactg ggtgcgccag   180
gcccctggca agggcctgga gtgggtggcc tccatctctc catactatgg ctacacctcc   240
tatgccgact ctgtgaaggg ccggtttaca atcagcgccg ataccccaa gaacacagcc   300 tatctgcaga tgaattccct gagggcagag gacaccgccg tgtactattg cgccagacac   360
```

```
ggctacgccc tggattattg gggccagggc accctggtga cagtgagctc cggcagcaca    420
tccggatctg gcaagccagg ctctggagag ggaagcacca aggcgacat  ccagatgaca    480 cagtccccat ctagcctgag cgcctccgtg ggcgataggg tgaccatcac atgtcgcgcc    540
tctcagagcg tgtcctctgc cgtggcatgg taccagcaga agcccggcaa ggcccctaag    600
ctgctgatct acagcgccag ctccctgtat tccggcgtgc cttctcggtt ctccggctct    660
agaagcggca ccgactttac cctgacaatc tctagcctgc agcccgagga tttcgccaca    720
tactattgtc agcagagcgt gtgggtgggc tactccctga tcacctttgg ccagggcaca    780
aaggtggaga tcaaggagca gaagctgatc agcgaggagg acctgaatcc cggggccgaa    840
gcagcagcaa aggaggccgc agcgaaggaa gcagctgcga aggccggatc catggatatc    900
cagatgaccc agtccccgag ctccctgtcc gcctctgtgg gcgatagggt caccatcacc    960
tgccgtgcca gtcaggacat ccgtaattat ctgaactggt atcaacagaa accaggaaaa   1020
gctccgaaac tactgattta ctatacctcc cgcctggagt ctggagtccc ttctcgcttc   1080
tctggttctg gttctgggac ggattacact ctgaccatca gcagtctgca accggaagac   1140
ttcgcaactt attactgtca gcaaggtaat actctgccgt ggacgttcgg acagggcacc   1200
aaggtggaga tcaaggcgg  cggcggaagt ggaggaggag gctcaggcgg aggagggagc   1260
gaggttcagc tggtggagtc tggcggtggc ctggtgcagc caggggctc  actccgtttg   1320 tcctgtgcag cttctggcta ctcctttacc ggctacacta tgaactgggt gcgtcaggcc   1380
ccaggtaagg gcctggaatg ggttgcactg attaatcctt ataaaggtgt tagtacctac   1440
aaccagaagt tcaaggaccg tttcactata agcgtagata atccaaaaa  cacagcctac   1500 ctgcaaatga acagcctgcg tgctgaggac actgccgtct attattgtgc tagaagcgga   1560
tactacggcg atagtgactg gtattttgac gtgtggggtc aaggaaccct ggtcaccgtc   1620
tcctcgacta gtggcggagg aggatcactc gagagcggac aggtgctgct ggaatccaat   1680
atcaaagtcc tgcccacttg gtctaccccc gtgcagccta tggctctgat tgtgctggga   1740
ggagtcgcag gactgctgct gtttatcggg ctgggaattt tcttttgcgt gcgctgccgg   1800
caccggagaa ggcaggccga gcgcatgagc cagatcaagc gactgctgag cgagaagaaa   1860
acctgtcagt gtccccatag attccagaag acctgttcac ccatt               1905
```

<210> SEQ ID NO 56
<211> LENGTH: 635
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 56

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Gln Pro Gly Gly Ser Leu Arg Leu Ser Cys Ala Ala Ser Gly Phe
            35                  40                  45

Asn Ile Tyr Tyr Ser Tyr Met His Trp Val Arg Gln Ala Pro Gly Lys
        50                  55                  60

Gly Leu Glu Trp Val Ala Ser Ile Ser Pro Tyr Tyr Gly Tyr Thr Ser
65                  70                  75                  80

Tyr Ala Asp Ser Val Lys Gly Arg Phe Thr Ile Ser Ala Asp Thr Ser

```
                    85                  90                  95
Lys Asn Thr Ala Tyr Leu Gln Met Asn Ser Leu Arg Ala Glu Asp Thr
                100                 105                 110

Ala Val Tyr Tyr Cys Ala Arg His Gly Tyr Ala Leu Asp Tyr Trp Gly
            115                 120                 125

Gln Gly Thr Leu Val Thr Val Ser Ser Gly Ser Thr Ser Gly Ser Gly
        130                 135                 140

Lys Pro Gly Ser Gly Glu Gly Ser Thr Lys Gly Asp Ile Gln Met Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Ser Val Ser Ser Ala Val Ala Trp Tyr Gln
            180                 185                 190

Gln Lys Pro Gly Lys Ala Pro Lys Leu Leu Ile Tyr Ser Ala Ser Ser
        195                 200                 205

Leu Tyr Ser Gly Val Pro Ser Arg Phe Ser Gly Ser Arg Ser Gly Thr
    210                 215                 220

Asp Phe Thr Leu Thr Ile Ser Ser Leu Gln Pro Glu Asp Phe Ala Thr
225                 230                 235                 240

Tyr Tyr Cys Gln Gln Ser Val Trp Val Gly Tyr Ser Leu Ile Thr Phe
                245                 250                 255

Gly Gln Gly Thr Lys Val Glu Ile Lys Glu Gln Lys Leu Ile Ser Glu
            260                 265                 270

Glu Asp Leu Asn Pro Gly Ala Glu Ala Ala Lys Glu Ala Ala Ala
        275                 280                 285

Lys Glu Ala Ala Ala Lys Ala Gly Ser Met Asp Ile Gln Met Thr Gln
290                 295                 300

Ser Pro Ser Ser Leu Ser Ala Ser Val Gly Asp Arg Val Thr Ile Thr
305                 310                 315                 320

Cys Arg Ala Ser Gln Asp Ile Arg Asn Tyr Leu Asn Trp Tyr Gln Gln
                325                 330                 335

Lys Pro Gly Lys Ala Pro Lys Leu Leu Ile Tyr Tyr Thr Ser Arg Leu
            340                 345                 350

Glu Ser Gly Val Pro Ser Arg Phe Ser Gly Ser Gly Ser Gly Thr Asp
        355                 360                 365

Tyr Thr Leu Thr Ile Ser Ser Leu Gln Pro Glu Asp Phe Ala Thr Tyr
    370                 375                 380

Tyr Cys Gln Gln Gly Asn Thr Leu Pro Trp Thr Phe Gly Gln Gly Thr
385                 390                 395                 400

Lys Val Glu Ile Lys Gly Gly Gly Gly Ser Gly Gly Gly Gly Ser Gly
                405                 410                 415

Gly Gly Gly Ser Glu Val Gln Leu Val Glu Ser Gly Gly Gly Leu Val
            420                 425                 430

Gln Pro Gly Gly Ser Leu Arg Leu Ser Cys Ala Ala Ser Gly Tyr Ser
        435                 440                 445

Phe Thr Gly Tyr Thr Met Asn Trp Val Arg Gln Ala Pro Gly Lys Gly
    450                 455                 460

Leu Glu Trp Val Ala Leu Ile Asn Pro Tyr Lys Gly Val Ser Thr Tyr
465                 470                 475                 480

Asn Gln Lys Phe Lys Asp Arg Phe Thr Ile Ser Val Asp Lys Ser Lys
                485                 490                 495

Asn Thr Ala Tyr Leu Gln Met Asn Ser Leu Arg Ala Glu Asp Thr Ala
            500                 505                 510
```

```
Val Tyr Tyr Cys Ala Arg Ser Gly Tyr Tyr Gly Asp Ser Asp Trp Tyr
        515                 520                 525

Phe Asp Val Trp Gly Gln Gly Thr Leu Val Thr Val Ser Ser Thr Ser
    530                 535                 540

Gly Gly Gly Gly Ser Leu Glu Ser Gly Gln Val Leu Leu Glu Ser Asn
545                 550                 555                 560

Ile Lys Val Leu Pro Thr Trp Ser Thr Pro Val Gln Pro Met Ala Leu
                565                 570                 575

Ile Val Leu Gly Gly Val Ala Gly Leu Leu Leu Phe Ile Gly Leu Gly
                580                 585                 590

Ile Phe Phe Cys Val Arg Cys Arg His Arg Arg Gln Ala Glu Arg
        595                 600                 605

Met Ser Gln Ile Lys Arg Leu Leu Ser Glu Lys Lys Thr Cys Gln Cys
        610                 615                 620

Pro His Arg Phe Gln Lys Thr Cys Ser Pro Ile
625                 630                 635
```

<210> SEQ ID NO 57
<211> LENGTH: 1905
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

| | |
|---|---|
| atggccctgc cagtgaccgc cctgctgctg ccactggccc tgctgctgca cgccgcccgg | 60 |
| cctgacatcc agatgacaca gtccccaagc tccctgtccg cctctgtggg cgatagggtg | 120 |
| accatcacat gcagggcaag ccagtccgtg tctagcgccg tggcatggta ccagcagaag | 180 |
| cccggcaagg cccctaagct gctgatctac agcgcctcct ctctgtattc cggcgtgcca | 240 |
| tctcggttct ctggcagcag atccggcacc gactttaccc tgacaatcag ctccctgcag | 300 |
| cccgaggatt tcgccacata ctattgccag cagagcgtgt gggtgggcta ctccctgatc | 360 |
| acctttggcc agggcacaaa ggtggagatc aagggatcta ccagcggatc cggcaagcct | 420 |
| ggcagcggag agggatccac aaagggagag gtgcagctgg tggagtctgg aggaggcctg | 480 |
| gtgcagcctg cggctctct gaggctgagc tgtgcagcat ccggcttcaa catctactat | 540 |
| agctacatgc actgggtgcg ccaggccccc ggcaagggcc tggagtgggt ggcctctatc | 600 |
| agcccttact atggctacac ctcttatgcc gacagcgtga agggccggtt tacaatctcc | 660 |
| gccgataccc taagaacac agcctatctg cagatgaatt ccctgagggc agaggacacc | 720 |
| gccgtgtact attgtgccag acacggctac gccctggatt attggggcca gggcaccctg | 780 |
| gtgacagtgt ctagcgagca aagctgatc agcgaggagg acctgaatcc cggggccgaa | 840 |
| gcagcagcaa aggaggccgc agcgaaggaa gcagctgcga aggccggatc catggatatc | 900 |
| cagatgaccc agtccccgag ctccctgtcc gcctctgtgg gcgatagggt caccatcacc | 960 |
| tgccgtgcca gtcaggacat ccgtaattat ctgaactggt atcaacagaa accaggaaaa | 1020 |
| gctccgaaac tactgattta ctatacctcc cgcctggagt ctggagtccc ttctcgcttc | 1080 |
| tctggttctg gttctgggac ggattacact ctgaccatca gcagtctgca accggaagac | 1140 |
| ttcgcaactt attactgtca gcaaggtaat actctgccgt ggacgttcgg acagggcacc | 1200 |
| aagtggagag tcaaaggcgg cggcggaagt ggaggaggag ctcaggcgg aggagggagc | 1260 |
| gaggttcagc tggtggagtc tggcggtggc ctggtgcagc caggggggctc actccgtttg | 1320 |

```
tcctgtgcag cttctggcta ctcctttacc ggctacacta tgaactgggt gcgtcaggcc      1380
ccaggtaagg gcctggaatg ggttgcactg attaatcctt ataaaggtgt tagtacctac      1440
aaccagaagt tcaaggaccg tttcactata agcgtagata atccaaaaa cacagcctac       1500 ctgcaaatga acagcctgcg tgctgaggac actgccgtct attattgtgc tagaagcgga      1560
tactacggcg atagtgactg gtattttgac gtgtggggtc aaggaaccct ggtcaccgtc      1620
tcctcgacta gtggcggagg aggatcactc gagagcggac aggtgctgct ggaatccaat      1680
atcaaagtcc tgcccacttg gtctacccc gtgcagccta tggctctgat tgtgctggga       1740
ggagtcgcag gactgctgct gtttatcggg ctgggaatt tcttttgcgt gcgctgccgg       1800
caccggagaa ggcaggccga gcgcatgagc cagatcaagc gactgctgag cgagaagaaa      1860
acctgtcagt gtccccatag attccagaag acctgttcac ccatt                     1905
```

<210> SEQ ID NO 58
<211> LENGTH: 635
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Met Ala Leu Pro Val Thr Ala Leu Leu Pro Leu Ala Leu Leu Leu
1               5                  10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Ser Val Ser Ser Ala Val Ala Trp Tyr Gln Gln Lys Pro Gly Lys Ala
    50                  55                  60

Pro Lys Leu Leu Ile Tyr Ser Ala Ser Ser Leu Tyr Ser Gly Val Pro
65                  70                  75                  80

Ser Arg Phe Ser Gly Ser Arg Ser Gly Thr Asp Phe Thr Leu Thr Ile
                85                  90                  95

Ser Ser Leu Gln Pro Glu Asp Phe Ala Thr Tyr Tyr Cys Gln Gln Ser
            100                 105                 110

Val Trp Val Gly Tyr Ser Leu Ile Thr Phe Gly Gln Gly Thr Lys Val
        115                 120                 125

Glu Ile Lys Gly Ser Thr Ser Gly Ser Gly Lys Pro Gly Ser Gly Glu
    130                 135                 140

Gly Ser Thr Lys Gly Glu Val Gln Leu Val Glu Ser Gly Gly Gly Leu
145                 150                 155                 160

Val Gln Pro Gly Gly Ser Leu Arg Leu Ser Cys Ala Ala Ser Gly Phe
                165                 170                 175

Asn Ile Tyr Tyr Ser Tyr Met His Trp Val Arg Gln Ala Pro Gly Lys
            180                 185                 190

Gly Leu Glu Trp Val Ala Ser Ile Ser Pro Tyr Tyr Gly Tyr Thr Ser
        195                 200                 205

Tyr Ala Asp Ser Val Lys Gly Arg Phe Thr Ile Ser Ala Asp Thr Ser
    210                 215                 220

Lys Asn Thr Ala Tyr Leu Gln Met Asn Ser Leu Arg Ala Glu Asp Thr
225                 230                 235                 240

Ala Val Tyr Tyr Cys Ala Arg His Gly Tyr Ala Leu Asp Tyr Trp Gly
                245                 250                 255
```

Gln Gly Thr Leu Val Thr Val Ser Ser Glu Gln Lys Leu Ile Ser Glu
        260                 265                 270

Glu Asp Leu Asn Pro Gly Ala Glu Ala Ala Lys Glu Ala Ala Ala
        275                 280                 285

Lys Glu Ala Ala Lys Ala Gly Ser Met Asp Ile Gln Met Thr Gln
    290                 295                 300

Ser Pro Ser Ser Leu Ser Ala Ser Val Gly Asp Arg Val Thr Ile Thr
305                 310                 315                 320

Cys Arg Ala Ser Gln Asp Ile Arg Asn Tyr Leu Asn Trp Tyr Gln Gln
                325                 330                 335

Lys Pro Gly Lys Ala Pro Lys Leu Leu Ile Tyr Tyr Thr Ser Arg Leu
            340                 345                 350

Glu Ser Gly Val Pro Ser Arg Phe Ser Gly Ser Gly Ser Gly Thr Asp
        355                 360                 365

Tyr Thr Leu Thr Ile Ser Ser Leu Gln Pro Glu Asp Phe Ala Thr Tyr
    370                 375                 380

Tyr Cys Gln Gln Gly Asn Thr Leu Pro Trp Thr Phe Gly Gln Gly Thr
385                 390                 395                 400

Lys Val Glu Ile Lys Gly Gly Gly Gly Ser Gly Gly Gly Gly Ser Gly
                405                 410                 415

Gly Gly Gly Ser Glu Val Gln Leu Val Glu Ser Gly Gly Gly Leu Val
            420                 425                 430

Gln Pro Gly Gly Ser Leu Arg Leu Ser Cys Ala Ala Ser Gly Tyr Ser
        435                 440                 445

Phe Thr Gly Tyr Thr Met Asn Trp Val Arg Gln Ala Pro Gly Lys Gly
    450                 455                 460

Leu Glu Trp Val Ala Leu Ile Asn Pro Tyr Lys Gly Val Ser Thr Tyr
465                 470                 475                 480

Asn Gln Lys Phe Lys Asp Arg Phe Thr Ile Ser Val Asp Lys Ser Lys
                485                 490                 495

Asn Thr Ala Tyr Leu Gln Met Asn Ser Leu Arg Ala Glu Asp Thr Ala
            500                 505                 510

Val Tyr Tyr Cys Ala Arg Ser Gly Tyr Tyr Gly Asp Ser Asp Trp Tyr
        515                 520                 525

Phe Asp Val Trp Gly Gln Gly Thr Leu Val Thr Val Ser Ser Thr Ser
    530                 535                 540

Gly Gly Gly Gly Ser Leu Glu Ser Gly Gln Val Leu Leu Glu Ser Asn
545                 550                 555                 560

Ile Lys Val Leu Pro Thr Trp Ser Thr Pro Val Gln Pro Met Ala Leu
                565                 570                 575

Ile Val Leu Gly Gly Val Ala Gly Leu Leu Leu Phe Ile Gly Leu Gly
            580                 585                 590

Ile Phe Phe Cys Val Arg Cys Arg His Arg Arg Gln Ala Glu Arg
        595                 600                 605

Met Ser Gln Ile Lys Arg Leu Leu Ser Glu Lys Lys Thr Cys Gln Cys
    610                 615                 620

Pro His Arg Phe Gln Lys Thr Cys Ser Pro Ile
625                 630                 635

<210> SEQ ID NO 59
<211> LENGTH: 1914
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 59

```
atggccctgc cagtgaccgc cctgctgctg ccactggccc tgctgctgca cgccgccaga      60
cccgaggtgc agctggtgga gtctggagga ggcctggtgc agcctggcgg ctccctgagg     120
ctgtcttgcg cagcaagcgg cttcaacatc tactatagct acatgcactg ggtgcgccag     180
gcccctggca agggcctgga gtgggtggcc tccatctctc atactatgg ctacacctcc      240
tatgccgact ctgtgaaggg ccggtttaca atcagcgccg atacctccaa gaacacagcc     300
tatctgcaga tgaattccct gagggcagag gacaccgccg tgtactattg cgccagacac     360
ggctacgccc tggattattg gggccagggc accctggtga cagtgagctc cggcagcaca     420
tccggatctg gcaagccagg ctctggagag gaagcacca agggcgacat ccagatgaca     480
cagtccccat ctagcctgag cgcctccgtg ggcgataggg tgaccatcac atgtcgcgcc     540
tctcagagcg tgtcctctgc cgtggcatgg taccagcaga agcccggcaa ggcccctaag     600
ctgctgatct acagcgccag ctccctgtat ccggcgtgc cttctcggtt ctccggctct      660
agaagcggca ccgactttac cctgacaatc tctagcctgc agcccgagga tttcgccaca     720
tactattgtc agcagagcgt gtgggtgggc tactccctga tcacctttgg ccagggcaca     780
aaggtggaga tcaaggagca gaagctgatc agcgaggagg acctgaatcc cggggggagga    840
ggagggagcg ggggaggagg cagcggcggg ggaggctctg gaggaggagg gagcggatcc     900
atggatatcc agatgaccca gtccccgagc tccctgtccg cctctgtggg cgataggggtc     960
accatcacct gccgtgccag tcaggacatc cgtaattatc tgaactggta tcaacagaaa    1020
ccaggaaaag ctccgaaact actgatttac tatacctccc gcctggagtc tggagtccct    1080
tctcgcttct ctggttctgg ttctgggacg gattacactc tgaccatcag cagtctgcaa    1140
ccggaagact tcgcaactta ttactgtcag caaggtaata tctctgccgtg gacgttcgga    1200
cagggcacca aggtggagat caaaggcggc ggcggaagtg gaggaggagg ctcaggcgga    1260
ggagggagcg aggttcagct ggtggagtct ggcggtggcc tggtgcagcc aggggggctca    1320
ctccgtttgt cctgtgcagc ttctggctac tcctttaccg gctacactat gaactgggtg    1380
cgtcaggccc caggtaaggg cctggaatgg gttgcactga ttaatcctta taaaggtgtt    1440
agtacctaca accagaagtt caaggaccgt ttcactataa gctagataa atccaaaaac     1500
acagcctacc tgcaaatgaa cagcctgcgt gctgaggaca ctgccgtcta ttattgtgct    1560
agaagcggat actacggcga tagtgactgg tattttgacg tgtggggtca aggaaccctg    1620
gtcaccgtct cctcgactag tggcggagga ggatcactcg agagcggaca ggtgctgctg    1680
gaatccaata tcaaagtcct gcccacttgg tctaccccg tgcagcctat ggctctgatt    1740
gtgctgggag gagtcgcagg actgctgctg tttatcgggc tgggaatttt cttttgcgtg    1800
cgctgccggc accggagaag gcaggccgag cgcatgagcc agatcaagcg actgctgagc    1860
gagaagaaaa cctgtcagtg tccccataga ttccagaaga cctgttcacc catt           1914
```

<210> SEQ ID NO 60
<211> LENGTH: 638
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 60

```
Met Ala Leu Pro Val Thr Ala Leu Leu Leu Pro Leu Ala Leu Leu Leu
1               5                   10                  15
His Ala Ala Arg Pro Glu Val Gln Leu Val Glu Ser Gly Gly Gly Leu
                20                  25                  30
Val Gln Pro Gly Gly Ser Leu Arg Leu Ser Cys Ala Ala Ser Gly Phe
            35                  40                  45
Asn Ile Tyr Tyr Ser Tyr Met His Trp Val Arg Gln Ala Pro Gly Lys
        50                  55                  60
Gly Leu Glu Trp Val Ala Ser Ile Ser Pro Tyr Gly Tyr Thr Ser
65                  70                  75                  80
Tyr Ala Asp Ser Val Lys Gly Arg Phe Thr Ile Ser Ala Asp Thr Ser
                85                  90                  95
Lys Asn Thr Ala Tyr Leu Gln Met Asn Ser Leu Arg Ala Glu Asp Thr
            100                 105                 110
Ala Val Tyr Tyr Cys Ala Arg His Gly Tyr Ala Leu Asp Tyr Trp Gly
        115                 120                 125
Gln Gly Thr Leu Val Thr Val Ser Ser Gly Ser Thr Ser Gly Ser Gly
        130                 135                 140
Lys Pro Gly Ser Gly Glu Gly Ser Thr Lys Gly Asp Ile Gln Met Thr
145                 150                 155                 160
Gln Ser Pro Ser Ser Leu Ser Ala Ser Val Gly Asp Arg Val Thr Ile
                165                 170                 175
Thr Cys Arg Ala Ser Gln Ser Val Ser Ser Ala Val Ala Trp Tyr Gln
            180                 185                 190
Gln Lys Pro Gly Lys Ala Pro Lys Leu Leu Ile Tyr Ser Ala Ser Ser
        195                 200                 205
Leu Tyr Ser Gly Val Pro Ser Arg Phe Ser Gly Ser Arg Ser Gly Thr
        210                 215                 220
Asp Phe Thr Leu Thr Ile Ser Ser Leu Gln Pro Glu Asp Phe Ala Thr
225                 230                 235                 240
Tyr Tyr Cys Gln Gln Ser Val Trp Val Gly Tyr Ser Leu Ile Thr Phe
                245                 250                 255
Gly Gln Gly Thr Lys Val Glu Ile Lys Glu Gln Lys Leu Ile Ser Glu
            260                 265                 270
Glu Asp Leu Asn Pro Gly Gly Gly Gly Ser Gly Gly Gly Gly Ser
        275                 280                 285
Gly Gly Gly Gly Ser Gly Gly Gly Ser Gly Ser Met Asp Ile Gln
        290                 295                 300
Met Thr Gln Ser Pro Ser Ser Leu Ser Ala Ser Val Gly Asp Arg Val
305                 310                 315                 320
Thr Ile Thr Cys Arg Ala Ser Gln Asp Ile Arg Asn Tyr Leu Asn Trp
                325                 330                 335
Tyr Gln Gln Lys Pro Gly Lys Ala Pro Lys Leu Leu Ile Tyr Tyr Thr
            340                 345                 350
Ser Arg Leu Glu Ser Gly Val Pro Ser Arg Phe Ser Gly Ser Gly Ser
        355                 360                 365
Gly Thr Asp Tyr Thr Leu Thr Ile Ser Ser Leu Gln Pro Glu Asp Phe
        370                 375                 380
Ala Thr Tyr Tyr Cys Gln Gln Gly Asn Thr Leu Pro Trp Thr Phe Gly
385                 390                 395                 400
Gln Gly Thr Lys Val Glu Ile Lys Gly Gly Gly Gly Ser Gly Gly Gly
                405                 410                 415
```

Gly Ser Gly Gly Gly Ser Glu Val Gln Leu Val Glu Ser Gly Gly
                420                 425                 430

Gly Leu Val Gln Pro Gly Ser Leu Arg Leu Ser Cys Ala Ala Ser
            435                 440                 445

Gly Tyr Ser Phe Thr Gly Tyr Thr Met Asn Trp Val Arg Gln Ala Pro
        450                 455                 460

Gly Lys Gly Leu Glu Trp Val Ala Leu Ile Asn Pro Tyr Lys Gly Val
465                 470                 475                 480

Ser Thr Tyr Asn Gln Lys Phe Lys Asp Arg Phe Thr Ile Ser Val Asp
                485                 490                 495

Lys Ser Lys Asn Thr Ala Tyr Leu Gln Met Asn Ser Leu Arg Ala Glu
            500                 505                 510

Asp Thr Ala Val Tyr Tyr Cys Ala Arg Ser Gly Tyr Tyr Gly Asp Ser
        515                 520                 525

Asp Trp Tyr Phe Asp Val Trp Gly Gln Gly Thr Leu Val Thr Val Ser
    530                 535                 540

Ser Thr Ser Gly Gly Gly Gly Ser Leu Glu Ser Gly Gln Val Leu Leu
545                 550                 555                 560

Glu Ser Asn Ile Lys Val Leu Pro Thr Trp Ser Thr Pro Val Gln Pro
                565                 570                 575

Met Ala Leu Ile Val Leu Gly Gly Val Ala Gly Leu Leu Leu Phe Ile
            580                 585                 590

Gly Leu Gly Ile Phe Phe Cys Val Arg Cys Arg His Arg Arg Arg Gln
        595                 600                 605

Ala Glu Arg Met Ser Gln Ile Lys Arg Leu Leu Ser Glu Lys Lys Thr
    610                 615                 620

Cys Gln Cys Pro His Arg Phe Gln Lys Thr Cys Ser Pro Ile
625                 630                 635

<210> SEQ ID NO 61
<211> LENGTH: 1914
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atggccctgc cagtgaccgc cctgctgctg ccactggccc tgctgctgca cgccgcccgg     60
cctgacatcc agatgacaca gtccccaagc tccctgtccg cctctgtggg cgatagggtg    120
accatcacat gcagggcaag ccagtccgtg tctagcgccg tggcatggta ccagcagaag    180
cccggcaagg cccctaagct gctgatctac agcgcctcct ctctgtattc cggcgtgcca    240
tctcggttct ctggcagcag atccggcacc gactttaccc tgacaatcag ctcccctgcag   300 cccgaggatt tcgccacata ctattgccag cagagcgtgt gggtgggcta ctccctgatc    360
acctttggcc agggcacaaa ggtggagatc aaggatctac cagcggatc cggcaagcct    420 ggcagcggag agggatccac aaagggagag gtgcagctgg tggagtctgg aggaggcctg    480
gtgcagcctg gcggctctct gaggctgagc tgtgcagcat ccggcttcaa catctactat    540
agctacatgc actgggtgcg ccaggccccc ggcaagggcc tggagtgggt ggcctctatc    600
agcccttact atggctacac ctcttatgcc gacagcgtga agggccggtt acaatctcc     660 gccgatacct ctaagaacac agcctatctg cagatgaatt ccctgagggc agaggacacc    720
gccgtgtact attgtgccag acacggctac gccctggatt attggggcca ggcaccctg    780

```
gtgacagtgt ctagcgagca gaagctgatc agcgaggagg acctgaatcc cggggggagga      840 ggagggagcg ggggaggagg cagcggcggg ggaggctctg gaggaggagg gagcggatcc      900
atggatatcc agatgaccca gtccccgagc tccctgtccg cctctgtggg cgatagggtc      960
accatcacct gccgtgccag tcaggacatc cgtaattatc tgaactggta tcaacagaaa     1020
ccaggaaaag ctccgaaact actgatttac tatacctccc gcctggagtc tggagtccct     1080
tctcgcttct ctggttctgg ttctgggacg gattacactc tgaccatcag cagtctgcaa     1140
ccggaagact cgcaactta ttactgtcag caaggtaata ctctgccgtg gacgttcgga     1200
cagggcacca aggtggagat caaaggcggc ggcggaagtg gaggaggagg ctcaggcgga     1260
ggagggagcg aggttcagct ggtggagtct ggcggtggcc tggtgcagcc agggggctca     1320
ctccgtttgt cctgtgcagc ttctggctac tcctttaccg gctacactat gaactgggtg     1380
cgtcaggccc caggtaaggg cctggaatgg gttgcactga ttaatcctta taaggtgttt     1440
agtacctaca accagaagtt caaggaccgt ttcactataa gcgtagataa atccaaaaac     1500
acagcctacc tgcaaatgaa cagcctgcgt gctgaggaca ctgccgtcta ttattgtgct     1560
agaagcggat actacggcga tagtgactgg tattttgacg tgtggggtca aggaaccctg     1620
gtcaccgtct cctcgactag tggcggagga ggatcactcg agagcggaca ggtgctgctg     1680
gaatccaata tcaaagtcct gcccacttgg tctaccccg tgcagcctat ggctctgatt     1740
gtgctgggag gagtcgcagg actgctgctg tttatcgggc tgggaatttt cttttgcgtg     1800
cgctgccggc accggagaag gcaggccgag cgcatgagcc agatcaagcg actgctgagc     1860
gagaagaaaa cctgtcagtg tccccataga ttccagaaga cctgttcacc catt           1914
```

<210> SEQ ID NO 62
<211> LENGTH: 638
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Ser Val Ser Ser Ala Val Ala Trp Tyr Gln Gln Lys Pro Gly Lys Ala
    50                  55                  60

Pro Lys Leu Leu Ile Tyr Ser Ala Ser Ser Leu Tyr Ser Gly Val Pro
65                  70                  75                  80

Ser Arg Phe Ser Gly Ser Arg Ser Gly Thr Asp Phe Thr Leu Thr Ile
                85                  90                  95

Ser Ser Leu Gln Pro Glu Asp Phe Ala Thr Tyr Tyr Cys Gln Gln Ser
            100                 105                 110

Val Trp Val Gly Tyr Ser Leu Ile Thr Phe Gly Gln Gly Thr Lys Val
        115                 120                 125

Glu Ile Lys Gly Ser Thr Ser Gly Ser Gly Lys Pro Gly Ser Gly Glu
    130                 135                 140

Gly Ser Thr Lys Gly Glu Val Gln Leu Val Glu Ser Gly Gly Gly Leu
145                 150                 155                 160
```

```
Val Gln Pro Gly Gly Ser Leu Arg Leu Ser Cys Ala Ala Ser Gly Phe
            165                 170                 175
Asn Ile Tyr Tyr Ser Tyr Met His Trp Val Arg Gln Ala Pro Gly Lys
        180                 185                 190
Gly Leu Glu Trp Val Ala Ser Ile Ser Pro Tyr Tyr Gly Tyr Thr Ser
        195                 200                 205
Tyr Ala Asp Ser Val Lys Gly Arg Phe Thr Ile Ser Ala Asp Thr Ser
        210                 215                 220
Lys Asn Thr Ala Tyr Leu Gln Met Asn Ser Leu Arg Ala Glu Asp Thr
225                 230                 235                 240
Ala Val Tyr Tyr Cys Ala Arg His Gly Tyr Ala Leu Asp Tyr Trp Gly
                245                 250                 255
Gln Gly Thr Leu Val Thr Val Ser Ser Glu Gln Lys Leu Ile Ser Glu
            260                 265                 270
Glu Asp Leu Asn Pro Gly Gly Gly Gly Ser Gly Gly Gly Gly Ser
        275                 280                 285
Gly Gly Gly Gly Ser Gly Gly Gly Ser Gly Ser Met Asp Ile Gln
        290                 295                 300
Met Thr Gln Ser Pro Ser Ser Leu Ser Ala Ser Val Gly Asp Arg Val
305                 310                 315                 320
Thr Ile Thr Cys Arg Ala Ser Gln Asp Ile Arg Asn Tyr Leu Asn Trp
                325                 330                 335
Tyr Gln Gln Lys Pro Gly Lys Ala Pro Lys Leu Leu Ile Tyr Tyr Thr
                340                 345                 350
Ser Arg Leu Glu Ser Gly Val Pro Ser Arg Phe Ser Gly Ser Gly Ser
            355                 360                 365
Gly Thr Asp Tyr Thr Leu Thr Ile Ser Ser Leu Gln Pro Glu Asp Phe
        370                 375                 380
Ala Thr Tyr Tyr Cys Gln Gln Gly Asn Thr Leu Pro Trp Thr Phe Gly
385                 390                 395                 400
Gln Gly Thr Lys Val Glu Ile Lys Gly Gly Gly Gly Ser Gly Gly Gly
                405                 410                 415
Gly Ser Gly Gly Gly Gly Ser Glu Val Gln Leu Val Glu Ser Gly Gly
            420                 425                 430
Gly Leu Val Gln Pro Gly Gly Ser Leu Arg Leu Ser Cys Ala Ala Ser
        435                 440                 445
Gly Tyr Ser Phe Thr Gly Tyr Thr Met Asn Trp Val Arg Gln Ala Pro
        450                 455                 460
Gly Lys Gly Leu Glu Trp Val Ala Leu Ile Asn Pro Tyr Lys Gly Val
465                 470                 475                 480
Ser Thr Tyr Asn Gln Lys Phe Lys Asp Arg Phe Thr Ile Ser Val Asp
                485                 490                 495
Lys Ser Lys Asn Thr Ala Tyr Leu Gln Met Asn Ser Leu Arg Ala Glu
                500                 505                 510
Asp Thr Ala Val Tyr Tyr Cys Ala Arg Ser Gly Tyr Tyr Gly Asp Ser
            515                 520                 525
Asp Trp Tyr Phe Asp Val Trp Gly Gln Gly Thr Leu Val Thr Val Ser
        530                 535                 540
Ser Thr Ser Gly Gly Gly Gly Ser Leu Glu Gly Gln Val Leu Leu
545                 550                 555                 560
Glu Ser Asn Ile Lys Val Leu Pro Thr Trp Ser Thr Pro Val Gln Pro
                565                 570                 575
Met Ala Leu Ile Val Leu Gly Gly Val Ala Gly Leu Leu Leu Phe Ile
```

|     | 580 |     |     |     | 585 |     |     |     | 590 |     |
| --- | --- | --- | --- | --- | --- | --- | --- | --- | --- | --- |
| Gly | Leu | Gly | Ile | Phe | Phe | Cys | Val | Arg | Cys | Arg | His | Arg | Arg | Gln |

Gly Leu Gly Ile Phe Phe Cys Val Arg Cys Arg His Arg Arg Gln
            595                 600                 605

Ala Glu Arg Met Ser Gln Ile Lys Arg Leu Leu Ser Glu Lys Lys Thr
    610                 615                 620

Cys Gln Cys Pro His Arg Phe Gln Lys Thr Cys Ser Pro Ile
625                 630                 635

<210> SEQ ID NO 63
<211> LENGTH: 1917
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
atggctttgc ctgtcacggc tcttctgctc cctctggccc tgcttctgca cgcggcgcga    60
cccgatatcc agatgactca gacgacctca tcattgtccg ccagtttggg ggacagggtt   120
acaatatcct gccgggcgag ccaagacatc agtaaatatc ttaattggta ccagcagaaa   180
ccagatggta cagtaaaact tcttatctac cacacctctc ggctccactc tggggttccc   240
tctaggttca gtggtagtgg gtcaggcacc gactacagcc ttacgataag caacttggaa   300
caggaggata tcgcaactta cttctgccaa cagggaaata ccctgcctta cgttcggt    360
ggaggcacta aactggagat cactgggtca acctctggta gcggtaagcc tggctccggc   420
gaaggctcca caaagggtga ggtgaaactc caagagtcag gtcccggttt ggtagccccc   480
tcacaaagtt tgtcagttac ttgtaccgta agcggcgttt ccctgcccga ttacggtgtg   540
agctggataa gcagccacc gagaaaaggt cttgaatggc tgggagtgat ctggggggtct   600
gagacaacgt attacaactc agctcttaag agcaggctta cgatcattaa agataacagc   660
aaatctcaag tgttcctcaa aatgaatagc cttcaaactg atgatactgc catctattat   720
tgtgctaagc attattacta tggcggcagt tacgcaatgg attattgggg gcaaggtacc   780
tcagtcactg taagcagcga acagaagctc atttctgaag aagacctcaa ccccggaggg   840
ggaggggggaa gtgggggagg gggtagtggt ggcggaggat caggcggggg gggatcagga   900
tccatggata tccagatgac ccagtccccg agccctctgt ccgcctctgt gggcgatagg   960
gtcaccatca cctgccgtgc cagtcaggac atccgtaatt atctgaactg gtatcaacag  1020
aaaccaggaa aagctccgaa actactgatt tactataccc cccgcctgga gtctggagtc  1080
ccttctcgct ctctctggttc tggttctggg acggattaca ctctgaccat cagcagtctg  1140
caaccggaag acttcgcaac ttattactgt cagcaaggta atactctgcc gtggacgttc  1200
ggacagggca ccaaggtgga gatcaaaggc ggcggcggaa gtggaggagg aggctcaggc  1260
ggaggaggga gcgaggttca gctggtggag tctggcggtg gcctggtgca gccgggggggc  1320
tcactccgtt tgtcctgtgc agcttctggc tactcctta ccggctacac tatgaactgg  1380
gtgcgtcagg ccccaggtaa gggcctggaa tgggttgcac tgattaatcc taccaaaggt  1440
gttagtacct acaaccagaa gttcaaggac cgtttcacta taagcgtaga taatccaaaa  1500
aacacagcct acctgcaaat gaacagcctg cgtgctgagg acactgccgt ctattattgt  1560
gctagaagcg atactacgg cgatagtgac tggtattttg acgtgtggggg tcaaggaacc  1620
ctggtcaccg tctcctcgac tagtggcgga ggaggatcac tcgagagcgg acaggtgctg  1680
ctggaatcca atatcaaagt cctgcccact tggtctaccc ccgtgcagcc tatggctctg  1740
```

```
attgtgctgg gaggagtcgc aggactgctg ctgtttatcg ggctgggaat tttcttttgc    1800
gtgcgctgcc ggcaccggag aaggcaggcc gagcgcatga ccagatcaa gcgactgctg    1860 agcgagaaga aacctgtca gtgtccccat agattccaga agacctgttc acccatt       1917
```

<210> SEQ ID NO 64
<211> LENGTH: 639
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Ser Thr Ser Gly Ser Gly Lys Pro Gly Ser Gly Glu Gly Ser Thr
130                 135                 140

Lys Gly Glu Val Lys Leu Gln Glu Ser Gly Pro Gly Leu Val Ala Pro
145                 150                 155                 160

Ser Gln Ser Leu Ser Val Thr Cys Thr Val Ser Gly Val Ser Leu Pro
                165                 170                 175

Asp Tyr Gly Val Ser Trp Ile Arg Gln Pro Pro Arg Lys Gly Leu Glu
            180                 185                 190

Trp Leu Gly Val Ile Trp Gly Ser Glu Thr Thr Tyr Tyr Asn Ser Ala
        195                 200                 205

Leu Lys Ser Arg Leu Thr Ile Ile Lys Asp Asn Ser Lys Ser Gln Val
        210                 215                 220

Phe Leu Lys Met Asn Ser Leu Gln Thr Asp Asp Thr Ala Ile Tyr Tyr
225                 230                 235                 240

Cys Ala Lys His Tyr Tyr Tyr Gly Gly Ser Tyr Ala Met Asp Tyr Trp
                245                 250                 255

Gly Gln Gly Thr Ser Val Thr Val Ser Ser Glu Gln Lys Leu Ile Ser
            260                 265                 270

Glu Glu Asp Leu Asn Pro Gly Gly Gly Gly Ser Gly Gly Gly Gly
        275                 280                 285

Ser Gly Gly Gly Gly Ser Gly Gly Gly Ser Gly Ser Met Asp Ile
        290                 295                 300

Gln Met Thr Gln Ser Pro Ser Ser Leu Ser Ala Ser Val Gly Asp Arg
305                 310                 315                 320

Val Thr Ile Thr Cys Arg Ala Ser Gln Asp Ile Arg Asn Tyr Leu Asn
```

```
                   325                 330                 335
Trp Tyr Gln Gln Lys Pro Gly Lys Ala Pro Lys Leu Ile Tyr Tyr
                340                 345                 350
Thr Ser Arg Leu Glu Ser Gly Val Pro Ser Arg Phe Ser Gly Ser
                355                 360                 365
Ser Gly Thr Asp Tyr Thr Leu Thr Ile Ser Ser Leu Gln Pro Glu Asp
    370                 375                 380
Phe Ala Thr Tyr Tyr Cys Gln Gln Gly Asn Thr Leu Pro Trp Thr Phe
385                 390                 395                 400
Gly Gln Gly Thr Lys Val Glu Ile Lys Gly Gly Gly Ser Gly Gly
                405                 410                 415
Gly Gly Ser Gly Gly Gly Ser Glu Val Gln Leu Val Glu Ser Gly
                420                 425                 430
Gly Gly Leu Val Gln Pro Gly Gly Ser Leu Arg Leu Ser Cys Ala Ala
                435                 440                 445
Ser Gly Tyr Ser Phe Thr Gly Tyr Thr Met Asn Trp Val Arg Gln Ala
    450                 455                 460
Pro Gly Lys Gly Leu Glu Trp Val Ala Leu Ile Asn Pro Thr Lys Gly
465                 470                 475                 480
Val Ser Thr Tyr Asn Gln Lys Phe Lys Asp Arg Phe Thr Ile Ser Val
                485                 490                 495
Asp Lys Ser Lys Asn Thr Ala Tyr Leu Gln Met Asn Ser Leu Arg Ala
                500                 505                 510
Glu Asp Thr Ala Val Tyr Tyr Cys Ala Arg Ser Gly Tyr Tyr Gly Asp
                515                 520                 525
Ser Asp Trp Tyr Phe Asp Val Trp Gly Gln Gly Thr Leu Val Thr Val
    530                 535                 540
Ser Ser Thr Ser Gly Gly Gly Gly Ser Leu Glu Ser Gly Gln Val Leu
545                 550                 555                 560
Leu Glu Ser Asn Ile Lys Val Leu Pro Thr Trp Ser Thr Pro Val Gln
                565                 570                 575
Pro Met Ala Leu Ile Val Leu Gly Gly Val Ala Gly Leu Leu Leu Phe
                580                 585                 590
Ile Gly Leu Gly Ile Phe Phe Cys Val Arg Cys Arg His Arg Arg
                595                 600                 605
Gln Ala Glu Arg Met Ser Gln Ile Lys Arg Leu Leu Ser Glu Lys Lys
    610                 615                 620
Thr Cys Gln Cys Pro His Arg Phe Gln Lys Thr Cys Ser Pro Ile
625                 630                 635
```

<210> SEQ ID NO 65
<211> LENGTH: 1566
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
atggagaccc cgcccagct gctgttcctg ctgctgctgt ggctgcccga caccaccggc      60
atgtcacggg gctccgacct gggcaaaaag ctgctggagg ccgctagggc cgggcaggac    120
gatgaagtga gaatcctgat ggccaacggg gctgacgtga atgctaagga tgagtacggc    180
ctgacccccc tgtatctggc tacagcacac ggccatctgg agatcgtgga agtcctgctg    240
aaaaacggag ccgacgtgaa tgcagtcgat gccattgggt tcactcctct gcacctggca    300

```
gcctttatcg gacatctgga gattgcagaa gtgctgctga agcacggcgc tgacgtgaac    360
gcacaggata agttcggaaa aaccgctttt gacatcagca ttggcaacgg aaatgaagac    420
ctggctgaaa tcctgcagaa actgaatgaa cagaaactga ttagcgaaga agacctgaac    480 cccggggag gaggagggag cggggagga ggcagcggcg ggggaggctc tggaggagga      540
gggagcggat ccatggatat ccagatgacc cagtccccga gctccctgtc cgcctctgtg    600
ggcgataggg tcaccatcac ctgccgtgcc agtcaggaca tccgtaatta tctgaactgg    660
tatcaacaga aaccaggaaa agctccgaaa ctactgattt actataccct ccgcctggag    720
tctggagtcc cttctcgctt ctctggttct ggttctggga cggattacac tctgaccatc    780
agcagtctgc aaccggaaga cttcgcaact tattactgtc agcaaggtaa tactctgccg    840
tggacgttcg gacagggcac caaggtggag atcaaaggcg gcggcggaag tggaggagga    900
ggctcaggcg gaggagggag cgaggttcag ctggtggagt ctggcggtgg cctggtgcag    960 ccaggggct cactccgttt gtcctgtgca gcttctggct actcctttac cggctacact     1020
atgaactggg tgcgtcaggc cccaggtaag ggcctggaat gggttgcact gattaatcct    1080
tataaaggtg ttagtaccta caaccagaag ttcaaggacc gtttcactat aagcgtagat    1140
aaatccaaaa acacagccta cctgcaaatg aacagcctgc gtgctgagga cactgccgtc    1200
tattattgtg ctagaagcgg atactacggc gatagtgact ggtattttga cgtgtggggt    1260
caaggaaccc tggtcaccgt ctcctcgact agtggcggag gaggatcact cgagagcgga    1320
caggtgctgc tggaatccaa tatcaaagtc ctgcccactt ggtctacccc cgtgcagcct    1380
atggctctga ttgtgctggg aggagtcgca ggactgctgc tgtttatcgg ctgggaatt    1440 ttcttttgcg tgcgctgccg gcaccggaga aggcaggccg agcgcatgag ccagatcaag    1500
cgactgctga gcgagaagaa aacctgtcag tgtccccata gattccagaa gacctgttca    1560
cccatt                                                              1566
```

<210> SEQ ID NO 66  
<211> LENGTH: 522  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 66

```
Met Glu Thr Pro Ala Gln Leu Leu Phe Leu Leu Leu Trp Leu Pro
1               5                   10                  15

Asp Thr Thr Gly Met Ser Arg Gly Ser Asp Leu Gly Lys Lys Leu Leu
            20                  25                  30

Glu Ala Ala Arg Ala Gly Gln Asp Asp Glu Val Arg Ile Leu Met Ala
        35                  40                  45

Asn Gly Ala Asp Val Asn Ala Lys Asp Glu Tyr Gly Leu Thr Pro Leu
    50                  55                  60

Tyr Leu Ala Thr Ala His Gly His Leu Glu Ile Val Glu Val Leu Leu
65                  70                  75                  80

Lys Asn Gly Ala Asp Val Asn Ala Val Asp Ala Ile Gly Phe Thr Pro
                85                  90                  95

Leu His Leu Ala Ala Phe Ile Gly His Leu Glu Ile Ala Glu Val Leu
            100                 105                 110

Leu Lys His Gly Ala Asp Val Asn Ala Gln Asp Lys Phe Gly Lys Thr
        115                 120                 125
```

```
Ala Phe Asp Ile Ser Ile Gly Asn Gly Asn Glu Asp Leu Ala Glu Ile
            130                 135                 140

Leu Gln Lys Leu Asn Glu Gln Lys Leu Ile Ser Glu Glu Asp Leu Asn
145                 150                 155                 160

Pro Gly Gly Gly Gly Ser Gly Gly Gly Ser Gly Gly Gly Gly
                165                 170                 175

Ser Gly Gly Gly Ser Gly Ser Met Asp Ile Gln Met Thr Gln Ser
            180                 185                 190

Pro Ser Ser Leu Ser Ala Ser Val Gly Asp Arg Val Thr Ile Thr Cys
            195                 200                 205

Arg Ala Ser Gln Asp Ile Arg Asn Tyr Leu Asn Trp Tyr Gln Gln Lys
            210                 215                 220

Pro Gly Lys Ala Pro Lys Leu Leu Ile Tyr Tyr Thr Ser Arg Leu Glu
225                 230                 235                 240

Ser Gly Val Pro Ser Arg Phe Ser Gly Ser Gly Ser Gly Thr Asp Tyr
                245                 250                 255

Thr Leu Thr Ile Ser Ser Leu Gln Pro Glu Asp Phe Ala Thr Tyr Tyr
            260                 265                 270

Cys Gln Gln Gly Asn Thr Leu Pro Trp Thr Phe Gly Gln Gly Thr Lys
            275                 280                 285

Val Glu Ile Lys Gly Gly Gly Gly Ser Gly Gly Gly Gly Ser Gly Gly
290                 295                 300

Gly Gly Ser Glu Val Gln Leu Val Glu Ser Gly Gly Gly Leu Val Gln
305                 310                 315                 320

Pro Gly Gly Ser Leu Arg Leu Ser Cys Ala Ala Ser Gly Tyr Ser Phe
                325                 330                 335

Thr Gly Tyr Thr Met Asn Trp Val Arg Gln Ala Pro Gly Lys Gly Leu
            340                 345                 350

Glu Trp Val Ala Leu Ile Asn Pro Tyr Lys Gly Val Ser Thr Tyr Asn
            355                 360                 365

Gln Lys Phe Lys Asp Arg Phe Thr Ile Ser Val Asp Lys Ser Lys Asn
            370                 375                 380

Thr Ala Tyr Leu Gln Met Asn Ser Leu Arg Ala Glu Asp Thr Ala Val
385                 390                 395                 400

Tyr Tyr Cys Ala Arg Ser Gly Tyr Tyr Gly Asp Ser Asp Trp Tyr Phe
                405                 410                 415

Asp Val Trp Gly Gln Gly Thr Leu Val Thr Val Ser Ser Thr Ser Gly
            420                 425                 430

Gly Gly Gly Ser Leu Glu Ser Gly Gln Val Leu Leu Glu Ser Asn Ile
            435                 440                 445

Lys Val Leu Pro Thr Trp Ser Thr Pro Val Gln Pro Met Ala Leu Ile
450                 455                 460

Val Leu Gly Gly Val Ala Gly Leu Leu Leu Phe Ile Gly Leu Gly Ile
465                 470                 475                 480

Phe Phe Cys Val Arg Cys Arg His Arg Arg Arg Gln Ala Glu Arg Met
                485                 490                 495

Ser Gln Ile Lys Arg Leu Leu Ser Glu Lys Lys Thr Cys Gln Cys Pro
            500                 505                 510

His Arg Phe Gln Lys Thr Cys Ser Pro Ile
            515                 520

<210> SEQ ID NO 67
<211> LENGTH: 1569
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
atggccttac cagtgaccgc cttgctcctg ccgctggcct tgctgctcca cgccgccagg      60
ccgatgtcac ggggctccga cctgggcaaa aagctgctgg aggccgctag gccgggcag     120
gacgatgaag tgagaatcct gatggccaac ggggctgacg tgaatgctaa ggatgagtac    180
ggcctgaccc ccctgtatct ggctacagca cacggccatc tggagatcgt ggaagtcctg    240
ctgaaaaacg gagccgacgt gaatgcagtc gatgccattg ggttcactcc tctgcacctg    300
gcagccttta tcggacatct ggagattgca gaagtgctgc tgaagcacgg cgctgacgtg    360
aacgcacagg ataagttcgg aaaaaccgct tttgacatca gcattggcaa cggaaatgaa    420
gacctggctg aaatcctgca gaaactgaat gaacagaaac tgattagcga agaagacctg    480
aaccccgggg gaggaggagg gagcggggga ggaggcagcg gcggggagg ctctggagga     540
ggagggagcg gatccatgga tatccagatg acccagtccc cgagctccct gtccgcctct    600
gtgggcgata gggtcaccat cacctgccgt gccagtcagg acatccgtaa ttatctgaac    660
tggtatcaac agaaaccagg aaaagctccg aaactactga tttactatac ctcccgcctg    720
gagtctggag tcccttctcg cttctctggt tctggttctg ggacggatta cactctgacc    780
atcagcagtc tgcaaccgga agacttcgca acttattact gtcagcaagg taatactctg    840
ccgtggacgt tcggacaggg caccaaggtg gagatcaaag cggcggcgg aagtggagga     900
ggaggctcag cggaggagg gagcgaggtt cagctggtgg agtctggcgg tggcctggtg    960
cagccagggg gctcactccg tttgtcctgt gcagcttctg gctactcctt taccggctac  1020
actatgaact gggtgcgtca ggcccccaggt aagggcctgg aatgggttgc actgattaat  1080
ccttataaag tgttagtac ctacaaccag aagttcaagg accgtttcac tataagcgta    1140
gataaatcca aaaacacagc ctacctgcaa atgaacagcc tgcgtgctga ggacactgcc   1200
gtctattatt gtgctagaag cggatactac ggcgatagtg actggtattt tgacgtgtgg  1260
ggtcaaggaa ccctggtcac cgtctcctcg actagtggcg gaggaggatc actcgagagc   1320
ggacaggtgc tgctggaatc caatatcaaa gtcctgccca cttggtctac ccccgtgcag   1380
cctatggctc tgattgtgct gggaggagtc gcaggactgc tgctgtttat cgggctggga   1440
atttctttt gcgtgcgctg ccggcaccgg agaaggcagg ccgagcgcat gagccagatc    1500
aagcgactgc tgagcgagaa gaaaacctgt cagtgtcccc atagattcca gaagacctgt   1560
tcacccatt                                                           1569
```

<210> SEQ ID NO 68
<211> LENGTH: 523
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Met Ala Leu Pro Val Thr Ala Leu Leu Leu Pro Leu Ala Leu Leu Leu
1               5                  10                  15

His Ala Ala Arg Pro Met Ser Arg Gly Ser Asp Leu Gly Lys Lys Leu
            20                  25                  30
```

Leu Glu Ala Ala Arg Ala Gly Gln Asp Asp Glu Val Arg Ile Leu Met
            35                  40                  45

Ala Asn Gly Ala Asp Val Asn Ala Lys Asp Glu Tyr Gly Leu Thr Pro
 50                  55                  60

Leu Tyr Leu Ala Thr Ala His Gly His Leu Glu Ile Val Glu Val Leu
 65                  70                  75                  80

Leu Lys Asn Gly Ala Asp Val Asn Ala Val Asp Ala Ile Gly Phe Thr
                 85                  90                  95

Pro Leu His Leu Ala Ala Phe Ile Gly His Leu Glu Ile Ala Glu Val
            100                 105                 110

Leu Leu Lys His Gly Ala Asp Val Asn Ala Gln Asp Lys Phe Gly Lys
            115                 120                 125

Thr Ala Phe Asp Ile Ser Ile Gly Asn Gly Asn Glu Asp Leu Ala Glu
            130                 135                 140

Ile Leu Gln Lys Leu Asn Glu Gln Lys Leu Ile Ser Glu Glu Asp Leu
145                 150                 155                 160

Asn Pro Gly Gly Gly Gly Ser Gly Gly Gly Ser Gly Gly Gly
                165                 170                 175

Gly Ser Gly Gly Gly Gly Ser Gly Ser Met Asp Ile Gln Met Thr Gln
            180                 185                 190

Ser Pro Ser Ser Leu Ser Ala Ser Val Gly Asp Arg Val Thr Ile Thr
            195                 200                 205

Cys Arg Ala Ser Gln Asp Ile Arg Asn Tyr Leu Asn Trp Tyr Gln Gln
            210                 215                 220

Lys Pro Gly Lys Ala Pro Lys Leu Leu Ile Tyr Tyr Thr Ser Arg Leu
225                 230                 235                 240

Glu Ser Gly Val Pro Ser Arg Phe Ser Gly Ser Gly Ser Gly Thr Asp
                245                 250                 255

Tyr Thr Leu Thr Ile Ser Ser Leu Gln Pro Glu Asp Phe Ala Thr Tyr
            260                 265                 270

Tyr Cys Gln Gln Gly Asn Thr Leu Pro Trp Thr Phe Gly Gln Gly Thr
            275                 280                 285

Lys Val Glu Ile Lys Gly Gly Gly Gly Ser Gly Gly Gly Gly Ser Gly
            290                 295                 300

Gly Gly Ser Glu Val Gln Leu Val Glu Ser Gly Gly Gly Leu Val
305                 310                 315                 320

Gln Pro Gly Gly Ser Leu Arg Leu Ser Cys Ala Ala Ser Gly Tyr Ser
                325                 330                 335

Phe Thr Gly Tyr Thr Met Asn Trp Val Arg Gln Ala Pro Gly Lys Gly
            340                 345                 350

Leu Glu Trp Val Ala Leu Ile Asn Pro Tyr Lys Gly Val Ser Thr Tyr
            355                 360                 365

Asn Gln Lys Phe Lys Asp Arg Phe Thr Ile Ser Val Asp Lys Ser Lys
370                 375                 380

Asn Thr Ala Tyr Leu Gln Met Asn Ser Leu Arg Ala Glu Asp Thr Ala
385                 390                 395                 400

Val Tyr Tyr Cys Ala Arg Ser Gly Tyr Tyr Gly Asp Ser Asp Trp Tyr
                405                 410                 415

Phe Asp Val Trp Gly Gln Gly Thr Leu Val Thr Val Ser Ser Thr Ser
            420                 425                 430

Gly Gly Gly Gly Ser Leu Glu Ser Gly Gln Val Leu Leu Glu Ser Asn
            435                 440                 445

Ile Lys Val Leu Pro Thr Trp Ser Thr Pro Val Gln Pro Met Ala Leu

```
                450             455             460
Ile Val Leu Gly Gly Val Ala Gly Leu Leu Phe Ile Gly Leu Gly
465                 470             475             480

Ile Phe Phe Cys Val Arg Cys Arg His Arg Arg Gln Ala Glu Arg
                485             490             495

Met Ser Gln Ile Lys Arg Leu Leu Ser Glu Lys Lys Thr Cys Gln Cys
            500             505             510

Pro His Arg Phe Gln Lys Thr Cys Ser Pro Ile
        515             520
```

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Gly Gly Gly Gly Ser Gly Gly Gly Ser Gly Gly Gly Ser Gly
1               5               10              15

Gly Gly Gly Ser
            20
```

<210> SEQ ID NO 70
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70

```
ggaggaggag ggagcggggg aggaggcagc ggcggggag gctctggagg aggaggagc        60
```

<210> SEQ ID NO 71
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
atggacatcc agatgactca gaccacaagc tccctgtctg caagtctggg cgaccgggtg        60
acaatctcct gcagagcctc tcaggatatt aggaactacc tgaattggta tcagcagaaa       120
cctgatggca cagtcaagct gctgatctac tataccagcc ggctgcactc aggcgtgcca       180
agcaaattct caggaagcgg ctccgggact gactactccc tgaccatctc taacctggag       240
caggaagata ttgctaccta tttctgccag cagggcaata cactgccctg acttttgcc        300 ggaggcacca aactggagat caagggggga ggcgggagtg gaggcggggg atcaggagga       360
ggaggcagcg gaggaggagg gtccgaggtc cagctgcagc agagcggacc agaactggtg       420
aagcccggag caagtatgaa aatctcctgt aaggcctcag gatacagctt caccggctat       480
acaatgaact gggtgaaaca gtcccatggc aagaacctgg aatggatggg ctgattaat       540 cctaccaaag gcgtcagcac ctataatcag aagtttaaag acaaggccac actgactgtg       600
gataagtcta gttcaaccgc ttacatggag ctgctgtccc tgacatctga agacagtgcc       660
gtgtactatt gtgctcggtc tggctactat ggggacagtg attggtactt cgatgtctgg       720
```
ggacagggca ctaccctgac cgtgttttct 750

<210> SEQ ID NO 72
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Asn
                20                  25                  30

Tyr Leu Asn Trp Tyr Gln Gln Lys Pro Asp Gly Thr Val Lys Leu Leu
            35                  40                  45

Ile Tyr Tyr Thr Ser Arg Leu His Ser Gly Val Pro Ser Lys Phe Ser
        50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Trp Thr Phe Ala Gly Gly Thr Lys Leu Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Gln Gln Ser Gly Pro Glu Leu Val Lys Pro Gly Ala
    130                 135                 140

Ser Met Lys Ile Ser Cys Lys Ala Ser Gly Tyr Ser Phe Thr Gly Tyr
145                 150                 155                 160

Thr Met Asn Trp Val Lys Gln Ser His Gly Lys Asn Leu Glu Trp Met
                165                 170                 175

Gly Leu Ile Asn Pro Thr Lys Gly Val Ser Thr Tyr Asn Gln Lys Phe
            180                 185                 190

Lys Asp Lys Ala Thr Leu Thr Val Asp Lys Ser Ser Ser Thr Ala Tyr
        195                 200                 205

Met Glu Leu Leu Ser Leu Thr Ser Glu Asp Ser Ala Val Tyr Tyr Cys
    210                 215                 220

Ala Arg Ser Gly Tyr Tyr Gly Asp Ser Asp Trp Tyr Phe Asp Val Trp
225                 230                 235                 240

Gly Gln Gly Thr Thr Leu Thr Val Phe Ser
                245                 250

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Gly Gly Gly Ser
1               5

<210> SEQ ID NO 74
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 74

Gly Gly Gly Gly Ser Gly Gly Gly Gly Ser Gly Gly Gly Gly Ser
1               5                   10                  15
```